United States Patent
Cubillos-Ruiz et al.

(10) Patent No.: US 10,421,965 B2
(45) Date of Patent: *Sep. 24, 2019

(54) COMPOUNDS FOR INDUCING ANTI-TUMOR IMMUNITY AND METHODS THEREOF

(71) Applicant: Cornell University, Ithaca, NY (US)

(72) Inventors: Juan R. Cubillos-Ruiz, New York, NY (US); Laurie H. Glimcher, New York, NY (US)

(73) Assignee: Cornell University, Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/877,864

(22) Filed: Jan. 23, 2018

(65) Prior Publication Data

US 2018/0258426 A1    Sep. 13, 2018

Related U.S. Application Data

(63) Continuation of application No. 15/024,215, filed as application No. PCT/US2014/057525 on Sep. 25, 2014, now Pat. No. 9,957,506.

(60) Provisional application No. 61/882,461, filed on Sep. 25, 2013.

(51) Int. Cl.
| | |
|---|---|
| C07H 21/04 | (2006.01) |
| C12N 15/113 | (2010.01) |
| A61K 31/713 | (2006.01) |
| A61K 45/06 | (2006.01) |

(52) U.S. Cl.
CPC .......... *C12N 15/113* (2013.01); *A61K 31/713* (2013.01); *A61K 45/06* (2013.01); *C12N 15/1137* (2013.01); *C12Y 207/11* (2013.01); *C12N 2310/11* (2013.01); *C12N 2310/14* (2013.01); *C12N 2320/31* (2013.01)

(58) Field of Classification Search
CPC .................................................. C07H 21/04
See application file for complete search history.

(56) References Cited

U.S. PATENT DOCUMENTS

| | | | |
|---|---|---|---|
| 4,522,811 A | 6/1985 | Eppstein et al. | |
| 4,683,194 A | 7/1987 | Saiki et al. | |
| 4,683,195 A | 7/1987 | Mullis et al. | |
| 4,683,202 A | 7/1987 | Mullis | |
| 4,812,128 A | 3/1989 | Mikelsaar | |
| 4,868,116 A | 9/1989 | Morgan et al. | |
| 4,873,316 A | 10/1989 | Meade et al. | |
| 4,879,214 A | 11/1989 | Kornher et al. | |
| 4,879,215 A | 11/1989 | Weng et al. | |
| 4,906,122 A | 3/1990 | Barrett et al. | |
| 4,980,286 A | 12/1990 | Morgan et al. | |
| 4,987,071 A | 1/1991 | Cech et al. | |
| 5,030,103 A | 7/1991 | Buist et al. | |
| 5,116,742 A | 5/1992 | Cech et al. | |
| 5,166,320 A | 11/1992 | Wu et al. | |
| 5,223,409 A | 6/1993 | Ladner et al. | |
| 5,233,409 A | 8/1993 | Schwab | |
| 5,283,317 A | 2/1994 | Saifer et al. | |
| 5,399,346 A | 3/1995 | Anderson et al. | |
| 5,491,084 A | 2/1996 | Chalfie et al. | |
| 5,498,531 A | 3/1996 | Jarrell | |
| 5,583,973 A | 12/1996 | Delisi et al. | |
| 5,589,369 A | 12/1996 | Seidman et al. | |
| 5,591,669 A | 1/1997 | Krimpenfort et al. | |
| 5,612,894 A | 3/1997 | Wertz | |
| 5,650,298 A | 7/1997 | Bujard et al. | |
| 5,658,570 A | 8/1997 | Newman et al. | |
| 5,693,780 A | 12/1997 | Newman et al. | |
| 5,730,975 A | 3/1998 | Hotamisligil et al. | |
| 5,756,096 A | 5/1998 | Newman et al. | |
| 5,811,524 A | 9/1998 | Brams et al. | |
| 5,908,762 A | 6/1999 | Ono et al. | |
| 5,939,598 A | 8/1999 | Kucherlapati et al. | |
| 5,945,307 A | 8/1999 | Glucksmann et al. | |
| 6,037,148 A | 3/2000 | Khodadoust | |
| 6,075,181 A | 6/2000 | Kucherlapati et al. | |
| 6,080,576 A | 6/2000 | Zambrowicz et al. | |
| 6,093,573 A | 7/2000 | Beamer et al. | |
| 6,329,422 B1 | 12/2001 | Fischer et al. | |
| 6,400,487 B1 | 6/2002 | Harris et al. | |
| 6,410,516 B1 | 6/2002 | Baltimore et al. | |
| 6,413,735 B1 | 7/2002 | Lau | |
| 6,630,312 B2 | 10/2003 | Shoelson | |
| 6,632,608 B2 | 10/2003 | Glimcher et al. | |
| 6,632,641 B1 | 10/2003 | Brennan et al. | |
| 7,220,539 B1 | 5/2007 | Du et al. | |
| 7,306,905 B2 | 12/2007 | Ron et al. | |
| 7,358,415 B2 | 4/2008 | Glimcher et al. | |

(Continued)

FOREIGN PATENT DOCUMENTS

| | | |
|---|---|---|
| EP | 0857780 A1 | 8/1998 |
| EP | 1669067 A2 | 6/2006 |

(Continued)

OTHER PUBLICATIONS

"U.S. Appl. No. 15/024,215, Notice of Allowance dated Jan. 30, 2018", 8 pgs.
"U.S. Appl. No. 15/921,322, Non Final Office Action dated May 18, 2018", 13 pgs.
"European Application Serial No. 14781414.9, Communication Pursuant to Article 94(3) EPC dated Feb. 16, 2018", 3 pgs.
"European Application Serial No. 14781414.9, Response filed Jun. 18, 2018 to Communication Pursuant to Article 94(3) EPC dated Feb. 16, 2018", 198 pgs.
"U.S. Appl. No. 15/024,215, Examiner Interview Summary dated Aug. 30, 2017", 3 pgs.

(Continued)

*Primary Examiner* — Kimberly Chong
(74) *Attorney, Agent, or Firm* — Schwegman Lundberg & Woessner, P.A.

(57) ABSTRACT

Described herein is a previously unknown function of XBP1 in controlling anti-tumor immunity. It is shown that inhibiting XBP1 in tumor-associated dendritic cells inhibits tumor growth and induces protective anti-tumor immune responses.

12 Claims, 36 Drawing Sheets

Specification includes a Sequence Listing.

(56) References Cited

U.S. PATENT DOCUMENTS

| | | | |
|---|---|---|---|
| 8,227,184 B2 | 7/2012 | Glimcher et al. |
| 8,434,740 B2 | 5/2013 | Logtenberg |
| 8,765,932 B2 | 7/2014 | Fitzgerald et al. |
| 8,940,479 B2 | 1/2015 | Lee et al. |
| 9,957,506 B2 | 5/2018 | Cubillos-Ruiz et al. |
| 2002/0059652 A1 | 5/2002 | Glimcher et al. |
| 2003/0096762 A1 | 5/2003 | Fischer et al. |
| 2003/0224428 A1 | 12/2003 | Ron et al. |
| 2004/0077020 A1 | 4/2004 | Mannick et al. |
| 2004/0110236 A1 | 6/2004 | Glimcher et al. |
| 2004/0170622 A1 | 9/2004 | Glimcher et al. |
| 2004/0197272 A1 | 10/2004 | Fischer et al. |
| 2005/0059052 A1 | 3/2005 | Kaufman et al. |
| 2005/0059652 A1 | 3/2005 | Hamann et al. |
| 2005/0250182 A1 | 11/2005 | Kaufman et al. |
| 2006/0057104 A1 | 3/2006 | Cheng et al. |
| 2006/0063187 A1 | 3/2006 | Hotamisligil et al. |
| 2006/0073213 A1 | 4/2006 | Hotamisligil et al. |
| 2006/0148739 A1 | 7/2006 | Kotani et al. |
| 2007/0141074 A1 | 6/2007 | Schubert |
| 2007/0196335 A1 | 8/2007 | Pardoll et al. |
| 2008/0241114 A1 | 10/2008 | Glimcher et al. |
| 2009/0186893 A1 | 7/2009 | Patterson et al. |
| 2009/0232738 A1 | 9/2009 | Glimcher et al. |
| 2009/0275638 A1 | 11/2009 | Fitzgerald et al. |
| 2009/0291857 A1 | 11/2009 | Koong et al. |
| 2010/0075894 A1 | 3/2010 | Hotamisligil et al. |
| 2010/0266618 A1 | 10/2010 | Stojdl et al. |
| 2011/0052669 A1 | 3/2011 | Lee et al. |
| 2011/0142799 A1 | 6/2011 | Glimcher et al. |
| 2012/0141539 A1 | 6/2012 | Glimcher |
| 2012/0270877 A1 | 10/2012 | Zeng et al. |
| 2012/0322814 A1 | 12/2012 | Korennykh et al. |
| 2014/0030294 A1 | 1/2014 | Glimcher |
| 2014/0088148 A1 | 3/2014 | Dakshanamurthy et al. |
| 2014/0170622 A1 | 6/2014 | Pastrick et al. |
| 2015/0018406 A1 | 1/2015 | Glimcher et al. |
| 2016/0083361 A1 | 3/2016 | Del Valle et al. |
| 2016/0237429 A1 | 8/2016 | Cubillos-Ruiz et al. |
| 2018/0201933 A1 | 7/2018 | Cubillios-Ruiz et al. |

FOREIGN PATENT DOCUMENTS

| | | |
|---|---|---|
| EP | 3049521 B1 | 3/2019 |
| WO | WO-89002468 A1 | 3/1989 |
| WO | WO-89005345 A1 | 6/1989 |
| WO | WO-89007136 A2 | 8/1989 |
| WO | WO-9011345 A1 | 10/1990 |
| WO | WO-9101140 A1 | 2/1991 |
| WO | WO-9117271 A1 | 11/1991 |
| WO | WO-9201047 A1 | 1/1992 |
| WO | WO-92007573 A1 | 5/1992 |
| WO | WO-9209680 A1 | 6/1992 |
| WO | WO-9209690 A2 | 6/1992 |
| WO | WO-9215679 A1 | 9/1992 |
| WO | WO-9218619 A1 | 10/1992 |
| WO | WO-9220791 A1 | 11/1992 |
| WO | WO-9301288 A1 | 1/1993 |
| WO | WO-9304169 A1 | 3/1993 |
| WO | WO-9323431 A1 | 11/1993 |
| WO | WO-9402610 A1 | 2/1994 |
| WO | WO-9410300 A1 | 5/1994 |
| WO | WO-9416101 A2 | 7/1994 |
| WO | WO-9418317 A1 | 8/1994 |
| WO | WO-9429442 A2 | 12/1994 |
| WO | WO-9503832 A1 | 2/1995 |
| WO | WO-9601313 A1 | 1/1996 |
| WO | WO-9623898 A1 | 8/1996 |
| WO | WO-9739721 A2 | 10/1997 |
| WO | WO-9918953 A1 | 4/1999 |
| WO | WO-0149717 A2 | 7/2001 |
| WO | WO-0172783 A2 | 10/2001 |
| WO | WO-02085396 A1 | 10/2002 |
| WO | WO-03089622 A2 | 10/2003 |
| WO | WO-2004020610 A2 | 3/2004 |
| WO | WO-2004037373 A2 | 5/2004 |
| WO | WO-2005034737 A2 | 4/2005 |
| WO | WO-2006031930 A2 | 3/2006 |
| WO | WO-2006031931 A2 | 3/2006 |
| WO | WO-07041282 A2 | 4/2007 |
| WO | WO-07053747 A2 | 5/2007 |
| WO | WO-2007101224 A2 | 9/2007 |
| WO | WO-2008039445 A2 | 4/2008 |
| WO | WO-08143876 A2 | 11/2008 |
| WO | WO-2008141129 A1 | 11/2008 |
| WO | WO-2009091815 A2 | 7/2009 |
| WO | WO-2009129465 A2 | 10/2009 |
| WO | WO-2010008860 A1 | 1/2010 |
| WO | WO-2010014905 A2 | 2/2010 |
| WO | WO-2010031056 A2 | 3/2010 |
| WO | WO-2010088498 A1 | 8/2010 |
| WO | WO-2010141619 A1 | 12/2010 |
| WO | WO-2010151827 A1 | 12/2010 |
| WO | WO-2011022316 A1 | 2/2011 |
| WO | WO-2012109238 | 8/2012 |
| WO | WO-2012138715 A2 | 10/2012 |
| WO | WO-2013134774 | 9/2013 |
| WO | WO-2013142571 A2 | 9/2013 |
| WO | WO-2015/048331 A1 | 4/2015 |
| WO | WO-2015048331 | 4/2015 |

OTHER PUBLICATIONS

"U.S. Appl. No. 15/024,215, Final Office Action dated Sep. 29, 2017", 12 pgs.

"U.S. Appl. No. 15/024,215, Non Final Office Action dated Jun. 23, 2017", 14 pgs.

"U.S. Appl. No. 15/024,215, Notice of Allowance dated Dec. 21, 2017", 4 pgs.

"U.S. Appl. No. 15/024,215, Preliminary Amendment filed Mar. 20, 2017", 7 pgs.

"U.S. Appl. No. 15/024,215, Preliminary Amendment filed Mar. 23, 2016", 8 pgs.

"U.S. Appl. No. 15/024,215, Preliminary Amendment filed May 17, 2016", 4 pgs.

"U.S. Appl. No. 15/024,215, Response filed Sep. 19, 2017 to Non Final Office Action dated Jun. 23, 2017", 11 pgs.

"U.S. Appl. No. 15/024,215, Response filed Nov. 9, 2017 to Final Office Action dated Sep. 29, 2017", 9 pgs.

"U.S. Appl. No. 15/024,215, Response filed May 24, 2017 to Restriction Requirement dated Apr. 17, 2017", 7 pgs.

"U.S. Appl. No. 15/024,215, Restriction Requirement dated Apr. 17, 2017", 9 pgs.

"Autophagy", Wikipedia,, [Online] Retrieved from the Internet : <http://en.wikipedia.org/wiki/Autophagy>, (2012), 6 pgs.

"European Application Serial No. 03749316.0, Communication Pursuant to Article 94(3) EPC dated Jul. 10, 2009", 6 pgs.

"European Application Serial No. 03749316.0, Supplementary Partial European Search Report dated Nov. 26, 2007", 7 pgs.

"European Application Serial No. 05013817.1, Communication Pursuant to Article 94(3) EPC dated May 3, 2010", 6 pgs.

"European Application Serial No. 05013817.1, Partial European Search Report dated Mar. 17, 2006", 7 pgs.

"European Application Serial No. 14781414.9, Communication pursuant to Article 94(3) EPC dated May 30, 2017", 4 pgs.

"European Application Serial No. 14781414.9, Response Filed Jun. 30, 2017 to Communication pursuant to Article 94(3) EPC dated May 30, 2017", 191 pgs.

"European Application Serial No. 14781414.9, Response filed Nov. 15, 2016 to Communication pursuant to Rules 161(1) and 162 EPC dated May 6, 2016", 17 pgs.

"GenBank GI:4827058 for X-box binding protein 1", x-box-binding protein-1 [*Homo sapiens*], 2018.

"International Application Serial No. PCT/US2003/27404, International Preliminary Report on Patentability dated Apr. 21, 2006", 4 pgs.

"International Application Serial No. PCT/US2009/030976, International Preliminary Report on Patentability dated Jul. 29, 2010", 7 Pgs.

(56) References Cited

OTHER PUBLICATIONS

"International Application Serial No. PCT/US2009/030976, International Search Report dated Jul. 9, 2009", 5 pgs.
"International Application Serial No. PCT/US2009/030976, Written Opinion dated Jul. 9, 2009", 5 pgs.
"International Application Serial No. PCT/US2009/048321, International Preliminary Report on Patentability dated Jan. 13, 2011", 8 pgs.
"International Application Serial No. PCT/US2009/048321, International Search Report dated Dec. 8, 2009", 6 pgs.
"International Application Serial No. PCT/US2012/024140, International Preliminary Report on Patentability dated Aug. 22, 2013", 7 pgs.
"International Application Serial No. PCT/US2012/024140, International Search Report dated Aug. 17, 2012", 4 pgs.
"International Application Serial No. PCT/US2012/024140, Written Opinion dated Aug. 17, 2012", 5 pgs.
"International Application Serial No. PCT/US2013/030251, International Preliminary Report on Patentability dated Sep. 18, 2014", 8 pgs.
"International Application Serial No. PCT/US2013/030251, International Search Report dated Jun. 26, 2013", 7 pgs.
"International Application Serial No. PCT/US2013/030251 , Written Opinion dated Jun. 26, 2013", 7 pgs.
"International Application Serial No. PCT/US2013/033094, International Search Report dated Oct. 9, 2013", 8 pgs.
"International Application Serial No. PCT/US2013/033094, Written Opinion dated Oct. 9, 2013", 10 pgs.
"International Application Serial No. PCT/US2014/057525, International Preliminary Report on Patentability dated Apr. 7, 2016", 9 pgs.
"International Application Serial No. PCT/US2014/057525, International Search Report dated Nov. 24, 2014", 4 pgs.
"International Application Serial No. PCT/US2014/057525, Written Opinion dated Nov. 24, 2014", 7 pgs.
"Japanese Application Serial No. 2004-533014, Office Action dated Aug. 21, 2009", 9 pgs.
"Statin", [Online] retrieved from the Internet: <http://en.wikipedia.org/wiki/Statin>, (2008), 8 pgs.
"Thermo Scientific Pierce Protein Interaction Technical Handbook", version 2, (2010), 73 pgs.
"XBP1 antibody (ab37152)", Abcam, [Online] Retrieved from the Internet : <http://www.abcam.com/XBP1-antibody-ab37152.html, (2011), 4 pgs.
ABCAM, "IRE1 antibody (ab45973)", [Online] Retrieved from the Internet <http://www.abcam.com/IRE1-antibody-ab45973.html>, (2011), 4 pgs.
Acosta-Alvear, D, et al., "XBP1 controls diverse cell type- and condition specific-transcriptional regulatory networks", Molecular Cell, vol. 27, (2007), 53-66.
Acsadi, et al., "Human Dystrophin Expression in mdx Allter Intramuscular Injection of DNA Constructs", Nature, 333, (1991), 815-818.
Aghajanian, et al., "A phase I trial of the novel proteasome inhibitor PS341 in advanced solid tumor malignancies", Clin Cancer Res, vol. 8, (2002), 2505-2511.
Ahern, H, "Biochemical Reagent kits offer scientists good return on investment", The Scientist, vol. 9(15), (1995), 20 pgs.
Ahn, J, et al., "Dietary resveratrol alters lipid metabolism-related gene expression of mice on an atherogenic diet", J. Hepatology vol. 49 (6), (2008), 1019-1028.
Ahonen, et al., "The CD40-TRAF6 Axis Controls Affinity Maturation and the Generation of Long-Lived Plasma Cells", Nat Immunol. 3(5), (2002), 451-456.
Akira, et al., "NF-IL6 and NF-Kappa B in Cytokine Gene Regulation", Adv Immunol., 65:, (1997), 1-46.
Al-Hajj, Muhammad, et al., "Prospective identification of tumorigenic breast cancer cells", Proc. Natl. Acad. Sci. USA, 100(7), (2003), 3983-3988.

Altmeyer, et al., "Reversal of EBV Immortalization Precedes Apoptosis in IL-6-induced Human B Cell Terminal Differentiation", Immunity, vol. 7, (1997), 667-677.
Alton, et al., "Nucleotide Sequence Analysis of the Chloramphenicol Resistance Transposon Tn9", Nature 282:, (1979), 864-869.
Amit, I, et al., "Unbiased Reconstruction of a Mammalian Transcriptional Network Mediating Pathogen Responses", Science, vol. 326, (2009), 257-263.
Andersson, L, et al., "Pharmacology of apolipoprotein A-1", Current Opinion in Lipidology, vol. 8, (1997), 225-228.
Andre, Patrice, et al., "An inhibitor of HIV-1 protease modulates proteasome activity, antigen presentation, and T cell responses.", Proc Natl Acad Sci U S A., 95(22), (Oct. 27, 1998), 13120-13124.
Aragon, T, et al., "Messenger RNA targeting to endoplasmic reticulum stress signalling sites", Nature, 457, (2009), 736-740.
Araki, E, et al., "Endoplasmic reticulum stress and diabetes mellitus", Internal Medicine, vol. 42(1), (2003), 7-14.
Aridor, M, "Traffic jam: a compendium of human diseases that affect intracellular transport processes", Traffic, vol. 1 (11), (2000), 836-851.
Aridor, M, "Traffic jams II: an update of diseases of intracellular transport", Traffic, vol. 3(11), (2002), 781-790.
Arpin, et al., "Generation of Memory B Cells and Plasma Cells In Vitro", Science 268, (1995), 720.
Arrnentano, et al., "Expression of Human Factor IX in Rabbit Hepatocytes by Retrovirus-Mediated Gene Transfer: Potential for Gene Therapy of Hemophilia B", Proc. Nat!. Acad. Sci. USA, vol. 87, (1990), 6141-6145.
Askari, et al., "Molecular Medicine Antisense-Oligonucleotide Therapy", N. Engl. J. Med., 334:, (1996), 316-311.
Atkin, J, et al., "Endoplasmic reticulum stress and induction of the unfolded protein response in human sporadic amyotrophic lateral sclerosis", Neurobiology of Disease, vol. 30, (2008), 400-407.
Atkin, J, et al., "Induction of the Unfolded Protein Response in Familial Amyotrophic Lateral Sclerosis and Association of Protein-disulfide Isomerase with Superoxide Dismutase 1", The Journal of Biological Chemistry, vol. 281 (40), (2006), 30152-30165.
Atkinson, et al., "The NOD mouse model of type 1 diabetes: As good as it gets?", Nature Medicine, 5(6), (1999), 601-604.
Attisano, et al., "Signal Transduction by the TGF beta Superfamily", Science 296:, (2002), 1646-1647.
Auf, G, et al., "Inositol-requiring enzyme 1 is a key regulator of angiogenesis and invasion in malignant glioma", PNAS, vol. 107(35), (2010), 15553-15558.
Bagchi, Aranya, et al., "MyD88-Dependent and MyD88-Independent Pathways in Synergy, Priming, and Tolerance between TLR Agonists", J. Immun., 178, (2007), 1164-1171.
Bai, et al., "A Mouse Model to Test the In Vivo Efficacy of Chemical Chaperones", J. of Pharm. and Toxicol. Methods, 40(1), (1998), 39-45.
Baldwin, et al., "Cloning of the Luciferase Structural Genes From Vibrio Harveyi and Expression of Bioluminescence in *Escherichia coli*", Biochemistry 23, (1984), 3663-366.
Bancroft, A J, et al., "Cytokine Production in BALB/c Mice Immunized with Radiation Attenuated Third Stage Larvae of the Filarial Nematode, *Brigia pahangi*", J. Immunol, vol. 150(4), (1993), 1395-1402.
Banerji, et al., "A Lymphocyte-Specific Cellular Enhancer Is Located Downstream of the Joining Region in Immunoglobulin Heavy Chain Genes", Cell 33:, (1983), 729-740.
Bantignies, et al., "Genetic characterization of transactivation of the human T-cell leukemia virus type 1 promoter: Binding of Tax to Tax-responsive element 1 is mediated by the cyclic AMP responsive members of the CREB/ATF family of transcription factors", Mol Cell Biol., vol. 16(5),, (1996), 2174-2182.
Barbas, Carlos F, et al., "Assembly of combinatorial antibody libraries on phage surfaces: the gene III site", Proc Natl Acad Sci U S A., 88(18), (Sep. 15, 1991), 7978-82.
Barnard, G A, "A New Test for 2×2 Table", Nature, vol. 156, (1945), 177-178.
Barnard, G A, "Significant Tests for 2×2 Tables", Biometrika, vol. 34, (1947), 123-138.

(56) References Cited

OTHER PUBLICATIONS

Barnett, B, et al., "Regulatory T cells in ovarian cancer: biology and therapeutic potential", Am J Reprod Immunol, vol. 54, (2005), 369-377.
Barouch, D H, et al., "Immunogenicity of recombinant adenovirus serotype 35 vaccine in the presence of pre-existing anti-Ad5 immunity", J Immunol., vol. 172, (2004), 6290-6297.
Barr, et al., "Identification of the Critical Features of a Small Peptide Inhibitor of JNK Activity", J. Bioi. Chern., 277:, (2002), 10987-10997.
Barski, A, et al., "High-resolution profiling of histone methylations in the human genome", Cell, vol. 129, (2007), 823-837.
Bartel, et al., "Elimination of False Positives That Arise in Using the Two-Hybrid Systems", Biotechniques, 14, (1993), 920-924.
Bartel, David P., et al., "Isolation of New Ribozymes from a Large Pool of Random Sequence", Science, 261(5127), (1993), 1411-1418.
Barthel, et al., "RNA Interference-based Strategies for Metabolic Syndrome Treatment", Horm. Metab. Res., 37:, (2005), 59-62.
Bazter, M A, et al., "Enhanced evolutionary PCR using oligonucleotides with inosine at the 3'-terrninus", Nucleic Acid Res., vol. 19(18), (1991), 5081.
Beerli, et al., "Autocrine Inhibition of the Epidermal Growth Factor Receptor by Intracellular Expression of a Single-Chain Antibody", Biochem. Biophys. Res. Commun. 204, (1994), 666-672.
Beerli, et al., "Intracellular Expression of Single Chain Antibodies Reverts ErbB-2 Transformation", J. Biol. Chem., vol. 269, (1994), 23931-23936.
Beg, Amer A., et al., "Embryonic lethality and liver degeneration in mice lacking the ReIA component of NF-KB", Nature, 376, (1995), 167-170.
Ben, Baruch A, et al., "Inflammation-associated immune suppression in cancer: the roles played by cytokines, chemokines and additional mediators", Seminars in Cancer Biology, vol. 16, (2006), 38-52.
Bennet, et al., "Antisense Therapy for Angioplasty Restenosis. Some Critical Considerations", Circulation, 92:, (1995), 1981-1993.
Bennet, et al., "JNK: A New Therapeutic Target for Diabetes", Current Opinion in Pharmacology, 3:, (2003), 420-425.
Berkner, K., "Development of adenovirus vectors for the expression of heterologous genes", BioTechniques, 6(7), (Jul.-Aug. 1988), 616-629.
Bernardi, et al., "Mitochondria and Cell Death", Eur. Biochem. vol. 264, (1998), 687.
Bertolotti, A, et al., "Dynamic interaction of BiP and ER stress transducers in the unfolded-protein response", Nat Cell Biol., 2:, (2000), 326-332.
Bhowmick, N A, et al., "Stromal fibroblasts in cancer initiation and progression", Nature, vol. 432, (2004), 332-337.
Biocca, et al., "Expression and Targeting of Intracellular Antibodies in Mammalian Cells", EMBO J. vol. 9, (1990), 101-108.
Biocca, et al., "Intracellular Immunization With Cytosolic Recombinant Antibodies", Biotechnology 12, (1994), 396-399.
Blackman, et al., "A Model System for Peptide Hormone Action in Differentiation: Interleukin 2 Induces a B Lymphoma to Transcribe the J Chain Gene", Cell 47, (1986), 609-617.
Blick, T, et al., "Epithelial Mesenchymal Transition Traits in Human Breast Cancer Cell Lines Parallel the CD44hi/CD24lo/− Stem Cell Phenotype in Human Breast Cancer", J Mammary Gland Biol Neoplasia, vol. 15, (2010), 235-252.
Blumenthal, A, et al., "Common and unique gene expression signatures of human macrophages in response to four strains of *Mycobacterium avium* that differ in their growth and persistence characteristics", Infect Immun., 73, (2005), 3330-3341.
Boder, Eric T., et al., "Directed Evolution of Antibody Fragments With Monovalent Femtomolar Antigen-Binding Affinity", Proc. Natl. Soc. Sci. USA, 97(20), (Sep. 26, 2000), 10701-10705.
Boeglin, et al., "Soluble CD40L and TLR Agonist synergize Murine B Cell Proliferation", Eur. J. Immunol., (2009), S55-S279.

Boes, et al., "Enhanced B-1 Cell Development, but Impaired IgG Antibody Responses in Mice Deficient in Secreted IgM", J Immunol., 160, (1998), 4776-4787.
Bogoyevitch, et al., "Targeting the JNK MAPK Cascade for Inhibition: Basic Science and Therapeutic Potential", Biochimica et Biophysica Acta, 1697, (2004), 89-101.
Boldrick, J C, et al., "Stereotyped and specific gene expression programs in human innate immune responses to bacteria", Proc Natl Acad Sci USA, vol. 99, (2002), 972-977.
Bollard, C M, et al., "Complete responses of relapsed lymphoma following genetic modification of tumor-antigen presenting cells and T-lymphocyte transfer", Blood, vol. 110, (2007), 2838-2845.
Bonapace, et al., "Chemical Chaperones protect from the effect of apoptosis-inducing mutation in carbonic anhydrase IV identified in retinitis pigmentosa 17", PNAS, 101 {33}:, (2004), 12300-12305.
Boobbyer, et al., "New Hydrogen-Bond Potentials for Use in Determining Energetically Favorable Binding Sites on Molecules of Known Structure", J Med. Chern. 32, (1989), 1083.
Bos, R, et al., "Levels of hypoxia-inducible factor-1alpha independently predict prognosis in patients with lymph node negative breast carcinoma", Cancer, vol. 97 (6), (2003), 1573-1581.
Bossy-Weyzel, et al., "Assay for Cytochrome c Release From Mitochondria During Apoptosis", Methods in Enzymol., 322, (2000), 235-242.
Bradley, "Modifying the Mammalian Genome by Gene targeting", Current Opinion in Biotechnology, vol. 2, (1991), 823-829.
Bradner, J E, et al., "A robust small-molecule microarray platfolTT for screening cell lysates", Chem Biol., vol. 13(5), (2006), 493-504.
Brauweiler, et al., "A molecular mechanism for human T-cell leukemia virus latency and Tax transactivation", J Biol Chem., vol. 270(21), (1994), 12814-12822.
Breitling, R., et al., "Rank products: a simple, yet powerful, new method to detect differentially regulated genes in replicated microarray experiments", FEBS Lett., 573(1-3), (2004), 83-92.
Brinster, et al., "Regulation of Metallothionein-Thymidine Kinase Fusion Plasmids Injected in Mouse Eggs", Nature, vol. 296, (1982), 39-42.
Brown, et al., "Protein antigens of normal and malignant human cells identified by immunoprecipitation with monoclonal antibodies", J Biol Chem., vol. 255(11), (1980), 4980-4983.
Brown, et al., "Structural Characterization of Human Melanoma-Associated Antigen p97 With Monoclonal Antibodies", J Immunol., 127, (1981), 539-546.
Bunin, B., et al., "A General and Expedient Method for the Solid-Phase Synthesis of 1, 4-Benzodiazephine Derivatives", J. Am. Chem. Soc., 114, (1992), 10997-10998.
Burdin, et al., "Endogenous IL-6 and IL-10 Contribute to the Differentiation of CD40-Activated Human B", J Immunol., 154, (1995), 2533-2544.
Burg, et al., "Effects of Glycine Belaine and Glycerophosphocholine on Thermal Stability of Ribonuclease", Am. J. Physiol. Renal Physiol., vol. 43:, (1998), F762-F765.
Bush, et al., "Proteasome inhibition leads to a heat-shock response, induction of endoplasmic reticulum chaperones, and thermotolerance", J Biol Chem., vol. 272(141),, (1997), 9086-9092.
Bushman, et al., "RNA Interference: Applications in Vertebrates", Mol Ther., vol. 7(1), (2003), 9-10.
Byrne, et al., "Multiplex Gene Regulation: A Two-Tiered Approach to Transgene Regulation in Transgenic Mice", PNAS. USA, vol. 86, (1989), 5473-5477.
Calame, "Plasma Cells: Finding New Light AI the End of B Cell Development", Nat. Immunol., vol. 2(12), (2001), 1103-1108.
Calame, et al., "Transcriptional Controlling Elements in the Immunoglobulin and T Cell Receptor Loci", Adv. Immunol vol. 43, (1988), 235-275.
Calfon, et al., "IRE1 couples endoplasmic reticulum load to secretory capacity by processing the XBP-1 mRNA", (2002), 92-96 pgs.
Callahan, M J, et al., "Increased HLA-DMB expression in the tumor epithelium is associated with increased CTL infillralion and improved prognosis in advanced-stage serous ovarian cancer", Clin Cancer Res., vol. 14, (2008), 7667-7673.

(56) References Cited

OTHER PUBLICATIONS

Campanero, M, et al., "Regulation of E2F through ubiquitin-proteasome-dependent degradation: Stabilization by the pRB tumor suppressor protein", Proc. Natl. Acad. Sci. USA, vol. 94, (1997), 2221-2226.

Camper, et al., "Postnatal Repression of the a-Felopro1ein Gene Is Enhancer Independent", Genes Dev., vol. 3, (1989), 537-546.

Cane, et al., "Harnessing the Biosynthelic Code: Combinations, Permutations, and Mutations", Science, vol. 282, (1998), 63.

Cao, W, et al., "Oxidized lipids block antigen cross-presentation by dendritic cells in cancer", J Immunol., vol. 192, (2014), 2920-2931.

Carell, T, et al., "A Novel Procedure for the Synthesis of Libraries Containing Small Organic Molecules", Angew Chem Int Ed Engl, 33(20), (1994), 2059-2061.

Carell, T., et al., "A Solution-Phase Screening Procedure for the Isolation of Active Compounds from a Library of Molecules", Angew Chem Int Ed Engl, 33(20), (1994), 2061-2064.

Carlson, et al., "A New Means of Inducibly Inactivating a Cellular Protein", Mol. Cell. Biol., vol. 8, (1988), 2638-2646.

Carlson, et al., "A New Use for Intracellular Antibody Expression: Inactivation of Human Immunodeficiency Virus Type I", PNAS, USA, vol. 90, (1993), 7427-7428.

Carrasco, D R, et al., "The differentiation and stress response factor XBP-1 drives multiple myeloma pathogenesis", Cancer Cell, vol. 11, (2007), 349-360.

Cassol, et al., "Stability of Dried Blood Spot Specimens for Detection of Human Immunodeficiency Virus DNA by Polymerase Chain Reaction", Journal of Clinical Microbiology, vol. 30(12), (1992), 3039-3042.

Caton, M L, et al., "Notch-RBP-J signaling controls the homeostasis of CD8-dendritic cells in the spleen", J Exp Med., vol. 204, (2007), 1653-1664.

Chapman, et al., "Translational Attenuation Mediated by an mRNA Intron", Curr Biol., vol. 7, (1997), 85-89.

Cheang, M C, "Basal-like breast cancer defined by five biomarkers has superior prognostic value than triple-negative phenotype", Clin Cancer Res., vol. 14(5), (2008), 1368-1376.

Chen, et al., "Combined Intra-nd Extra-cellular Immunization Against Human Immunodeficiency Virus Type 1 Infection With a Human Anti-gp 120 Antibody", PNAS, USA, vol. 91, (1994), 5932-5936.

Chen, et al., "Intracellular Antibodies as a New Class of Therapeutic Molecules for Gene Therapy", Human Gene Therapy, 5, (1994), 595-601.

Chen, B P, et al., "Analysis of ATF3, a transcription factor induced by physiological stresses and modulated by Jadd153/Chop10", Mol. Cell Biol., vol. 16, (1996), 1157-1168.

Chen, C, et al., "In Vitro Induction of T Cell Anergy by Blocking B7 and Early T Cell Costimulatory Molecule ETC-1/B7-2", Immunity, vol. 1, (1994), 147-154.

Chen, H, et al., "Regulation and Activities of .alpha.-Fetoprotein", Critical Reviews in Eukaryotic Gene Expression 7(1&2), (1997), 11-41.

Chen, L, et al., "HIV protease inhibitor lopinavir-induced TNF-alpha and IL-6 expression is coupled to the unfolded protein response and ERK signaling pathways in macrophages", Biochem Pharmacol., vol. 78, (2009), 70-77.

Chen, X, et al., "Integration of external signaling pathways with the core transcriptional network in embryonic stem cells", Cell, vol. 133, (2008), 1106-1117.

Chen, X, et al., "XBP1 promotes triple-negative breast cancer by controlling the HIF1alpha pathway", Nature, vol. 508, (2014), 103-107.

Chen, Y, et al., "Identification of mitogen-activated protein kinase signaling pathways that confer resistance to endoplasmic reticulum stress in *Saccharomyces cerevisiae*", Mol Cancer Res., vol. 3(12), (2005), 669-677.

Chevalier, et al., "Interaction of murine BiP/GRP78 with the Dna homologue MTJ1", J Biol Chem., vol. 275(26),, (2000), 19620-1962.

Cho, C. Y., et al., "An Unnatural Biopolymer", Science, 261, (Sep. 1993), 1303-1305.

Choe, et al., "IL-10 Interrupts Memory B Cell Expansion in the Germinal Center by Inducing Differentiation Into Plasma Cells", Eur J Immunol., 28:, (1998), 508-515.

Chow, et al., "Anti-HIV drugs for cancer therapeutics: back to the future?", Lancet Oncol., 61-71.

Chowdhury, J., et al., "Long-Term Improvement of Hypercholesterolemia After ex Vivo Gene Therapy in LDLR-Deficient Rabbits", Science, vol. 254, (Dec. 20, 1991), 1802-1805.

Clackson, T., et al., "Making Antibody Fragments Using Phage Display Libraries", Nature, 352(6336), (1991), 624-628.

Clarke, Michael F, et al., "Cancer Stem Cells—Perspectives on Current Status and Future Directions: AACR Workshop on Cancer Stem Cells", American Association for Cancer Research, 66. 19, [Online]. Retrieved from the Internet:<:www.aacrjournals.org>, (Oct. 1, 2006), 9339-9344.

Clauss, et al., "The Basic Domain/Leucine Zipper Protein hXBP-1 Preferentially Binds to and Transactivates CRE-like Sequences Containing an ACGT Core", Nucleic Acids Research, vol. 24, (1996), 1855.

Clauss, I M, et al., "In Situ Hybridization Studies Suggest a Role for the Basic Region-Leucine Zipper Protein hXBP-1 in Exocrine Gland and Skeletal Development During Mouse Embryogenesis", Dev. Dynamics 197, (1993), 146-156.

Clerici, Mario, et al., "A TH1-TH2 switch is a critical step in the etiology of HIV infection", Immunology Today, vol. 14(3), (1993), 107-111.

Cohen, et al., "Emerging Technologies for Sequencing Antisense Oligonucleotides: Capillary Electrophoresis and Mass Spectrometry", Adv. Chromatgr. 36, (1996), 127-162.

Collison, K S, et al., "Effect of dietary monosodium glutamate on trans fat-induced nonalcoholic fatty liver disease", The Journal of Lipid Research, vol. 50 (8), (2008), 1521-1537.

Conejo-Garcia, J R, et al., "Tumor-infiltrating dendritic cell precursors recruited by a beta-defensin contribute to Vasculogenesis under the influence of Vegf-A", Nat Med. vol. 10, (2004), 950-958.

Conejo-Garcia, J R, et al., "Vascular leukocytes contribute to tumor vascularization", Blood, vol. 105, (2005), 679-681.

Conley, S J, et al., "Antiangiogenic agents increase breast cancer stem cells via the generation of tumor hypoxia", PNAS USA, vol. 109(8), (2012), 2784-2789.

Cotton, "Current Methods of Mutation Detection", Mulot Res., 285, (1992), 125-144.

Cotton, et al., "Reactivity of Cytosine and Thymine in Single-Base-Pair Mismalhces With Hydroxylamine and Osmium Tetroxide and Its Application to the Study of mutations", PNAS, vol. 85(12), (1988), 4397-4401.

Cottrell, et al., "Silence of the Strands: RNA Interference in Eukaryotic Pathogens", Trends Microbioll., (2003), 37-43.

Coussens, L M, et al., "Inflammation and cancer", Nature, vol. 420, (2002), 860-867.

Coussens, Lisa M, et al., "MMP-9 Supplied by Bone Marrow-Derived Cells Contributes to Skin Carcinogenesis", Cell, 103, (Oct. 2000), 481-490.

Cox, et al., "A Novel Mechanism for Regulating Activity of a Transcription Factor Thal Controls the Unfolded Protein Response", Cell, vol. 87, (1996), 391-404.

Cox, J, et al., "Transcriptional induction of genes encoding endoplasmic reticulum resident proteins requires a transmembrane protein kinase", Cell, 73, (1993), 1197-1206.

Creighton, C J, "Residual breast cancers after conventional therapy display mesenchymal as well as tumor-initialing features", PNAS, USA, vol. 106(33), (2009), 13820-13825.

Cressman, et al., "Liver Failure and Defective Hepatocyte Regeneration in Interleukin-6-Deficient Mice", Science, 274, (1996), 1379-1383.

Cristiano, et al., "Hepatic Gene Therapy: Adenovirus Enhancement of Receptor-Mediated Gene Delivery and Expression in Primary Hepatocytes", PNAS, USA, vol. 90(6), (1993), 2122-2126.

Cubillos-Ruiz, J R, et al., "Blocking ovarian cancer progression by targeting tumor microenvironmenial leukocytes", Cell Cycle, vol. 9, (2010), 260-268.

(56) References Cited

OTHER PUBLICATIONS

Cubillos-Ruiz, J R, et al., "Polyethylenimine-based siRNA nanocomplexes reprogram tumor-associated dendrilic cells via TLR5 lo elicit therapeutic antitumor immunity", J Clin Invest, vol. 119, (2009), 2231-2244.

Cubillos-Ruiz, J R, et al., "Reprogramming tumor-associated dendrilic cells in vivo using microRNA mimelics triggers protective immunity against ovarian cancer", Cancer Res, (2012).

Cubillos-Ruiz, J R, et al., "Reprogramming Tumor-Associated Dendritic Cells In Vivo Using miRNA Mimetics Triggers Protective Immunity against Ovarian Cancer", Cancer Research, vol. 72(7), (2012), 1683-1693.

Cull, et al., "Screening for Receptor Ligands Using Large Libraries of Pep tides Linked to the C Terminus of the Iac Repressor", PNAS USA, vol. 89, (1992), 1865-1869.

Cullen, B R, et al., "Secreted Placental Alkaline-Phosphatase as a Eukaryotic Reporter Gene", Methods in Enzymology, 216, (1992), 362-368.

Curiel, D. T., et al., "Adenovirus enhancement of transferrin-polylysine-mediated gene delivery", Proc Natl Acad Sci USA., 88(19), (Oct. 1, 1991), 8850-4.

Curiel, T J, et al., "Blockade of B7-H1 improves myeloid dendritic cell-mediated antitumor immunity", Nat Med., vol. 9, (2003), 562-567.

Cwirla, S. E., et al., "Peptides on Phage: a Vast Library of Peptides for Identifying Ligands", Proc. Natl. Acad. Sci. USA, 87(16), (1990), 6378-6382.

Dai, et al., "Gene Therapy Via Primary Myoblasts: Long-Term Expression of Factor IX Protein Following Transplantation In Vivo", PNAS, USA, vol. 89, (1992), 10892-10895.

Dai, et al., "Genetic polymorph isms of human CYP2C8 and their effects on metabolism of anticancer drug: Paclitaxel", FASEB Journal, vol. 14, No. 8, p. 162, Publisher: Federation Amer. Soc. Exp. Bioi., Rockville, MD, XP009002862, ISSN:0892-6638, (May 11, 2000).

Dallman, M J, "Cytokines and transplantation: Th1/Th2 regulation of the immune response to solid organ transplants in the adult", Curr. Opin. Immunol. vol. 7,, (1995), 632-638.

Danos, et al., "Safe and Efficient Generation of Recombinant Retroviruses With Amphotropic and Ecotropic Host Ranges", PNAS, USA., vol. 85, (1988), 6460-6464.

Darzynkiewicz, et al., "Analysis of Apoptotic Cells by Flow and Laser Scanning Cytometry", Methods in Enzymol 322, (2000), 18-39.

Daugherty, et al., "Flow Cytometric Screening of Cell-Based Libraries", J Immunol. Methods, 243, (2000), 211-227.

Davies, Michael P.A., et al., "Expression and splicing of the unfolded protein response gene XBP-1 are significantly associated with clinical outcome of endocrine-treated breast cancer", International Journal of Cancer, vol. 123(1),, (2008), 85-88.

De, Palma M, et al., "Tie 2-expressing monocytes: regulation of tumor angiogenesis and therapeutic implications", Trends Immunol., vol. 28, (2007), 519-524.

De, Paula Daniel, et al., "Hydrophobization and bioconjugation for enhanced siRNA delivery and targeting", RNA, vol. 13, (2007), 431-456.

De, Raedt T, et al., "Exploiting cancer cell vulnerabilities to develop a combination therapy for Ras-driven tumors", Cancer Cell, vol. 20, (2011), 400-413.

Dean, M, et al., "Tumour Stem Cells and Orig Resistance", Nat Rev Cancer, vol. 5, (2005), 275-284.

Delepine, et al., "EIF2AK3, Encoding Translation Initiation Factor 2-a Kinase 3, Is Mutated in Patients with Wolcotl-Rallison Syndrome", Nat. Genet, 25, (2000), 406-409.

Desjarlias, et al., "Using Shape Complementarily as an Initial Screen in Designing Ligands for a Receptor Binding Site of Known Three-Dimensional Structure", J. Med. Chern., 31, (1988), 722.

Devlin, et al., "Random Peptide Libraries: A Source of Specific Protein Binding Molecules", Science, vol. 249, (1990), 404-406.

Dewet, et al., "Firefty Luciferase Gene: Structure and Expression in Mammalian Cells", Mol. Cell. Biol., vol. 7, (1987), 725-737.

Dewitt, S. H., et al., ""Diversomers": An Approach to Nonpeptide, Nonologomeric Chemical Diversity", Proc. Nat. Acad. Sci. USA, 90(15), (1993), 6909-6913.

Didierlaurent, A M, et al., "AS04, an aluminum salt- and TLR4 agonist-based adjuvant system, induces a transient localized innate immune response leading to enhanced adaptive immunity", J Immunol., vol. 183, (2009), 6186-6197.

Ding, L, et al., "Ligand-independent activation of estrogen receptor alpha by XBP-1", Nucleic Acids Res., vol. 31(18), (2003), 5266-5274.

Ding, Wen-Xing, et al., "Differential Effects of Endoplasmic Reticulum Stress-Induced Autophagy on Cell Survival", The Journal of Biological Chemistry, vol. 282(7),, (2007), 4702-4710.

Ding, Wen-Xing, et al., "Linking of Autophagy to Ubiquitin-Proteasome System Is Important for the Regulation of Endoplasmic Reticulum Stress and Cell Viability", The American Journal, vol. 171(2),, (2007), 513-524.

Dinulescu, D M, et al., "Role of K-ras and Pten in the development of mouse models of endometriosis and endometrioid ovarian cancer", Nat Med., vol. 11, (2005), 63-70.

Dioufa N, et al., "Atypical induction of the unfolded protein response by mifepristone", Endocrine, vol. 38, No. 2, (Jul. 11, 2010), 167-173.

Dontu, G., et al., "In vitro Propagation and Transcriptional Profiling of Human Mammary Stem/Progenitor Cells", Genes & Development, 17, (2003), 1253-1270.

Douglasj, Mahoney, et al., "Virus-tumor interactome screen reveals ER stress response can reprogram resistant cancers for oncolytic virus-triggered Caspase-2 cell death", Cancer Cell, Cell Press, US, vol. 20, No. 4, (Sep. 13, 2011), 443-456.

Dranoff, G, "Cytokines in cancer pathogenesis and cancer therapy", Nature Reviews Cancer, vol. 4, (2004), 11-22.

Duan, L, et al., "Potent Inhibition of Human Immunodeficiency Virus Type 1 Replication by an Intracellular anti-REV single chain antibody", PNAS, vol. 91, (1994), 5075-5079.

Dudley, M E, et al., "Cancer regression and autoimmunity in patients after clonal repopulation with antitumor lymphocytes", Science, vol. 298, (2002), 850-854.

Dunn, G P, et al., "Cancer immunoediting: from immunosurveillance to tumor escape", Nature Immunology, vol. 3, (2002), 991-998.

Ebrahimpour, P, et al., "Metabolic Syndrome and Related Insulin Levels in Obese Children", Metab. Syndr. Reial. Disord., vol. 4(3), (2006), 172-178.

Edlund, et al., "Cell Specific Expression of the Rat Insulin Gene: Evidence for Role of Two Distinct 5' Flanking Elements", Science, 230:, (1985), 912-916.

Eggerding, et al., "A One-Step Coupled Amplification and Oligonucleotide Ligation Procedure for Multiplex Genetic Typing", PCR Methods Appl., vol. 4, (1995), 337.

Eggerding, et al., "Fluorescence-Based Oligonucleotide Ligation Assay for Analysis of Cystic Fibrosis Tranmembrane Conductance Regulator Gene Mutations", Hum. Mutat., 5: 153, (1995), 153-165.

Eglitis, et al., "Gene Expression in Mice After High Efficiency Retrovirai-Mediated Gene Transfer", Science, 230:, (1985), 1395-1398.

Else, K J, et al., "Cytokine-mediated Regulation of Chronic Intestinal Helminth Infection", The Journal of Experimental Medicine, vol. 179, (1994), 347-351.

Engebrecht, et al., "Identification of Genes and Gene Products Necessary for Bacterial Bioluminescence", PNAS, vol. 1, (1984), 4154-4158.

Engel, et al., "Unfolding new roles for XBP1 in immunity", Nature Immunology, (2010), 365-367.

Engelke, et al., "Direct Sequencing of Enzymatically Amplified Human Genomic DNA", PNAS, USA, vol. 85, (1988), 544-548.

Eppstein, D A, et al., "Biological activity of liposome-encapsulated murine interferon gamma is mediated by a cell membrane receptor", PNAS, vol. 82 (11), (1985), 3688-3692.

(56) References Cited

OTHER PUBLICATIONS

Erb, E., et al., "Recursive deconvolution of combinatorial chemical libraries", Proc. Natl. Acad. Sci. USA, 91(24), (1994), 11422-11426.
Evans, J, et al., "Enhancement of antigen-specific immunity via the TLR4 Liglands MPL adjuvant and Ribi.529", Expert Rev Vaccines, vol. 2, (2003), 219-229.
Falo, L D, et al., "Targeting antigen into the phagocytic pathway in vivo induces protective tumour immunity", Nat Med. 1, (1995), 649-653.
Fanlei, Hu, et al., "ER stress and its regulator X-box-binding protein-1 enhance polyIC-induced innate immune response in dendritic cells", European Journal of Immunology, vol. 41, No. 4, (Apr. 14, 2011), 1086-1097.
Fassler, R, et al., "Consequences of lack of .beta.1 integrin gene expression in mice", Genes & Development 9, (1995), 1896-1908.
Fauci, A. S., "The human immunodeficiency virus: infectivity and mechanisms of pathogenesis", Science, 239(4840), (1988), 617-22.
Feldman, Douglas E, et al., "The unfolded protein response: A novel component of the hypoxic stress response in tumors", Molecular Cancer Research, American Association for Cancer Research, US, vol. 3, No. 11, (Nov. 1, 2005), 597-605.
Felici, et al., "Selection of Antibody Ligands From a Large Library of Oligopeptides Expressed on a Multivalent Exposition Vector", J Mol Biol, 222, (1991), 301-310.
Ferry, et al., "Retroviral-Mediated Gene Transfer Into Hepatocytes In Vivo", PNAS, USA, vol. 88, (1991), 8377-8381.
Fischer, et al., "Partial Restoration of Defective Chloride Conductance in IIF508 CF Mice by Trimethylamine Oxide", Am. J. Physiol. Lung Cell Mol., vol. 281, (2001), L52-L57.
Flesken, Nikitin A, et al., "Induction of carcinogenesis by concurrent inactivation of p53 and Rb1 in the mouse ovarian surface epithelium", Cancer Res., vol. 63, (2003), 3459-3463.
Flotte, et al., "Gene Expression From Adeno-Associated Virus Vectors in Airway Epithelial Cells", Am J Respir. Cell. Mol. Biol., vol. 7, (1992), 349-356.
Flotte, T. R., "Expression of the Cystic Fibrosis Transmembrane Conductance Regulator From a Novel Adeno-Associated Virus Promoter", The Journal of Biological Chemistry, 268(5), (1993), 3781-3790.
Fodor, et al., "Multiplexed Biochemical Assays With Biological Chips", Nature, vol. 364, (1993), 555-556.
Foti, et al., "Conservation and divergence of the yeast and mammalian unfolded protein response. Activation of specific mammalian endoplasmic reticulum stress element of the grp78/BiP promoter by yeast Hac1", J Biol Chem., vol. 274 (43), (1999), 30402-30409.
Foulkes, W D, et al., "Triple-negative breast cancer", N Engl J Med., vol. 363(20), (2010), 1938-1948.
Fowler, D H, et al., "Donor CD4-Enriched Cells of Th2 Cytokine Phenotype Regulate Grall-Versus-Host Disease Nithout Impairing Allogeneic Engraftment in Sublethally Irradiated Mice", Blood, vol. 84(10), (1994), 3540-3549.
Fowler, D H, et al., "Donor Lymphoid Cells of Th2 Cytokine Phenotype Reduce Lethal Grall Versus Host Disease and Facilitate Fully Allogeneic Cell Transfers in Sublethally Irradiated Mice", Advances in Bone Marrow Purging and Processing: FourthInternational Symposium. Prog. Clin. Biol. Res., vol. 389, (1994), 533-540.
Frank-Kamenetsky, Maria, "Therapeutic RNAi targeting PCSK9 acutely lowers plasma cholesterol in rodents and LDL cholesterol in nonhuman primates", Proc. Natl. Acad.Sci. USA, 105(33), (2008), 11915-11920.
Friedlander, R, et al., "A regulatory link between ER-associated protein degradation and the unfolded protein response", Nature Cell Biology, 2, (2000), 379-384.
Fuchs, et al., "Targeting Recombinant Antibodies to the Surface of *Escherichia coli*: Fusion to a Peptidoglycan Associated Lipoprotein", Bio/Technology, 9, (1991), 1370-1372.

Fujimoto, T, et al,, "Upregulation and overexpression of human x-box binding protein 1 (hXBP-1) gene in primary breast cancers", Breast Cancer, vol. 10 (4),, (2003), 301-306.
Gabay, C, et al., "Acute-Phase Proteins and Other Systemic Responses to Inftammation", New England Journal of Medicine, vol. 340(6), (1999), 448-454.
Galfre, G., et al., "Antibodies to major histocompatibility antigens produced by hybrid cell lines", Nature, 266, (1977), 550-552.
Gallop, et al., "Applications of Combinatorial Technologies to Drug Delivery. 1. Background and Peptide Combinatorial Libraries", J. Med. Chem., 37(9), (1994), 1233-1251.
Garrad, et al., "FAB Assembly and enrichment in a Monovalent Phage Display System", Bio/Technology, vol. 9, (1991), 1373-1377.
Garrett, W S, et al., "Communicable ulcerative colitis induced by T-bet deficiency in the innate immune system", Cell. vol. 131, (2007), 33-45.
Gass, J, et al., "The unfolded protein response of B-lymphocytes: PERK-independent development of antibodysecreting cells", Molecular Immunology, vol. 45, (2008), 1035-1043.
Gasser, S, et al., "The DNA damage pathway regulates innate immune system ligands of the NKG2D receptor", Nature, vol. 436, (2005), 1186-1190.
Gaultier, et al., "a-DNA IV: a-Anomeric and p-Anomeric Tetrathymidylates Covalently Linked to Intercalating Oxazolopyridocarbazole. Synthesis, Physicochemical Properties and Poly (rA) Binding", Nucleic Acids. Res., vol. 15, (1987), 6625-6641.
Geething, et al., "Signal transduction pathway mediating the endoplasmic reticulum unfolded protein response: IRE1 and the ER chaperones", Molecular Biology. Vanderbilt University, Nashville, TN.
Gefter, Malcolm L, et al., "A Simple Method for Polyethylene Glycol-Promoted Hybridization of Mouse Myeloma Cells", Somatic Cell Genetics, 3, (1977), 231-236.
Genestier, et al., "TLR Agonists Selectively Promote Terminal Plasma Cell Differentiation of B Cell Subsets Specialized in Thymus-Independent Responses", The Journal of Immunology, vol. 178, (2007), 7779-7786.
Gething, et al., "Protein Folding in the Cell", Nature 355, (1992), 33-45.
Ghosh, R, et al., "Transcriptional regulation of VEGF-A by the unfolded protein response pathway", Plos One, vol. 5(3), (2010), 1-12.
Gilchrist, M, et al., "Systems biology approaches identify ATF3 as a negative regulator of Toll-like receptor 4", Nature, 441, (2006), 173-178.
Ginestier, C, et al., "ALDH1 is a marker of normal and malignant human mammary stem cells and a predictor of poor clinical outcome", Cell Stem Cell, vol. 1 (5), (2007), 555-567.
Ginsberg, Henry N, et al., "Metabolic Syndrome: Focus on Dyslipidemia", Obesity, vol. 14, (2006), 41S-49S.
Glimcher, et al., "From Sugar to Fat: How the Transcription Factor XBP1 Regulates Hepatic Lipogenesis", Ann. NY. Acad. Sci., vol. 1173, (2009), E2-E9.
Gomez, B P, et al., "Human X-box binding protein-1 confers both estrogen independence and antiestrogen resistance in breast cancer cell lines", FASEB J., vol. 21, (2007), 4013-4027.
Gonzalez, et al., "Mechanism of Non-Spliceosomal mRNA Splicing in the Unfolded Protein Response Pathway", EMB, vol. 18(11), (1999), 3119-3132.
Goodford, et al., "A Computational Procedure for Determining Energetically Favorable Binding Sites on Biologically important Macromolecules", J Med. Chem., vol. 28, (1985), 849.
Gorczynski, R M, et al., "Interleukin 12 in Combination With Anti-Interleukin 10 Reverses Graft Prolongation After Portal Venous Immunization", Transplantation, vol. 60(11),, (1995), 1337-1341.
Gossen, M., "Tight Control of Gene Expression in Mammalian Cells by Tetracycline-Responsive Promoters", Proc. Natl. Acad. Sci. USA, 89, (1992), 5547-5551.
Gossen, M., et al., "Transcriptional Activation by Tetracyclines in Mammalian Cells", Science, 268(5218), (1995), 1766-1769.

(56) References Cited

OTHER PUBLICATIONS

Gram, H., et al., "In vitro Section and Affinity Maturation of Antibodies From a Naive Combinational Immunoglobulin Library", Proc. Natl. Acad. Sci. USA, 89(8), (1992), 3576-3580.

Greenbaum, "Insulin resistance in type 1 diabetes", Diabetes/Metabolism Research and Reviews, (2002), 192-200.

Griffin, et al., "DNA Sequencing: Recent Innovations and Future Trends", Appl. Biochem. Biotechnol, 38, (1993), 147-159.

Griffiths, et al., "Human Anti-Self Antibodies With High Specificity From Phage Display Libraries", EMBO J., vol. 12, (1993), 725-734.

Gross, Atan, et al., "BCL-2 Family Members and the Mitochondria in Apoptosis", Genes and Development, 13, (1999), 1899-1911.

Gruber, et al., "Differential effects of HIV-1 protease inhibitors on dendritic cell immunophenotype and function", J. Biol. Chern., 276(51), (2001), 47840-47843.

Grzych, J M, et al., "Egg Deposition is the Major Stimulus for the Production of Th2 Cytokines in Murine Schistosomiasis Mansoni", J. Immunol., vol. 146(4),, (1991), 1322-1327.

Gu, F, et al., "Protein-tyrosine phosphatase 1B potentiates IRE1 signaling during endoplasmic reticulum stress", Journal of Biological Chemistry, vol. 279(48), (2004), 49689-49693.

Gualdi, Rossana, et al., "Hepatic specification of the gut endoderm in vitro: cell signaling and transcriptional control", Genes & Development, 10, (1996), 1670-1682.

Gunes, C, et al., "Embryonic lethality and liver degeneration in mice lackin the metal-responsive transcriptional activator MTF-1", EMBO J., vol. 17,, (1998), 2846-2854.

Haj-Ahmad, "Development of a Helper-Independent Human Adenovirus Vector and Its Use in the Transfer of the Herpes Simplex Virus Thymidine Kinase Gene", J. Viral., vol. 57, (1986), 267.

Hall, et al., "Expression and Regulation of *Escherichia coli* Lacz Gene Fusions in Mammalian Cells", J. Mel.Appl. Gen vol. 2, (1983), 101-109.

Hallek, et al., "Multiple Myeloma: Increasing Evidence for a Multistep Transformation Process", Blood, vol. 91(1), (1998), 3-21.

Hamanishi, J, et al., "Programmed cell death 1 ligand 1 and tumor-infiltrating COB+ T lymphocytes are prognostic factors of human ovarian cancer", PNAS, USA, vol. 104, (2007), 3360-3365.

Hampton, et al., "ER Stress Response: Getting the UPR Hand on Misfolded Proteins", Curro; Biol., 10, (2000), R518.

Han, et al., "IRE1a Kinase Activation Modes Control Alternate Endoribonuclease Outputs to Determine Divergent Cell Fates", 1-21 pgs.

Han, L Y, et al., "HLA class I antigen processing machinery component expression and intra tumoral T-Cell infiltrate as independent prognostic markers in ovarian carcinoma", Clin Cancer Res., vol. 14, (2008), 3372-3379.

Hanahan, Douglas, et al., "Hallmarks of Cancer: The Next Generation", Cell, 144(5), (2011), 646-674.

Hanes, Jozef, et al., "Picomolar affinity antibodies from a fully synthetic naive library selected and evolved by ribosome display", Nature Biotechnology, 18(12), (Dec. 2000), 1287-1291.

Harding, et al., "An integrated stress response regulates amino acid metabolism and resistance to oxidative stress", Mol Cell., vol. 11(3), (2003), 619-633.

Harding, et al., "Diabetes Mellitus and Exocrine Pancreatic Dysfunctional Perk-1-Mice Reveals a Role for Translational Control in Secretary Cell Survival", Molecular Cell, 7, (2001), 1153-1163.

Harding, et al., "Enodplasmic Reticulum Stress and the Development of Diabetes" Diabetes, vol. 51 (3):, (2002), S455-S461.

Harding, et al., "Protein Translation and Folding Are Coupled by an Endoplasmic-Reticulum-Resident Kinase", Nature, 397, (1999), 271-274.

Harding, et al., "Regulated translation initiation controls stress-induced gene expression in mammalian cells", Mol Cell vol. 6(5), (2000), 1099-1108.

Harding, et al., "Transcriptional and Translational Control in the Mammalian Unfolded Protein Response", Annu. Rev. Cell Dev. Biol., vol. 18, (2002), 575.

Haselhoff, et al., "Simple RNA Enzymes With New and Highly Specific Endoribonuclease Activities", Nature, 334:, (1988), 585-591.

Hawkins, R. E, "Selection of Phage Antibodies by Binding Affinity. Mimicking Affinity Maturation.", Journal of Molecular Biology, 254, (1992), 889-896.

Hay, et al., "Bacteriophage Cloning and *Escherichia coli* Expression of a Human IgM Fab", Hum Antibod Hybridomas vol. 3, (1992), 81-85.

Hayahsi, K, et al., "PCR-SSCP: a simple and sensitive method for detection of mutations in the genomic DNA", PCR Methods Appl., vol. 1 (1), (1991), 34-38.

Hayashi, "PCR-SSCP: A Method for Detection of Mutations", Genet Anal Tech App., 9, (1992), 73-79.

Haze, et al.; "Identification of the G13 {cAMP-Response-Element-Binding Protein-Related protein Gene Product Related to Activating Transcription Factor 6 as a Transcriptional Activator of the Mammalian Unfolded Protein Response", Biochem J., vol. 355, (2001), 19-28.

Healy, S J, et al., "Targeting the endoplasmic reticulum-stress response as an anticancer strategy", Eur J Pharmaco. vol. 1625(1-3), (2009), 234-246.

Heddlesten, J M, et al., "Hypoxia inducible factors in cancer stem cells", Br J Cancer, vol. 102, (2009), 789-795.

Heikkila, et al., "The prevention of alloxan-induced diabetes in mice by dimethyl sulfoxide", European Journal of Pharmacology, Elsvier, BV, NL, 44(2), (1977), 191-193.

Helene, et al., "Control of Gene Expression by Triple Helix-Fonning Oligonucleotides", Ann. N.Y. Acad Sci. 660, (1992), 27-36.

Helene, et al., "The Anti-Gene Strategy: Control of Gene Expression by Triplex-Forming-Oligonucleotides", Anticancer Drug Des., 6(6), (1991), 569-584.

Hentsch, B, et al., "Hlx homeo box gene is essential for an inductive tissue interaction that drives expansion of embryonic liver and gut", Genes Dev., vol. 10, (1996), 70-79.

Herber, D L, et al., "Lipid accumulation and dendritic cell dysfunction in cancer", Nat Med., vol. 16, (2010), 880-886.

Hermonat, Paul, et al., "Use of adeno-associated virus as a mammalian DNA cloning vector: Transduction of neomycin resistance into mammalian tissue culture cells", Proc. Natl. Acad. Sci. USA, vol. 81, (Oct. 1984), 6466-6470.

Hershkowitz, "Identification of conserved gene expression features between murine mammary carcinoma models and human breast tumors", Genome Biol., vol. 8{5), (2007), R76.

Herz, et al., "Adenovirus-Mediated Transfer of Low Density Lipoprotein Receptor Gene Acutely Accelerates Cholesterol Clearance in Normal Mice", PNAS, USA, vol. 90, (1993), 2812-2816.

Hetz, et al., "Fine-Tuning of the Unfolded Protein Response: Assembling the IRE1 a Interactome", Mol. Cell, (2009), 551-561 pgs.

Hetz, C, et al., "Proapoptotic BAX and BAK modulate the unfolded protein response by a direct interaction with IRE1alpha", Science, 31, (2006), 572-576.

Hetz, C, et al., "Targeting the unfolded protein response in disease", Nature Reviews Drug Discovery, vol. 12, (2013), 703-719.

Hetz, Claudio, et al., "The Unfolded Protein Response: Intergrating Stress Signals Through the Stress Sensor IRE1 alpha", Physiol Rev., vol. 91, (2011), 1219-1243.

Hetz, Claudio, et al., "Unfolded protein response transcription factor XBP-1 does not influence prion replication of pathogenesis", PNAS, vol. 105(2), 2008), 757-762.

Hetz, Claudio, et al., "XBP-1 and the UPRosome: Mastering Secretory Cell Function", Current Immunology Reviews, vol. 4, (2008), 1-10.

Hetz, Claudio, et al., "XBP-1 deficiency in the nervous system protects against amyotrophic lateral sclerosis by increasing autophagy", Genes & Development, vol. 23, (2009), 2294-2306.

Hirano, et al., "Excessive Production of Interleukin 61B Cell Stimulatory Factor-2 in Rheumatoid Arthritis", Eur. J. Immunol.18, (1988), 1797-1801.

Hirano, et al., "Interleukin 6 and Plasma Cell Neoplasias", Prog. Growth Fact Res., 1, (1989), 133-142.

(56) References Cited

OTHER PUBLICATIONS

Hirosumi, et al., "A Central Role for JNK. In Obesity and Insulin Resistance", Nature, 420, 333-336.
Hirsch, Emilio, et al., "Impaired migration but not differentiation of haematopoietic stem cells in the absence of .beta.1 Integrins", Nature, vol. 380, (1996), 171-175.
Hodge, et al., "Hyperproliferation and Dysregulation of IL-4 Expression in NF-ATp-Deficient Mice", Immunity, vol. 4, (1996), 397-405.
Hollien, J, et al., "Decay of endoplasmic reticulum-localized mRNAs during the unfolded protein response", Science, 313, (2006), 104-107.
Hollien, J, et al., "Regulated Ire1-dependent decay of messenger RNAs in mammalian cells", J Cell Biol., vol. 186, (2009), 323-331.
Hoogenboom, et al., "Multi-Subunit Proteins on the Surface of Filamentous Phage: Methodologies for Displaying Antibody {Fab) Heavy and Light Chains", NucAcid Res., vol. 19, (1991), 4133-4137.
Horii, et al., "Involvement of IL-6 in Mesangial Proliferative Glomerulonephritis", J Immunol., 143 (12), (1989), 3949-3955.
Horwell, et al., "'Targeted' Molecular Diversity: Design and Development Non-Peptide Antagonists for Cholecystokinin and Tachykinin Receptors", Immunopharmacology, vol. 33, (1996), 68.
Hosokawa, et al., "A novel ER a-mannosidase-like protein accelerates ER-associated degradation", EMBO Rep., vol. 2 (5), (2001), 415-422.
Hosokawa, N, et al., "EDEM accelerates ERAD by preventing aberrant dimer formation of misfolded alpha1-antitrypsin", Genes to Cells, vol. 11,, (2006), 465-476.
Hosseini, Hassan, et al., "Protection against experimental autoimmune encephalomyelitis by a proteasome modulator", Journal of Neuroimmunology, 188, (2001), 233-244.
Hotamisligil, "Inflammatory Pathways and Insulin Action", International Journal of Obesity, 27, (2003), S53-S55.
Houghten, R. A, et al., "The use of synthetic peptide combinatorial libraries for the identification of bioactive peptides", BioTechniques, 13(3), (Sep. 1992), 412-421.
Houghten, Richard A, et al., "Generation and use of synthetic peptide combinatorial libraries for basic research and drug discovery", Nature, 354(6348), (Nov. 7, 1991), 84-86.
Hoyer-Hansen, M, et al., "Connecting endoplasmic reticulum stress to autophagy by unfolded protein response and Calcium", Cell Death and Differentiation, vol. 14,, (2007), 1576-1582.
Huang, Da Wei, et al., "Systematic and Integrative Analysis of Large Gene Lists Using DAVID Bioinformatics Resources", Nature Protocols, 4.1, (Dec. 2008), 44-57.
Huang, Q, et al., "The plasticity of dendritic cell responses to pathogens and their components", Science, vol. 294, (2001), 870-875.
Huarte, E, et al., "Depletion of dendritic cells delays ovarian cancer progression by boosting antitumor immunity", Cancer Res., vol. 68, (2008), 7684-7691.
Huber, Brian, et al., "Retroviral-mediated gene therapy for the treatment of hepatocellular carcinoma: An innovative approach for cancer therapy", Proc. Natl. Acad. Sci. USA, 88, (1991), 8039-8043.
Hudis, C A, "Triple-negative breast cancer: an unmet medical need", Oncologist, vol. 16 Suppl 1, (2011), 1-11.
Hughes, et al., "Apoptotic Nuclease Assays", Methods in Enzymol., vol. 322, (2000), 47-62.
Hur, K Y, et al., "IRE1 activation protects mice against acetaminophen-induced hepatotoxicity", The EMBO Journal, vol. 30(7), (2012), 1357-1418.
Huse, et al., "Generation of a large combinatorial library of the immunoglobulin repertoire in phage lambda", Science, 246, (1989), 1275-1281.
Hussein, Y R, et al., "Glut-1 Expression Correlates with Basal-like Breast Cancer", vol. 4(6), (2011), 321-327.
Hwu, et al., "Functional and Molecular Characterization of Tumor-Infiltrating Lymphocytes Transduced With Tumor Necrosis Factor-a eDNA for the Gene Therapy of Cancer InHumans", J. Immunol., vol. 150, (1993), 4104-4115.
Hynes, et al., "Hormone-Responsive Expression of an Endogenous Proviral Gene of Mouse Mammary Tumor Virus After Molecular Cloning and Gene Transfer Into Cultured Cells", Proc. Natl. Acad. Sci. USA, vol. 78, (1981), 2038-2042.
Ilieva, E, et al., "Oxidative and endoplasmic reticulum stress interplay in sporadic amyotrophic lateral sclerosis", Brain, vol. 130,, (2007), 3111-3123.
Iliopoulos, D, et al., "An epigenetic switch involving NF-kappaB, Lin28, Let-7 MicroRNA, and IL6 links inflammation to cell transformation", Cell, vol. 139(4), (2009), 693-706.
Iliopoulos, D, et al., "Inducible formation of breast cancer stem cells and their dynamic equilibrium with non-stem Cancer cells via IL6 secretion", PNAS, USA, vol. 108(4), (2011), 1397-1402.
Iliopoulos, D, et al., "Loss of miR-200 inhibition of Suz12 leads to polycomb-mediated repression required for the formation and maintenance of cancer stem cells", Mol Cell., vol. 39(5), (2010), 761-772.
Illera, et al., "Apoptosis in Splenic B Lymphocytes. Regulation by Protein Kinase C and IL-4", J. Immunol., vol. 151(6), (1993), 2965-2973.
Inoue, et al., "Potent Inhibition of Human Immunodeficiency Virus Type 1 Replication by an Intracellular Anti-Rev Single-Chain Antibody", PNAS, USA, vol. 91, (1997), 5075-5079.
Inoue, et al., "Sequence-Dependent Hydrolysis of RNA Using Modified Oligonucleotide Splints and RNase H", FEBS Lett vol. 215, (1987), 327-330.
Inoue, et al., "Synthesis and Hybridization Studies on Two Complementary Non(2'-0-Methyl)Ribonucleotides", Nucleic Acids Res. ,vol. 15, (1987), 6131-6148.
Inouye, et al., "Potent Inhibition of Human Immunodeficiency Virus Type 1 in Primary T Cells and Alveolar Macrophage by a Combination Anti-Rev Strategy Delivered in an Adeno-Associated Virus Vector", Journal of Virology, vol. 71 (5), (1997), 4071-4078.
Irizarry, R A, et al., "Summaries of Affymetrix GeneChip probe level data", Nucleic Acids Res., vol. 31 (4), (2003), e15.
Irving, et al., "Ribosome Display and Affinity Maturation: From Antibodies to Single Vdomans and Steps Towards Cancer Therapeutics", J. Immunol. Methods., vol. 248, (2001), 31-35.
Ishii, K, et al., "Host Innate Immune Receptors and Beyond: Making Sense of Microbial Infections", Cell Host & Microbe, vol. 3:, (2008), 352-363.
Israel, et al., "Highly Inducible Expression From Vectors Containing Multiple ORE's in CHO Cells Overexpressing the Glucocorticoid Receptor", Nucl. Acids Res., vol. 17, (1989), 2589-2604.
Iwabuchi, et al., "Use of the Two-Hybrid System to Identify the Domain Ofp53 Involved Oligomerization", Oncogene, vol. 8, (1993), 1693-1696.
Iwakoshi, et al., "Plasma cell differentiation and the unfolded protein response intersect at the transcription factor XBP-1", Nat Immunol., vol. 4(4),, (2003), 321-329.
Iwakoshi, et al., "The transcription factor XBP-1 is essential for the development and survival of dendritic cells", J Exp Med. vol. 204, (2007), 2267-2275.
Iwakoshi, et al., "The X-box Binding Protein-I Transcription Factor Is Required for Plasma Cell Differentiation and the Unfolded Protein Response", Immunological Reviews, vol. 194, (2003), 29-38.
Iwawaki, T, et al., "Function of IRE1 alpha in the placenta is essential for placental development and embryonic viabilily", PNAS, vol. 106, (2009), 16657-16662.
Jacks, T, et al., "Effects of an Rb mutation in the mouse", Nature, vol. 359, (1992), 295-300.
Jackson, E L, et al., "Analysis of lung tumor initiation and progression using conditional expression of oncogenic K-ras", Genes Dev., vol. 15, (2001), 3243-3248.
Janeway, C, et al., "Innate immune recognition", Annu Rev Immunol., vol. 20, (2002), 197-216.

(56) References Cited

OTHER PUBLICATIONS

Jogi, A, et al., "Hypoxia alters gene expression in human neuroblastoma cells toward an immature and neural crestlike phenotype", PNAS USA, vol. 99 (10), (2002), 7021-7026.
Johnson, C P, et al., "Forced unfolding of proteins within cells", Science, vol. 317, (2007), 663-666.
Jonkers, J, et al., "Synergistic tumor suppressor activity of BRCA2 and p53 in a conditional mouse model for breast Cancer", Nat Genet., vol. 29, (2001), 418-425.
Kadato, K, et al., "Ranking differentially expressed genes from Affymetrix gene expression data-methods with reproducibility, sensitivity, and specificity", Algorithm Mol Biol., vol. 47, (2009), 7 pgs.
Kaelin, W G, et al., "Oxygen sensing by metazoans: the central role of the HIF hydroxylase pathway", Mol Cell., vol. 30 (4 ), (2008), 393-402
Kakiuchi, et al., "Impaired feedback regulation of XBP1 as a genetic risk factor for bipolar disorder", Nat Genet. vol. 35 (2), (2003), 171-175.
Karin, et al., "Phosphorylation meets ubiquitination: the control of NF-[kappa]B activity", Annu Rev Immunol., vol. 18, (2000), 621-663.
Kaser, et al., "Transcription Factor XBP1 Regulates Paneth Cell Function and Inflammation in the Intestine", vol. 1 (1), (2007), 1-2.
Kaser, A, et al., "001 Transcription Factor XBP1 Regulates Paneth Cell Function and Inflammation in the Intestine", Abstracts of the ECCO Congress, Innsbruck, Austria 1-3, (Mar. 2007), 2 pgs.
Kaser, A, et al., "Endoplasmic reticulum stress in the intestinal epithelium and inflammatory bowel disease", Seminars in Immunology, W.B. Saunders Company, PA, US, 21 (3), (2009), 156-163.
Kaser, A, et al., "XBP1 links ER stress to intestinal inflammation and confers genetic risk for human inflammatory bowel disease", Cell, vol. 134, (2008), 743-756.
Katze, "Regulation of the interferon-induced PKR: can viruses cope?", Trends Microbiol. vol. 3(2), (1995), 75-78.
Kauffman, et al., "Stress Signaling From the Lumen of the Endoplasmic Reticulum: Coordination of Gene Transcriptional and Translational Controls", Genes Dev., vol. 13, (1999), 1211-1233.
Kauffman, et al., "Translational efficiency of polycistronic mRNAs and their utilization to express heterologous genes in mammalian cells", EMBO J. vol. 6, (1987), 187-195.
Kaufman, et al., "The Unfolded Protein Response in Nutrient Sensing and Differentiation", Nat. Rev. Mol. Cell Biol., vol. 3, (2002), 411.
Kaufman, D R, et al., "Route of adenovirus-based HIV-1 vaccine delivery impacts the phenotype and trafficking of vaccine-elicited COB+ T lymphocytes", J Virol, vol. 84, (2010), 5986-5996.
Kaufman, D R, et al., "Trafficking of antigen-specific COB+ T lymphocytes to mucosal surfaces following intramuscular vaccination", J Immunol., 181, (2008), 4188-4198.
Kaufman, R J, et al., "Inositol-requiring 1/X-box-binding protein 1 is a regulatory hub that links endoplasmic reticulum homeostasis with innate immunity and metabolism", EMBO Mol Med., vol. 2,, (2010), 189-192.
Kaufman, R J, "Orchestrating the unfolded protein response in health and disease", The Journal of Clinical Investigation, vol. 110(10), (2002), 389-1398.
Kawahara, et al., "Endoplasmic Reticulum Stress-Induced mRNA Splicing Permits Synthesis of Transcription Factor HaC1/ERN4 That Activates the Unfolded Protein Response", Mol. Biol. Cell., vol. 8, (1997), 1845-1862.
Kawahara, et al., "Unconventional Splicing of HaC1/ERN4 mRNA Required for the Unfolded Protein Response. Sequence-Specific and Non-Sequential Cleavage of the Sites", J. Biol Chern., vol. 273, (1998), 1802-1807.
Kawai, T, et al., "TLR signaling", Semin Immunol., 19, (2007), 24-32.
Kawano, et al., "Autocrine Generation and Requirement of BSF-2/IL-6 for Human Multiple Myelomas", Nature, vol. 332, (1988), 83-85.

Kay, et al., "Hepatic gene therapy: persistent expression of human alpha 1-antitrypsin in mice after direct gene delivery in vivo", Human Gene Therapy, vol. 3, (1992), 641-647.
Keen, et al., "Rapid Detection of Single Base Mismatches as Heteroduplexes on Hydrolink Gels", Trends Genet, vol. 7, (1991), 5.
Keith, B, et al., "Hypoxia-inducible factors, stem cells, and cancer", Cell, vol. 129, (2007), 465-472.
Kessel, et al., "Murine Developmental Control Genes", Science, vol. 249, (1990), 374-379.
Khoury, S J, et al., "Oral Tolerance to Myelin Basic Protein and Natural Recovery from Experimental Autoimmune Encephalomyelitis Are Associated with Downregulation of Inflammatory Cytokines and Differential Upregulation of Transforming Growth Factor.beta., Interleukin 4, and Pr", J. Exp. Med., vol. 176, (1992), 1355-1364.
Kieran, D, et al., "Deletion of the BH3-only protein puma protects motoneurons from ER stress-induced apoptosis and delays motoneuron loss in ALS mice", PNAS, vol., (2007), 20606-20611.
Kikuchi, et al., "Functional analysis of human P5, a protein disulfide isomerase homologue", J Biochem {Tokyo)., vol. 132(3), (2002), 451-455.
Kikuchi, H, et al., "Spinal cord endoplasmic reticulum stress associated with a microsomal accumuilation of mutant superoxide dismutase-1 in an ALS model", PNAS, vol. 103(15), (2006), 6025-6030.
Kinnebrew, M A, et al., "Bacterial flagellin stimulates Toll-like receptor 5-dependent defense against vancomycinesistant Enterococcus infection", J Infect Dis., vol. 201 (4),, (2010), 534-543.
Kishimoto, et al., "RTF: AB-ZIP Transcription Factor That Is Closely Related to the Human XBP/TREB5 and Is Activated by Hepatocellular Carcinoma in Rats", Biochem. Biophys. Res. Commun, vol. 223, (1996), 746-751.
Kishimoto, et al., "The Biology of Inlerleukin-6", Blood, vol. 74(1), (1989), 1-10.
Kishimoto, T, et al., "Enhanced Expression of a New Class of Liver-enriched b-Zip Transcription Factors Hepatocarcinogenesis-related Transcription Factor, in Hepatocellular Carcinomas of Rats and Humans", Cell Growth & Differentiation, vol. 9, (1998), 337-334.
Kisselev, et al., "Proteasome inhibitors: from research tools to drug candidates", Chem Biol., vol. 8(8),, (2001), 739-758.
Klisch, T J, et al., "In vivo Aloh1 targetome reveals how a proneural transcription factor regulates cerebellar development", PNAS, vol. 108, (2011), 3288-2393.
Klock, et al., "Oestrogen and Glucocorticoid Responsive Elements Are Closely Related But Distinct", Nature, vol. 329, (1987), 734-736.
Kohler, G., et al., "Continuous Cultures of Fused Cells Secreting Antibody of Predefined Specificity", Nature, 256(5517), (Aug. 7, 1975), 495-497.
Kokura, K, et al., "Identity between rat htf and human xbp-1 genes: determination of gene structure, target sequence, and transcription promotion function for HTF", GenBank Accession No. BAA82600, Gene, vol. 241 (2), (2000), 297-307.
Komatsu, M, et al., "Loss of autophagy in the central nervous system causes neurodegeneration in mice", Nature, vol. 441, (2006), 880-884.
Kono, H, et al., "How dying cells alert the immune system to danger", Nat Rev Immunol., vol. 8(4), (2008), 279-289.
Koong, Albert C, "Focussed Review: Targeting XBP-1 as a novel anti-cancer strategy", Cancer Biology & Therapy, vol. 5 (7), (2006), 756-759.
Koong, Albert C, "Targeting XBP-1 as a novei anti-cancer strategy", Cancer Biology & Therapy, 5{7), (2006), 756-759.
Kopf, et al., "Immune Responses of IL-4, IL-5, IL-6 Deficient Mice", Immunol Rev., vol. 148, (1995), 45-69.
Kopf, et al., "Impaired Immune and Acute-phase Responses in Interleukin-6-Deficient Mice", Nature, vol. 368, (1994), 339-342.
Korennykh, A V, et al., "The unfolded protein response signals through high-order assembly of Ire1", Nature, vol. 457, (2009), 687-693.

(56) References Cited

OTHER PUBLICATIONS

Kovacsovics-Bankowski, M, et al., "Efficient major histocompatibility complex class I presentation of exogenous antigen upon phagocytosis by macrophages", PNAS USA, vol. 90, (1993), 4942-4946.

Kovalchuk, et al., "IL-6 Transgenic Mouse Model for Extraosseous Plasmacytoma", PNAS, USA, vol. 99(3), (2002), 1509-1514.

Kozutsumi, et al., "The Presence of Malfolded Proteins in the Endoplasmic Reticulum Signals the Induction of Glucose-Regulated Proteins", Nature, vol. 332, (1988), 462-464.

Kullberg, M. C., et al., "Infection With Schislosoma mansoni Allers Th1!Th2 Cytokine Responses to a Non-Parasite Antigen", J. Immunol., vol. 148(10), (1992), 3264-3270.

Kurisu, et al., "MDG1/ERdj4, an ER-resident DnaJ family member, suppresses cell death induced by ER stress", Genes Cells, vol. 8(2), (2003), 189-202.

Kuznetsov, et al., "Multiple Molecular Chaperones Complex With Misfolded Large Oligomeric Glycoproteins in the Endoplasmic Reticulum", J. Biol. Chem., vol. 272, (1997), 3057.

Lam, et al., "Application of Combinatorial Library Methods in Cancer Research and Drug Discovery", Anticancer Drug Des, vol. 12, (1997), 145.

Lam, Kit S, et al., "A new type of synthetic peptide library for identifying ligand-binding activity", Nature, 354(6348), (Nov. 7, 1991), 82-84.

Landegren, Ulf, et al., "A ILgase-Mediated Gene Detection Technique", Science, 241, (1988), 1077-1080.

Langer, R, et al., "Biocompalibility of polymeric delivery systems for Macromolecules", J. Biomed Maler Res., vol. 15, (1981), 167-277.

Langmead, Ben, et al., "Ultrafast and memory-efficient alignment of short DNA sequences to the human genome", Genome Biology, 10(3), Article R25, (2009), 1-10.

Lawrence, et al., "Clix: A Search Algorithm for Finding Novel Ligands Capable of Binding Proteins of Known Three Dimensional Structure", Proteins, vol. 12, (1992), 31.

Lebrun, P, et al., "Dissociation by methylamine of insulin release from glucose-induced electrical activity in isolated mouse islets of Langerhans", Metabolism, Clinical and Experimental, W.B. Saunders Co., Philadelphia, PA, 34(12), (Dec. 1, 1985), 1122-1127.

Lee, et al., "Glucocorticoids regulate expression of dihydrofolate reductase cDNA in mouse mammary tumour virus chimaeric plasmids", Nature, vol. 294, (1981), 228-232.

Lee, et al., "IRE I-Mediated Unconventional mRNA Splicing and S2P-Mediated ATF6 Cleavage Merge to Regulate XBPI in Signaling the Unfolded Protein Response", Genes Dev: vol. 16(4), (2002), 452-466.

Lee, et al., "Mammalian Stress Response: Induction of the Glucose-Regulated Protein Family", Curr. Opin. Cell Biol., vol. 4, (1992) 267-273.

Lee, et al., "The Glucose-Regulated Proteins: Stress Induction and Clinical Applications", Trends Biochem. Sci., vol. 26, (2001), 504-510.

Lee, A H, et al., "Prolesome inhibitors disrupt the unfolded protein response in myeloma cells", PNAS, vol. 100 (17), (2003), 9946-9951.

Lee, A H, et al., "Regulation of Hepatic Lipogenesis by the Transcription Factor XBP1", Science, vol. 320, (2008), 1492-1496.

Lee, A H, et al., "Tumour necrosis factor-alpha and interferon-gamma synergistically activate the RANTES promoter through nuclear factor kappaB and interferon regulatory factor 1 (IRF-1) transcription factors", Biochem J., 350, (2000), 131-8.

Lee, A H, et al., "XBP-1 is required for biogenesis of cellular secretory machinery of exocrine glands", EMBO J., vol. 24, (2005), 4368-4380.

Lee, A H, et al., "XBP-1 regulates a subset of endoplasmic reticulum resident chaperone genes in the unfolded protein response", Mol Cell Biol., vol. 23, (2003), 7448-7459.

Lee, D. H, et al., "Proteasome inhibitors: valuable new tools for cell biologists", Trends Cell Biol., 8(10), (Oct. 1998), 397-403.

Lee, Eva Y-H-P, et al., "Mice deficient for Rb are nonviable and show defects in neurogenesis and haemalopoiesis", Nature, vol. 359, (1992), 288-294.

Lee, K P, et al., "Structure of the dual enzyme Ire1 reveals the basis for catalysis and regulation in nonconventional RNA splicing", Cell, vol. 132(1), (2008), 89-100.

Lee, T G, et al., "Purification and partial characterization of a cellular inhibitor of the inlerferoninduced protein kinase of M, 68,000 from influenza virus-infected cells", Proc Nall Sci USA, vol. 87(16), (1990), 6208-6812.

Leen, A M, et al., "Monoculture-derived T lymphocytes specific for multiple viruses expand and produce clinically relevant effects in immunocompromised individuals", Nat Med., vol. 12, (2006), 1160-1166.

Lehmann, B D, "Identification of human triple-negative breast cancer subtypes and preclinical models for selection of targeted therapies", J. Clinical Invest., vol. 121 (7), (2011), 2750-2767.

Lemarchand, et al., "Adenovirus-Mediated Transfer of a Recombinant Human UI Antitrypsin cDNA to Human Endothelial Cells", PNAS, USA, vol. 89, (1992), 6482-6486.

Lemasters, et al., "Mitochondrial permeability transition: a common pathway to necrosis and apoptosis", Biochem. Biophys. Res Commin., vol. 304(3), (2003), 463-470.

Lembo, A, et al., "Administration of a synthetic TLR4 agonist protects mice from pneumonic tularemia.", J Immunol., 180(11), 7574-81.

Leonard, et al., "Role of Jak Kinases and STAT's in Cytokine Signal Transduction", Int. J Hematol., vol. 73, (2001), 271.

Leonard, et al., "Role of the Common Cytokine Receptor y Chain in Cytokine Signaling and Lymphoid Development", Immun. Reviews, vol. 14, 8 pgs.

Lerner, "How to Make a Hybridoma", Yale J Biol. Med., vol. 54(5), (1981), 387-402.

Leung, Hagesteinjn C, et al., "Xbp1s-negative tumor B cells and pre-plasmablasts mediate therapeutic proteasome inhibitor resistance in multiple myeloma", Cancer Cell., vol. 24(3), (2013), 289-304.

Levy, Adam E, et al., "Administration of Ingraft Inlerleukin-4 Prolongs Cardiac Allografl Survival in Rais Treated With Donor-specific Transfusion/Cyclosporine", Transplantation, vol. 60(5), (1995), 405-406.

Li, et al., "Targeted Mutation of the DNA Methyltransferase Gene Results in Embryonic Lethality", Cell, vol. 69:, (1992), 915.

Li, B, et al., "RSEM: accurate transcript quantification from RNA-Seq data with or without a reference genome", BMC Bioinformatics, vol. 12, (2011), 323.

Li, X, "Intrinsic resistance of tumorigenic breast cancer cells to chemotherapy", J. Nall Cancer Inst., vol. 100(9), (2008), 672-679.

Li, Z, et al., "Hypoxia-inducible factors regulate tumorigenic capacity of glioma stem cells", Cancer Cell, vol. 15(6), (2009), 501-513.

Lin, et al., "Repression of C-MYC Transcription by Blimp-I, An Inducer of Terminal B Cell Differentiation", Science, vol. 276, (1997), 596-599.

Lindsten, et al., "A transgenic mouse model of the ubiquitin/proteasome system", Nat Biolechnol, vol. 21(8), (2003), 897-902.

Ling, S C, et al., "Response of myeloma to the proteasome inhibitor bortezomib is correlated with the unfolded protein response regulator XBP-1", Haematologica. vol. 97(1), (2012), 64-72.

Liou, H C, et al., "", GenBank Accession No. P17861, Science, vol. 247, (1990), 1581-1584.

Liou, H C, et al., "A new member of the leucine zipper class of proteins that binds to the HLA DR alpha promoter", Science, vol. 247, (1990), 1581-1584.

Liou, H C, et al., "An HLA-DR alpha promoter DNA-binding is expressed ubiquitously and maps to human chromosomes 22 and 5", Immunogenetics, vol. 34(5), (1991), 286-292.

Lisbona, F, et al., "BAX inhibitor-1 is a negative regulator of the ER stress sensor IRE1alpha", Mol Cell, vol. 33(6), (2009), 679-691.

Litvak, V, et al., "Function of C/EBP delta in a regulatory circuit that discriminates between transient and persistent TLR4-induced signals", Nat Immunol., vol. 10, (2009), 437-443.

(56) References Cited

OTHER PUBLICATIONS

Litvak, V, et al., "Role of the Transcript factor of C/EBPdelta in a regulatory circuit that discriminates between transient and persistent TLR4-induced signals", Nat Immunol., vol. 10, (2009), 437-443.
Liu, et al., "Regulation of B-Cell Commitment to Plasma Cells or to Memory B Cells", Sem Immunol., vol. 9, (1997), 235-240.
Liu, C Y, et al., "Ligand-independent dimerization activates the stress response kinases IRE1 and PERK in the lumen of the endoplasmic reticulum", J Biol Chem., vol. 275(32), (2000), 24881-24885.
Liu, J, et al., "Modulation of DNA vaccine-elicited COB+ T-lymphocyte epitope immunodominance hierarchies", J Virol, vol. 80, (2006), 11991-11997.
Liu, X S, "An algorithm for finding protein-DNA binding sites with applications to chromatin-immunoprecipitation microarray experiments", Nat Biotechnol., vol. 20(8), (2002), 835-839.
Locksley, R M, et al., "Helper T-cell subsets in mouse leishmaniasis: induction, expansion and effector function", Immunoparasitiology Today, vol. 1, (1991), A58-A61.
Lorenzo, et al., "Cytofluorometric Quantitation of Nuclear Apoptosis Induced in a Cell-Free System", Methods in Enzymol., vol. 322, (2000), 198-201.
Luo, D, et al., "AIP1 is critical in transducing IRE1-mediated endoplasmic reticulum stress response", Journal of Biological Chemistry, vol. 283(18), (2008), 11905-11912.
Luo, H C, et al., "Spontaneous calcification of arteries and cartilage in mice lacking matrix GLA protein", Nature vol. 386(6620), (1997), 78-81.
Luo, Hongyu, et al., "A Proteasome Inhibitor Effectively Prevents Mouse Heart Allograft Rejection", Transplantation, vol. 72, No. 2, (Jul. 27, 2001), 196-202.
Lupien, M, et al., "FoxA 1 translates epigenetic signatures into enhancer-driven lineage-specific transcription", Cell, vol. 132(6), (2008), 958-970.
Ma, Y, et al., "Plasma cell differentiation initiates a limited ER stress response by specifically suppressing the PERK-dependent branch of the unfolded protein response", Cell Stress and Chaperones, vol. 15, (2010), 281-293.
Ma, Y, et al., "The role of the unfolded protein response in tumor development: friend or foe?", Nat Rev Cancer, vol. 4, (2004), 966-977.
Ma, Y, et al., "The unfolding tale of the unfolded protein response", Cell, vol. 107(7), (2001).
Madura, et al., "N-recognin/Ubc2 interactions in the N-end rule pathway", J. Biol. Chem., vol. 268(16), (1993), 12046-12054.
Maeda, H, et al., "Adoptive transfer of a Th2-like cell line prolongs MHC class II antigen disparate skin allografl survival in the mouse", International Immunology, vol. 6(6), (1994), 855-862.
Maekawa, T, et al., "Mouse ATF-2 null mutants display features of a severe type of meconium aspiration syndrome", The Journal of Biological Chemistry, vol. 274(25), (1999), 17813-17819.
Maher, et al., "DNA Triple-Helix-Formation: An Approach to Artificial Gene Repressors?", Bioassays, vol. 14(12), (1992), 807-815.
Mahoney, D, et al., "Virus-tumor interactome screen reveals ER stress response can reprogram resistant cancers for oncolytic virus-triggered Caspase-2 cell death", Cancer Cell, Cell Press, US, 20(4), (2011), 443-456.
Malyala, P, et al., "Enhancing the therapeutic efficacy of CpG oligonucleotides using biodegradable microparticles", Adv Drug Deliv Rev., 61, (2009), 218-225.
Malyala, P, et al., "The potency of the adjuvant, CpG oligos, is enhanced by encapsulation in PLG microparticles", Pharm Sci., 97, (2008), 1155-1164.
Mani, S. A, et al., "The epithelial-mesenchymal transition generates cells with properties of stem cells", Cell, 133(4), (May 16, 2008), 704-15.
Manning, et al., "Targeting JNK for Therapeutic Benefit: From Junk to Gold?", Nature Reviews, vol. 2, (2003), 554-565.
Mantovani, et al., "Neutrophils in the activation and regulation of innate and adaptive immunity", Nature Reviews Immunol., vol. 11, (2011), 519-531.
Mantovani, Alberto, et al., "Cancer-related inflammation", Nature, 454, (2008), 436-444.
Marasco, W A, et al., "Design, intracellular expression, and activity of a human anti-human immunodeficiency virus type 1 gp120 single-chain antibody", PNAS USA, vol. 90(16), (1993), 7889-7893.
Marotta, L L, et al., "The JAK2/STAT3 signaling pathway is required for growth of CD44?CD24? stem cell-like breast cancer cells in human tumors", J Clin Invest., vol. 121(7), (2011), 2723-2735.
Martinon, F, et al., "Regulation of innate immunity by signaling pathways emerging from the endoplasmic reticulum", Current Opinion in Immunology, vol. 23, (2010), 1-6.
Martinon, F, et al., "TLR activation of the transcription factor XBP1 regulates innate immune responses in macrophages", NalImmunol. vol. 11, (2010), 411-418.
Matsui, et al., "B cell response pathways regulated by IL-5 and IL-2. Secretory microH chain-mRNA and J chain mRNA expression are separately controlled events", J Immunol., vol. 142(8), (1989), 2918-2923.
Matsuzaki, et al., "Identification of transcriptional activation domain of TREB5, a CREC/ATF family I protein that Binds to HTLV-1 enhancer", J Biochem {Tokyo), vol. 117(2), (1995), 303-338.
Matus, S, et al., "The Stress Rheostat: An Interplay Between the Unfolded Protein Response (UPR) and Autophagy in Neurodegeneration", Current Molecular Medicine, vol. 8, 157-172.
Maxam, et al., "A new method for sequencing DNA", PNAS, vol. 74, (1977), 560-564.
Mayo, et al., "The Mouse Metallothionein-I Gene Is Transcriptionally Regulated by Cadmium Following Transfection Into Human or Mouse Cells", Cell, vol. 29, (1982), 99-108.
McCafferty, et al., "Phage Antibodies: Filamentous Phage Displaying Antibody Variable Domains", Nature, vol. 348, (1990), 552-554.
McConnell, et al., "The Cytosensor Microphysiometer: Biological Applications of Silicon Technology", Science, vol. 257, (1992), 1906-1912.
McDonnell, V M, "Antisense-oligonucleotide therapy", N Eng. J Med., vol. 334, (1996), 316-318.
McHeyzer, Williams, et al., "B Cell Memory and the Long-Lived Plasma Cell", Curr Opin Immunolll, (1999), 172-179.
McLaughlin, Susan K., et al., "Adeno-associated virus general transduction vectors: analysis of proviral structures", Journal of Virology, 62 (6), (Jun. 1988), pp. 1963-1973.
McLean, Cory Y., et al., "GREAT improves functional interpretation of cis-regulatory regions", Nature Biotechnology, 28(5), (May 2010), 495-501.
McManus, Michael, et al., "Gene Silencing in Mammals by Small Interfering RNAs", Nature Reviews Genetics, 3(10), (Oct. 2002), 737-747.
Medzhitov, R, "Origin and physiological roles of inftammation", Nature, 454, (2008), 428-435.
Medzhitov, R, "Recognition of microorganisms and activation of the immune response", Nature, vol. 449 (7164), (2007), 819-826.
Melville, et al., "The cellular inhibitor of the PKR protein kinase, P58,r ,is an influenza virus activated co-chaperone that modulates heat shock protein activity", J Biol Chem., vol. 274(6), (1999), 3797-3803.
Meng, et al., "Orientational Sampling and Rigid-Body Minimization on Molecular Docking", Proteins, vol. 17, (1993), 266.
Meng, E. C., et al., "Automated Docking With Grid-Based Energy Evaluation", Journal of Computational Chemistry, 13(4), (1992), 505-524.
Meng, L., et al., "Epoxomicin, a potent and selective proteasome inhibitor, exhibits in vivo antiinflammatory activity.", Proc Natl Acad Sci U S A., 96(18), (Aug. 31, 1999), 10403-8.
Meng, Lihao, et al., "Eponemycin Exerts Its Antitumor Effect through the Inhibition of Proteasome Function", Cancer Research, vol. 59, (Jun. 15, 1999), 2798-2801.
Mercola, et al., "Antisense Approaches to Cancer Gene Therapy", Cancer Gene Therapy, 2, (1995), 47-59.

(56) References Cited

OTHER PUBLICATIONS

Meredith, M M, et al., "Expression of the zinc finger transcription factor zDC (Zbtb46, Btbd4) defines the classical dendritic cell lineage", J Exp Med., vol. 209, (2012), 1153-1165.
Meusser, B, et al., "ERAD: the long road to destruction", Nature Cell Biology, vol. 7(8), (2005), 766-772.
Mhashilkar, et al., "Inhibition of HIV-I Tat-Mediated LTR Transactivation and HIV-I Infection by Anti-Tat Single Chain Intrabodies", EMBO J., vol. 14, (1995), 1542-1551.
Mihara, et al., "Interleukin-6 {IL-6) Induces the Proliferation of Synovial Fibroblastic CellsIn the Presence of Soluble IL-6 Receptor", Brit. J Rheumatol., vol. 34, (1995), 321-325.
Mikkelsen, T S, et al., "Genome-wide maps of chromatin state in pluripotent and lineage-committed cells", Nature, vol. 448, (2007), 553-560.
Miller, et al., "Progress Toward Human Gene Therapy", Blood, vol. 76(2), (1990), 271-278.
Mineo, et al., "Chemical Specificity of Short-Chain Fatty Acids in stimulating insulin and glucagon secretion in sheep", American Journal of Physiology., vol. 267(2, PI. 1),, (1994), E234-E241.
Miura, et al., "Transient Transfection Assay of Cell Death Genes", Methods in Enzymol., vol. 322, (2000), 480-92.
Miyasaka, et al., "Constitutive Production of Interleukin 61 B Cell Stimulatory Factor-2 From Inflammatory Synovium", Clin. Immunol. and Immunopathol., vol. 52, (1989), 238-247.
Molinari, et al., "Role of EDEM in the release of misfolded glycoproteins from the calnexin cycle", Science, vol. 299, (2000), 1397-1400.
Montagner, M, et al., "SHARP1 suppresses breast cancer metastasis by promoting degradation of hypoxia-inducible actors", Nature, vol. 487(7407), (2012), 380-384.
Moore, M W, et al., "Introduction of soluble protein into the class I pathway of antigen processing and presentation", Cell, vol. 54, (1988), 777-785.
Morgan, R A, et al., "Cancer regression in patients after transfer of genetically engineered lymphocytes", Science, vol. 314, (2006), 126-129.
Mori, et al., "A Transmembrane Protein With a cdc2+/CDC28-Relaled Kinase Activity Is Required for Signaling From the ER to the Nucleus", Cell, vol. 74, (1993), 743-756.
Morse, et al., "Induction of Cell Cycle Arrest and B Cell Terminal Differentiation by CDK Inhibitor p18 INK4c and 11-6", Immunity, vol. 6, (1997), 47-56.
Mucenski, M L, et al., "A Functional c-myb Gene Is Required for Nonrnal Murine Fetal Hepatic Hematopoiesis", Cell, vol. 65, (1991), 677-689.
Murphy, I, et al., "Synucleinopathies: a pathological and molecular review", Clinical Neurosci Res, (2001), 445-455.
Muzyczka, N., "Use of Adeno-Associated Virus as a General Transduction Vector for Mammalian Cells", In: Current Topics in Microbiology and Immunology, 158, Springer-Verlag, Berlin: R.W. Compans, et al., (Eds.), (1992), pp. 97-129.
Myers, et al., "Detection of Single Base Substitutions by Ribonuclease Cleavage AI Mismatches in RNA: DNA Duplexes", Science, vol. 230, (1985), 1242.
Myers, et al., "Detection of Single Base Substitutions in Total Genomic DNA", Nature, vol. 313, (1985), 495.
Nagata, T, et al., "Increased ER stress during motor neuron degeneration in a transgenic mouse model of amyotrophic lateral sclerosis", Neurological Research, vol. 29, (2007), 767-771.
Nakatani, et al., "Involvement of endoplasmic reticulum stress in insulin resistance and diabetes", Journal of Biological Chemistry, vol. 280(1), (2005), 847-851.
Nakazawa, et al., "UV and Skin Cancer: Specific p53 Gene Mutation in Normal-Skin as a Biologically Relevant Exposure Measurement", PNAS, vol. 91, (1994), 360-364.
Nau, G J, et al., "Human macrophage activation programs induced by bacterial pathogens", PNAS, USA, vol. 99, (2002), 1503-1508.

Nelms, et al., "The IL-4 Receptor: Signaling Mechanisms and Biologic Functions", Annu. Rev. Immunol., vol. 17, (1999), 701-738.
Nesbeth, Y, et al., "CCL5-mediated endogenous antitumor immunity elicited by adoptively transferred lymphocytes and dendrilic cell depletion", Cancer Res., vol. 6, (2009), 6331-6338.
Nesbeth, Y C, et al., "CD4+ T cells elicit host immune responses to MHC class II-negative ovarian cancer through CCL5 secretion and CD40-mediated licensing of dendritic cells", J Immunol., vol. 184, (2010), 5654-5662.
Neve, R. M, et al., "A collection of breast cancer cell lines for the study of functionally distinct cancer subtypes", Cancer Cell., 10(6), (Dec. 2006), 515-27.
Newman, J, et al., "Comprehensive identification of Human bZIP Interactions with Coiled-Coil Arrays", Science, vol. 300, (2003), 2097-2101.
Newmann, et al., "Primaiization" of recombinant antibodies for immunoltherapy of human diseases: a macaque/human Chimeric antibody against human CD4, Biotechnology, vol. 10, (1992), 1455-1460.
Nickerson, Deborah A., et al., "Automated DNA diagnostics using an ELISA-based oligonucleotide ligation assay", Proc. Natl. Acad. Sci. USA; vol. 87, pp. 8923-8927, Nov. 1990, (Aug. 16, 1990), 8923-8927.
Nikiforov, et al., "Genetic Bil Analysis: a solid phase method for typing single nucleotide polymorphisms", Nucleic Acids Rev., vol. 22(20), (1994), 4167-4175.
Nikiforov, et al., "The use of 96-well polystyrene plates for DNA hybridization-based assays: an evaluation of different approaches to oligonucleolide immobilization", Anal Biochem, vol. 227, (1995), 201.
Nikiforov, et al., "The use of phosphorolhioate primers and exonuclease hydrolysis for the preparation of singlestranded PCR products and their detection by solid-phase hybridization", PCR Methods Appl., vol. 3, (1994), 285-291.
Nishiloh, H, et al., "ASK1 is essential for endoplasmic reticulum stress-induced neuronal cell death triggered by expanded polyglutamine repeats", Genes and Development, vol. 16, (2003), 1394-1397.
Oda, et al., "EDEM as an acceptor of terminally misfolded glycoproteins released from calnexin", Science, vol. 299,, (2003), 1394-1397.
Ogata, M, et al., "Autophagy Is Activated for Cell Survival after Endoplasmic Reticulum Stress", Molecular and Cellular Biology, vol. 26(24), (2006), 9220-9231.
Ohtsuka, et al., "Mammalian HSP40/DNAJ homologs: cloning of novel cDNAs and a proposal for their classification and nomenclature", Cell Stress Chaperones, vol. 5(2), (2000), 98-112.
Ohtsuka, E., et al., "An alternative approach to deoxyoligonucleotides as hybridization probes by insertion of deoxyinosine at ambiguous codon positions", J. Biol. Chem., 260(5), (Mar. 10, 1985), 2605-8.
Okada, et al., "Distinct roles of activating transcription factor 6 {ATF6) and double-stranded RNA-activated protein kinase-like endoplasmic reticulum kinase {PERK) in transcription during the mammalian unfolded protein response", Biochem J., vol. 366{Pt 2), (2002), 585-594.
O'Neill, L, et al., "The family of five: TIR-domain-containing adaptors in Toll-like receptor signalling", Nat Rev Immunol, vol. 7, (2007), 353-364.
Ono, et al., "Human X-Box-Binding Protein 1 Is Required for the Transcription of a Subset of Human Class II Major Histocompalibility Genes and Forms a helerodimer With c-fos", PNAS, USA, vol. 88, (1991), 4309-4312.
Ota, T, et al., "Inhibition of apolipoprolein B100 secretion by lipid-induced hepatic endoplasmic reticulum stress in rodents", The Journal of Clinical Investigation, vol. 118(1), (2008), 316-332.
Ozcan, et al., "Chemical Chaperones Reduce ER Stress and Restore Glucose Homeostasis in a Mouse Model of Type 2 Diabetes", Science, (2006), 1137-1140.
Ozcan, et al., "Endoplasmic Reticulum Stress Links Obesity, Insulin Action, and Type 2 Diabetes", Science, vol. 306, (2004), 457-461.
Pang, et al., "Addressing insulin resistance in Type I diabetes", Diabetic Medicine, vol. 25, (2008), 1015-1024.

(56) References Cited

OTHER PUBLICATIONS

Papandreou, I, et al., "Identification of an Ire1 alpha endonuclease specific inhibitor with cytotoxic activity against human multiple myeloma", Blood, vol. 117, (2011), 1311-1314.
Parker, R, et al., "Endoplasmic Reticulum Stress Links Dyslipidemia to Inhibition of Proleasome Activity and Glucose transport by HIV Protease Inhibitors", Molecular Pharmacology, vol. 67(6), (2005), 1909-1919.
Pati, et al., "Antitumorigenic effects of HIV protease inhibitor rilonavir: inhibition of Kaposi sarcoma", Blood, vol. 15,99(10), (2002), 3771-3779.
Patil, et al., "Intracellular Signaling From the Endoplasmic Reticulum to the Nucleus: The Unfolded Protein Response in Yeast and Mammals", Curr Opin Cell Biol., vol. 13, (2001), 349-355.
Patrick, L, "Nonalcoholic Fatty Liver Disease: Relationship to Insulin Sensitivity and Oxidative Stress. Treatment Approaches using Vitamin E, Magnesium, and Betaine", Alternative Medicine Review, Thorne Research, Inc., Sandpoint, US, vol. 7(4), (Jan. 1, 2002), 276-291.
Paul, W, et al., "Lymphocyte Responses and Cytokines", Cell, vol. 76,, (1994), 241-251.
Pearce, E J, et al., "Downregulation of Th1 Cytokine Production Accompanies Induction of Th2 Responses by a Parasitic Helminth, *Schistosoma mansoni*", J. Exp. Med., vol. 173, (1991), 159-166.
Pearlman, E, et al., "Induction of Murine T-Helper-Cell Responses to the Filarial Nematode *Brugia malayi*", Infection and Immunity, vol. 61(3), (1993), 1105-1112.
Peisach, E, et al., "Interaction of a peptidomimetic aminimide inhibitor with elastase", Science, vol. 269{5220),, (1995), 66-69.
Peng, et al., "NFATc1 and NFATc2 together control both T and B cell activation and differentiation", Immunity, vol. 14, (2001), 13-20.
Perou, C. M, et al., "Molecular portraits of human breast tumours", Nature, 406(6797), (Aug. 17, 2000), 747-52.
Persing, D H, et al., "Taking toll: lipid A mimelics as adjuvanls and immunomodulalors", Trends Microbiol., vol. 10, (2002), S32-37.
Pinkert, et al., "An Albumin Enhancer Localed 10 kb Upstream Functions Along With Its Promoter to Direct Efficient Liver-Specific Expression in Transgenic Mice", Genes Dev., vol. 1, (1987), 268-277.
Piret, J P, et al., "CoC12, a chemical inducer of hypoxia-inducible factor-1, and hypoxia reduce apoptotic cell death in hepatoma cell line HepG2", Ann N Y Acad Sci., vol. 973,, (2002), 443-447.
Pisa, P, et al., "Selective expression of interleukin 10, interferon y, and granulocyte-macrophage colony-stimulating actor in ovarian cancer biopsies", PNAS USA, vol. 89, (1992), 7708-7712.
Prols, et al., "Upregulation of the Cochaperone Mdg1 in Endothelial Cells is Induced by Stress and During in vitro Angiogenesis", Exp. Cell Res., vol. 269, (2001), 42-53.
Quantin, B., et al., "Adenovirus as an Expression Vector in Muscle Cells in Vivo", Proc. Natl. Acad. Sci. USA, 89, (Apr. 1992), 2581-2584.
Queen, et al., "Immunoglobin Gene Transcription Is Activated by Downstream Sequence Elements", Cell, vol. 33, (1983), 741-748.
Rakha, E A, et al., "Triple-negative breast cancer: distinguishing between basal and nonbasal subtypes", Clin Cancer Res., vol. 15(7):, (2009), 2302-2310.
Randall, et al., "Interleukin-5 (IL-5) and IL-6 define two molecularly distinct pathways of B-cell differentiation", Mol Cell Biol., vol. 13(7), (1993), 3929-3936.
Ranger, et al., "Inhibitory function of two NFAT family members in lymphoid homeostasis and Th2 development", Immunity, vol. 9(5),, (1998), 627-635.
Rao, R, et al., "Misfolded proteins, endoplasmic reticulum stress and neurodegeneration", Current Opinion in Cell Biology, vol. 16, (2004), 653-662.
Rapoport, M, et al., "Interleukin 4 Reverses T Cell Proliferative Unresponsiveness and Prevents the Onset of diabetes in Nonobese Diabetic Mice", J. Exp. Med., vol. 178, (1993), 87-99.
Rasanen, K, et al., "Activation of fibroblasts in cancer stroma", Experimental Cell Research, vol. 316, (2010), 2713-2722.
Ravasi, T, et al., "Systems biology of transcription control in macrophages", Bioessays, vol. 29, (2007), 1215-1226.
Raychaudhuri, S, et al., "Fully mobilizing host defense: building better vaccines", Nat Blotechnol., vol. 16, (1998), 1025-1031.
Raychaudhuri, S, et al., "Identifying relationships among genomic disease regions: predicting genes at pathogenic SNP associations and rare deletions", PLoS Genet 5, e1000534, (2009), 15 pgs.
Reddy, J, et al., "Lipid Metabolism and Liver Inflammation II. Fatty liver disease and fatty acid oxidation", Am. J. Physiol. Gastrointest Liver Physiol., vol. 290, (2006), G852-G858.
Reed, J C, "Mechanisms of apoptosis avoidance in cancer", Current Opinion in Oncology, vol. 11, (1999), 68-75.
Reimold, et al., "Plasma cell differentiation requires the transcription factor XBP-1", Nature, vol. 412(6844), (2001), 300-307.
Reimold, A M, et al., "An essential role in liver development for transcription factor XBP-1", Genes & Development 14, (2000), 152-157.
Reimold, A, et al., "Chondrodysplasia and neurological abnormalities in ATF-2-deficient mice", Nature, vol. 379, (1996), 262-265.
Reimold, A, et al., "Control of Terminal B Cell Differentiation by Transcription Factor XBP-1", vol. 42(9 Suppl.):S58, Poster No. 52, (1999).
Reimold, A, et al., "Transcription Factor B Cell Lineage-specific Activator Protein Regulates the Gene for Human XBox Binding Protein 1", J. Exp. Med., vol. 183, (1996), 393-401.
Rengarajan, et al., "Sequential involvement of NFAT and Egr transcription factors in FasL regulation", Immunity, vol. 12(3), (2000), 293-300.
Ricardo, S, et al., "Breast cancer stem cell markers CD44, CD24 and ALDH1: expression distribution within intrinsic molecular subtype", J Clin Palhol., vol. 64(11), (2011), 937-946.
Richardson, et al., "Phenotypic knockout of the high-affinity human interleukin 2 receptor by intracellular single-chain antibodies against the alpha subunit of the receptor", PNAS, USA, vol. 92(8), (1995), 3137-3141.
Richardson, C E, et al., "An essential role for XBP-1 in host protection against immune activation in C.elegans", Nature, vol. 463, (2010), 1092-1095.
Roach, J C, et al., "Transcription factor expression in lipopolysaccharide-activated peripheral-blood-derived mononuclear cells", PNAS USA, vol. 104, (2007), 16245-16250.
Robertson, G, et al., "Genome-wide profiles of STAT1 DNA association using chromatin immunoprecipitation and massively parallel sequencing", Nat Methods, vol. 4, (2007), 651-657
Robinson, M D, et al., "A scaling normalization method for differential expression analysis of RNA-seq data", Genome Biology, vol. 11, (2010), R25.
Roby, K F, et al., "Development of a syngeneic mouse model for events related to ovarian cancer", Carcinogenesis, vol. 21, (2000), 585-591.
Rock, et al., "Degradation of cell proteins and the generation of MHC class I-presented peptides", Annu Rev lmmunol, vol. 17, (1999), 739-779.
Rock, K L, et al., "Analysis of the role of MHC class II presentation in the stimulation of cytotoxic T lymphocytes by antigens targeted into the exogenous antigen-MHC class I presentation pathway", J Immunol., vol. 156, (1996), 3721-3726.
Romero-Ramirez, Lorenzo, et al., "X box-binding protein 1 regulates angiogenesis in human pancreatic adenocarcinomas", Transl. Oncol., vol. 2(1), (2009), 31-38.
Romero-Ramirez, Lorenzo, et al., "XBP1 is essential for survival under hypoxic conditions and is required for tumor growth", Cancer Research, American Association for Cancer Research, US, vol. 64, No. 17, (Sep. 1, 2004), 5943-5947.
Ron, D, et al., "Signal integration in the endoplasmic reticulum unfolded protein response", Nature Reviews Molecular Cell Biology, vol. 8, (Jul. 2007), 519-529.
Rondinone, "Therapeutic potential of RNAi in metabolic diseases", Bio Techniques, vol. 40, (2006), S31-S36.
Rong, J, et al., "Bifunctional Apoptosis REgulator (BAR), an endoplasmic reticulum-associated E3 ubiquitin ligase, modulates

(56) References Cited

OTHER PUBLICATIONS

BI-1 protein stability and function in ER stress", Journal of Biological Chemistry, vol. 286 (2), (2010), 1453-1463.
Rosenbaum, et al., "Temperature-gradient gel electrophoresis. Thermodynamic analysis of nucleic acids and proteins in purified form and in cellular extracts", Biophys Chem., vol. 265, (1987), 1275.
Rosenfeld, M. A., "Adenovirus-Mediated Transfer of a Recombinant a1-Antitrypsin Gene to the Lung Epithelium in Vivo", Science, 252(5004), (Apr. 19, 1991), 431-434.
Rosenfeld, Melissa, et al., "In Vivo Transfer of the Human Cystic Fibrosis Transmembrane Conductance Regulator Gene to the Airway Epithelium", Cell, 68, (1992), 143-155.
Rossi, et al., "Therapeutic Antisense and Ribozymes", Br. Med. Bull., vol. 51, (1995), 217-225.
Rossolini, G. M., et al., "Use of deoxyinosine-containing primers vs degenerate primers for polymerase chain reaction based on ambiguous sequence information", Mol. Cell. Probes, 8(2), (Apr. 1994), 91-8.
Rudge, et al., "Interleukin 4 reduces expression of inhibitory receptors on B cells and abolishes CD22 and Fe gamma RII-mediated B cell suppression", J Exp Med., vol. 195(8), (2002), 1079-1085.
Rudolph, D, et al., "Impaired fetal T cell development and perinatal lethality in mice lacking the cAMP response elemenl binding protein", PNAS US A., vol. 95(8), (1998), 4481-4486.
Ruegsegger, et al., "Block of HAC1 mRNA Translation by Long-Range Base Pairing Is Released by Cytoplasmic Splicing Upon Induction of the Unfolded Protein Response", Cell, vol. 107, (2001), 103-114.
Saiki, et al., "Analysis of Enzymatically Amplified (3-Globin and HLA-DQa DNA With Allele-Specific Oligonucleotide Probes", Nature, vol. 324, (1986), 163.
Saiki, et al., "Genetic analysis of amplified DNA with immobilized sequence-specific oligonucleotide probes", PNAS. USA, vol. 86(16), (1989), 6230-6234.
Saleeba, et al., "Chemical cleavage of mismatch to detect mutations", Methods Enzymol., vol. 217, (1992), 286-295.
Saltiel, et al., "Insulin signalling and the regulation of glucose and lipid metabolism", Nature., vol. 414(6865), (2011), 799-806.
Samoilova, et al., "IL-6-deficient mice are resistant to experimental autoimmune encephalomyelitis: roles of 1L-6 in the activation and differentiation of autoreactive T cells", J Immunol., vol. 161 (12), (1998), 6480-6486.
Samuel, "The eIF-2a protein kinases, regulators of translation in eukaryotes from yeasts to humans", J Biol Chem., vol. 268(11), (1993), 7603-7606.
Samulski, R. J., "Helper-Free Stocks of Recombinant Adeno-Associated Viruses: Normal Integration Does Not Require Viral Gene Expression", Journal of Virology, 63(9), (1989), 3822-3828.
Sanger, F., "DNA sequencing with chain-terminating inhibitors", Proceedings of the National Academy of Sciences USA, 74 (12), (Dec. 1977), 5463-5467.
Sato, E Olson, et al., "Intraepithelial CD8+ tumor-infiltrating lymphocytes and a high CD8+/regulatory T cell ratio are associated with favorable prognosis in ovarian cancer", PNAS USA, vol. 102, (2005), 18538-18543.
Satpathy, A T, et al., "Zbtb46 expression distinguishes classical dendritic cells and their committed progenitors from other immune lineages", J Exp Med., vol. 209, (2012), 1135-1152.
Scarlett, U K, et al., "In situ stimulation of CD40 and Toll-like receptor 3 transforms ovarian cancer-infiltrating dendritic cells from immunosuppressive to immunostimuiatory cells", Cancer Res., vol. 69,, (2009), 7329-7337.
Scarlett, U K, et al., "Ovarian cancer progression is controlled by phenotypic changes in dendritic cells", J Exp Med, (2012).
Scheuner, et al., "Translational Control Is Required for the Unfolded Protein Response and in Vivo Glucose Homeostasis", Mol. Cell., vol. 7, (2001), 1165.
Schmalzing, et al., "Microchip electrophoresis: a method for high-speed SNP detection", Nucleic Acids Research, vol. 28(9), (2000), 1-6.
Schmidt, C, et al., "Scatter factor/hepatocyte growth factor is essential for liver development", Nature, vol. 373,, (1995), 699-702.
Schmitz, et al., "Transcriptional activation induced in Macrophages by toll-like receptor {TLR) ligands: from expression Profiling to a model of TLR signaling", European Journal of Immunology 34, (2004), 2863-2873.
Schmitz, Peiffer, et al., "IRS-I Regulation in Health and Disease", fUBMB Life, vol. 55(7), (2003), 367-374.
Schraml, B U, et al., "Genetic tracing via DNGR-1 expression history defines dendritic cells as a hematopoietic ineage", Cell, vol. 154, (2013), 843-858.
Schroder, et al., "Control of glycosylalion of MHC class II-associated invariant chain Cy transloco-associaled RAMP4", EMBO J, vol. 18(17), (1999), 4804-4815.
Schurr, J R, et al., "Central role of toll-like receptor 4 signaling and host defense in experimental pneumonia caused by Gram-negative bacteria", Infect Immun., vol. 73, (2005), 532-545.
Schwab, L P, et al., "Hypoxia-inducible factor 1 promotes primary tumor growth and tumor-initiating cell activity in breast cancer", Breast Cancer Res., vol. 14(1), (2012), R6.
Scott, J. K., et al., "Searching for Peptide Ligands with an Epitope Library", Science, 249, (1990), 386-390.
Searle, et al., "Building a metal-responsive promoter with synthetic regulatory elements", Mol. Cel. Biol, vol. 5:, (1985), 1480-1489.
Seed, et al., "An LF A-3 cDNA Encodes a Phosphplipid-Linked Membrane Protein homologous to Its Receptor CD2", Nature, vol. 329, (1987), 840.
Semenza, G L, "Defining the role of hypoxia-inducible factor 1 in cancer biology and therapeutics", Oncogene, vol. 29(5), (2010), 625-634.
Semenza, G L, "HIF-1, O(2), and the 3 PHDs: how animal cells signal hypoxia to the nucleus", Cell, vol. 107(1), (2011), 1-3.
Semenza, G L, "Targeting HIF-1 for cancer therapy", Nat Rev Cancer, vol. 3(10), (2003), 721-732.
Servillo, G, et al., "Transcription factor CREM coordinates the liming of hepatocyte proliferation in the regenerating liver", Genes & Development, vol. 12, (1998), 3639-3643.
Sgadari, et al., "HIV protease inhibitors are potent anti-angiogenic molecules and promote regression of Kaposi sarcoma", Nat Med. vol. 8(3), (2002), 225-232.
Sha, H, et al., "The IRE1-XBP1 pathway of the unfolded protein response is required for adipogenesis", Cell Metabolism, vol. 9 (6), (2009), 556-564.
Shaffer, et al., "XBP1, Downstream of Blimp-1, Expands the Secretory Apparatus and Other Organelles, and Increases Protein Synthesis in Plasma Cell Differentiation", Immunity, 21, (2004), 81-93.
Shamu, et al., "Oligomerization and Phosphorylation of the Ire 1 p Kinase During Intracellular Signaling From the Endoplasmic Reticulum to the Nucleus", EMBO J 15, (1996), 3028-3039.
Shapira, S D, et al., "A physical and regulatory map of host-influenza interactions reveals pathways in H1N1 infection", Cell, vol. 139, (2009), 1255-1267.
Sharp, et al., "RNA Interference", Genes and Development, 287, (2001), 485-490.
Sharp, et al., "RNA Interference", P.D. 287, (2000), 2431-2432.
Shearer, G, et al., "T helper cell immune dysfunction in asymptomatic, HIV-1-seropositive individuals: the role ofTH1-TH2 cross-regulation", Chem. Immunol., vol. 54, (1992), 21-43.
Shen, et al., "Complementary Signaling Pathways Regulate the Unfolded Protein Response and Are Required for C. Elegans Development", Cell, vol. 107, (2001), 893-903.
Shen, et al., "ER stress regulation of ATF6 localization by dissociation of BiP/GRP78 Binding and unmasking of Golgi localization signals", Dev Cell., vol. 3(1), (2002), 99-111.
Shen, et al., "Identification and Characterization of a Novel Endoplasmic Reticulum {ER} Dnaj Homologue which Stimulates ATPase Activity of BiP in vitro and is Induced by ER Stress", J. Bio Chem., vol. 277 (18), (2001), 15947-15956.

(56) References Cited

OTHER PUBLICATIONS

Shi, et al., "Identification and Characterization of Pancreatic Eukaryotic Initiation Factor 2 a-Subunit Kinase, PEK, Involved in Translational Control", Mol. Cell Biol., vol. 18, (1998), 7499-7509.
Shi, et al., "When Translation Meets Metabolism: Multiple Links to Diabetes", Endocrine Reviews, vol. 24(1), (2003), 91-101.
Sidman, K R, et al., "Controlled release of macromolecules and pharmaceuticals from synthetic polypeptides based on glutamic acid", Biopolymers, vol. 22(1), (1983), 547-556.
Sidrauski, et al., "The Transmembrane Kinase Ire1p Is a Site-Specific Endonuclease That Initiates mRNA Splicing in the Unfolded Protein Response", Cell, vol. 90, (1997), 1031-1039.
Sidrauski, et al., "tRNA ligase is required for regulated mRNA splicing in the unfolded protein response", Cell., vol. 87(3), (1996), 405-413.
Sigma-Aldrich, "Lipoprotein Function and Lipid Transport", http://www.sigmaaldrich.com/Area.sub.Jf.sub.Interest/Biochemicals/Enzyme, (2008), 3 pgs.
Silze, T, et al., "The fibroblast: sentinel cell and local immune modulator in tumor tissue", International Journal of Cancer, vol. 108, (2004), 173-180.
Simon, A K, et al., "Divergent T-cell cytokine patterns in inflammatory arthritis", Proc. Natl. Acad. Sci. USA, vol. 91,, (1994), 8562-8566.
Singh, M, et al., "Polylactide-co-glycolide microparticles with surface adsorbed antigens as vaccine delivery systems", Curr Drug Deliv., vol. 3, (2006), 115-120.
Singh, S P, et al., "Fat accumulation in Caenorhabditis elegans triggered by the electrophilic lipid peroxidation product 4-hydroxynonenal (4-HNE)", Aging, vol. 1, (2009), 68-80.
Singh, S P, et al., "Role of the electrophilic lipid peroxidation product 4-hydroxynonenal in the development and maintenance of obesity in mice", Biochemistry, vol. 47, (2008), 3900-3911.
Sjolander, et al., "Integrated Fluid Handling System for Biomolecular Interaction Analysis", Anal. Chem., vol. 63, (1991), 2338-2345.
Smalley, M, et al., "Stem cells and breast cancer: A field in transit", Nat Rev Cancer, vol. 3(11), (2003), 832-844.
Smyth, G K, et al., "Statistical issues in cDNA microarray data analysis", Methods Mol Biol., vol. 224, (2003), 111-136.
So, J S, et al., "Silencing of lipid metabolism genes through IRE1alpha-mediated mRNA decay lowers plasma lipids in mice", Cell Metab., vol. 16, (2012), 487-499.
Songyang, et al., "SH2 Domains Recognize Specific Phosphopeptide Sequences", Cell 72, (1993), 767-778.
Sriburi, R, et al., "Coordinate Regulation of Phospholipid Biosynthesis and Secretory Pathway Gene Expression in KBP-1{S)-induced Endoplasmic Reticulum Biogenesis", The Journal of Biological Chemistry, vol. 282 (10),, (2007), 7024-7034.
Sriburi, R, et al., "XBP1: a link between the unfolded protein response, lipid biosynthesis, and biogenesis of the endoplasmic reticulum", The Journal of Cell Biology, vol. 167(1), (2004), 35-41.
Stingl, J, et al., "Molecular heterogeneity of breast carcinomas and the cancer stem cell hypothesis", Nat Rev Cancer, vol. 7(10):, (2007), 791-799.
Stoerker, et al., "Rapid Genotyping by MALDI-Monitored Nuclease Selection From Probe; Libraries", Nature Biotechnology, vol. 18, (2000), 1213.
Stoichet, et al., "Structure-Based Discovery Of Inhibitors Of Thymidylate Synthase", Science, vol. 259, (1993), 1445.
Struhl, K, "Transcriptional noise and the fidelity of initiation by RNA polymerase II", Nat Struct Mol Bioi., vol. 14, (2007), 103-105.
Suckow, M, "Cancer vaccines: Harnessing the potential of antitumor immunity", The Veterinary Journal, vol. 198, (2013), 28-33.
Sui, Guangchao, "A DNA Vector-Based RNAi Technology to Supress Gene Expression in Mammalian Cells", Proceedings of the National Academy of Sciences, 99(8), (Apr. 16, 2002), 5515-5520.
Sullivan, B M, et al., "Antigen-driven effector CD8 T cell function regulated by T-bet", Proc Nall Acad Sci USA, vol. 100, (2003), 15818-15823.
Szabo, et al., "Surface Plasmon Resonance and Its Use in Biomolecular Interaction Analysis (BIA)", Curro Opin. Struct. Biol., vol. 5, (1995), 699-705.
Takahashi, T, et al., "Antiobesity agent for treating and preventing obesity, comprises extract of betaine, dandelion, turmeric, red pepper and/or Lonicera japonoica,as active ingredients", DERWENT, (Jan. 1, 1900).
Takatsu, et al., "Cytokines Involved in B-Cell Differentiation and Their Sites of Action", Proc Soc Exp Biol & Med., vol. 215, (1997), 121-133.
Takeuchi, T., et al., "Heart allografts in murine systems. The differential activation of Th2-like effector cells in peripheral tolerance.", Transplantation. 53(6), (1992), 1281-91.
Tan, E Y, et al., "The key hypoxia regulated gene CAIX is upregulated in basal-like breast tumours and is associated with resistance to chemotherapy", J Cancer, vol. 100(2), (2009), 405-411.
Tang, Q, et al., "A comprehensive view of nuclear receptor cancer cistromes", Cancer Res., vol. 71(22), (2011), 6940-6947.
Taub, R, "Transcriptional control of liver regeneration", FASEB J., vol. 10, (1996), 413-427.
Thai, N, et al., "Cytokine mRNA Profiles in Mouse Orthotopic Liver Transplantation", Transplantation, vol. 59 (2), (1995), 274-281.
Thomas, et al., "Site-Directed Mutagenesis by Gene Targeting in Mouse Embryo-Derived Stem Cells", Cell 51, (1987), 503.
Thomas, Karn, et al., "Homogeneous Datasets of Triple Negative Breast Cancers Enable the Identification of Novel Prognostic and Predictive Signatures", PLOS ONE, vol. 6, No. 12, (Dec. 29, 2011), e28403-e28403.
Thompson, et al., "BAFF-R, A Newly Identified TNF Receptor That Specifically Interacts With BAFF", Science 293, (2001), 2108-2111.
Tirasophon, et al., "A stress response pathway from the endoplasmic reticulum to the nucleus requires a novel bifunctional protein kinase/Endoribonuclease (Ire1p) in mammalian cells", Genes Dev., vol. 12(12), (1998), 1812-1824.
Tirasophon, et al., "The Endoribonuclease Activity of Mammalian IREI Autoregulates Its mRNA and Is Required for the Unfolded Protein Response", Genes Dev., vol. 14, (2000), 2725-2736.
Todd, D, et al., "XBP1 governs late events in plasma cell differentiation and is not required for antigen specific memory B cell development", J Exp Med., vol. 206, (2009), 2151-2159.
Toh, et al., "Isolation and Characterization of a Rat Liver Alkaline Phosphatase Gene", Eur. J Biochem., vol. 182, (1989), 231-238.
Tratschin, et al., "A Human Parvovirus, Adeno-Associated Virus, as a Eucary", Mol. Cell. Biol., vol. 4:, (1985), 2072-2081.
Tratschin, et al., "Adeno-associated virus vector for high-frequency integration, expression, and rescue of genes in mammalian cells", Mol Cell Biol., vol. 5(11), (1985), 3251-60.
Tratschin, et al., "Genetic analysis of adeno-associated virus: properties of deletion mutants constructed in vitro and evidence for an adeno-associated virus replication function", J Virol., vol. 51 (3), (1984), 611-619.
Trojanowski, J Q, "Parkinson's Disease and Related Synucleinopathies are a New Class; of Nervous System Amyloidoses", Neurotoxicology, vol. 23(4-5), (2002), 457-460.
Tsunekawa, et al., "Protection of pancreatic-cells by exendin-4 may involve the reduction of endoplasmic reticulum stress: in vivo and in vitro studies", J. Endocrinology, 193, (2007), 65-74.
Turner, et al., "Blimp-1, a novel zinc finger-containing protein that can drive the maturation of B lymphocytes into immunoglobulin-secreting cells", Cell, vol. 77, (1994), 297-306.
Turner, B, et al., "ER Stress and UPR in Familial Amyotrophic Lateral Sclerosis", Current Molecular Medicine, vol. 6,, (2006), 79-86.
Turner, M, et al., "HLA-B27 misfolding in transgenic rats is associated with activation of the unfolded protein response", Journal of Immunology, vol. 175, (2005), 2438-2448.
Tuschl, et al., "Targeted mRNA degradation by double-stranded RNA in vitro", Genes Dev., vol. 13(24), (1999), 3191-3197.
Tzakis, A G, et al., "Early Tolerance in Pediatric Liver Allografl Recipients", J. Pediatr. Surg., vol. 29(6), (1994), 754-756.

(56) References Cited

OTHER PUBLICATIONS

Uehara, Y, et al., "Placental defect and embryonic lethality in mice lacking hepatocyte growth factor/scatter factor", Nature, vol. 373, (1995), 702-705.
Urano, et al., "A survival pathway for Caenorhabditis elegans with a blocked unfolded protein response", J Cell Biol. vol. 158(4), (2002), 639-646.
Urano, et al., "IRE1 and Efferent Signaling From the Endoplasmic Reticulum", J Cell Sci., vol. 113(21), (2000), 3697-3702.
Urano, F, et al., "Coupling of stress in the ER to activation of JNK protein kinases by transmembrane protein kinase IRE1", Science, vol. 287, (2000), 664-666.
Urushitani, M, et al., "Chromogranin-mediated secretion of mutant superoxide dismutase proteins linked to amyotrophic lateral sclerosis", Nature Neuroscience, vol. 9(1), (2006), 108-118.
Uysal, et al., "Protection from obesity-induced insulin resistance in mice lacking TNF-alpha function", Nature, vol. 389, (1997), 610-614.
Van, Beusechem, et al., "Long-Term Expression of Human Adenosine Deaminase in Rhesus Monkeys Transplanted Nith Retrovirus-Infected Bone-Marrow Cells", Proc. Natl. Acad. Sci. USA 89, (1992), 7640-7644.
Van, Huizen R, et al., "P58IPK, a novel endoplasmic reticulum stress-inducible protein and potential negative regulator of eIF2alpha signaling", Journal of Biological Chemistry, vol. 278(18),, (2003), 15558-15564.
Van, Limbergen J, et al., "The genetics of Crohn's disease", Annual Review of Genomics and Human Genetics 2009 vol. 10, (May 2009), 89-116.
Vargo, Gogola T, et al., "Modelling breast cancer: one size does not fit all", Cancer, vol. 7(9), (2007), 659-672.
Visvader, J E, et al., "Cancer stem cells in solid tumours: accumulating evidence and unresolved questions", Nat Rev Cancer, vol. 8(10), (2008), 755-768.
Vladykovskaya, E, et al., "Lipid peroxidation product 4-hydroxy-trans-2-nonenal causes endothelial activation by inducing endoplasmic reticulum stress", J Biol Chem., vol. 287, (2012), 11398-11409.
Vlug, A, et al., "ATF3 expression precedes death of spinal motoneurons in amyotrophic lateral sclerosis-SOD1 transgenic mice and correlates with c-Jun phosphorylation, CHOP expression, somatodendritic ubiquitination and Golgi fragmentation", European Journal of Neuroscience, vol. 22,, (2005), 1881-1894.
Volkmann, K, et al., "Potent and selective inhibitors of the inositol-requiring enzyme 1 endoribonuclease", J Biol Chem., vol. 286 (14), (2011), 12743-12755.
Vranic, S, et al., "Angiogenesis in triple-negative adenoid cystic carcinomas of the breast", Virchows Archiv., Springer, Berlin, DE, vol. 459 (4), (2011), 377-382.
Wagner, et al., "Gene inhibition using antisense oligodeoxynucleotides", Nature, vol. 372, (1994), 333-335.
Walter, P, et al., "The unfolded protein response: from stress pathway to homeostatic regulation", Science, vol. 334 (6059), (2011), 1081-1086.
Wang, et al., "Activation of ATF6 and an ATF6 DNA binding site by the endoplasmic reticulum stress response", J Biol Chem., vol. 275(35), (2000), 27013-27020.
Wang, et al., "Cloning of mammalian Ire1 reveals diversity in the ER stress responses", EMBO J., vol. 17(19), (1998), 5708-5717.
Wang, et al., "Oligomeric complexes involved in translocation of proteins across the membrane of the endoplasmic reticulum", FECS Lett., vol. 457(3),, (1999), 316-322.
Wang, F M, et al., "Resveratrol triggers the pro-apoptotic endoplasmic reticulum stress response and represses pro-survival XBP1 signaling in human multiple myeloma cells", Exp Hematol., vol. 39(10), (2011), 999-1006.
Wang, Y, et al., "Targeting HIF1 eliminates cancer stem cells in hematological malignancies", Cell Stem Cell, vol. 8(4), (2011), 399-411.
Weintraub, et al., "Antisense RNA as a Molecular Tool for Genetic Analysis", Reviews-Trends in Genetics, vol. 1(1), (1986).

Welch, et al., "Influence of Molecular and Chemical Chaperones on Protein Folding", Cell Stress Chaperones, vol. 1, (1996), 109-115.
Welch, et al., "Mammalian stress response: cell physiology, structure/function of stress proteins, and implications for medicine and disease", Physiol Rev., vol. 72(4), (1992), 1063-1081.
Welihinda, et al., "The unfolded protein response pathway in *Saccharomyces cerevisiae*. Oligomerization and transphosphorylation of Ire1p (Ern1p) are required for kinase activation", J Biol Chem., vol. 271(30), (1996), 18181-18187.
Wen, et al., "Identification of c-myc promoter-binding protein and X-box binding protein 1 as Interleukin-6 target genes in human multiple myeloma cells", Int. Journal of Oncology, vol. 15, (1999), 173-178.
Werge, et al., "Cloning and Intracellular Expression of a Monoclonal Antibody to the 21 ras Protein", FEBS Letters 274, (1990), 193-198.
Whelan, et al., "The HIV protease inhibitor Indinavir reduces immature dendritic cell transendothelial migration", Eur. J. Immunol 33, (2003), 2520-2530.
Whiteside, T L, "Immune suppression in cancer: effects on immune cells, mechanisms and future therapeutic intervention", Seminars in Cancer Biol., vol. 16(1), (2006), 3-15.
Whiteside, T L, "The tumor microenvironment and its role in promoting tumor growth", Oncogene, vol. 27:, (2008), 5904-5912.
Wilcox, W R, et al., "Lysosomal storage disorders: the need for better pediatric recognition and comprehensive care", J. Pediatric, vol. 144, (2004), S3-S4.
Wilson, et al., "Hepatocyte-directed gene transfer in vivo leads to transient improvement of hypercholesterolemia in low density lipoprolein receptor-deficient rabbits", J Biol Chem., vol. 267(2), (1992), 963-967.
Wilson, et al., "Retrovirus-mediated transduction of adult hepatocytes", Proc Natl Acad Sci USA., vol. 85(9), (1988), 3014-3018.
Wilson, et al., "The use of mRNA display to select high-affinity protein-binding peptides", PNAS, USA, vol. 98 (7), (2001), 3750-3755.
Winoto, et al., "A novel, inducible and T cell-specific enhancer located at the 3' end of the T cell receptor alpha locus", EMBO J., vol. 8(3), (1989), 729-733.
Wiseman, R, et al., "Flavonol activation defines an unanticipated ligand-binding site in the kinase-RNase domain of IRE1", Molecular Cell, vol. 38(2),, (2009), 291-304.
Wolff, J. A., et al., "Direct Gene Transfer into Mouse Muscle in Vivo", Science, 247, 1465-1468.
Won, Herrath, et al., "Animal models of human type 1 diabetes", Nature Immunology, 10(2), (2009), 129-132.
Wondisford, et al., "Cloning of the human thyrotropin beta-subunit gene and transient expression of biologically active human thyrotropin after gene transfection", Mol. Endocrinol. 2, (1988), 32-39.
Wong, et al., "Characterization of beta-thalassaemia mutations using direct genomic sequencing of amplified single copy DNA", Nature, vol. 330(6146), (1987), 384-386.
Wong, C C, et al., "Hypoxia-inducible factor 1 is a master regulator of breast cancer metastatic niche formation", Proceedings of the National Academy of Sciences, vol. 108, No. 39, (Sep. 27, 2011), 16369-16374.
Woo, C W, et al., "Adaptive suppression of the ATF4-CHOP branch of the unfolded protein response by toll-like receptor signalling", Nat Cell Biol. vol. 11, (2009), 1473-1480.
Wootz, H, et al., "Caspase-12 cleavage and increased oxidative stress during mononeuron degeneration in transgenic mouse model of ALS", Biochemical and Biophysical Research Communications, vol. 322, (2004), 281-286.
Wootz, H, et al., "XIAP decreases caspase-12 cleavage and calpain activity in spinal cord of ALS transgenic mice", Experimental Cell Research, vol. 312,, (1890-1898), 2006.
Wouters, B G, et al., "Hypoxia signalling through mTOR and the unfolded protein response in cancer", Nat Rev Cancer, vol. 8(11), (2008), 851-864.
Wu, G. Y., et al., "Receptor-Mediated Gene Delivery and Expression in Vivo", The Journal of Biological Chemistry, 263(29), (1988), 14621-14624.

(56) References Cited

OTHER PUBLICATIONS

Wu, X, et al., "HIV protease inhibitors induce endoplasmic reticulum stress and disrupt barrier integrity in intestinal epithelial cells", Gastroenterology, Gastroenterology, vol. 138, (2010), 197-209.

Xia, X, et al., "Integrative analysis of HIF binding and transactivation reveals its role in maintaining hislone methylalion homeostasis", PNAS USA, vol. 106(11), (2009), 4260-4265.

Xiao-Mei, Zhu, et al., "Endoplasmic reticulum stress and its regulator XBP-1 contributes to dendritic cell maturation and activation induced by high mobility group box-1 protein", International Journal of Biochemistry and Cell Biology, Pergamon, GB, vol. 44, No. 7, (Mar. 27, 2012), 1097-1105.

Xu, et al., "The Role of CD40-CD 154 Interaction in Cell Immunoregulation", J Biomed Sci, (2004), 426-438.

Xu, Y, "DNA damage: a trigger of innate immunity but a requirement for adaptive immune homeostasis", Nat Rev Immunol., vol. 6, (2006), 261-270.

Y0shimura, T, et al., "Multiple cDNA closes encoding nuclear proteins that bind to the tax dependent enhancer of HTLV-1: all contain a leucine zipper structure and basic amino acid domain", EMBO, vol. 9(8), (1990), 2537-2542.

Yamaguchi, et al., "Stress-associated endoplasmic reticulum protein 1 (SERP1)/Ribosomel associated membrane protein 4 (RAMP4) stabilizes membrane proteins during stress and facilitates subsequent glycosylation", J Cell Biol. vol. 147(6), (1999), 1195-1204.

Yamamura, M, et al., "Local Expression of Antiinflammatory Cytokines in Cancer", The Journal of Clinical Investigation, vol. 91, (1993), 1005-1010.

Yan, et al., "Control of PERK elF2a kinase activity by the endoplasmic reticulum stress-induced molecular chaperone P581PK", PNAS USA., vol. 99(25),, (2002), 15920-15925.

Yan, Q, et al., "The hypoxia-inducible factor 2alpha N-terminal and C-terminal transactivation domains cooperate to promote renal tumorigenesis in vivo", Mol Cell Biol., vol. 27(6), (2007), 2092-102.

Yanagitani, K, et al., "Cotranslational targeting of XBP1 protein to the membrane promotes cytoplasmic splicing of its own mRNA", Mol Cell, vol. 34,, (2009), 191-200.

Yang, et al., "Ubiquitin protein ligase activity of IAPs and their degradation in proteasomes in response to apoptotic stimuli", Science, vol. 88(5467), (2000), 874-877.

Yang, L, et al., "FZD7 has a critical role in cell proliferation in triple negative breast cancer", Oncogene, vol. 30, No. 43, (Oct. 27, 2011), 4437-4446.

Ye, et al., "ER Stress Induces Cleavage of Membrane-Bound ATF6 by the Same Proteases Thal Process SREBPs", Mol Cell, vol. 6, (2000), 1355-1364.

Yeh, et al., "A cell-surface antigen which is present in the ganglioside fraction and shared by human melanomas", Int. J. Cancer, vol. 29, (1982), 269-275.

Yeh, et al., "Cell surface antigens of human melanoma identified by monoclonal antibody", Proc Nall Acad Sci USA. vol. 76(6), (1979), 2927-2931.

Yoneda, T, et al., "Activation of caspase-12, an endoplasmic reticulum (ER) resident caspase, through tumor necrosis actor receptor-associated factor 2-dependent mechanism in response to ER stress", Journal of Biological Chemistry, vol. 276(17),, (2001), 13935-13940.

Yoshida, et al., "A time-Dependent Phase Shift in the Mammalian Unfolded Protein Response", Dev Cell, vol. 4(2), (2003), 265-271.

Yoshida, et al., "ATF6 Activated by Proteolysis Binds in the Presence of NF-Y {CBF) Directly to the cis-Acling Element Responsible for the Mammalian Unfolded Protein Response", Molecular and Cellular Biology, vol. 20(18), (2000), 6755-6767.

Yoshida, et al., "Endoplasmic Reticulum Stress-Induced Fornnation of Transcription Factor Complex ERSF Including NF-Y {CBF) and Activating Transcription Factors 60. And 6p That Activates the Mammalian Unfolded Protein Response", Mol Cell Biol 21, (2001), 1239-1248.

Yoshida, et al., "Identification of the cis-Acting Endoplasmic Reticulum Stress Response Element Responsible for Transcriptional Induction of Mammalian Glucose-Regulated Proteins", J. Biol. Chem., vol. 273, (1998), 33741-33749.

Yoshida, et al., "XBPI mRNA Is Induced by ATF6 and Spliced by IREI in Response to ER Stress to Produce a Highly Active Transcription Factor", Cell, vol. 107, (2001), 881-891.

Yoshimura, et al., "Adenovirus-Mediated Transfer of a Recombinant al-Antitrypsin Gene to the Lung Epithelium In Vivo", Science, vol. 252, (1991), 431-434.

Yoshimura, K, et al., "Adenovirus-mediated augmentation of cell transfection with unmodified plasmid vectors", J Biol Chem., vol. 268(4), (1993), 2300-2003.

Yoshimura, T, et al., "Multiple cDNA clones encoding nuclear proteins that bind to the tax-dependent enhancer of HTLV-2: all contain a leucine zipper structure and basic amino acid domain", EMBO J., vol. 9(8), (1990), 2537-2542.

Yoshizaki, et al., "Pathogenic Significance of Interleukin-6 (IL-60/BSF-2) in Castleman's Disease", Blood 74, (1989), 1360-1367.

Yuan, et al., "Reversal of Obesity-and-Diet-Induced Insulin Resistance with Salicylates or Targeted Disruption of ikkbeta", Science, vol. 293, (2001), 1673.

Zamore, P. D, et al., "RNAi: Double-Stranded RNA Directs the ATP-Dependent Cleavage of mRNA at 21 to 23 Nucleotide Intervals", Cell, 101, (2000) 25-33.

Zanoboni, A, et al., "Stimulation of insulin secretion in man by oral glycerol administration", Metabolism, Clinical and Experimental, W.B. Saunders Co., Philadelphia, PA,vol. 25(1), (Jan. 1, 1976), 41-45.

Zervos, et al., "Mxi1, a protein that specifically interacts with Max to bind Myc-Max recognition sites", Cell 72:, (1993), 223-232.

Zhang, et al., "GRP78, but not Protein-disulfide Isomerase, Partially Reverses Hyperglycemia-induced Inhibition of Insulin Synthesis and Secretion in Pancreatic-cells", J. Biol. Chem., 284(8), (2009), 5289-5298.

Zhang, J, et al., "Insulin inhibits transcription of IRS-2 gene in rat liver through an insulin response element (IRE) that resembles IREs of other insulin-repressed genes", PNAS, vol. 98(7), (2001), 3756-3761.

Zhang, K, et al., "From endoplasmic-reticulum stress to the inflammatory response", Nature, vol. 454, (2008), 455-462.

Zhang, K, et al., "The unfolded protein response sensor IRE1alpha is required at 2 distinct steps in B cell lymphopoiesis", J Clin Invest., vol. 115, (2005), 268-281.

Zhang, K, et al., "The unfolded protein response transducer IRE1alpha prevents ER stress-induced hepatic steatosis", EMBO J., vol. 30(7), (2011), 1357-1375.

Zhang, L, et al., "Intratumoral T cells, recurrence, and survival in epithelial ovarian cancer", N Engl J Med., vol. 348, (2003), 203-213.

Zhang, Q, et al., "Control of cyclin D1 and breast tumorigenesis by the EgIN2 prolyl hydroxylase", Cancer Cell, vol. 16(5), (2009), 413-424.

Zhao, et al., "Endoplasmic reticulum stress in health and disease", Current Opinion in Cell Biology, vol. 18, (2006), 444-452.

Zhou, et al., "HIV Protease Inhibitors Activate the Unfolded Protein Response in Macrophages: Implication for Atherosclerosis and Cardiovascular Disease", Mol. Pharmacol, (2005), 690-700 pgs.

Zhou, H, et al., "HIV protease inhibitors increase TNF-alpha and IL-6 expression in macrophages: involvement of the RNA-binding protein HuR", vol. 195, (2007), 134-143.

Zhou, J, et al., "The crystal structure of human IRE1 luminal domain reveals a conserved dimerization interface required for activation of the unfolded protein response", PNAS USA, vol. 103(39), (2006), 14343-14348.

Zhu, et al., "Interaction of ATF6 and serum response factor", Mol Cell Biol. vol. 17(9), (1997), 4957-4966.

Zhu, X, et al., "Endoplasmic reticulum stress and its regulator XBP-1 contributes to dendritic cell maturation and activation induced by high mobility group box-1 protein", International Journal of Biochemistry and Cell Biology. Pergamon. GB., vol. 44. No. 7,, (Mar. 2012), 1097-1105.

(56) References Cited

OTHER PUBLICATIONS

Zimmet, et al., "Global and societal implications of the diabetes epidemic", Nature., vol. 414(6865), (2001), 782-787.
Zollner, et al., "Proteasome inhibition reduces superantigen-medialed T cell activation and the severity of psoriasis in a SCID-hu model", J Clin Invest. vol. 109(5), (2002), 671-679.
Zou, W, "Immunosuppressive networks in the tumour environment and their therapeutic relevance", Nat Rev Cancer, vol. 5, (2005), 263-274.
Zubler, "Key Differentiation steps in normal C cells and in myeloma cells", Semin Hematol., vol. 34 {Supp 1}, (1997), 13-22.
Zuckermann, R N., et al., "Discovery of Nanomolar Ligands for 7-Transmembrane G-Protein-Coupled Receptors from a Diverse N-(Substituted]glycine Peptoid Library", Journal of Medicinal Chemistry, 37(17), (Aug. 19, 1994), 2678-2685.
U.S. Appl. No. 15/024,215, filed Mar. 23, 2016, Compounds for Inducing Anti-Tumor Immunity and Methods Thereof.
PCT/US2014/057525, Sep. 25, 2014, Compounds for Inducing Anti-Tumor Immunity and Methods Thereof.
"U.S. Appl. No. 15/921,322, Advisory Action dated Mar. 15, 2019", 7 pgs.
"U.S. Appl. No. 15/921,322, Final Office Action dated Dec. 31, 2018", 12 pgs.
"U.S. Appl. No. 15/921,322, Preliminary Amendment filed Mar. 15, 2018", 4 pgs.
"U.S. Appl. No. 15/921,322, Response filed Feb. 28, 2019 to Final Office Action dated Dec. 31, 2018", 8 pgs.
"U.S. Appl. No. 15/921,322, Second Preliminary Amendment filed Mar. 16, 2018", 4 pgs.
"U.S. Appl. No. 15/921,322, Response filed Apr. 29, 2019 to Advisory Action dated Mar. 15, 2019", 5 pgs.
"U.S. Appl. No. 15/921,322, Examiner Interview Summary dated Apr. 25, 2019", 3 pgs.
"U.S. Appl. No. 15/921,322, Notice of Allowance dated May 28, 2019", 7 pgs.
"European Application Serial No. 19160532.8, Extended European Search Report dated Jun. 17, 2019", 9 pgs.
Rosenblatt, Jacalyn, et al., "Vaccination with dendritic cell/tumor fusion cells results in cellular and humoral antitumor immune responses in patients with multiple myeloma", *Blood*, 117(2), (Jan. 13, 2011), 393-402.

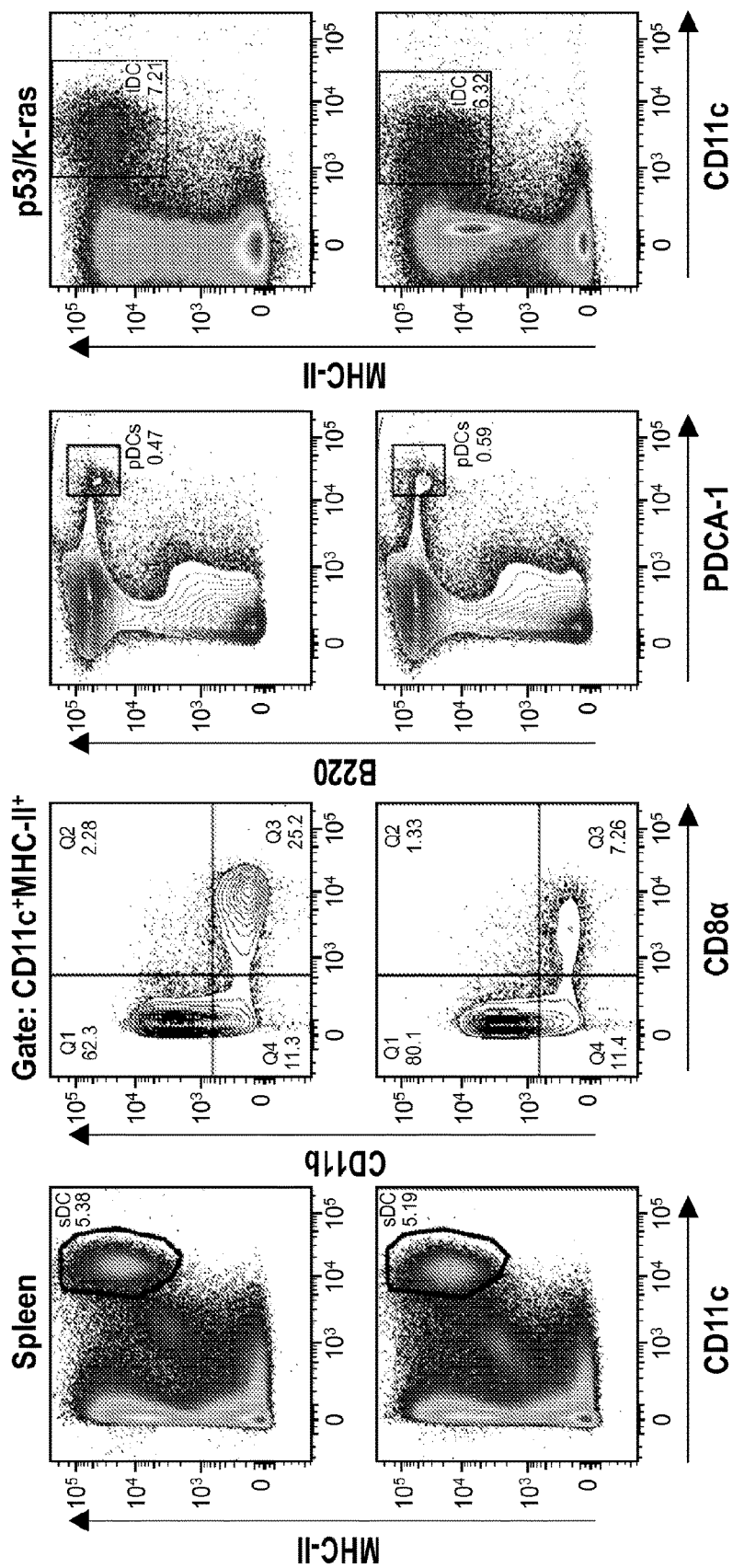

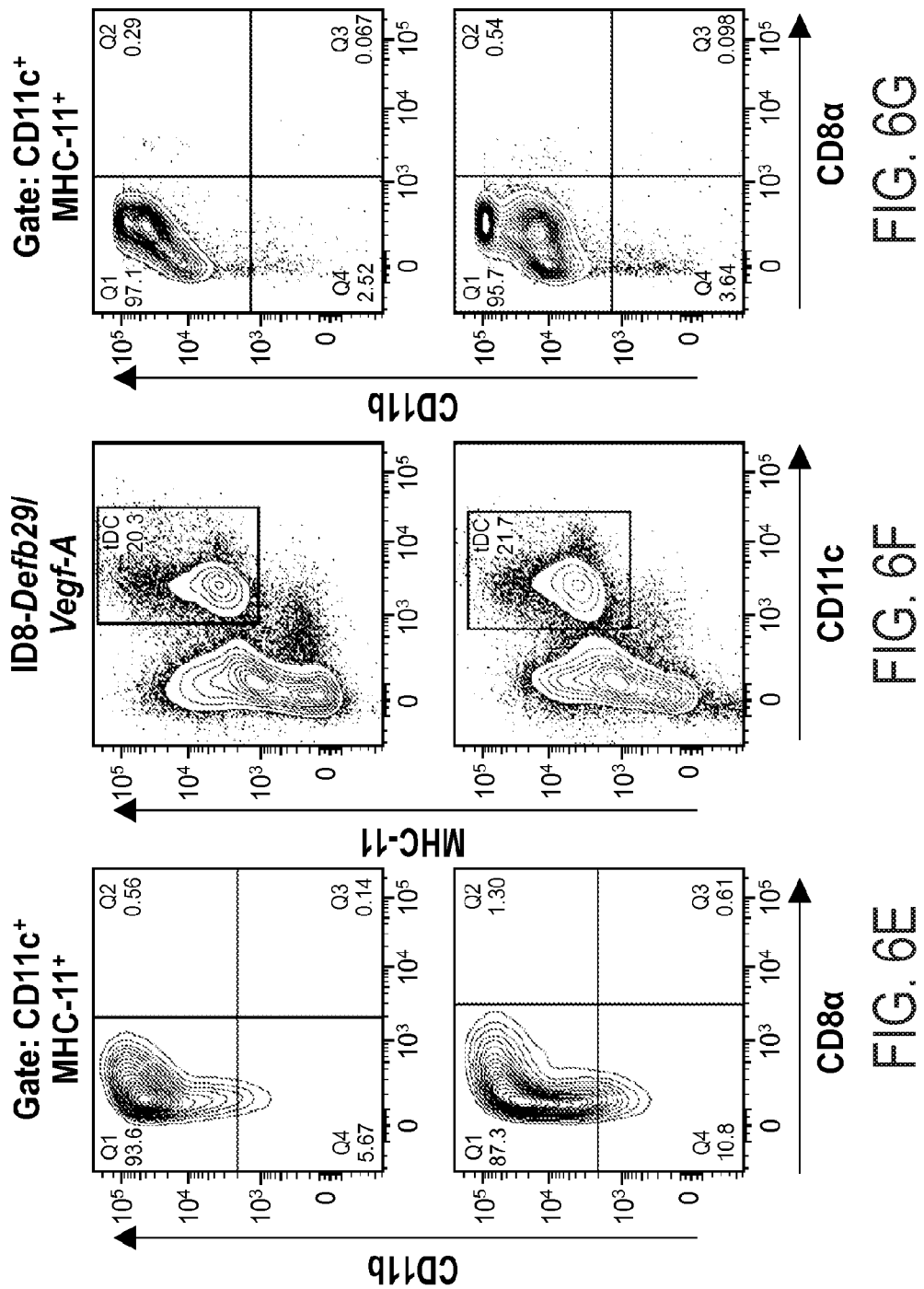

| Regulator | Type | Fold | Targets | p | Prediction | Z |
|---|---|---|---|---|---|---|
| XBP1 | TF | -1.84 | 24 | $1\times10^{-9}$ | Inhibited | -3.17 |
| MKL2 | TF | | 15 | $2\times10^{-9}$ | Inhibited | -3.16 |
| TGFB1 | GF | | 95 | $3\times10^{-13}$ | Inhibited | -2.73 |
| SRF | TF | | 26 | $2\times10^{-7}$ | Inhibited | -2.71 |
| CD38 | enzyme | | 18 | $2\times10^{-7}$ | Inhibited | -2.35 |
| MKL1 | TF | -1.55 | 16 | $7\times10^{-8}$ | Inhibited | -2.33 |
| ITK | kinase | 1.80 | 13 | $1\times10^{-7}$ | Activated | 2.02 |
| NCR1 | receptor | 2.87 | 6 | $7\times10^{-8}$ | Activated | 2.22 |
| IL2 | cytokine | | 48 | $1\times10^{-14}$ | Activated | 2.77 |

TF = transcription factor, GF = growth factor, Z = prediction Z-score

FIG. 8A

| Functional cluster | GO terms | Description | Enr | P | FDR | N | %↓ |
|---|---|---|---|---|---|---|---|
| Carbohydrate metabolic process | GO:0044262 | cellular carbohydrate metabolic process | 2.2 | 0.0006 | 1% | 24 | 96% |
| | GO:0005975 | carbohydrate metabolic process | 1.9 | 0.0013 | 2% | 29 | 97% |
| Protein localization and transport | GO:0045184 | establishment of protein localization | 1.7 | 0.0022 | 3% | 37 | 78% |
| | GO:0015031 | protein transport | 1.7 | 0.0034 | 5% | 36 | 81% |
| | GO:0008104 | protein localization | 1.6 | 0.0067 | 9% | 39 | 77% |
| Regulation of cell communication | GO:0010646 | regulation of cell communication | 1.6 | 0.0034 | 5% | 41 | 68% |
| Lipid metabolic process | GO:0006629 | lipid metabolic process | 1.6 | 0.0094 | 13% | 38 | 67% |

Enr=enrichment fold, N=number of involved genes, %↓ =% of involved genes that are downregulated

FIG. 8D

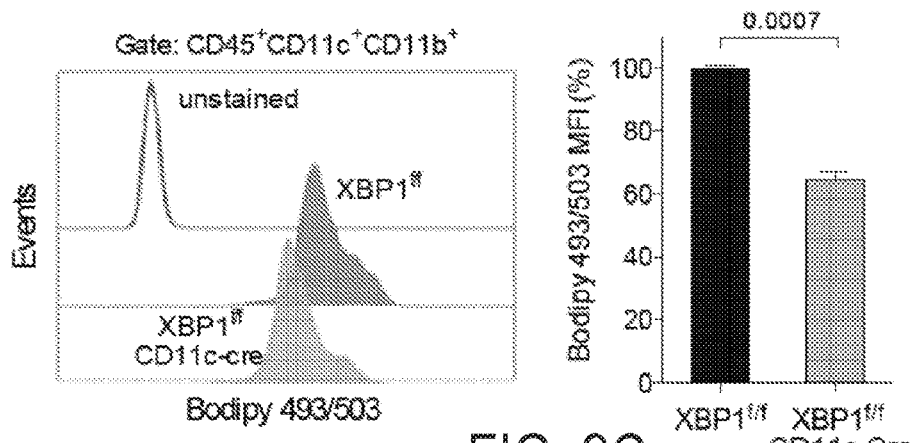
FIG. 9C
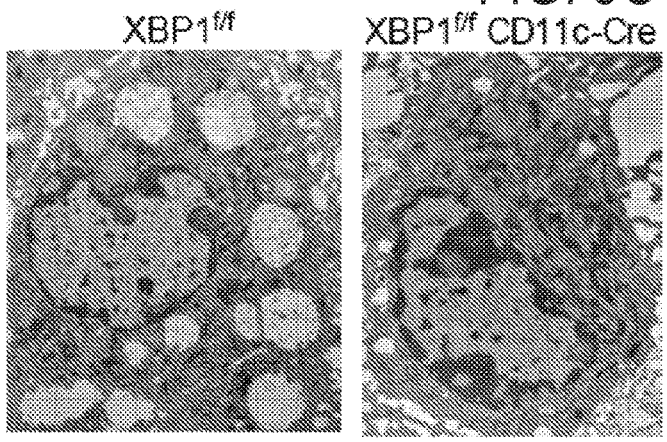
FIG. 9D
FIG. 9E
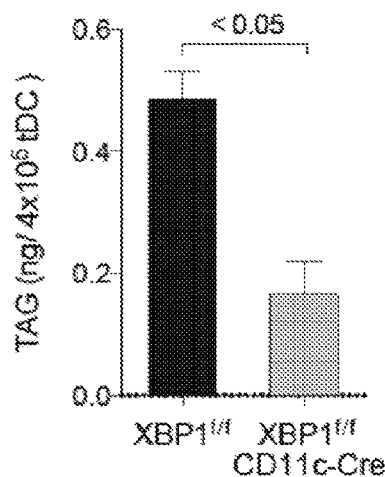
FIG. 9F
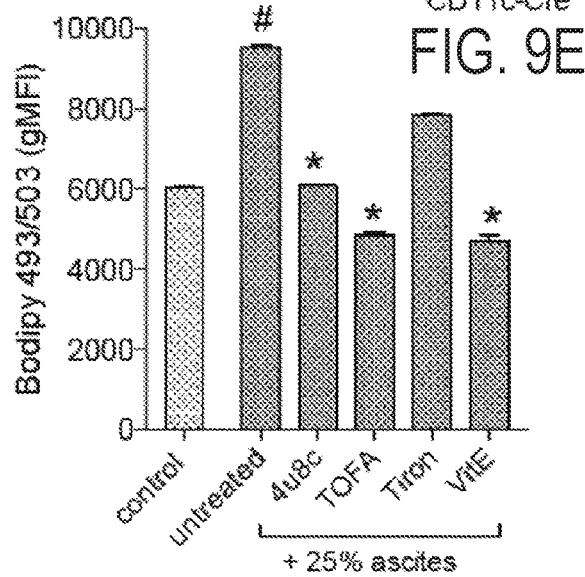
FIG. 9G

COMPOUNDS FOR INDUCING ANTI-TUMOR IMMUNITY AND METHODS THEREOF

RELATED APPLICATIONS

This application is a continuation of U.S. patent application Ser. No. 15/024,215, filed Mar. 23, 2016, which is a National Stage application claiming priority to PCT/US2014/057525, filed Sep. 25, 2014, which application claims the benefit of U.S. Provisional Patent Application Ser. No. 61/882,461, filed Sep. 25, 2013, where the entire content of each of the above-referenced patent applications is incorporated by reference as if fully set forth herein.

FEDERALLY SPONSORED RESEARCH

This invention was made with U.S. Government support under Grant Number AI089967 awarded by the National Institutes of Health. The U.S. Government has certain rights in this invention.

BACKGROUND OF THE INVENTION

The Endoplasmic Reticulum (ER) functions primarily to process newly synthesized secretory and transmembrane proteins. However, abnormal accumulation of unfolded proteins in this compartment causes a state of "ER stress", which is a hallmark feature of secretory cells and many diseases, including diabetes, neurodegeneration and cancer (Hetz et al., *Nature Reviews Drug Discover* 2013; 12, 703-719). Adaptation to protein-folding stress is mediated by the activation of an integrated signal transduction pathway known as the ER stress response, or the unfolded protein response (UPR). This coordinated pathway signals through three distinct stress sensors located at the ER membrane: IRE-1α, ATF6, and PERK (Hetz et al., *Nature Reviews Drug Discover* 2013; 12, 703-719). The most conserved arm of the UPR involves IRE-1α. During ER stress, this kinase oligomerizes, autophosphorylates, and uses its endoribonuclease activity to excise a 26-nucleotide fragment from the unspliced XBP1 mRNA (Yoshida et al., *Cell* 2001; 107; 881-891). These events give rise to functional XBP1, a potent multitasking transcription factor that promotes the expression of ER chaperones and regulates distinct sets of target genes in a cell type-specific manner (Acosta-Alvear et al., *Mol Cell* 2007; 27, 53-66; Lee et al., *Mol Cell Biol* 2003; 23, 7448-7459; Yoshida et al., *Cell* 2001; 107; 881-891). Importantly, while XBP1 has been shown to control the maintenance of various immune cells under non-pathological conditions, a role for this transcription factor as a negative regulator of anti-tumor responses and normal immune function in cancer has never been reported.

Aggressive tumors have evolved strategies to thrive in adverse conditions such as hypoxia, nutrient starvation and high metabolic demand. Cancer cells constantly undergo ER stress, but they ensure survival by adjusting the ER protein folding capacity via the UPR (Hetz et al., *Nature Reviews Drug Discover* 2013; 12, 703-719). In malignant cells, XBP1 confers drug resistance by preventing drug-induced cell-cycle arrest and mitochondrial permeability and apoptosis (Gomez et al., *FASEB J* 2007; 21, 4013-4027). XBP1 drives the pathogenesis of multiple myeloma (Carrasco et al., *Cancer Cell* 2007; 11, 349-360; Lee et al., *Proc Natl Acad Sci USA* 2003; 100, 9446-9951) and of chronic lymphocytic leukemia (Sriburi et al., *J Cell Biol* 2004; 167, 35-41). Further, it was recently demonstrated that XBP1 fosters triple-negative breast cancer progression by promoting tumor cell survival and metastatic capacity under hypoxic conditions (Chen et al., *Nature* 2014; 508, 103-107). While XBP1 expression in cancer cells has been shown to directly support tumorigenesis, the role of this ER stress sensor in sculpting a tumor-permissive immune milieu has not been established.

In most solid cancers, nonmalignant cells such as leukocytes, vascular cells and fibroblasts, stimulate tumor development and progression (Bhowmick et al., *Nature* 2004; 432, 332-337; Whiteside. *Oncogene* 2008; 27, 5904-5912). Leukocyte recruitment to established cancers results in diverse pro-tumoral effects including the secretion of growth factors that enhance tumor cell proliferation and metastasis (Coussens et al., *Cell* 2000; 103, 481-490; Coussens and Werb, *Nature* 2002; 420, 860-867; Mantovani et al., *Nature* 2008; 454, 436-444); the induction of tumor vascularization via paracrine mechanisms (De Palma et al., *Trends Immunol* 2007; 28, 519-524); and the orchestration of immunosuppressive networks (Zou, *Nat Rev Cancer* 2005; 5, 263-274) that restrain the protective role of the scarce leukocyte subsets with inherent anti-tumor capacity. Ovarian tumors subvert the normal activity of infiltrating dendritic cells (DCs) to inhibit the function of otherwise protective anti-tumor T cells (Cubillos-Ruiz et al., *J Clin Invest* 2009; 119, 2231-2244; Curiel et al., *Nat Med* 2003; 9, 562-567; Huarte et al., *Cancer Res* 2008; 68, 7684-7691; Scarlett et al., *Cancer Res* 2009; 69, 7329-7337; Scarlett et al., *J Exp Med* 2012). Eliminating or "re-programming" tumor-associated DCs (tDCs) in vivo has been demonstrated to abrogate ovarian cancer progression (Cubillos-Ruiz et al., *J Clin Invest* 2009; 119, 2231-2244; Curiel et al., *Nat Med* 2003; 9, 562-567; Huarte et al., *Cancer Res* 2008; 68, 7684-7691; Nesbeth et al., *Cancer Res* 2009; 69, 6331-6338; Nesbeth et al., *J Immunol* 2010; 184, 5654-5662; Scarlett et al., *Cancer Res* 2009; 69, 7329-7337; Scarlett et al., *J Exp Med* 2012), but the precise molecular pathways that tumors exploit in DCs to co-opt their normal activity remain poorly understood, and therefore available therapeutics are limited.

SUMMARY OF THE INVENTION

Dendritic cells (DCs) are required to initiate and sustain anti-cancer immunity. However, tumors efficiently manipulate DC function to evade immune control. The Endoplasmic Reticulum (ER) stress response has been shown to operate in malignant cells to support tumor growth, but prior to the discovery of the present invention, its role in sculpting the immune response to cancer was elusive. The present invention is based, at least in part, on the new finding that constitutive activation of the ER stress sensor XBP1 in tumor-associated DCs (tDCs) drives ovarian cancer progression. Here, it is reported that, XBP1-deficient tDCs showed reduced intracellular lipid accumulation and demonstrated improved antigen-presenting capacity, leading to enhanced intra-tumoral T cell activation and increased host survival. The present invention is also based, at least in part, on the new finding that therapeutic XBP1 silencing using siRNA-loaded nanoparticles restored proper tDC function in situ and extended host survival by inducing protective anti-tumor immunity. In particular, the instant inventors have discovered that tumors rely on DC-intrinsic XBP1 to elude immune control. These findings, for the first time, reveal a key function for XBP1 in anti-tumor immunity, opening new avenues for therapeutics that target the ER stress response.

Such therapeutics could potentially inhibit tumor growth directly while simultaneously inducing robust anti-tumor immunity.

In one embodiment, the present invention pertains to the unexpected discovery that the ER stress sensor, XBP1 functions as a crucial driver of DC dysfunction in the tumor microenvironment. In another embodiment, the present invention provides that the ER stress sensor XBP1 is constitutively active in ovarian cancer associated dendritic cells (DCs). In another embodiment, the present invention provides that the lipid peroxidation byproduct 4-HNE triggers ER stress and XBP1 activation in DCs. In another embodiment, the present invention provides that XBP1 regulates lipid metabolism and antigen presentation by tumor-associated DCs. In other embodiments, the invention provides that targeting XBP1 in tumor-associated DCs (tDCs) extends host survival by enhancing anti-tumor immunity.

Accordingly, in one aspect, the invention pertains to a method for enhancing or inducing an anti-tumor immune response in a subject, including administering to the subject an effective amount of a direct or indirect inhibitor of XBP1, thereby enhancing or inducing the anti-tumor immune response in the subject.

In another aspect, the invention pertains to a method for treating or reducing the progression of ovarian cancer in a subject, including administering to the subject an effective amount of a direct or indirect inhibitor of XBP1, thereby treating or reducing the progression of ovarian cancer in the subject.

In another aspect, the invention pertains to a method for inducing, enhancing or promoting the immune response of cancer-associated dendritic cells in a subject including administering to the subject an effective amount of a direct or indirect inhibitor of XBP1, thereby inducing, enhancing or promoting the immune response of cancer-associated dendritic cells in the subject.

In one embodiment, the subject has ovarian cancer. In another embodiment, the subject has primary ovarian cancer or metastatic ovarian cancer. In another embodiment, the subject has a carcinoma, an adenocarcinoma, an epithelial cancer, a germ cell cancer or a stromal tumor.

In another embodiment, the anti-tumor immune response is induced or enhanced in T cells in the subject. For example, intra-tumoral T cells may be activated in the subject. In certain embodiments, the anti-tumor immune response may be antigen presentation by T cells. In other embodiments, the anti-tumor immune response may be an immunogenic function.

In one embodiment, the inhibitor of XBP1 is a direct inhibitor. In another embodiment, the inhibitor of XBP1 is an indirect inhibitor.

For example, the inhibitor of XBP1 may be a nucleic acid molecule that is antisense to an XBP1-encoding nucleic acid molecule, an XBP1 shRNA, and XBP1 siRNA, a microRNA that targets XBP1, a nanoparticle-encapsulated XBP1 siRNA, an XBP1 siRNA-PEI nanoparticle, a dominant negative XBP1 molecule, an XBP1-specific antibody or a small molecule inhibitor of XBP1.

In certain embodiments, the inhibitor of XBP1 is an agent that inhibits IRE-1α or an agent that inhibits the generation of functional XBP1. For example, the inhibitor of IRE-1α may be an IRE-1α shRNA, an IRE-1α siRNA, or a nanoparticle-encapsulated IRE-1α siRNA. For example, an agent that inhibits the generation of functional XBP1 may be an agent that inhibits an endonuclease that produces functional XBP1.

In one embodiment, the inhibitor of XBP1 is administered systemically, parenterally, or at tumor locations in the subject. For example, the inhibitor of XBP1 may be administered at the site of the ovarian cancer or ovarian tumor.

In another embodiment, the inhibitor of XBP1 targets tumor-associated dendritic cells (tDCs)

In certain embodiments, the inhibitor of XBP1 is administered in combination with a second cancer therapeutic agent. For example, the inhibitor of XBP1 may be administered in combination with a chemotherapeutic agent.

In another embodiment, treatment of the subject with a direct or indirect inhibitor of XBP1 induces extended survival of the subject.

In another aspect, the invention pertains to a method for enhancing or inducing an anti-tumor immune response in a subject including administering to the subject an effective amount of a direct or indirect inhibitor of IRE-1α, thereby enhancing or inducing the anti-tumor response in the subject.

In one embodiment, the subject has ovarian cancer. In another embodiment, the subject has a carcinoma, an adenocarcinoma, an epithelial cancer, a germ cell cancer or a stromal tumor.

In another embodiment, the anti-tumor immune response is induced or enhanced in T cells in the subject. For example, intra-tumoral T cells may be activated in the subject.

In one embodiment, the inhibitor of IRE-1α is a direct inhibitor. In another embodiment, the inhibitor of IRE-1α is an indirect inhibitor.

For example, the inhibitor of IRE-1α may be a nucleic acid molecule that is antisense to an IRE-1α-encoding nucleic acid molecule, an IRE-1α shRNA, and IR-E1α siRNA, a microRNA that targets IRE-1α, a nanoparticle-encapsulated IRE-1α siRNA, an IRE-1α siRNA-PEI nanoparticle, a dominant negative IRE-1α molecule, an IRE-1α-specific antibody and a small molecule inhibitor of IRE-1α.

In one embodiment, the inhibitor of IRE-1α is administered systemically, parenterally, or at tumor locations in the subject. For example, the inhibitor of IRE-1α may be administered at the site of the ovarian cancer or ovarian tumor.

In another embodiment, the inhibitor of IRE-1α targets tumor-associated dendritic cells (tDCs)

In certain embodiments, the inhibitor of IRE-1α is administered in combination with a second cancer therapeutic agent. For example, the inhibitor of IRE-1α may be administered in combination with a chemotherapeutic agent.

In another embodiment, treatment of the subject with a direct or indirect inhibitor of IRE-1α induces extended survival of the subject.

In another aspect, the invention pertains to a method for activating or enhancing Type 1 immunity in ovarian cancer-infiltrating T cells in a subject including administering to the subject an effective amount of a direct or indirect inhibitor of XBP1, thereby activating or enhancing Type 1 immunity in ovarian cancer-infiltrating T cells in the subject.

In yet another aspect, the invention pertains to a method for reducing ER stress in tumor-associated dendritic cells (tDCs) in a subject including administering to the subject an effective amount of a direct or indirect inhibitor of 4-HNE to inhibit XBP1 activation, thereby reducing ER stress in tumor-associated dendritic cells in the subject.

In a further aspect, the invention pertains to a method for reducing or preventing intracellular lipid accumulation in tumor-associated dendritic cells (DCs) including administering to the subject an effective amount of a direct or indirect inhibitor of XBP1, thereby reducing or preventing intracellular lipid accumulation in tumor-associated dendritic cells in the subject.

In one embodiment, the number of cytosolic lipid droplets in the dendritic cell is reduced. In another embodiment, the intracellular levels of total triglycerides is reduced.

In another aspect, the invention pertains to a method for enhancing or inducing T cell activation at a tumor site in a subject including administering to the subject an effective amount of a direct or indirect inhibitor of XBP1, thereby enhancing or including T cell activation at the tumor site in the subject.

In yet another aspect, the invention pertains to a method for inducing, enhancing or promoting the antigen presenting capacity of tumor-associated dendritic cells (DCs) in a subject including administering to the subject an effective amount of a direct or indirect inhibitor of XBP1 thereby inducing, enhancing or promoting the antigen presenting capacity of tumor-associated dendritic cells in the subject.

In yet another aspect, the invention pertains to a method for inducing, enhancing or promoting the antigen presenting capacity of tumor-associated dendritic cells (tDCs) in a subject including contacting dendritic cells with an effective amount of a direct or indirect inhibitor of XBP1 and then administering the dendritic cells to the subject, thereby inducing, enhancing or promoting the antigen presenting capacity of tumor-associated dendritic cells in the subject.

In a further aspect, the invention pertains to a method of identifying a compound useful in enhancing or inducing anti-tumor immunity in a subject, including providing an indicator composition comprising XBP1, or biologically active portions thereof; contacting the indicator composition with each member of a library of test compounds; selecting from the library of test compounds a compound of interest that interacts with XBP1, or biologically active portions thereof; and contacting ovarian cancer cells with the compound of interest, wherein the ability of the compound to enhance or induce anti-tumor immunity in the subject is indicated by the ability of the compound to inhibit growth of ovarian cancer cells as compared to the growth of ovarian cancer cells in the absence of the compound.

BRIEF DESCRIPTION OF THE DRAWINGS

FIG. 1A: depicts the gating strategy used to isolate human ovarian cancer-associated DCs present in solid tumors.

FIG. 1B: depicts the gating strategy used to isolate human ovarian cancer-associated DCs present in malignant ascites specimens.

FIG. 1C: depicts the gating strategy used to isolate tDCs from p53-Kras-driven primary ovarian tumors of mice bearing advanced metastatic ID8-Defb29-VegfA ovarian tumors.

FIG. 1D: depicts the gating strategy used to isolate tDCs from malignant ovarian ascites of mice bearing advanced metastatic ID8-Defb29-VegfA ovarian tumors.

FIG. 1E: graphically depicts robust expression of Clec9A/DNGR-1 and Zbtb46 by murine $CD45^+CD11c^+MHC-II^+CD11b^+CD8\alpha^-$ tumor-infiltrating myeloid cells, reinforcing their identity as genuine classical DCs (cDCs). These two markers distinguish cDCs and their committed progenitors from other closely related mononuclear phagocytic lineages.

FIG. 1F: depicts the gating strategy to isolate control $CD45^+CD11c^+MHC-II^+CD11b^+CD8\alpha^-$ DCs from the spleen (sDCs).

FIG. 2A: depicts PCR analysis of Xbp1 mRNA splicing in ovarian cancer tDCs from human (1-12) and mouse (p53/K-ras and ID8-Def29/Vegf-A) origin. XBP1u, unspliced form; XBP1s, spliced form; Actb, β-actin.

FIG. 2B: graphically depicts expression of total XBP1 mRNA (Left) and spliced XBP1 (XBP1s) mRNA (Right). Expression of the indicated transcript was determined by RT-qPCR. sDC, splenic DCs.

FIG. 2C: depicts a western blot of XBP1s protein expression in nuclear extracts obtained from the indicated DCs. Lamin B was used as loading control. In all cases data are representative of 3 independent experiments with similar results.

FIG. 2D: graphically depicts expression of ERdj4 mRNA (Left) and Sec61a1 mRNA (Right). Expression of the indicated transcript was determined by RT-qPCR.

FIG. 2E: graphically depicts expression of BiP mRNA (Left) and CHOP mRNA (Right). Expression of the indicated transcript was determined by RT-qPCR.

FIG. 2F: graphically depicts the expression of CHOP in tDCs sorted from human patient ovarian cancer specimens (determined by RT-qPCR) correlated with the percentage of $CD45^+CD3^+$ T cells present in each individual tumor (circle) or ascites (square) sample. r, Spearman's Rank correlation coefficient.

FIGS. 3A-D: graphically depict the effect of diverse cytokines on XBP1 activation by DCs. Splicing and upregulation of XBP1 was determined by RT-qPCR analysis.

FIGS. 3E-F: graphically depict the effect of hypoxia-mimicking conditions on XBP1 activation by DCs.

FIG. 4A: depicts increased intracellular lipid content in tDCs compared with control sDCs from naïve or tumor-bearing mice (Ovca). Representative FACS analysis of lipid staining for DCs from the indicated sources (Left). Intracellular lipid quantification expressed as mean fluorescence intensity (MFI) of Bodipy 493/503 staining (Right).

FIG. 4B: graphically depicts the quantification of intracellular ROS levels in DCs expressed as geometric MFI (gMFI) of DCFDA staining.

FIG. 4C: graphically depicts the levels of 4-HNE-protein adducts in cell-free malignant ascites obtained from hosts bearing metastatic ovarian cancer.

FIG. 4D: graphically depicts the quantification of total intracellular 4-HNE-protein adducts in tDCs isolated from metastatic ovarian cancer ascites samples of human and mouse origin.

FIG. 4E: graphically depicts the intracellular levels of 4-HNE-protein adducts in tDCs isolated from mice with advanced ID8-Defb29-VegfA ovarian tumors and exposed to cell-free malignant ascites in the presence or absence of Vitamin E (VitE).

FIG. 4F: graphically depicts the rapid generation of intracellular 4-HNE-protein adducts in naïve sDCs incubated with increasing concentrations of purified 4-HNE.

FIGS. 4G-H: depict the quantification of XBP1s gene expression in sDCs exposed for 3 h to increasing amounts of purified 4-HNE. Data are representative of at least two independent experiments with similar results.

FIG. 4I: depict the quantification of total XBP1 (left) and ERdj4 (right) gene expression in sDCs exposed for 3 h to increasing amounts of purified 4-HNE. Data are representative of at least two independent experiments with similar results.

FIG. 4J: depict the quantification of total BiP (left) and CHOP (right) gene expression in sDCs exposed for 3 h to increasing amounts of purified 4-HNE. Data are representative of at least two independent experiments with similar results.

FIG. 5A: depicts a Schematic of Xbp1 exon 2 deletion.

FIG. 5B: graphically depicts deletion efficiency of XBP1, which was determined by RT-qPCR using primers that selectively amplify exon 2 of Xbp1 (see methods).

FIG. 5C: depicts induction of canonical XBP1 target genes ERdj4 (Left) and Sec61 (Right) upon stimulation (determined via RT-qPCR). Data were normalized to endogenous Actb expression in each sample. Data are representative of at least three independent experiments with similar results.

FIG. 6A-I: Shows the assessment of immune cell population in conditional knockout mice FIGS. 6A-C: depict representative FACS analysis of DC populations in the spleen.

FIG. 6D-E: depict representative FACS analysis of DC populations in infiltrating p53/K-ras ovarian tumors.

FIG. 6F-G: depict representative FACS analysis of DC populations in malignant ID8-Defb29/Vegf-A ovarian cancer ascites of XBP1$^{f/f}$ (top) or XBP1$^{f/f}$ CD11c-Cre (bottom) mice.

FIG. 6H-I: depicts the proportions (FIG. 6H) and absolute numbers (FIG. 6I) of depicted immune cell populations in the spleen of wild type or conditional knockout mice. pDC, plasmacytoid DCs. Data are representative of 3 mice per group. *P<0.05

FIG. 7A: depicts p53/K-ras-driven ovarian tumors generated in hosts reconstituted with bone marrow from either XBP1$^{f/f}$ (top) or XBP1$^{f/f}$ CD11c-Cre (bottom) donor mice as described in the methods and primary tumors were resected 48 days after intrabursal injection of Cre-expressing adenovirus (ADV-Cre).

FIG. 7B: graphically depicts growth kinetics of p53/K-ras-driven ovarian tumors in hosts reconstituted with bone marrow from the indicated genotypes.

FIG. 7C: graphically depicts the proportion of hosts presenting p53/K-ras-derived metastatic lesions in the peritoneal cavity 48 days after tumor induction.

FIG. 7D: depicts mice of the indicated genotypes implanted with ID8-Defb29-VegfA ovarian cancer cells via intraperitoneal (i.p.) injection.

FIG. 7E: graphically depicts peritoneal metastases evaluated 3-4 weeks after tumor implantation (n=3 mice per group). **P<0.001.

FIG. 7F: graphically depicts malignant ascites generation in tumor-bearing mice expressed as percent weight gain due to progressive accumulation of peritoneal fluid. *P<0.05.

FIG. 7G: depicts reduced splenomegaly in tumor-bearing mice deficient for XBP1 in CD11c$^+$ DCs.

FIG. 7H: depicts overall survival rates in mice bearing aggressive ID8-Defb29-VegfA tumors. Data are representative of at least two independent experiments with similar results using 4-6 mice per group. **P<0.001.

FIG. 7I: depicts overall survival rates in mice bearing parental ID8 tumors. Data are representative of at least two independent experiments with similar results using 4-6 mice per group. **P<0.001.

FIG. 8A-D: Shows transcriptional analysis of ovarian cancer-associated DCs devoid of XBP1.

FIG. 8A: depicts the top transcriptional regulators associated with differentially expressed gene signatures in wild type vs. XBP1-deficient DCs isolated from mice bearing ID8-Defb29/Vegf-A ovarian tumors for 3 weeks.

FIG. 8B: depicts the main ER stress-related gene network controlled by XBP1 in tDCs based on Ingenuity Pathway Analysis (IPA).

FIG. 8C: depicts the expression levels of previously reported RIDD targets in XBP1-deficient tDCs.

FIG. 8D: depicts the top significantly affected biological processes identified in tDCs devoid of XBP1 (see methods).

FIG. 9A-G: Shows that XBP1 disrupts lipid homeostasis in ovarian cancer-associated DCs.

FIG. 9A: depicts the downregulation of genes involved in the UPR/ER stress response in tDCs devoid of XBP1. WT, XBP1$^{f/f}$ tDC. XBP1$^{def}$, XBP1$^{f/f}$ CD11c-Cre tDC (n=3/group). FDR, false discovery rate. RPKM, transcript abundance expressed as reads per kilobase per million reads.

FIG. 9B: depicts the downregulation of genes involved in the lipid metabolism in tDCs devoid of XBP1. WT, XBP1$^{f/f}$ tDC. XBP1$^{def}$, XBP1$^{f/f}$ CD11c-Cre tDC (n=3/group). FDR, false discovery rate. RPKM, transcript abundance expressed as reads per kilobase per million reads.

FIG. 9C: depicts decreased intracellular lipid content in XBP1$^{f/f}$ CD11c-Cre tDCs (n=3 mice per group) from mice bearing ID8-Defb29-VegfA tumors for 3 weeks evidenced by Bodipy493/503 staining.

FIG. 9D: depicts electron micrographs (12,000×) demonstrating large intracellular lipid bodies in XBP1-sufficient, but not XBP1-deficient tDC.

FIG. 9E: graphically depicts quantification of lipid bodies in tDCs sorted from mice bearing ID8-Defb29-VegfA ovarian tumors for 3-4 weeks.

FIG. 9F: graphically depicts quantification of intracellular triglycerides (TAG) in tDCs sorted from mice bearing ID8-Defb29-VegfA ovarian tumors for 3-4 weeks.

FIG. 9G: graphically depicts the intracellular lipid content of tDCs incubated in vitro with 25% cell-free ovarian cancer ascites supernatants in the presence of the indicated inhibitors. Intracellular lipid content was assessed 24 h later via Bodipy493/503 staining. Data are representative of 3 independent experiments with similar results. *P<0.05 compared with control tDC incubated in the absence of cell-free ascites supernatants. *P<0.05 compared with ascites-exposed tDC but left untreated.

FIG. 10A: depicts increased expression of XBP1-controlled lipid biosynthetic genes (Agpat6, Fasn, Lpar1) in tDCs isolated from mice bearing ID8-Defb29-Vegf-A ovarian tumors for 4-5 weeks compared with the indicated control sDCs.

FIG. 10B: graphically depicts rapid upregulation of XBP1 s, ERdj4 and XBP1-controlled lipid biosynthetic genes (Agpat6, Fasn, Lpar1) in naïve sDCs stimulated for 3 h with increasing concentrations of purified 4-HNE. Data are normalized to endogenous levels of β-actin in each sample, and are representative of three independent experiments with similar results.

FIG. 10C: graphically depicts the lipidomic profile of tDCs obtained from mice bearing ID8-Defb29/Vegf-A ovarian tumors for 4 weeks.

FIG. 10D: graphically depicts the lipidomic profile of cell-free ascites supernatants obtained from mice bearing ID8-Defb29/Vegf-A ovarian tumors for 4 weeks.

FIG. 10E: graphically depicts relative expression of genes encoding scavenger receptors (Cd36, Cd68, Msr1) in XBP1-deficient vs. wild type tDCs.

FIG. 10F: depicts representative FACS analysis of Bodipy 493/503 staining in tDCs exposed to cell-free ovarian cancer ascites in the presence or absence of inhibitory compounds.

FIG. 11A: shows a representative histogram analysis of surface molecule expression on tDCs from peritoneal wash samples of XBP1$^{f/f}$ (striped) or XBP1$^{f/f}$ CD11c-Cre (black) mice bearing ID8-Defb29-VegfA tumors for 3-4 weeks. Dotted histograms indicate isotype control staining.

FIG. 11B: graphically depicts quantification of the data shown in FIG. 5A expressed as geometric mean fluorescence intensity (gMFI) of staining (n=3 mice per group).

FIG. 11C: depicts CFSE-dilution analysis of OT-1 T cells cocultured with full-length OVA-pulsed tDCs isolated from the peritoneal cavity of XBP1$^{f/f}$ or XBP1$^{f/f}$ CD11c-Cre mice bearing ID8-Dejb29-VegfA ovarian tumors for 4 weeks (see methods for details).

FIG. 11D: graphically depicts the proportion of proliferating OT-1 T cells described in FIG. 5C.

FIGS. 11E and 11F: depict enhanced endogenous T cell activation at tumor sites in mice devoid of XBP1 in CD11c$^+$ tDCs. Peritoneal wash samples from wild type (XBP1$^{f/f}$, black bars) or XBP1-deficient (XBP1$^{f/f}$ CD11c-Cre, gray bars) mice were collected 2-3 weeks after peritoneal implantation of ID8-Defb29-VegfA cancer cells. Surface expression of CD44 and intracellular levels of tumoricidal IFN-γ were analyzed on CD3$^+$CD4$^+$ (FIG. 11E) or CD3$^+$CD8$^+$ (FIG. 11F) tumor-infiltrating T cells (TILs). In all cases, data are representative of at least two independent experiments using 3-4 mice group.

FIG. 12A: depicts CFSE-dilution analysis of OT-1 T cells cocultured with full length OVA-pulsed CD11c$^+$MHC-II$^+$CD11b$^+$CD8α$^-$ DCs isolated from the spleen (sDC) of XBP1$^{f/f}$ or XBP1$^{f/f}$ CD11c-Cre mice.

FIG. 12B: graphically depicts the proportion of proliferating OT-1 T cells described in FIG. 12A. Data are representative of two independent experiments with similar results.

FIG. 13A: depicts the selective uptake of rhodamine-labeled nanoparticles by CD11c$^+$ tDC in the peritoneal cavity. Top, control untreated mice. Bottom, representative data from mice receiving Rhodamine-labeled siRNA-PEI nanocomplexes.

FIG. 13B-C: graphically depicts the biodistribution and silencing activity of intraperitoneally injected siRNA-PEI nanoparticles. CD45$^+$CD11c$^+$Rhodamine$^+$ tDCs were FACS-sorted from peritoneal wash samples 3 days after nanoparticle injection and gene expression levels were determined via RT-qPCR. Data are representative of three independent silencing experiments with 2-3 mice per group and all data were normalized to endogenous Actb expression.

FIG. 14A: shows representative CFSE dilution of OT-1 T cells proliferating in vivo at tumor sites in full-length OVA-pulsed untreated mice or after administration of immunostimulatory nanocomplexes carrying luciferase-matching (siLuc-PEI) or XBP1-specific (siXBP1-PEI) siRNA (see methods for details).

FIG. 14B: graphically depicts the proportion of OT-1 T cells in the ascites of treated mice (n=3/group) three days after transfer.

FIG. 14C: graphically depicts the division (Left) and proliferation (Right) index of transferred OT-1 T cells shown in FIG. 6B.

FIGS. 14D-H: show enhanced anti-tumor immune responses in mice treated with DC-targeting. XBP1-silencing nanocomplexes. ID8-Defb29/Vegf-A tumor-bearing mice (n=3/group) were treated at days 8, 13, 18 and 23 post-tumor injection and peritoneal lavage samples were analyzed at day 27. FIG. 14D graphically depicts the proportion of metastatic spheroid tumor cells (CD45$^-$SSC$^{hi}$) found in the peritoneal cavity of treated mice. FIG. 14E shows representative pictures of peritoneal lavages obtained from treated mice. FIG. 14F graphically depicts the proportion of antigen-experienced (CD44$^+$), activated (CD69$^+$) CD4$^+$ (Left) and CD8$^+$ (Right) T cells infiltrating tumor locations determined by FACS analyses (gated on CD3$^+$ cells).

FIG. 14G-H show representative ELISA-based analysis showing increased IFN-γ and Granzyme B secretion by peritoneal (FIG. 14G) and splenic (FIG. 14H) T cells isolated from mice treated with XBP1-silencing nanoparticles.

FIGS. 14I-J: depict overall survival rates in wild type (FIG. 14I) or Rag2-deficient (FIG. 14J) ovarian cancer-bearing mice (n=6/group) treated with nanocomplexes at days 12, 16, 20, 24, 28 and 32 after implantation of ID8-Defb29/Vegf-A cancer cells. In all cases, data are representative of at least two independent experiments with similar results. ***P<0.001. Log-Rank Test.

DETAILED DESCRIPTION OF THE INVENTION

Definitions

Figure 1A:
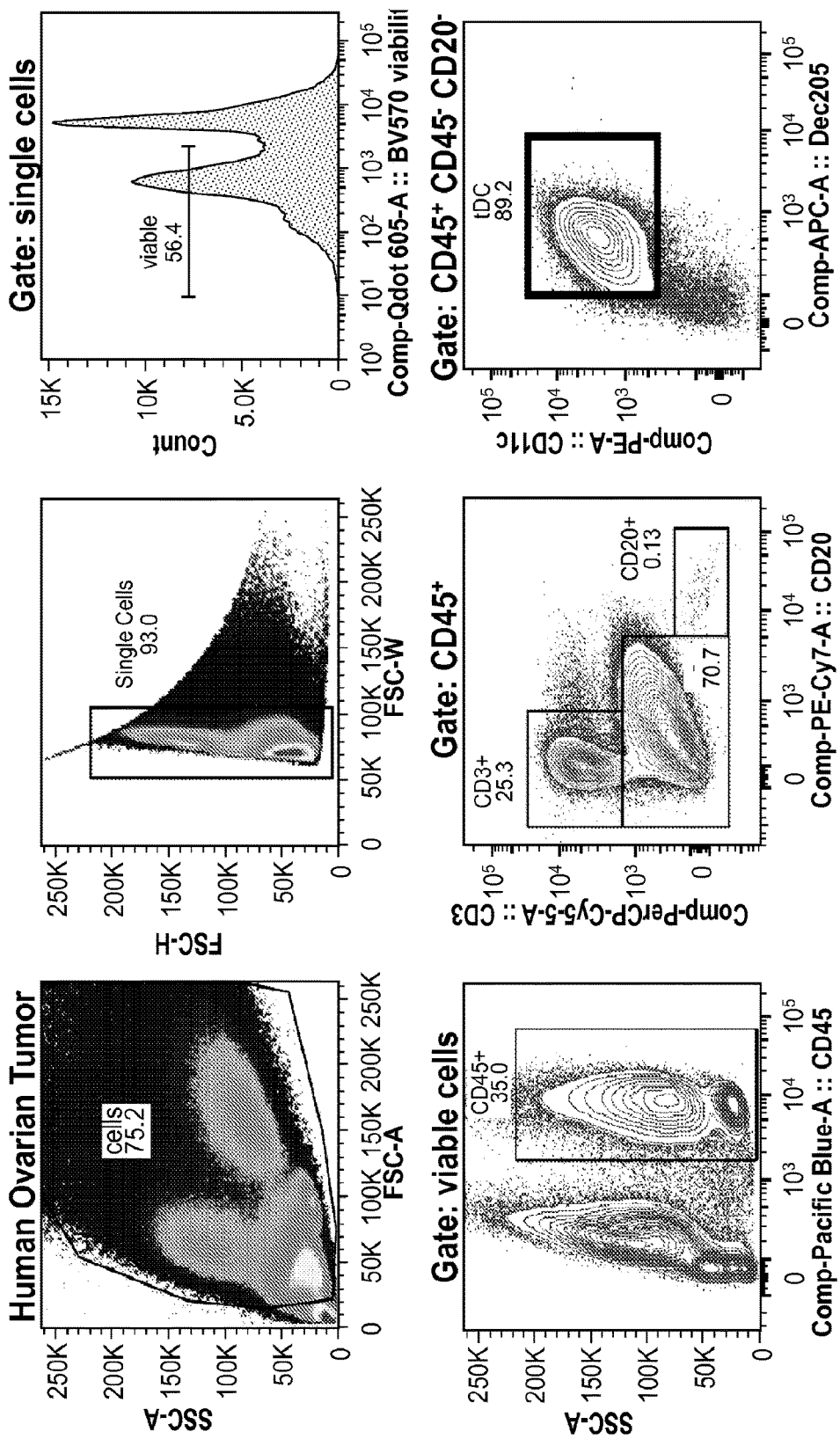
FIG. 1A-F: Shows the gating strategy used for FACS analysis
Figure 1B:
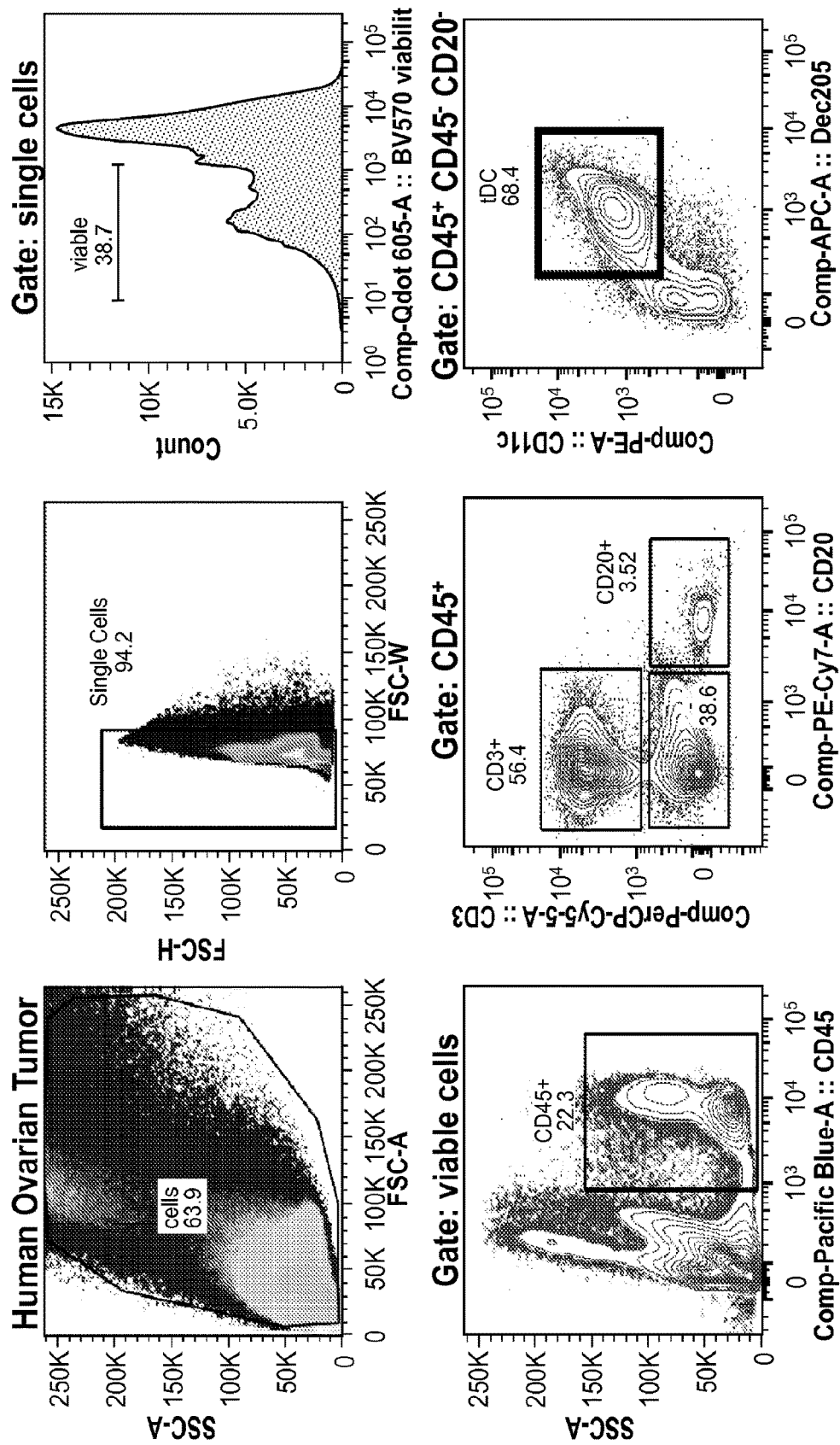
Figure 1C:
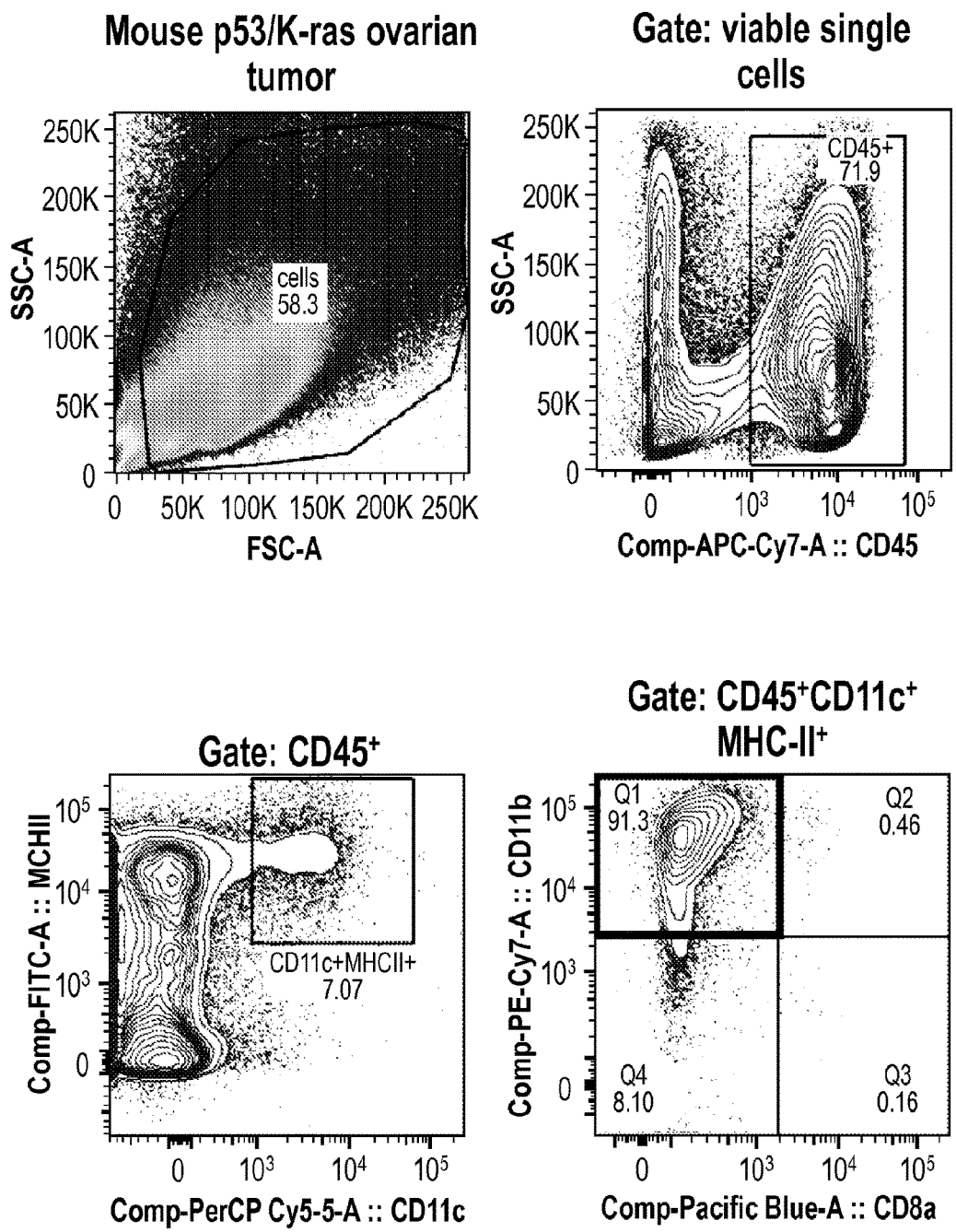
Figure 1D:
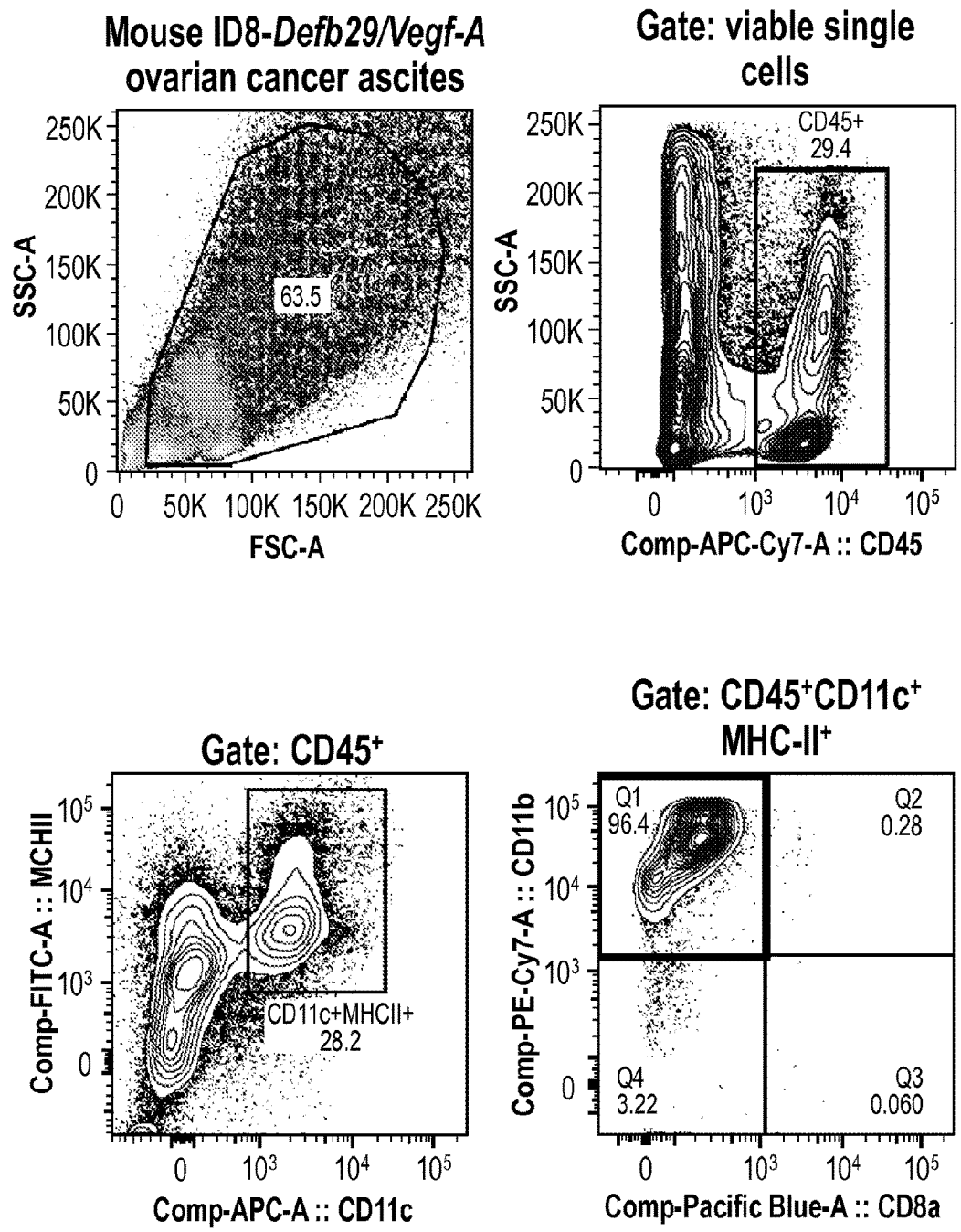
Figure 1E:
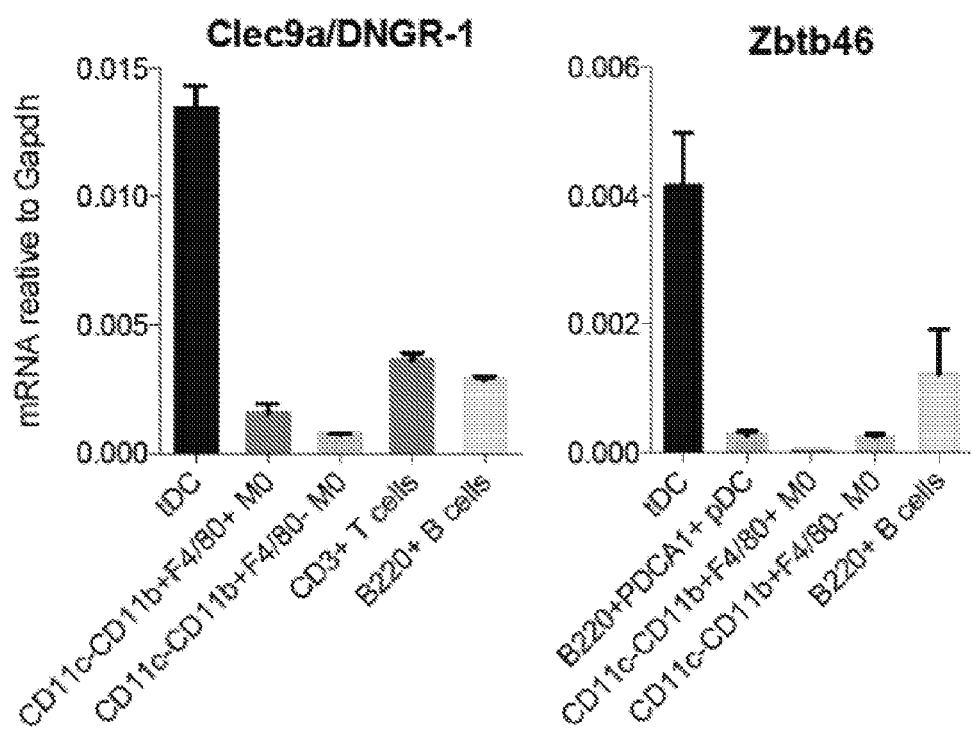
Figure 1F:
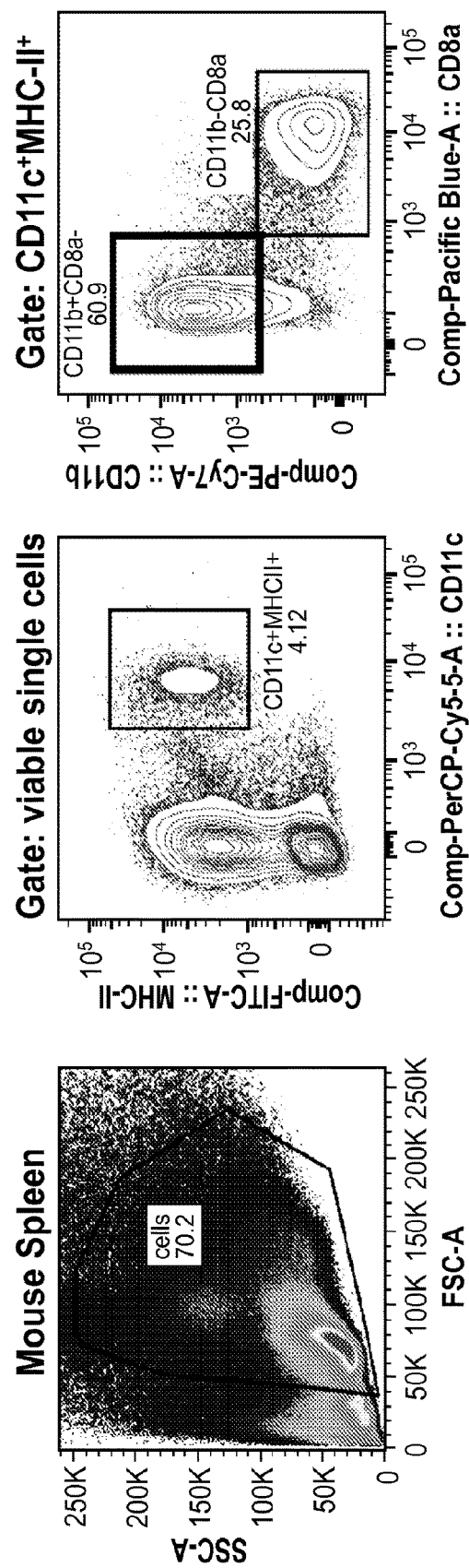

Terms used in the claims and specification are defined as set forth below unless otherwise specified.

"Polypeptide." "peptide", and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

"Nucleic acid" refers to deoxyribonucleotides or ribonucleotides and polymers thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions can be achieved by generating sequences in which the third position of one or more selected (or all) codons is substituted with mixed-base and/or deoxyinosine residues (Batzer et al., Nucleic Acid Res. 19:5081, 1991; Ohtsuka et al. Biol. Chem. 260: 2605-2608, 1985); and Cassol et al, 1992; Rossolini et al, Mol. Cell. Probes 8:91-98, 1994). For arginine and leucine, modifications at the second base can also be conservative. The term nucleic acid is used interchangeably with gene. cDNA, and mRNA encoded by a gene. Polynucleotides used herein can be composed of any polyribonucleotide or polydeoxribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, the polynucleotide can be composed of triple-stranded regions comprising RNA or DNA or both RNA and DNA. A polynucleotide can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

As used herein, the term "ER stress" refers to a perturbation in ER function and dysregulation of ER homeostasis due to an internal or external cellular insult. ER stress elicits a signaling cascade (i.e., the unfolded protein response) to mitigate stress.

The term "Unfolded Protein Response" (UPR) or the "Unfolded Protein Response pathway" refers to an adaptive response to the accumulation of unfolded proteins in the ER and includes the transcriptional activation of genes encoding chaperones and folding catalysts and protein degrading complexes as well as translational attenuation to limit further accumulation of unfolded proteins. Both surface and secreted proteins are synthesized in the endoplasmic reticulum (ER) where they need to fold and assemble prior to being transported.

As used herein, the term "dendritic cell" refers to a type of specialized antigen presenting cell (APC) involved in innate and adaptive immunity. Also referred to as "DC." Dendritic cells may be present in the tumor microenvironment and these are referred to as "tumor-associated dendritic cells" or "tDCs."

As used herein, the term "anti-tumor immunity" refers to an immune response induced upon recognition of cancer antigens by immune cells.

As used herein, the term "T cell activation" refers to cellular activation of resting T cells manifesting a variety of responses (For example, T cell proliferation, cytokine secretion and/or effector function). T cell activation may be induced by stimulation of the T cell receptor (TCR) with antigen/MHC complex.

As used herein, the term "antigen presenting capacity" refers to the ability of antigen presenting cells (APCs) to present antigen to T lymphocytes to elicit an immune response. In certain embodiments, the immune response is a type I immunity response. In certain embodiments, the antigen presenting capacity is determined by measuring infiltration and activation of T cells at tumor locations and/or secretion of IFN-γ and Granzyme B ex vivo by APCs (i.e., dendritic cells).

As used herein, the term "anti-tumor T cells" refers to T lymphocytes that have been activated by APCs, wherein the antigen is a tumor-associated antigen. These T lymphocytes will subsequently induce the killing of malignant cells.

As used herein, the term "anti-tumor response" refers to at least one of the following: tumor necrosis, tumor regression, tumor inflammation, tumor infiltration by activated T lymphocytes, or activation of tumor infiltrating lymphocytes. In certain embodiments, activation of lymphocytes is due to presentation of a tumor-associated antigen by APCs.

As used herein, the term "extended survival" refers to increasing overall or progression free survival in a treated subject relative to an untreated control.

As used herein, the term "test sample" is a sample isolated, obtained or derived from a subject. e.g., a human subject. The term "subject" or "host" is intended to include living organisms, but preferred subjects or hosts are mammals, and in particular, humans or murines. The term "subject" or "host" also includes cells, such as prokaryotic or eukaryotic cells. In particularly preferred embodiments, the "test sample" is a sample isolated, obtained or derived from a subject, e.g., a female human.

The term "sufficient amount" or "amount sufficient to" means an amount sufficient to produce a desired effect. e.g., an amount sufficient to reduce the size of a tumor.

The term "therapeutically effective amount" is an amount that is effective to ameliorate a symptom of a disease. A therapeutically effective amount can be a "prophylactically effective amount" as prophylaxis can be considered therapy.

As used herein, "combination therapy" embraces administration of each agent or therapy in a sequential manner in a regiment that will provide beneficial effects of the combination and co-administration of these agents or therapies in a substantially simultaneous manner. Combination therapy also includes combinations where individual elements may be administered at different times and/or by different routes but which act in combination to provide a beneficial effect by co-action or pharmacokinetic and pharmacodynamics effect of each agent or tumor treatment approaches of the combination therapy. For example, the agents or therapies may be administered simultaneously, sequentially, or in a treatment regimen in a predetermined order.

As used herein, "about" will be understood by persons of ordinary skill and will vary to some extent depending on the context in which it is used. If there are uses of the term which are not clear to persons of ordinary skill given the context in which it is used, "about" will mean up to plus or minus 10% of the particular value.

It must be noted that, as used in the specification and the appended claims, the singular forms "a." "an" and "the" include plural referents unless the context clearly dictates otherwise.

Various aspects described herein are described in further detail in the following subsections.

ER Stress and UPR

The "Unfolded Protein Response" (UPR) or the "Unfolded Protein Response pathway" is initiated when there is an accumulation of unfolded proteins in the ER. This results in the transcriptional activation of genes encoding chaperones, folding catalysts, and protein degrading complexes, as well as translational attenuation to limit further accumulation of unfolded proteins.

Since the ER and the nucleus are located in separate compartments of the cell, the unfolded protein signal must be sensed in the lumen of the ER and transferred across the ER membrane and be received by the transcription machinery in the nucleus. The UPR performs this function for the cell. Activation of the UPR can be caused by treatment of cells with reducing agents like DTT, by inhibitors of core glycosylation like tunicamycin or by Ca-ionophores that deplete the ER calcium stores. First discovered in yeast, the UPR has now been described in C. elegans as well as in mammalian cells. In mammals, the UPR signal cascade is mediated by three ER transmembrane proteins: the protein-kinase and site-specific endoribonuclease IRE-1 alpha; the eukaryotic translation initiation factor 2 kinase, PERK/PEK; and the transcriptional activator ATF6. If the UPR cannot adapt to the presence of unfolded proteins in the ER, an apoptotic response is initiated leading to the activation of JNK protein kinase and caspases 7, 12, and 3. The most proximal signal from the lumen of the ER is received by a transmembrane endoribonuclease and kinase called IRE-1. Following ER stress, IRE-1 is essential for survival because it initiates splicing of the XBP1 mRNA, the spliced version of which activates the UPR.

The unfolded protein response (UPR) is a major cellular stress response pathway activated in tumors that allows them to adapt to the stresses of the tumor microenvironment. Similarly, the ER stress response has been shown to operate in malignant cells to support tumor growth. The present invention provides the novel discovery that constitutive activation of the ER stress sensor, XBP1, in cancer-associated DCs drives cancer progression (e.g., ovarian cancer progression). In certain embodiments, the ER stress response is dysregulated in cells present in the tumor microenvironment. In certain embodiments, the ER stress response is activated through signaling of the IRE-1/XBP1 pathway. In certain embodiments, the IRE-1/XBP1 pathway is constitutively active in cells present in the tumor microenvironment.

Accordingly, in one aspect, the invention pertains to a method for treating or reducing the progression of ovarian cancer in a subject, the method comprising administering to the subject a direct or indirect inhibitor of XBP1 or a direct or indirect inhibitor of IRE-1α such that progression of the ovarian cancer in the subject is inhibited. Non-limiting examples of direct inhibitors of XBP1 include a nucleic acid molecule that is antisense to an XBP1-encoding nucleic acid molecule, an XBP1 shRNA, an XBP siRNA, a nanoparticle-encapsulated XBP1 siRNA (e.g., polyethylenimine (PEI)-based nanoparticles encapsulating siRNA), a microRNA that targets XBP1, a dominant negative XBP1 molecule, an XBP1-specific antibody and small molecule inhibitors of XBP1. Non-limiting examples of indirect inhibitors of XBP1 include agents that target IRE-1, an endonuclease essential for proper splicing and activation of XBP1, such that inhibition of IRE-1 leads to inhibition of the production of the spliced, active form of XBP1. Non-limiting examples of IRE-1 inhibitors include a nucleic acid molecule that is antisense to an IRE-1-encoding nucleic acid molecule, an IRE-1 shRNA, an IRE-1 siRNA, a nanoparticle-encapsulated IRE-1 siRNA, a microRNA that targets IRE-1, a dominant negative IRE-1 molecule, an IRE-1-specific antibody and small molecule inhibitors of IRE-1.

XBP1

X-box binding protein-1 (XBP1) is a transcription factor that acts as an ER stress sensor by promoting the expression of ER chaperones and regulating distinct sets of target genes in a cell type-specific manner (Acosta-Alvear et al., 2007; Lee et al., 2003; Yoshida et al., 2001). In certain embodiments, XBP1 is spliced via IRE-1 activation. In certain embodiments, spliced XBP1 enhances transcription of ER chaperones.

The X-box binding human protein ("XBP1") is a DNA binding protein and has an amino acid sequence as described in, for example, Liou, H. C., et. al. 1990. Science 247, 1581-1584 and Yoshimura, T., et al. 1990. EMBO J. 9, 2537-2542, and other mammalian homologs thereof, such as described in Kishimoto T., et al. 1996. Biochem. Biophys. Res. Commun. 223, 746-751 (rat homologue). Exemplary proteins intended to be encompassed by the term "XBP1" include those having amino acid sequences disclosed in GenBank with accession numbers A36299 [gi: 105867], NP_005071 [gi: 4827058], P17861 [gi: 139787], CAA39149 [gi: 287645], and BAA82600 [gi: 5596360] or e.g., encoded by nucleic acid molecules such as those disclosed in GenBank with accession numbers AF027963 [gi: 13752783]; NM_013842 [gi: 13775155]; or M31627 [gi: 184485]. XBP1 is also referred to in the art as TREB5S or HTF (Yoshimura, T., et al. 1990. EMBO Journal. 9, 2537; Matsuzaki, Y., et al. 1995. J. Biochem. 117, 303). Like other members of the b-zip family, XBP1 has a basic region that mediates DNA-binding and an adjacent leucine zipper structure that mediates protein dimerization.

There are two forms of XBP-1 protein, unspliced and spliced, which differ in their sequence and activity. Unless the form is referred to explicitly herein, the term "XBP1" as used herein includes both the spliced and unspliced forms. Spliced XBP1 ("XBP1s") directly controls the activation of the UPR, while unspliced XBP1 functions to negatively regulate spliced XBP1.

"Spliced XBP1" ("XBP1s") refers to the spliced, processed form of the mammalian XBP1 mRNA or the corresponding protein. Human and murine XBP1 mRNA contain an open reading frame (ORF1) encoding bZIP proteins of 261 and 267 amino acids, respectively. Both mRNA's also contain another ORF, ORF2, partially overlapping but not in frame with ORF1. ORF2 encodes 222 amino acids in both human and murine cells. Human and murine ORF1 and ORF2 in the XBP1 mRNA share 75% and 89% identity respectively. In response to ER stress, XBP1 mRNA is processed by the ER transmembrane endoribonuclease and kinase IRE-1 which excises an intron from XBP1 mRNA. In murine and human cells, a 26 nucleotide intron is excised. The boundaries of the excised introns are encompassed in an RNA structure that includes two loops of seven residues held in place by short stems. The RNA sequences 5' to 3' to the boundaries of the excised introns form extensive base-pair interactions. Splicing out of 26 nucleotides in murine and human cells results in a frame shift at amino acid 165 (the numbering of XBP1 amino acids herein is based on GenBank accession number NM.sub.-013842 [gi: 13775155] and one of skill in the art can determine corresponding amino acid numbers for XBP1 from other organisms, e.g., by performing a simple alignment). This causes removal of the C-terminal 97 amino acids from the first open reading frame (ORF1) and addition of the 212 amino from ORF2 to the N-terminal 164 amino acids of ORF1 containing the b-ZIP domain. In mammalian cells, this splicing event results in the conversion of a 267 amino acid unspliced XBP1 protein to a 371 amino acid spliced XBP1 protein. The spliced XBP1 then translocates into the nucleus where it binds to its target sequences to induce their transcription.

"Unspliced XBP1" ("XBP1u") refers to the unprocessed XBP1 mRNA or the corresponding protein. As set forth above, unspliced murine XBP1 is 267 amino acids in length and spliced murine XBP1 is 371 amino acids in length. The sequence of unspliced XBP1 is known in the art and can be found. e.g., Liou, H. C., et. al. 1990. Science 247, 1581-1584 and Yoshimura, T., et al. 1990. EMBO J. 9, 2537-2542, or at GenBank accession numbers NM_005080 [gi: 14110394] or NM_013842 [gi: 13775155].

As used herein, the term "functional XBP1" refers to the spliced form of XBP1, which acts as a transcription factor to activate the UPR.

As used herein, the term "ratio of spliced to unspliced XBP1" refers to the amount of spliced XBP1 present in a cell or a cell-free system, relative to the amount or of unspliced XBP1 present in the cell or cell-free system. "The ratio of unspliced to spliced XBP1" refers to the amount of unspliced XBP1 compared to the amount of unspliced XBP1. "Increasing the ratio of spliced XBP1 to unspliced XBP1" encompasses increasing the amount of spliced XBP1 or decreasing the amount of unspliced XBP1 by, for example, promoting the degradation of unspliced XBP1. Increasing the ratio of unspliced XBP1 to spliced XBP1 can be accomplished, e.g., by decreasing the amount of spliced XBP1 or by increasing the amount of unspliced XBP1. Levels of spliced and unspliced XBP1 an be determined as described herein, e.g., by comparing amounts of each of the proteins which can be distinguished on the basis of their molecular weights or on the basis of their ability to be recognized by an antibody. In another embodiment described in more detail below, PCR can be performed employing primers which span the splice junction to identify unspliced XBP1 and spliced XBP1 and the ratio of these levels can be readily calculated.

The present invention pertains to the novel discovery that XBP1 is constitutively active in cancer-associated DCs, such as ovarian cancer-associated DCs. In one embodiment, the present invention is directed to the novel discovery that anti-tumor immunity is enhanced or increased in a subject by directly or indirectly inhibiting XBP1. In another embodiment, the present invention is directed to the discovery that ovarian cancer can be treated or reduced in a subject by administering an effective amount of a direct or indirect inhibitor of XBP1 to the subject.

IRE-1α

The term "IRE-1" or "IRE-1α" refers to an ER transmembrane endoribonuclease and kinase called "Serine/threonine-protein kinase/endoribonuclease." or alternatively, "Inositol-requiring protein 1", which oligomerizes and is activated by autophosphorylation upon sensing the presence of unfolded proteins, see, e.g., Shamu et al., (1996) EMBO J. 15: 3028-3039. In Saccharomyces cerevisiae, the UPR is controlled by IREp. In the mammalian genome, there are two homologs of IRE-1, IRE-1α and IRE-1β. IRE-1α is expressed in all cells and tissue whereas IRE-1β is primarily expressed in intestinal tissue. The endoribonucleases of either IRE-1α and IRE-1β are sufficient to activate the UPR. Accordingly, as used herein, the term "IRE-1" includes, e.g., IRE-1α, IRE-1β and IREp. In a preferred embodiment, IRE-1 refers to IRE-1α.

IRE-1 is a large protein having a transmembrane segment anchoring the protein to the ER membrane. A segment of the IRE-1 protein has homology to protein kinases and the C-terminal has some homology to RNAses. Over-expression of the IRE-1 gene leads to constitutive activation of the UPR. Phosphorylation of the IRE-1 protein occurs at specific serine or threonine residues in the protein.

IRE-1 senses the overabundance of unfolded proteins in the lumen of the ER. The oligomerization of this kinase leads to the activation of a C-terminal endoribonuclease by trans-autophosphorylation of its cytoplasmic domains. IRE-1 uses its endoribonuclease activity to excise an intron from XBP1 mRNA. Cleavage and removal of a small intron is followed by re-ligation of the 5' and 3' fragments to produce a processed mRNA that is translated more efficiently and encodes a more stable protein (Calfon et al. (2002) Nature 415(3): 92-95). The nucleotide specificity of the cleavage reaction for splicing XBP1 is well documented and closely resembles that for IRE-p mediated cleavage of HAC1 mRNA (Yoshida et al. (2001) Cell 107:881-891). In particular, IRE-1 mediated cleavage of murine XBP1 cDNA occurs at nucleotides 506 and 532 and results in the excision of a 26 base pair fragment. IRE-1 mediated cleavage of XBP1 derived from other species, including humans, occurs at nucleotides corresponding to nucleotides 506 and 532 of murine XBP1 cDNA, for example, between nucleotides 502 and 503 and 528 and 529 of human XBP1.

As used interchangeably herein, "IRE-1 activity." "biological activity of IRE-1" or "functional activity IRE-1," includes an activity exerted by IRE-1 on an IRE-1 responsive target or substrate, as determined in vivo, or in vitro, according to standard techniques (Tirasophon et al. 2000. Genes and Development Genes Dev. 2000 14: 2725-2736), IRE-1 activity can be a direct activity, such as a phosphorylation of a substrate (e.g., autokinase activity) or endoribonuclease activity on a substrate e.g., XBP1 mRNA. In another embodiment. IRE-1 activity is an indirect activity, such as a downstream event brought about by interaction of the IRE-1 protein with a IRE-1 target or substrate. As IRE-1 is in a signal transduction pathway involving XBP1, modulation of IRE-1 modulates a molecule in a signal transduction pathway involving XBP1. Modulators which modulate an XBP1 biological activity indirectly modulate expression and/or activity of a molecule in a signal transduction pathway involving XBP1, e.g., IRE-1, PERK, eIF2α or ATF6α.

The present invention provides the novel discovery that targeting the IRE-1α/XBP1 branch of the ER stress response in tumor-associated DCs induces protective immune responses against cancer (e.g., ovarian cancer). In some embodiment, the invention provides that inhibiting IRE-1α in tumor-associated DCs extends host survival by enhancing anti-tumor immunity.

Anti-Tumor Immunity

The immune system plays a critical role in protecting the host from cancer. Notably, the tumor microenvironment is an important aspect of cancer biology that contributes to tumor initiation, tumor progression, and responses to therapy. Cells and molecules of the immune system are a fundamental component of the tumor microenvironment.

Since tumor tissue is characterized by a variety of antigens not typically found in normal tissue, the immune system may mount a protective response. In certain embodiments, these antigens are referred to as "tumor-associated antigens (TAAs)." Innate immunity against the tumor is invoked very quickly. Macrophages, which are programmed to attack and destroy tumor cells in the similar fashion that they eliminate invading pathogens, are drawn to the tumor (Mantovani et al., *Nature Reviews Immunology* 2011; 11, 519-531). With time, adaptive anti-tumor immune responses develop. Dendritic cells migrate to the tumor as part of the innate immune response and serve as a link between innate and adaptive immunity. In certain embodiments, dendritic cells process tumor antigens and then directly interact with T and B cells, subsequently stimulating specific immune responses. The initial response of the immune system to a tumor is to recruit lymphocytes in an attempt to clear the tumor. Tumor-infiltrating lymphocytes (TILs) include cytotoxic T lymphocytes (CTLs), helper T cells, and natural killer (NK) cells. Proteins associated with tumorigenesis or malignant growth may also stimulate humoral immunity (Suckow, *The Veterinary Journal* 2013; 198, 28-33).

Coordination of the anti-tumor immune response requires communication between cells of the immune system, mostly carried out by cytokines (Dranoff, *Nature Reviews Cancer* 2004; 4, 11-22). For example, interleukin (IL)-6 produced by T lymphocytes and macrophages enhances the proliferation of both T and B lymphocytes. Likewise, interferon-gamma (IFNγ) is produced by NK cells, T lymphocytes, macrophages, and B lymphocytes and enhances tumor antigen presentation along with cell-mediated cytotoxicity.

The predominant cell type within tumor stroma is the fibroblast. Cancer-associated fibroblasts produce a variety of factors that promote proliferation and progression of cancer, including osteonectin, vascular endothelial growth factor (VEGF), and matrix metalloproteinases (MMPs). Many of these factors are widely produced by normal cells and therefore the immune system restricts itself from attacking these targets (Rasanen and Vaheri, *Experimental Cell Research* 2010; 316, 2713-2722).

In certain embodiments, the presence of a tumor serves as evidence that cancerous cells have successfully avoided immune elimination. This may occur due to immune selection pressure that favors growth of tumors that are less immunogenic (Dunn et. al, *Nature Immunology* 2002; 3, 991-998). Tumors may also escape through the expression of anti-apoptotic molecules (Reed. *Current Opinion in Oncology* 1999; 11, 68-75). Factors such as VEGF, soluble Fas, and transforming growth factor (TGF)-β, which are produced by tumor cells and tumor stroma, can suppress anti-tumor immune response (Ben-Baruch, *Seminars in Cancer Biology* 2006; 16, 38-52; Whiteside, *Seminars in Cancer Biology* 2006; 16, 3-15). Tumor stromal cells create an environment in which cancerous cells are exposed to growth factors while avoiding immune recognition. For example, thrombospondin-1 is produced by stromal cells and leads to immune suppression via activation of TGF-β (Silze et. al, *International Journal of Cancer* 2004; 108, 173-180).

Harnessing the inherent ability of T cells to eliminate tumor cells represents the most promising anti-cancer strategy since the development of chemotherapy, as demonstrated most recently by the dramatic shrinkage of melanoma in response to checkpoint blockers anti-CTLA4 and anti-PD1. In addition, recent reports demonstrate that adoptively transferred anti-tumor T cells (expanded from resected tumor specimens or genetically manipulated) can elicit robust and long-lasting anti-tumor responses (Bollard et al., 2007; Dudley et al., 2002; Leen et al., 2006; Morgan et al., 2006). However, in most cases, the optimal cytotoxic activity of such tumor-reactive T cells is drastically reduced because cancer-associated DCs are unable to support T cell function. (Barnett et al., 2005; Conejo-Garcia et al., 2004; Cubillos-Ruiz et al., 2009; Curiel et al., 2003; Huarte et al., 2008). The present invention reveals for the first time that DC-specific deletion of XBP1 can extend host survival by converting immunosuppressive tDCs into potent activators of Type 1 immunity in ovarian cancer-infiltrating T cells. Indeed, therapeutic silencing of XBP1 in tDCs using siRNA-encapsulating nanocarriers reversed their immunosuppressive phenotype and significantly prolonged host survival by inducing protective anti-tumor immune responses. Novel and more effective therapeutic strategies are needed to improve the dismal prognosis of metastatic ovarian cancer patients. The present invention demonstrates for the first time the feasibility and significant immunotherapeutic potential of targeting ER stress-driven XBP1 in tDCs using a safe and effective nanotechnology-based system that may slow or prevent the usually inevitable recurrence observed in metastatic ovarian cancer patients who have been "optimally" debulked. The present invention also provides that targeting the aberrant ER stress response in innate immune cells of the tumor microenvironment may also represent a viable therapeutic strategy to confront other lethal cancers that normally co-opt the immune response to promote malignant progression. Hence, the present invention provides for the first time that targeting the IRE-1α/XBP1 arm of the ER stress response in cancer-bearing hosts could be used to inhibit tumor growth while simultaneously inducing robust anti-tumor immunity.

In one embodiment, the present invention is directed to the novel discovery that constitutive activation of XBP1 in tumor-associated dendritic cells allows tumors to manipulate DC function and elude immune control. In another embodiment, the present invention is directed to the discovery that ablaiting XBP1 expression in tumor-associated dendritic cells enhances or induces anti-tumor immunity and extends host survival. In certain embodiments, inhibition of XBP1 enhances infiltration of activated T cells at tumor locations. In certain embodiments, inhibition of XBP1 enhances the capacity of infiltrating T cells to respond to tumor antigens.

Dendritic Cells

Dendritic cells (DC) are key regulators of both innate and adaptive immunity, and the array of immunoregulatory functions exhibited by these cells is dictated by their differentiation, maturation, and activation status. A major role of these cells is the induction of immunity to pathogens; however, recent data demonstrates that DCs are also critical regulators of anti-tumor immune responses. In certain embodiments, the generation of protective anti-tumor immunity depends on the presentation of tumor antigens by DCs to T cells. The control of DC survival plays an important role in regulating T cell activation and function.

DCs initiate an immune response by presenting a captured antigen, in the form of peptide-major histocompatability complex (MHC) molecule complexes, to naïve T cells in lymphoid tissues. Upon interaction with DCs, naïve CD4+ and CD8+ T cells can differentiate into antigen-specific effector cells. DCs also play a direct role in humoral immunity by interacting with B cells and indirectly by inducing the expansion and differentiation of CD4+ helper T cells.

Presentation of antigens to mount an immune response is one of the primary functions of dendritic cells. Tumor-associated DCs have the same function but the antigens are typically tumor-associated (TAA). Tumors can prevent antigen presentation and the establishment of tumor-specific immune responses through a variety of mechanisms. For example, tumors switch the differentiation of monocytes into macrophages and not DCs. or prevent the priming of tumor-specific T cells by DCs, through the mediation of IL-2 and macrophage colony-stimulating factor. In certain embodiments, tumors can interfere with DC maturation. For example, tumor cells can secrete IL-10 which leads to antigen-specific anergy of DCs. In certain embodiments, DCs are tumor-associated DCs (tDCs). These tDCs are present in the tumor microenvironment. The present invention, provides the novel discovery that tumors rely on DC-intrinsic XBP1 to elude immune control. The present invention also provides the novel discovery that inhibiting XBP1 in tumor-associated DCs extends host survival by enhancing anti-tumor immunity.

In one embodiment, the present invention is directed to the novel discovery that the ER stress sensor XBP1 is constitutively active in cancer-associated DCs, such as ovarian cancer-associated DCs. In another embodiment, the present invention pertains to the discovery that the lipid peroxidation byproduct 4-HNE triggers ER stress and XBP1 activation in DCs. In another embodiment, the present invention pertains to the discovery that XBP1 regulates lipid metabolism and antigen presentation by tumor-associated DCs.

XBP1 and Dendritic Cells

XBP1 is a transcription factor expressed in dendritic cells and activated by IRE-1α, an ER transmembrane kinase and endoribonuclease. XBP1 functions to regulate the ER stress response by maintaining ER homeostasis and preventing activation of cell death pathways caused by sustained ER stress. The ER stress response, or unfolded protein response (UPR) is activated when unfolded proteins accumulate in the ER and functions to regulate the balance between homeostasis and apoptosis. In certain embodiments, XBP1 plays a role in DC differentiation and survival. For example, XBP1-deficient cells are more sensitive to apoptosis (Iwakoshi 2007).

The instant inventors have discovered that XBP1 is constitutively active in tumor-associated dendritic cells.

In one embodiment, the present invention provides the novel discovery that XBP1 is a driver of dendritic cell dysfunction in the tumor microenvironment. In another embodiment, the present invention provides that XBP1 is constitutively active in cancer-associated dendritic cells, such as ovarian cancer-associated dendritic cells. In certain embodiments, XBP1-deficient tDCs demonstrate enhanced antigen-presenting capacity. In certain embodiments, silencing or inhibiting XBP1 improves host survival and induces anti-tumor immunity. In certain embodiments, the induction of anti-tumor immunity is carried out by activated infiltrating T cells that respond to tumor antigens.

XBP1 and Ovarian Cancer

During tumor development and progression, cancer cells encounter cytotoxic conditions such as hypoxia, nutrient deprivation, and low pH due to inadequate vascularization (Hanahan, D., et al. 2011. Cell 144, 646-74). To maintain survival and growth in the face of these physiologic stressors, a set of adaptive response pathways are induced. One adaptive pathway well studied in other contexts is the unfolded protein response (UPR), which is induced by factors affecting the endoplasmic reticulum (ER) such as changes in glycosylation, redox status, glucose availability, calcium homeostasis or the accumulation of unfolded or misfolded proteins (Hetz. C, et al. 2011. Physiol Rev 91, 1219-43). Notably, features of the tumor microenvironment, such as hypoxia and nutrient deprivation, can disrupt ER homeostasis by the perturbation of aerobic processes such as oligosaccharide modification, disulphide bond formation, isomerization, and protein quality control and export (Wouters, B. G., et al. 2008. Nat Rev Cancer 8, 851-64). In mammalian cells, the UPR is mediated by three ER-localized transmembrane protein sensors: Inositol-requiring transmembrane kinase/endonuclease-1 (IRE-1). PKR-like ER kinase (PERK) and activating transcription factor 6 (ATF6) (Walter, P., et al. 2011. Science 334, 1081-6). Of these. IRE-1 is the most evolutionarily conserved branch. An increase in the load of folding proteins in the ER activates IRE-1, an ER-resident kinase and endoribonuclease that acts as an ER-stress sensor. Activated IRE-1 removes a 26 bp intron from XBP1 mRNA and results in a frame shift in the coding sequence, with the spliced form encoding a 226 amino acid transcriptional activation domain (Calfon, M., et al. 2002. Nature 415, 92-6; Yoshida, H., et al. 2001. Cell 107, 881-91). In contrast to the unspliced XBP1 (XBP1u), which is unstable and quickly degraded, spliced XBP1 (XBP1s) is stable and is a potent inducer of target genes that orchestrate the cellular response to ER stress (Hetz, C. et al. 2011. Physiol Rev 91, 1219-43).

As described in detail above, the UPR is a major cellular stress response pathway activated in tumors that allows them to adapt to the stresses of the tumor microenvironment. Several studies have reported on the activation of the UPR in various human tumors and its relevance to combinatorial therapy (Carrasco, D. R., et al. 2007. Cancer Cell 11, 349-36; De Raedt, T., et al. 2011. Cancer Cell 20, 400-413; Healy, S. J., et al. 2009. Eur J Pharmacol 625, 234-246; Ma, Y., et al. 2004. Nat Rev Cancer 4, 966-977; Mahoney, D. J., et al. 2011. Cancer Cell 20, 443-456). However, the role of the UPR and XBP1 in anti-tumor immunity is largely unknown. Here, the instant inventors have identified a previously unknown function of XBP1 in anti-tumor immunity and ovarian cancer. Here, it is demonstrated that constitutive activation of XBP1, a key component of the most evolutionarily conserved branch of the UPR, allows tumors to evade immune control by crippling normal DC function. Furthermore, XBP1 deletion and/or silencing inhibits tumor growth and/or progression and induces robust anti-tumor immunity.

Tumors progress when the host fails to provide an effective anti-tumor immune response. Prior to the discovery of the present invention, the role of XBP1 in anti-tumor immunity was unknown. Herein the instant inventors have identified a role for XBP1 in eluding immune control and therefore inducing the progression of tumor development, such as ovarian tumor development. In certain embodiments, the present invention provides that XBP1 is constitutively active in tumor-associated dendritic cells present in ovarian tumors compared to normal dendritic cells. In certain embodiments, the present invention provides that constitutive activation of XBP1 is critical for the initiation and rapid progression of ovarian tumors. Notably, XBP1 deficient tDCs fail to initiate or progress tumor development (e.g., ovarian tumors). In certain embodiments, the rapid progression of ovarian tumors is a result of constitutively active XBP1 in tumor-associated dendritic cells. In certain embodiments, the present invention provides that tumor progression and/or tumor burden is reduced in XBP1-deficient tDCs, indicating an important role for XBP1 in the development and progression of ovarian tumors.

Lipid Metabolism and Peroxidation

Cancer-associated DCs accumulate substantial amounts of oxidized lipids, and this abnormal process negatively regulates their antigen-presenting capacity (Herber et al., 2010; Ramakrishnan et al., 2014). As provided by the instant invention, transcriptional and functional analyses of tDCs devoid of XBP1 suggest that this conserved ER stress sensor facilitates the aberrant lipid accumulation commonly observed in dysfunctional cancer-associated DCs.

Lipid oxidation by reactive oxygen species (ROS) generates reactive byproducts such as the unsaturated aldehyde 4-hydroxy-trans-2-nonenal (4-HNE), which has been shown to induce protein-folding stress by forming stable adducts with ER-resident chaperones (Vladykovskaya et al., 2012). For the first time, the present invention provides that 4-HNE, a lipid peroxidation byproduct available in the human and mouse ovarian cancer microenvironment, can rapidly trigger robust ER stress and XBP1 activation in naïve DCs. Interestingly, 4-HNE has been demonstrated to induce the unfolded protein response in endothelial cells by forming covalent adducts with ER resident chaperones, a process that promotes vascular inflammation (Vladykovskaya et al., 2012). The ER stress response has been linked to lipid biosynthesis (Lee et al., 2008; Sriburi et al., 2004). However, the present invention indicates that enhanced intracellular lipid accumulation by tDCs required ROS generation and IRE-1α/XBP1 activation. Interestingly, exposure to XBP1-activating 4-HNE has been shown to promote fat accumulation in worms and mice (Singh et al., 2008; Singh et al., 2009). Thus, in some embodiments, the present invention provides that reactive metabolic byproducts in the tumor microenvironment, like 4-HNE, can perpetuate ER stress in infiltrating immune cells such as tDCs. Constitutive activation of the IRE-1α/XBP1 arm through this process subsequently promotes abnormal intracellular lipid accumulation in tDCs via upregulation of lipid biosynthetic genes, which ultimately inhibits their natural capacity to support T cell-mediated anti-tumor responses.

In one embodiment, the present invention provides that XBP1-deficient tDCs display marked downregulation of genes involved in lipid metabolic pathways. These lipid biosynthetic genes are rapidly upregulated in naïve DCs exposed to 4-HNE, an XBP1-activation lipid peroxidation byproduct. This aberrant lipid accumulation by tDCs obstructs their normal antigen processing and presentation capacity (Herber et al., 2010; Ramakrisnan et al., 2014).

In one embodiment, the present invention provides that the lipid peroxidation byproduct 4-HNE triggers ER stress and XBP1 activation in DCs. In another embodiment, the present invention provides that XBP1 regulates lipid metabolism and antigen presentation by tumor-associated DCs. In one embodiment, the present invention provides that XBP1 deficient tDCs have reduced intracellular lipid accumulation and improved antigen presenting capacity, leading to enhanced intra-tumoral T cell activation and increased host survival.

Therapeutic Targeting of the UPR

In the present invention, an unexpected role for the ER stress sensor XBP1 as a central driver of DC malfunction in the tumor microenvironment has been discovered. These findings unveil a new mechanistic paradigm whereby a lethal cancer exploits the most conserved arm of the ER stress response in tumor-resident DCs to disrupt their lipid homeostasis, alter their local antigen-presenting capacity and ultimately evade T cell-mediated immune control. While the ER stress response, and especially XBP1 activation, has been previously shown to operate in cancer cells to promote tumorigenesis, the present invention now reveals that this integrated cellular pathway further supports malignant progression by inhibiting the development of protective anti-tumor immunity via manipulation of normal DC function.

The upstream kinase and endoribonuclease IRE-1, which drives the splicing of XBP1 mRNA, is a viable drug target. Recently, two groups have identified specific IRE-1 endoribonuclease inhibitors (Papandreou, I., et al. 2011. *Blood* 117, 1311-1314; Volkmann, K., et al. 2011. *J Biol Chem* 286, 12743-12755). Intriguingly, these compounds efficiently inhibit XBP1 splicing in vivo and dramatically impair tumor growth in a xenograft model (Mahoney, D. J., et al. 2011. *Cancer Cell* 20, 443-456; Papandreou, I., et al. 2011. *Blood* 117, 1311-1314; Volkmann, K., et al. 2011. *J Biol Chem* 286, 12743-12755). While large-scale small molecule screens have provided potentially promising candidates that target the IRE-1/XBP1 pathway, attention needs to be paid to the specificity and cytotoxity of these compounds in vivo. Recent advances in solving the crystal structure of IRE-1 (Korennykh, A. V., et al. 2009. *Nature* 457, 687-693; Lee, K. P., et al. 2008. *Cell* 132, 89-100; Zhou, J., et al. 2006. *Proc Natl Acad Sci USA* 103, 14343-14348) should accelerate the design of more potent and specific IRE-1 inhibitors. The use of UPR inhibitors in combination with standard chemotherapy may greatly enhance the effectiveness of anti-tumor therapies.

The methods of the invention using inhibitory compounds which inhibit the expression, processing, post-translational modification, or activity of XBP1 or a molecule in a biological pathway involving XBP1, such as IRE-1α, can be used to induce anti-tumor immunity or in the treatment of cancer (e.g., ovarian cancer). In one embodiment of the invention, an inhibitory compound can be used to inhibit (e.g., specifically inhibit) the expression, processing, post-translational modification, or activity of spliced XBP1. In another embodiment, an inhibitory compound can be used to inhibit (e.g., specifically inhibit) the expression, processing, post-translational modification, or activity of unspliced XBP1.

Inhibitory compounds of the invention can be, for example, intracellular binding molecules that act to directly or indirectly inhibit the expression, processing, post-translational modification, or activity of XBP1 or a molecule in a biological pathway involving XBP1, for example, IRE-1α. As used herein, the term "intracellular binding molecule" is intended to include molecules that act intracellularly to inhibit the processing expression or activity of a protein by binding to the protein or to a nucleic acid (e.g., an mRNA molecule) that encodes the protein. Examples of intracellular binding molecules, described in further detail below, include antisense nucleic acids, intracellular antibodies, peptidic compounds that inhibit the interaction of XBP1 or a molecule in a biological pathway involving XBP1 (e.g., IRE-1α) and a target molecule and chemical agents that specifically or directly inhibit XBP1 activity or the activity of a molecule in a biological pathway involving XBP1 (e.g., IRE-1α).

In one embodiment, an inhibitory compound of the invention is an antisense nucleic acid molecule that is complementary to a gene encoding XBP1 or a molecule in a signal transduction pathway involving XBP1, (e.g., IRE-1α or a molecule with which XBP1 interacts), or to a portion of said gene, or a recombinant expression vector encoding said antisense nucleic acid molecule. The use of antisense nucleic acids to downregulate the expression of a particular protein in a cell is well known in the art (see e.g., Weintraub, H. et al., Antisense RNA as a molecular tool for genetic analysis, *Reviews—Trends in Genetics*, Vol. 1(1) 1986; Askari, F. K, and McDonnell, W. M. (1996) *N. Eng. J. Med.* 334:316-318; Bennett, M. R. and Schwartz, S. M. (1995) *Circulation* 92:1981-1993; Mercola, D. and Cohen, J. S. (1995) *Cancer Gene Ther.* 2:47-59; Rossi, J. J. (1995) *Br. Med. Bull.* 51:217-225; Wagner, R. W. (1994) *Nature* 372:333-335). An antisense nucleic acid molecule comprises a nucleotide sequence that is complementary to the coding strand of another nucleic acid molecule (e.g., an mRNA sequence) and accordingly is capable of hydrogen bonding to the coding strand of the other nucleic acid molecule. Antisense sequences complementary to a sequence of an mRNA can be complementary to a sequence found in the coding region of the mRNA, the 5' or 3' untranslated region of the mRNA or a region bridging the coding region and an untranslated region (e.g., at the junction of the 5' untranslated region and the coding region). Furthermore, an antisense nucleic acid can be complementary in sequence to a regulatory region of the gene encoding the mRNA, for instance a transcription initiation sequence or regulatory element. Preferably, an antisense nucleic acid is designed so as to be complementary to a region preceding or spanning the initiation codon on the coding strand or in the 3' untranslated region of an mRNA. Given the known nucleotide sequence for the coding strand of the XBP1 gene and thus the known sequence of the XBP1 mRNA, antisense nucleic acids of the invention can be designed according to the rules of Watson and Crick base pairing. For example, the antisense oligonucleotide can be complementary to the region surrounding the translation start site of an XBP1. An antisense oligonucleotide can be, for example, about 5, 10, 15, 20, 25, 30, 35, 40, 45 or 50 nucleotides in length. Similarly, antisense nucleic acids targeting IRE-1α can also be designed according to the rules of Watson and Crick base pairing. An antisense nucleic acid of the invention can be constructed using chemical synthesis and enzymatic ligation reactions using procedures known in the art. To inhibit expression in cells, one or more antisense oligonucleotides can be used.

Alternatively, an antisense nucleic acid can be produced biologically using an expression vector into which all or a portion of a cDNA has been subcloned in an antisense orientation (i.e., nucleic acid transcribed from the inserted nucleic acid will be of an antisense orientation to a target nucleic acid of interest). The antisense expression vector can be in the form of, for example, a recombinant plasmid, phagemid or attenuated virus. The antisense expression vector can be introduced into cells using a standard transfection technique.

The antisense nucleic acid molecules of the invention are typically administered to a subject or generated in situ such that they hybridize with or bind to cellular mRNA and/or genomic DNA encoding a protein to thereby inhibit expression of the protein. e.g., by inhibiting transcription and/or translation. An example of a route of administration of an antisense nucleic acid molecule of the invention includes direct injection at a tissue site (e.g. a tumor site). Alternatively, an antisense nucleic acid molecule can be modified to target selected cells (for example, tumor-associated dendritic cells) and then administered systemically. For example, for systemic administration, an antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein.

In yet another embodiment, an antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215: 327-330).

In certain embodiments, an antisense nucleic acid molecule of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585-591)) can be used to catalytically cleave mRNA transcripts to thereby inhibit translation mRNAs. Alternatively, gene expression can be inhibited by targeting nucleotide sequences complementary to the regulatory region of a gene (e.g., an XBP1 promoter and/or enhancer) to form triple helical structures that prevent transcription of a gene in target cells. See generally, Helene, C. (1991) *Anticancer Drug Des.* 6(6): 569-84; Helene, C. et al. (1992) *Ann. N.Y. Acad. Sci.* 660:27-36; and Maher, L. J. (1992) *Bioassays* 14(12):807-15.

In another embodiment, a compound that promotes RNAi can be used to inhibit expression of XBP1 or a molecule in a biological pathway involving XBP1. The term "RNA interference" or "RNAi", as used herein, refers generally to a sequence-specific or selective process by which a target molecule (e.g., a target gene, protein or RNA) is downregulated. In certain embodiments, the process of "RNA interference" or "RNAi" features degradation of RNA molecules, e.g., RNA molecules within a cell, said degradation being triggered by an RNA agent. Degradation is catalyzed by an enzymatic, RNA-induced silencing complex (RISC). RNAi occurs in cells naturally to remove foreign RNAs (e.g., viral RNAs). Natural RNAi proceeds via fragments cleaved from free dsRNA which direct the degradative mechanism to other similar RNA sequences. Alternatively. RNAi can be initiated by the hand of man, for example, to silence the expression of target genes. RNA interference (RNAi) is a post-transcriptional, targeted gene-silencing technique that uses double-stranded RNA (dsRNA) to degrade messenger RNA (mRNA) containing the same sequence as the dsRNA (Sharp, P. A, and Zamore, P. D. 287, 2431-2432 (2000); Zamore, P. D., et al. *Cell* 101, 25-33 (2000). Tuschl, T. et al. *Genes Dev.* 13, 3191-3197 (1999); Cottrell T R, and Doering T L. 2003. Trends Microbiol. 11:37-43; Bushman F. 2003. Mol Therapy. 7:9-10; McManus M T and Sharp P A. 2002. Nat Rev Genet. 3:737-47). The process occurs when an endogenous ribonuclease cleaves the longer dsRNA into shorter. e.g., 21-23-nucleotide-long RNAs, termed small interfering RNAs or siRNAs. As used herein, the term "small interfering RNA" ("siRNA") (also referred to in the art as "short interfering RNAs") refers to an RNA agent, preferably a double-stranded agent, of about 10-50 nucleotides in length (the term "nucleotides" including nucleotide analogs), preferably between about 15-25 nucleotides in length, more preferably about 17, 18, 19, 20, 21, 22, 23, 24, or 25 nucleotides in length, the strands optionally having overhanging ends comprising, for example 1, 2 or 3 overhanging nucleotides (or nucleotide analogs), which is capable of directing or mediating RNA interference. Naturally-occurring siRNAs are generated from longer dsRNA molecules (e.g., >25 nucleotides in length) by a cell's RNAi machinery (e.g., Dicer or a homolog thereof). The smaller RNA segments then mediate the degradation of the target mRNA. Nanoparticle-encapsulated siRNA can also be used to downregulate a target molecule. Kits for synthesis of RNAi are commercially available from, e.g. New England Biolabs or Ambion. In one embodiment one or more of the chemistries described above for use in antisense RNA can be employed in molecules that mediate RNAi.

Alternatively, a compound that promotes RNAi can be expressed in a cell. e.g., a cell in a subject, to inhibit expression of XBP1 or a molecule in a biological pathway involving XBP1, such as IRE-1α. In contrast to siRNAs, shRNAs mimic the natural precursors of micro RNAs (miRNAs) and enter at the top of the gene silencing pathway. For this reason, shRNAs are believed to mediate gene silencing more efficiently by being fed through the entire natural gene silencing pathway. The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region, shRNAs may be substrates for the enzyme Dicer, and the products of Dicer cleavage may participate in RNAi. shRNAs may be derived from transcription of an endogenous gene encoding a shRNA, or may be derived from transcription of an exogenous gene introduced into a cell or organism on a vector. e.g., a plasmid vector or a viral vector. An exogenous gene encoding an shRNA can additionally be introduced into a cell or organism using other methods known in the art. e.g., lipofection, nucleofection, etc.

The requisite elements of a shRNA molecule include a first portion and a second portion, having sufficient complementarity to anneal or hybridize to form a duplex or double-stranded stem portion. The two portions need not be fully or perfectly complementary. The first and second "stem" portions are connected by a portion having a sequence that has insufficient sequence complementarity to anneal or hybridize to other portions of the shRNA. This latter portion is referred to as a "loop" portion in the shRNA molecule. The shRNA molecules are processed to generate siRNAs. shRNAs can also include one or more bulges, i.e., extra nucleotides that create a small nucleotide "loop" in a portion of the stem, for example a one-, two- or three-nucleotide loop. The stem portions can be the same length, or one portion can include an overhang of, for example, 1-5 nucleotides.

In certain embodiments, shRNAs of the invention include the sequences of a desired siRNA molecule described supra. In such embodiments, shRNA precursors include in the duplex stem the 21-23 or so nucleotide sequences of the siRNA, desired to be produced in vivo.

Another type of inhibitory compound that can be used to inhibit the expression and/or activity of XBP1 or a molecule in a biological pathway involving XBP1 (for example, IRE-1α) is an intracellular antibody specific for said protein. The use of intracellular antibodies to inhibit protein function in a cell is known in the art (see e.g., Carlson, J. R. (1988) *Mol. Cell. Biol.* 8:2638-2646; Biocca, S. et al. (1990) *EMBO J.* 9:101-108; Werge, T. M. et al. (1990) *FEBS Letters* 274:193-198; Carlson, J. R. (1993) *Proc. Natl. Acad. Sci. USA* 90:7427-7428; Marasco, W. A. et al. (1993) *Proc. Natl. Acad. Sci. USA* 90:7889-7893; Biocca, S. et al. (1994) *Bio/Technology* 12:396-399; Chen, S-Y. et al. (1994) *Human Gene Therapy* 5:595-601; Duan, L et al. (1994) *Proc. Natl. Acad. Sci. USA* 91:5075-5079; Chen, S-Y. et al. (1994) *Proc. Natl. Acad. Sci. USA* 91:5932-5936; Beerli, R. R. et al. (1994) *J. Biol. Chem.* 269:23931-23936; Beerli, R. R. et al. (1994) *Biochem. Biophys. Res. Commun.* 204:666-672; Mhashilkar, A. M. et al. (1995) *EMBO J.* 14:1542-1551; Richardson, J. H. et al. (1995) *Proc. Natl. Acad. Sci. USA* 92:3137-3141; PCT Publication No. WO 94/02610 by Marasco et al.; and PCT Publication No. WO 95/03832 by Duan et al.).

To inhibit protein activity using an intracellular antibody, a recombinant expression vector is prepared which encodes the antibody chains in a form such that, upon introduction of the vector into a cell, the antibody chains are expressed as a functional antibody in an intracellular compartment of the cell.

In another embodiment, an inhibitory compound of the invention is a peptidic compound derived from the XBP1 amino acid sequence or the amino acid sequence of a molecule in a biologicalon pathway involving XBP1.

The peptidic compounds of the invention can be made intracellularly in cells by introducing into the cells an expression vector encoding the peptide. Such expression vectors can be made by standard techniques using oligonucleotides that encode the amino acid sequence of the peptidic compound. The peptide can be expressed in intracellularly as a fusion with another protein or peptide (e.g., a GST fusion). Alternative to recombinant synthesis of the peptides in the cells, the peptides can be made by chemical synthesis using standard peptide synthesis techniques. Synthesized peptides can then be introduced into cells by a variety of means known in the art for introducing peptides into cells (e.g., liposome and the like).

In addition, dominant negative proteins (e.g., of XBP1 or IRE-1α) can be made which include XBP1 or IRE-1α (e.g., portions or variants thereof) that compete with native (i.e., wild-type) molecules, but which do not have the same biological activity. Such molecules effectively decrease, e.g., XBP1 IRE-1α activity in a cell.

Other inhibitory agents that can be used to specifically inhibit the activity of XBP1 or a molecule in a biological pathway involving XBP1 (e.g., IRE-1α) are chemical compounds that directly inhibit expression, processing, post-translational modification, and/or activity of XBP1. Such compounds can be identified using screening assays that select for such compounds, as described in detail above as well as using other art recognized techniques.

In certain embodiments, targeting XBP1 inhibits tumor growth. In certain embodiments, targeting XBP1 inhibits ovarian tumor growth.

The present invention provides that constitutive activation of the UPR in dendritic cells prevents a proper anti-tumor immune response. In certain embodiments, targeting XBP1 results in an anti-tumor immune response. In certain embodiments, the anti-tumor immune response is the proliferation and infiltration of T cells targeted for a specific tumor-associated antigen.

Screening Assays

In one aspect, the invention features methods for identifying compounds useful in enhancing or inducing anti-tumor immunity in a subject, such compounds have the potential for therapeutic use in the treatment of cancer, such as ovarian cancer. In other aspects, the invention features methods for identifying compounds useful in inhibiting the growth of ovarian cancer cells, such compounds having potential therapeutic use in the treatment of ovarian cancer. As described herein, the instant invention is based, at least in part, on the discovery of a previously unknown role for XBP1 in anti-tumor immunity and ovarian cancer, such a role being linked to anti-tumor immunity directed by tumor-associated dendritic cells. In exemplary aspects the invention features methods for identifying compounds useful for inducing or enhancing anti-tumor immunity and inhibiting the growth of ovarian cancer cells, the methods featuring screening or assaying for compounds that modulate, e.g., activate or increase, or inhibit or decrease, the activation of IRE-1/XBP1. In exemplary aspects, the methods comprise: providing an indicator composition comprising XBP1, or biologically active portions thereof; contacting the indicator composition with each member of a library of test compounds; selecting from the library of test compounds a compound of interest that interacts with XBP1, or biologically active portions thereof; and contacting ovarian cancer cells with the compound of interest, wherein the ability of the compound to enhance or induce anti-tumor immunity in the subject is indicated by the ability of the compound to inhibit growth of ovarian cancer cells as compared to the growth of ovarian cancer cells in the absence of the compound.

In another exemplary aspect, the methods comprise: providing an indicator composition comprising XBP1, or biologically active portions thereof; contacting the indicator composition with each member of a library of test compounds; and selecting from the library of test compounds a compound of interest that decreases the activity of XBP1, or biologically active portions thereof, wherein the ability of a compound to induce anti-tumor immunity or inhibit growth of ovarian cancer cells is indicated by a decrease in the activation as compared to the amount of activation in the absence of the compound.

As used herein, the term "contacting" (i.e., contacting a cell e.g. a cell, with a compound) includes incubating the compound and the cell together in vitro (e.g., adding the compound to cells in culture) as well as administering the compound to a subject such that the compound and cells of the subject are contacted in vivo. The term "contacting" does not include exposure of cells to an XBP1 modulator that may occur naturally in a subject (i.e., exposure that may occur as a result of a natural physiological process).

As used herein, the term "test compound" refers to a compound that has not previously been identified as, or recognized to be, a modulator of the activity being tested. The term "library of test compounds" refers to a panel comprising a multiplicity of test compounds.

As used herein, the term "indicator composition" refers to a composition that includes a protein of interest (e.g., XBP1 or a molecule in a biological pathway involving XBP1, such as IRE-1α), for example, a cell that naturally expresses the protein, a cell that has been engineered to express the protein by introducing one or more of expression vectors encoding the protein(s) into the cell, or a cell free composition that contains the protein(s) (e.g., purified naturally-occurring protein or recombinantly-engineered protein(s)).

As used herein, the term "cell" includes prokaryotic and eukaryotic cells. In one embodiment, a cell of the invention is a bacterial cell. In another embodiment, a cell of the invention is a fungal cell, such as a yeast cell. In another embodiment, a cell of the invention is a vertebrate cell, e.g., an avian or mammalian cell. In a preferred embodiment, a cell of the invention is a murine or human cell. As used herein, the term "engineered" (as in an engineered cell) refers to a cell into which a nucleic acid molecule e.g., encoding an XBP1 protein (e.g., a spliced and/or unspliced form of XBP1) has been introduced.

As used herein, the term "cell free composition" refers to an isolated composition, which does not contain intact cells. Examples of cell free compositions include cell extracts and compositions containing isolated proteins.

The cells used in the instant assays can be eukaryotic or prokaryotic in origin. For example, in one embodiment, the cell is a bacterial cell. In another embodiment, the cell is a fungal cell, e.g., a yeast cell. In another embodiment, the cell is a vertebrate cell, e.g., an avian or a mammalian cell. In a preferred embodiment, the cell is a human cell. The cells of the invention can express endogenous XBP1 or can be engineered to do so. For example, a cell that has been engineered to express the XBP1 protein can be produced by introducing into the cell an expression vector encoding the protein. Recombinant expression vectors can be used for expression of XBP1.

In another embodiment, the indicator composition is a cell free composition. XBP1 expressed by recombinant methods in a host cells or culture medium can be isolated from the host cells, or cell culture medium using standard methods for protein purification. For example, ion-exchange chromatography, gel filtration chromatography, ultrafiltration, electrophoresis, and immunoaffinity purification with antibodies can be used to produce a purified or semi-purified protein that can be used in a cell free composition. Alternatively, a lysate or an extract of cells expressing the protein of interest can be prepared for use as cell-free composition.

Pharmaceutical Compositions and Modes of Administration

Pharmaceutical compositions of the invention can be administered in combination therapy. i.e., combined with other agents. Agents include, but are not limited to, in vitro synthetically prepared chemical compositions, antibodies, antigen-binding regions, and combinations and conjugates thereof. In certain embodiments, an agent can act as an agonist, antagonist, allosteric modulator, or toxin.

In certain embodiments, the invention provides for pharmaceutical compositions comprising an XBP1 inhibitor or an inhibitor of a molecule in a biological pathway involving XBP1 (e.g., IRE-1α) with a pharmaceutically acceptable diluent, carrier, solubilizer, emulsifier, preservative and/or adjuvant. In certain embodiments, acceptable formulation materials preferably are nontoxic to recipients at the dosages and concentrations employed. In certain embodiments, the formulation material(s) are for s.c, and/or I.V. administration. In certain embodiments, the pharmaceutical composition can contain formulation materials for modifying, maintaining or preserving, for example, the pH, osmolality, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate. Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (Remington's Pharmaceutical Sciences, 18th Edition. A. R. Gennaro, ed., Mack Publishing Company (1995). In certain embodiments, the formulation comprises PBS; 20 mM NaOAC, pH 5.2, 50 mM NaCl; and/or 10 mM NAOAC, pH 5.2, 9% Sucrose. In certain embodiments, the optimal pharmaceutical composition will be determined by one skilled in the art depending upon, for example, the intended route of administration, delivery format and desired dosage.

See, for example, Remington's Pharmaceutical Sciences, supra. In certain embodiments, such compositions may influence the physical state, stability, rate of in vivo release and rate of in vivo clearance of an XBP1 inhibitor or an inhibitor of a molecule in a biological pathway involving XBP1 (e.g., IRE-1α).

In certain embodiments, the primary vehicle or carrier in a pharmaceutical composition can be either aqueous or non-aqueous in nature. For example, in certain embodiments, a suitable vehicle or carrier can be water for injection, physiological saline solution or artificial cerebrospinal fluid, possibly supplemented with other materials common in compositions for parenteral administration. In certain embodiments, the saline comprises isotonic phosphate-buffered saline. In certain embodiments, neutral buffered saline or saline mixed with serum albumin are further exemplary vehicles. In certain embodiments, pharmaceutical compositions comprise Tris buffer of about pH 7.0-8.5, or acetate buffer of about pH 4.0-5.5, which can further include sorbitol or a suitable substitute therefore. In certain embodiments, a composition comprising an XBP1 inhibitor or an inhibitor of a molecule in a biological pathway involving XBP1 (e.g., IRE-1α) can be prepared for storage by mixing the selected composition having the desired degree of purity with optional formulation agents (Remington's Pharmaceutical Sciences, supra) in the form of a lyophilized cake or an aqueous solution. Further, in certain embodiments, a composition comprising an XBP1 inhibitor or an inhibitor of a molecule in a biological pathway involving XBP1 (e.g., IRE-1α) can be formulated as a lyophilizate using appropriate excipients such as sucrose.

In certain embodiments, the pharmaceutical composition can be selected for parenteral delivery. In certain embodiments, the compositions can be selected for inhalation or for delivery through the digestive tract, such as orally. The preparation of such pharmaceutically acceptable compositions is within the ability of one skilled in the art.

In certain embodiments, the formulation components are present in concentrations that are acceptable to the site of administration. In certain embodiments, buffers are used to maintain the composition at physiological pH or at a slightly lower pH, typically within a pH range of from about 5 to about 8.

In certain embodiments, when parenteral administration is contemplated, a therapeutic composition can be in the form of a pyrogen-free, parenterally acceptable aqueous solution comprising a desired XBP1 inhibitor or an inhibitor of a molecule in a biological pathway involving XBP1 (e.g., IRE-1α) in a pharmaceutically acceptable vehicle. In certain embodiments, a vehicle for parenteral injection is sterile distilled water in which an XBP1 inhibitor or an inhibitor of a molecule in a biological pathway involving XBP1 (e.g., IRE-1α) is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that can provide for the controlled or sustained release of the product which can then be delivered via a depot injection. In certain embodiments, hyaluronic acid can also be used, and can have the effect of promoting sustained duration in the circulation. In certain embodiments, implantable drug delivery devices can be used to introduce the desired molecule.

In certain embodiments, a pharmaceutical composition can be formulated for inhalation. In certain embodiments, an XBP1 inhibitor or an inhibitor of a molecule in a biological pathway involving XBP1 (e.g., IRE-1α) can be formulated as a dry powder for inhalation. In certain embodiments, an inhalation solution comprising an XBP1 inhibitor or an inhibitor of a molecule in a biological pathway involving XBP1 (e.g., IRE-1α) can be formulated with a propellant for aerosol delivery. In certain embodiments, solutions can be nebulized. Pulmonary administration is further described in PCT application No. PCT/US94/001875, which describes pulmonary delivery of chemically modified proteins.

In certain embodiments, it is contemplated that formulations can be administered orally. In certain embodiments, an XBP1 inhibitor or an inhibitor of a molecule in a biological pathway involving XBP1 (e.g., IRE-1α) that is administered in this fashion can be formulated with or without those carriers customarily used in the compounding of solid dosage forms such as tablets and capsules. In certain embodiments, a capsule can be designed to release the active portion of the formulation at the point in the gastrointestinal tract when bioavailability is maximized and pre-systemic degradation is minimized. In certain embodiments, at least one additional agent can be included to facilitate absorption of an XBP1 inhibitor or absorption of an inhibitor of a molecule in a biological pathway involving XBP1 (e.g., IRE-1α). In certain embodiments, diluents, flavorings, low melting point waxes, vegetable oils, lubricants, suspending agents, tablet disintegrating agents, and binders can also be employed.

In certain embodiments, a pharmaceutical composition can involve an effective quantity of an XBP1 inhibitor or an inhibitor of a molecule in a biological pathway involving XBP1 (e.g., IRE-1α) in a mixture with non-toxic excipients, which are suitable for the manufacture of tablets. In certain embodiments, by dissolving the tablets in sterile water, or another appropriate vehicle, solutions can be prepared in unit-dose form. In certain embodiments, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving an XBP1 inhibitor or an inhibitor of a molecule in a biological pathway involving XBP1 (e.g., IRE-1α) in sustained- or controlled-delivery formulations. In certain embodiments, techniques for formulating a variety of other sustained- or controlled-delivery means, such as liposome carriers, bio-erodible microparticles or porous heads and depot injections, are also known to those skilled in the art. See for example, PCT Application No. PCT/US93/00829, which describes the controlled release of porous polymeric microparticles for the delivery of pharmaceutical compositions. In certain embodiments, sustained-release preparations can include semipermeable polymer matrices in the form of shaped articles, e.g. films, or microcapsules. Sustained release matrices can include polyesters, hydrogels, polylactides (U.S. Pat. No. 3,773,919 and EP 058.481), copolymers of L-glutamic acid and gamma ethyl-L-glutamate (Sidman et al., Biopolymers, 22:547-556 (1983)), poly (2-hydroxyethyl-methacrylate) (Langer et al., J. Biomed. Mater. Res., 15: 167-277 (1981) and Langer, Chem. Tech., 12:98-105 (1982)), ethylene vinyl acetate (Langer et al., supra) or poly-D(–)-3-hydroxybutyric acid (EP 133,988). In certain embodiments, sustained release compositions can also include liposomes, which can be prepared by any of several methods known in the art. See, e.g., Eppstein et al, Proc. Natl. Acad. Sci. USA, 82:3688-3692 (1985); EP 036,676; EP 088,046 and EP 143,949.

The pharmaceutical composition to be used for in vivo administration typically is sterile. In certain embodiments, this can be accomplished by filtration through sterile filtration membranes. In certain embodiments, where the composition is lyophilized, sterilization using this method can be conducted either prior to or following lyophilization and reconstitution. In certain embodiments, the composition for parenteral administration can be stored in lyophilized form or in a solution. In certain embodiments, parenteral compositions generally are placed into a container having a sterile access port, for example, an intravenous solution bag or vial having a stopper pierceable by a hypodermic injection needle.

In certain embodiments, once the pharmaceutical composition has been formulated, it can be stored in sterile vials as a solution, suspension, gel, emulsion, solid, or as a dehydrated or lyophilized powder. In certain embodiments, such formulations can be stored either in a ready-to-use form or in a form (e.g., lyophilized) that is reconstituted prior to administration.

In certain embodiments, kits are provided for producing a single-dose administration unit. In certain embodiments, the kit can contain both a first container having a dried protein and a second container having an aqueous formulation. In certain embodiments, kits containing single and multi-chambered pre-filled syringes (e.g., liquid syringes and lyosyringes) are included.

In certain embodiments, the effective amount of a pharmaceutical composition comprising an XBP1 inhibitor or an inhibitor of a molecule in a biological pathway involving XBP1 (e.g., IRE-1α), to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which an XBP1 inhibitor or an inhibitor of a molecule in a biological pathway involving XBP1 (e.g., IRE-1α) is being used, the route of administration, and the size (body weight, body surface or organ size) and/or condition (the age and general health) of the patient. In certain embodiments, the clinician can titer the dosage and modify the route of administration to obtain the optimal therapeutic effect.

In certain embodiments, the frequency of dosing will take into account the pharmacokinetic parameters of an XBP1 inhibitor or an inhibitor of a molecule in a biological pathway involving XBP1 (e.g., IRE-1α) in the formulation used. In certain embodiments, a clinician will administer the composition until a dosage is reached that achieves the desired effect. In certain embodiments, the composition can therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. In certain embodiments, appropriate dosages can be ascertained through use of appropriate dose-response data.

In certain embodiments, the mute of administration of the pharmaceutical composition is in accord with known methods, e.g. orally, systemically, locally, through injection by intravenous, intraperitoneal, intracerebral (intra-parenchymal), intracerebroventricular, intratumoral, intramuscular, subcutaneously, intra-ocular, intraarterial, intraportal, or intralesional routes; by sustained release systems or by implantation devices. In certain embodiments, the compositions can be administered by bolus injection or continuously by infusion, or by implantation device. In certain embodiments, individual elements of the combination therapy may be administered by different routes.

In certain embodiments, the composition can be administered locally via implantation of a membrane, sponge or another appropriate material onto which the desired molecule has been absorbed or encapsulated. In certain embodiments, where an implantation device is used, the device can be implanted into any suitable tissue or organ, and delivery of the desired molecule can be via diffusion, timed-release bolus, or continuous administration. In certain embodiments, it can be desirable to use a pharmaceutical composition comprising an XBP1 inhibitor or an inhibitor of a molecule in a biological pathway involving XBP1 (e.g., IRE-1α) in an ex vivo manner. In such instances, cells, tissues and/or organs that have been removed from the patient are exposed to a pharmaceutical composition comprising an XBP1 inhibitor or an inhibitor of a molecule in a biological pathway involving XBP1 (e.g., IRE-1α), after which the cells, tissues and/or organs are subsequently implanted back into the patient.

In certain embodiments, an XBP1 inhibitor or an inhibitor of a molecule in a biological pathway involving XBP1 (e.g., IRE-1α) can be delivered by implanting certain cells that have been genetically engineered, using methods such as those described herein, to express and secrete the polypeptides. In certain embodiments, such cells can be animal or human cells, and can be autologous, heterologous, or xenogeneic. In certain embodiments, the cells can be immortalized. In certain embodiments, in order to decrease the chance of an immunological response, the cells can be encapsulated to avoid infiltration of surrounding tissues. In certain embodiments, the encapsulation materials are typically biocompatible, semipermeable polymeric enclosures or membranes that allow the release of the protein product(s) but prevent the destruction of the cells by the patient's immune system or by other detrimental factors from the surrounding tissues.

In other embodiments, ex vivo treatment of dendritic cells with an inhibitor of XBP1 (e.g., siRNA) can be used to activate, induce, enhance or promote the antigen presenting capacity of dendritic cells. The activated dendritic cells can then be administered to a subject. In some embodiments, the dendritic cells may be tumor-associated dendritic cells.

This invention is further illustrated by the following examples which should not be construed as limiting. The contents of all references, patents, and published patent applications cited throughout this application, as well as the figures and the sequence listing, are hereby incorporated by reference.

EXAMPLES

Experimental Procedures
Tissues, Mice and Cell Lines

Stage III-IV human ovarian carcinoma specimens and malignant ascites samples were procured through Surgical Pathology at Weill Cornell Medical College/New York-Presbyterian Hospital under an approved protocol where research samples remained totally unidentified. Tumor single cell suspensions were generated as previously described (Conejo-Garcia et al., 2005). Malignant peritoneal ascites samples from patients with metastatic ovarian cancer were centrifuged for 10 min at 1300 rpm and red blood cells were lysed prior to FACS analysis. Mice were housed at the animal facilities of Harvard School of Public School, Weill Cornell Medical College, or The Wistar Institute. The Institutional Animal Care and Use Committee approved all animal experiments described in this study. XBP1$^{f/f}$ mice were generated as previously described (Lee et al., 2008) and have been backcrossed at least 15 generations onto C57BL/6 mice. Wild type, OT-1 transgenic. Itgax-Cre (CD11c-Cre) and Rag2-deficient mice, all in a full C57BL/6 background, were purchased from Jackson Laboratories (Bar Harbor, Me.).

Double transgenic LSL-K-ras$^{G12D/+}$p53$^{loxp/loxp}$ (p53/K-ras) mice were generated by obtaining LSL-K-ras$^{tm4Tyj}$ (Jackson et al., 2001) and Trp53$^{tm1/Brn}$ (Jonkers et al., 2001) from the NCI mouse models of human cancer consortium and bred to a full C57BL/6 background as previously reported (Scarlett et al., 2012), p53/K-ras mice were irradiated two consecutive days with 650 rads followed by reconstitution with bone marrow from XBP1$^{f/f}$ or XBP1$^{f/f}$ CD11c-Cre mice. 8 weeks post bone-marrow reconstitution autochthonous ovarian tumors were initiated by delivery of adenovirus-expressing Cre recombinase (ADV-Cre) into the ovarian bursa as previously reported (Dinulescu et al., 2005; Flesken-Nikitin et al., 2003; Scarlett et al., 2012). Seven weeks after tumor initiation, mice were sacrificed. Tumors, approximately 2-3 cm in diameter, were resected under sterile conditions after euthanizing the mouse. Specimens were then minced into pieces <3 mm in diameter and digested for 1 hour at 37° C. in RPMI containing 2 mg/mL collagenase Type D and 1 mg/ml DNAse I. The digested tissue pieces were then pressed through a 70 µm strainer to create a single cell suspension. Red blood cells were lysed using ACK lysis buffer and pellets from single-cell suspensions were resuspended to 50-100×10$^6$ cells/ml in freezing media (FBS containing 10% DMSO) and incubated on ice for 30 minutes. Tubes were then transferred to −80° C. for long-term storage.

Parental ID8 or aggressive ID8-Defb29/Vegf-A intraperitoneal ovarian tumors were generated as previously described (Conejo-Garcia et al., 2004; Roby et al., 2000). Briefly, 1-2×10$^6$ tumor cells were injected into wild type C57BL/6 mice or conditional XBP1-deficient mice. Implanted animals progressively developed multiple peritoneal masses and eventually massive ascites in ~35 days (ID8-Defb29/Vegf-A) or in ~2 months (parental ID8). Mice were weighted weekly to monitor malignant ascites accumulation and animals with severe abdominal distension were humanely euthanized.

Isolation of Human and Mouse DCs

Human patient ovarian cancer-associated DCs (CD45$^+$ CD3$^-$CD20$^-$ CD11c$^+$DEC205$^+$) were sorted from tumor single cell suspensions or malignant ascites using flow cytometry, following the gating strategy described in FIG. 1. During sorting, viable cells were identified using the LIVE/DEAD Fixable Yellow Dead Cell Stain Kit (Life Technologies). Mouse ovarian cancer-associated DCs (CD45$^+$ CD11c$^+$CD11b$^+$MHC-II$^+$CD8α$^-$) were sorted from single-cell suspensions of p53/K-ras-driven ovarian tumors or from peritoneal wash (10 ml 1×PBS) or total malignant ascites samples from mice bearing aggressive ID8-Defb29/Vegf-A intraperitoneal ovarian cancer, following the gating strategy described in FIG. 1. All fluorescently-labeled antibodies were from BioLegend. Control sDCs (CD45$^+$CD11c$^+$ CD11b$^+$MHC-II$^+$CD8α$^-$) were FACS sorted from spleens of naïve or ovarian cancer-bearing mice using Collagenase D and DNAse I treatment followed by incubation with the indicated antibodies.

Reagents and In Vitro Cellular Treatments

Murine recombinant cytokines were purchased from Peprotech. Cobalt chloride, Tunicamycin (used at 1 µg/ml), Tiron (used at 100-500 µM) and Vitamin E (α-tocopherol, used at 50-100 µM) were from Sigma. DCFDA staining was utilized for intracellular ROS detection (Abcam). Purified 4-HNE was obtained from Cayman Chemical and 4-HNE-protein adducts in ascites samples and DCs were detected and quantified through competitive ELISA (Cell Biolabs). TOFA (Cayman Chemical) was used at a final concentration of 5 µg/ml to inhibit fatty acid synthesis in DCs by blocking the synthesis of malonyl-CoA by acetyl-CoA carboxylase. The IRE-1α-specific inhibitor 4µ8c (Millipore) was used at a final concentration of 10 µM.

Conventional and Quantitative RT-PCR

Total RNA from human samples was isolated using the miRVANA miRNA isolation Kit (Life Technologies). RNA from mouse samples was isolated using the Qiazol reagent (Qiagen). 0.1-1 µg of RNA were used to generate cDNA using the High Capacity cDNA Reverse Transcription Kit (Life Technologies). Human and mouse Xbp1 splicing assays were performed as described (Lee et al., 2003a; Martinon et al., 2010) using conventional Reverse Transcription PCR (RT-PCR) and primers shown in Table 1. Gene expression analysis was done via Reverse Transcription quantitative PCR (RT-qPCR) using a Stratagene Mx3005 instrument and SYBR green I (Life Technologies). Murine XBP1s transcript expression was determined using a probe that spans the spliced-out version as previously demonstrated (Reimold et al., 2001). All primers used in this study are described in Table 1.

Western Blot

5×10$^6$ sDC or tDC were washed twice in IX cold PBS and nuclear proteins were purified using the Nuclear Extraction Kit (Life Technologies). Proteins were quantified using the BCA method (Pierce) and 15-20 µg of nuclear proteins were separated via SDS-PAGE and transferred onto nitrocellulose membranes following standard procedures. Anti-mouse XBP1 s (GL Biochem) was raised in rabbit using a peptide corresponding to the XBP1s C-terminus, and was used at a 1:500 dilution for immunoblotting. Goat anti-mouse Lamin B (Santa Cruz) was used at 1:2000. HRP-conjugated secondary antibodies to rabbit and mouse (Santa Cruz) were used at a 1:2000 dilution. SuperSignal West Femto (Pirce) was used as Chemiluminescent Substrate and blots were imaged using a FluorChemE instrument (ProteinSimple).

RNA-Seq and DC Transcriptional Profile tDCs were sorted from peritoneal wash samples of XBP1$^{f/f}$ or XBP1$^{f/f}$ CD11c-Cre female mice (n=3/group) bearing aggressive ID8-Defb29/Vegf-A ovarian tumors for 3 weeks. Total RNA was isolated using the miRVANA miRNA isolation Kit (Life Technologies) and further concentrated via RNeasy MinElute columns (Qiagen). RNA quality and integrity was confirmed in an Agilent Bioanalyzer 2100. In all cases RINs were 9.50 or higher. mRNA libraries were generated and sequenced at the Epigenomics Facility of Weill Cornell Medical College. Reads produced from 51 bp single end sequencing run were aligned against mouse genome (mm9) using Bowtie v0.12.8 (Langmead et al., 2009) algorithm. Mouse mm9 transcriptome information was obtained from UCSC Genome Browser and RSEM algorithm (Li and Dewey, 2011) was used to calculate number of aligned tags for each gene. Differential expression between two groups were tested by EdgeR (Robinson and Oshlack, 2010) and significance was defined using a False Discovery Rate (FDR) cutoff of 0.15. The most up-to-date gene information (official symbol and description) was obtained from NCBI Entrez information on May 15, 2014. Normalized expression RPKM values (Reads Per Kilobase of transcript per Million mapped reads) values were generated by EdgeR and used to demonstrate gene expression across samples as color-coded fold change of expression in a sample versus average expression across all samples. Functional enrichment analysis was done using QIAGEN's Ingenuity Pathway Analysis (IPA®, QIAGEN Redwood City, www.qiagen.com/ingenuity). For IPA upstream analysis, only regulators significant at $p<10^6$ with predicted activation/inhibition states (Z-score>2) were considered. Significantly affected biological processes were tested by using NCBI DAVID (Huang da et al., 2009) software using level 3 of GO biological processes and considering only FDR<0.15 results that showed at least 20 genes that constitute at least ⅔ of all involved in the process genes specifically up or down-regulated.

Flow Cytometry and Lipid Staining

Intracellular lipid content in DCs was evaluated via flow cytometry using 4,4-Difluoro-1,3,5,7,8-Pentamethyl-4-Bora-3a,4a-Diaza-s-Indacene (BODIPY 493/503. Life Technologies) as previously reported (Herber et al., 2010). Briefly, $5\times10^6$ cells from total spleen single cell suspensions or malignant peritoneal wash samples were conventionally stained for surface markers using fluorescently-labeled antibodies that do not overlap with BODIPY 493/503, namely CD11c-APC, CD45-APC-Cy7 and CD11b-Pacific Blue. Cells were washed twice with 1×PBS and stained with 500 μl of BODIPY 493/503 at 0.5 mg/ml in PBS for 15 min at room temperature in the dark. Cells were washed twice and analyzed by flow cytometry.

BODIPY 493/503 staining was detected in the PE channel. For intracellular cytokine staining, $5\times10^6$ cells isolated from malignant peritoneal wash samples of ovarian cancer-bearing mice were stimulated for 6 h in 10% FBS complete RPMI containing PMA (Calbiochem). Ionomycin (Calbiochem) and Brefeldin A (BioLegend). Cells were collected and stained for surface markers and intracellular cytokines following the FoxP3/Transcription Factor Staining buffer set (eBioscience). All antibodies were from BioLegend. Flow cytometry was performed on a LSRII instrument (BD Biosciences). Cell populations were sorted from peritoneal washes (10 ml 1×PBS) of ovarian carcinoma-bearing mice or from human ascites or tumor single-cell suspensions using a FACSAria sorter (BD Biosciences). Flow cytometry data was analyzed using FlowJo version 9 or 10.

Transmission Electron Microscopy and Lipidomics tDC were sorted from the peritoneal cavity of $XBP1^{f/f}$ or $XBP1^{f/f}$ CD11c-Cre female mice bearing ID8-Defb29/Vegf-A ovarian tumors for 3 to 4 weeks as shown in FIG. 1. Cells were washed twice with 1×PBS and pellets were fixed and sectioned for electron microscopy analysis (performed at the Electron Microscopy and Histology Core Facility of Weill Cornell Medical College) following standard methods. Alternatively, cell pellets from $0.5-1\times10^6$ sorted tDCs were frozen and total intracellular lipids were extracted and quantitatively analyzed via LC-MS at the Lipidomics Core Facility of Wayne State University School of Medicine.

Antigen Processing and Presentation

For in vitro antigen presentation experiments, tDC or sDC were sorted from the peritoneal cavity or spleen of $XBP1^{f/f}$ or $XBP1^{f/f}$ CD11c-Cre female mice bearing ID8-Defb29/Vegf-A ovarian tumors for 4 weeks (FIG. 1). tDCs were pulsed for overnight 50 μg/ml of full-length endotoxin-free OVA (SIGMA, Grade VII) in the presence or absence of Vitamin E (50 μg/ml) in media containing 25% cell-free ovarian cancer ascites supernatants. DCs were washed twice and cocultured for 3 days with CFSE-labeled CD8+ T cells immunopurified from OT-1 mice at a 1:10 (DC to T cell) ratio, as previously described (Scarlett et al., 2009).

For in vivo antigen presentation experiments, wild type C57BL/6 female mice bearing ID8-Defb29/Vegf-A ovarian tumors for three weeks were intraperitoneally injected with 0.6 mg of full length endotoxin-free OVA (SIGMA, grade VII) and 3 hours later, mice were left untreated or injected with siRNA-PEI nanoparticles (see below). 18 hours later, mice were transferred intraperitoneally with $2\times10^6$ CFSE-labeled T cells negatively purified from OT-1 transgenic mice. Peritoneal wash samples (10 mL) were collected after 72 hours and analyzed for CFSE dilution via FACS. Data were analyzed using FlowJo version 10. Division Index determines the average number of cell divisions that a cell in the original population has undergone. Proliferation Index shows the total number of divisions of only responding (proliferating) cells. Replication Index is the fold-expansion of the responding cells, thus indicating the expansion capability of the replicating cells.

Preparation of siRNA-PEI Nanoparticles and Therapeutic In Vivo Silencing

Endotoxin-free rhodamine-labeled and unconjugated polyethylenimine (PEI) for in vivo experiments "in vivo-jetPEI" was purchased from PolyPlus Transfection. To generate siRNA-PEI nanocomplexes, 50 μg of siRNA were complexed with "in vivo-jetPEI" at N/P ratio of 6, following the recommendations of the manufacturer and previously optimized conditions (Cubillos-Ruiz et al., 2009). All siRNA oligonucleotides were from IDT and included 2'-OMe modified nucleotides and specific phosphorothioate linkages, as previously reported (Piret et al., 2002). Sequences for the sense and antisense strands are as follows: siLuc sense: 5'-CuUACgcUGAguaCUUcGAdTsdT-3', siLuc antisense: 5'-UCgAAGUACUCAGCgUAAGdTsdT-3', siXBP1 sense: 5'-cAcccuGAAuucAuuGucudTsdT-3', siXBP1 antisense: 5'-AGAcAAUGAAUUcA-GGGUGdTsdT-3', silRE1a sense: 5'-AuGccGAAGuucA-GAuGGAdTsdT-3', silRE1a antisense: 5'-UC-cAUCUGAACUUCGGcAUdTsdT-3'. 2'-OMe modified nucleotides are in lower case. Phosphorothioate linkages are represented by "s" and "d" indicates DNA bases.

For in vivo biodistribution, phenotypic and silencing experiments, mice bearing ID8-Defb29/Vegf-A tumors for 3-4 weeks were intraperitoneally injected with rhodamine-labeled siXBP1-PEI or siLuc-PEI nanoparticles (50 μg of siRNA complexed with rhodamine-labeled "in vivo-jetPEI" at N/P 6, per mouse). Rhodamine$^+$CD45$^+$CD11c$^+$CD11b$^+$MHC-II$^+$ tDC were sorted after 3 days for downstream molecular biology analysis. For repeated siRNA treatments, wild-type C57BL/6 female mice were intraperitoneally injected with $1\times10^6$ aggressive ID8-Defb29/Vegf-A ovarian carcinoma cells, and mice received nanocomplexes (50 μg of siRNA complexed with "in vivo-jetPEI" at N/P 6, per mouse) at days 12, 16, 20, 24, 28 and 32 after tumor implantation.

Anti-Tumor Immune Responses and ELISA

Mice were intraperitoneally injected with ID8-Defb29/Vegf-A ovarian cancer cells and treated with siRNA-PEI nanoparticles (n=3/group) at days 8, 13, 18, and 23 after challenge. Total splenic T cells or Ficoll-enriched leukocytes ($2-3\times10^5$) from peritoneal wash samples were obtained 4 days after the last treatment (day 27) and cocultured in 10% FBS RPMI with $2-3\times10^4$ bone marrow-derived DCs previously pulsed overnight with irradiated ID8-Defb29/Vegf-A ovarian cancer cells. Supernatants were collected after 48-72 h of stimulation. IFN-γ and Granzyme B secretion cells was determined by ELISA using the Ready-SET-Go Kit (eBioscience).

Statistical Analysis

Unless noted otherwise, all experiments were repeated at least two times and results were similar between repeats. The correlation between CHOP expression in tDC and human intra-tumoral T cell infiltration was analyzed using the Spearman's Rank coefficient. Animal experiments used between 3 and 6 mice per group. A P value <0.05 was considered to be statistically significant. All statistical analyses were done using Graph Pad Prism 5.0. Differences between the means of experimental groups were calculated using a two-tailed unpaired Student's t test. Error bars represent standard error of the mean from independent samples assayed within the represented experiments. Survival rates were compared using the Log-Rank test. All survival experiments used at least 6 mice/group. This number provides a 5% significance level and 95% power to detect differences in survival of 20% or greater.

Example 1: Constitutive XBP1 Activation in Ovarian Cancer-Associated DCs

Innate myeloid cells with phenotypic and functional attributes of regulatory DCs commonly infiltrate ovarian tumors (Conejo-Garcia et al., 2004; Huarte et al., 2008; Scarlett et al., 2012). Rather than inducing anti-cancer immunity, these dysfunctional DCs facilitate malignant progression by preventing the activation and expansion of tumor-reactive T cells (Cubillos-Ruiz et al., 2010). To analyze XBP1 activation in human and mouse ovarian cancer-associated DCs, $CD45^+CD3^-CD20^-$ $CD11c^+DEC205^+$ tDCs were isolated via FACS from human patient ovarian tumors or metastatic ovarian cancer ascites samples. Murine $CD45^+CD11c^+$ $MHC-II^+$ $CD11b^+CD8\alpha^-$ tDCs were isolated from advanced p53/K-ras-driven ovarian tumors or from malignant ascites of mice bearing aggressive ID8-Defb29/Vegf-A ovarian carcinoma for 4-5 weeks and their identity as bonafide classical DCs was confirmed by quantifying Clec9A/DNGR-1 and Zbtb46 expression (FIG. 1). Splicing of the Xbp1 mRNA was evaluated using conventional PCR.

Figure 2A:
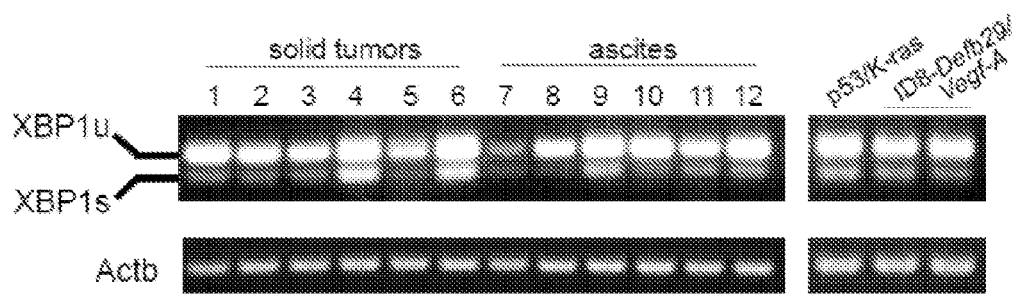
FIG. 2A-F: Shows constitutive XBP1 activation in human and mouse ovarian cancer-associated DCs.
Figure 2B:
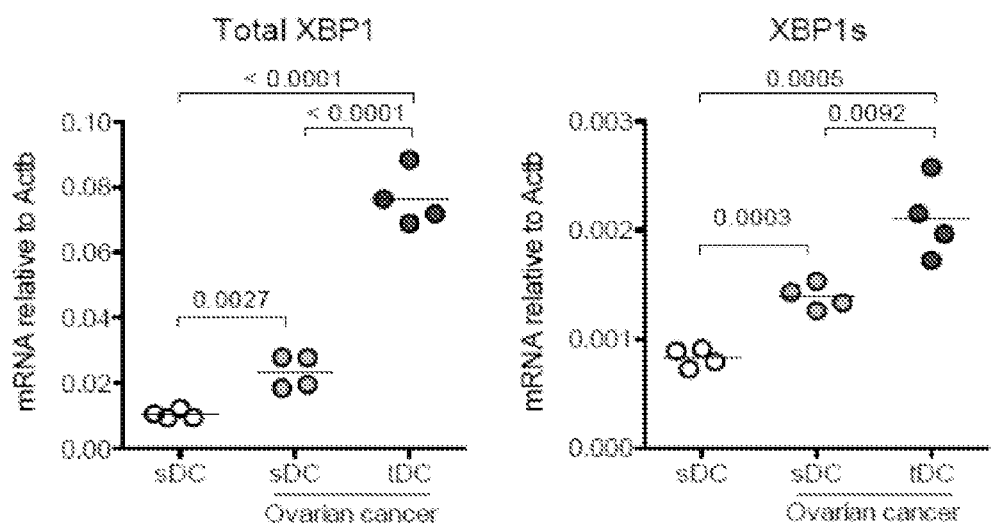
Figure 2C:
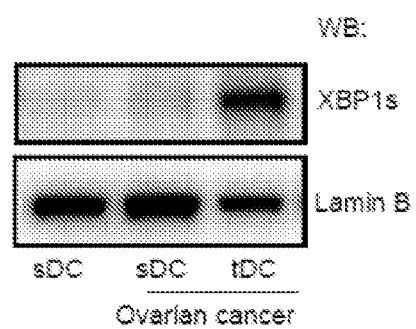
Figure 2D:
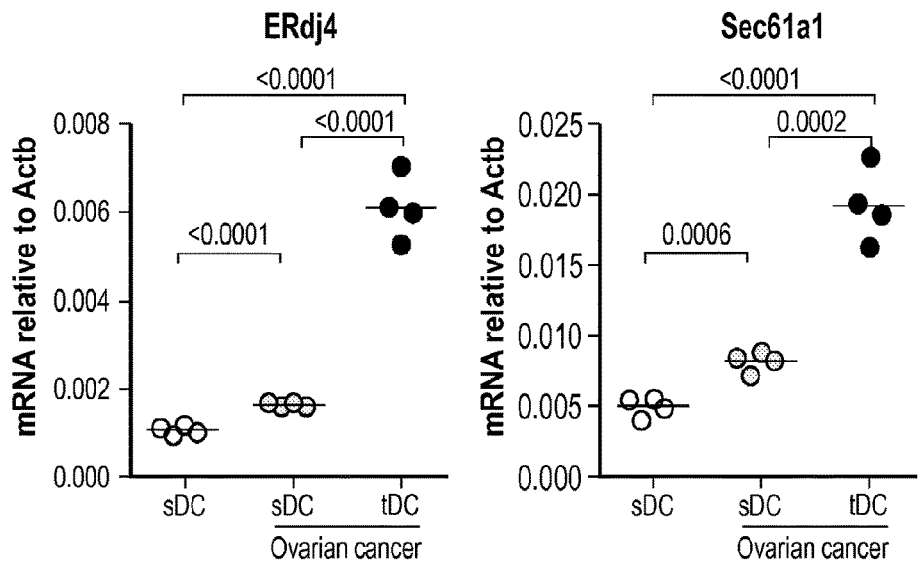
Figure 2E:
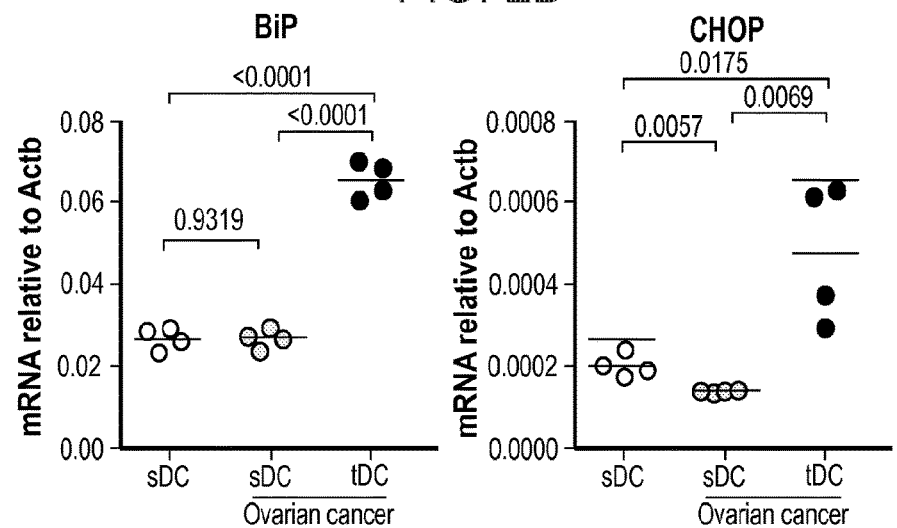
Figure 2F:
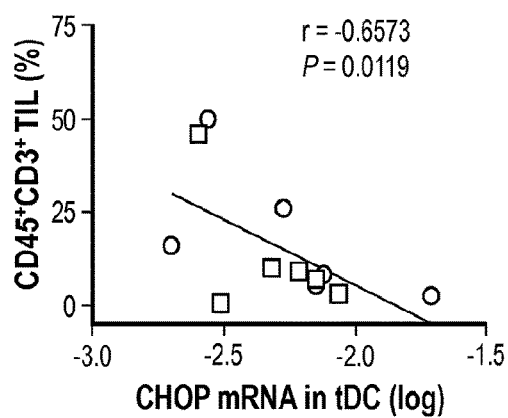

Malignant peritoneal fluid samples from patients with metastatic ovarian cancer were centrifuged for 10 min at 1300 rpm and total cells were used for FACS analysis. Solid primary or metastatic ovarian tumors were mechanically dissociated as described above. In both cases, $CD45^+CD3^-CD20^-CD11c^+DEC205^+$ tDCs were sorted via FACS for RNA extraction and gene expression quantification via RT-qPCR. The percentage of $CD45^+CD3^+$ T cells present in each sample was correlated with CHOP mRNA expression levels in sorted tDCs from the same specimen (FIG. 2F).

Notably, tumor-associated DCs (tDCs) isolated from multiple human patient ovarian cancer specimens (FIGS. 1A and 1B) or from preclinical models of aggressive primary and metastatic ovarian cancer (FIGS. 1C-1E) (Conejo-Garcia et al., 2004; Scarlett et al., 2012) exhibited constitutive splicing of the Xbp1 mRNA (FIG. 2A), a molecular event essential for generating fully functional XBP1 (Yoshida et al., 2001). Expression of the indicated transcripts was determined by RT-qPCR (FIG. 2B, 2D, 2E) (data are normalized to endogenous levels of Actb in each sample. $CD45^+CD11c^+MHC-II^+CD11b^+CD8\alpha^-$ sDCs were isolated from spleens of naïve or tumor-bearing mice), and quantitative analyses demonstrated increased expression of total and spliced Xbp1 mRNA in tDCs, compared with closely related $CD8\alpha-$ splenic DCs (sDCs) (FIG. 1E) isolated either from naïve or ovarian cancer-bearing mice (FIG. 2B).

Western blot analysis was used to assay the spliced form of XBP1 (XBP1s) protein expression in nuclear extracts obtained from the indicated DCs. Consistently, tDCs exhibited augmented XBP1 protein levels in the nucleus compared with control DCs obtained from non-tumor sites (FIG. 2C). Further confirming these findings, RT-PCR analysis showed marked upregulation of canonical XBP1 target genes ERdj4 and Sec61a1 (Acosta-Alvear et al., 2007; Lee et al., 2003b) (FIG. 2D), as well as increased expression of general ER stress response markers Hspa5 (BiP) and Ddit3 (CHOP) was evidenced only in tDCs (FIG. 2E).

The expression of CHOP in tDCs sorted from human patient ovarian cancer specimens was determined using RT-qPCR. Interestingly, CHOP expression levels in tDCs negatively correlated with T cell infiltration in several human ovarian cancer specimens analyzed, suggesting a potential role for ER-stressed tDCs in regulating anti-tumor immune responses (FIG. 2F). Together, these data indicate that DCs in the ovarian cancer microenvironment exhibit severe ER stress and robust XBP1 activation.

Example 2: Byproducts of Lipid Peroxidation Trigger ER Stress in DCs

Figure 3A:
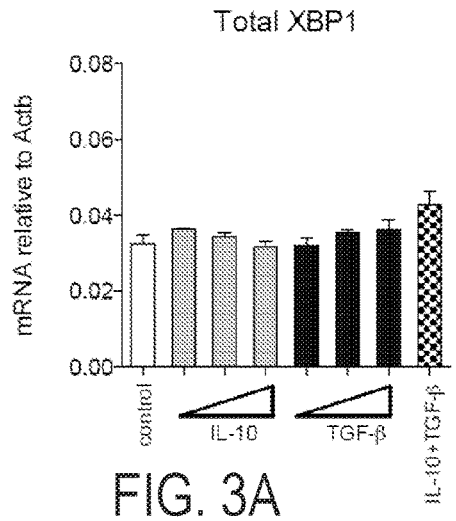
FIG. 3A-F: Shows the effect of diverse cytokines and hypoxia mimicking conditions on XBP1 activation by DCs
Figure 3B:
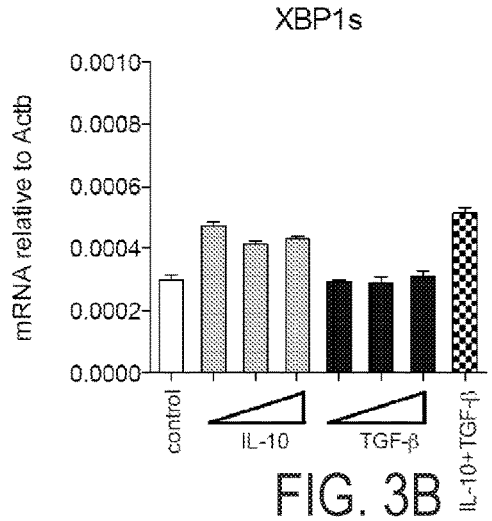
Figure 3C:
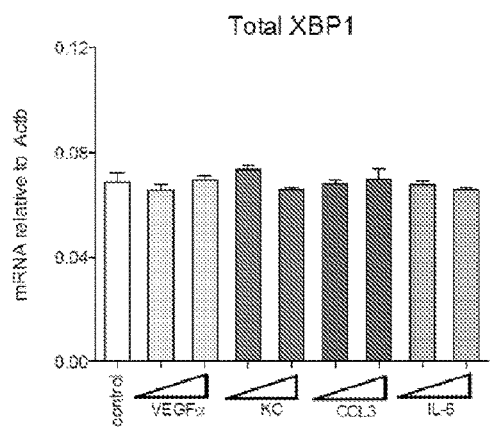
Figure 3D:
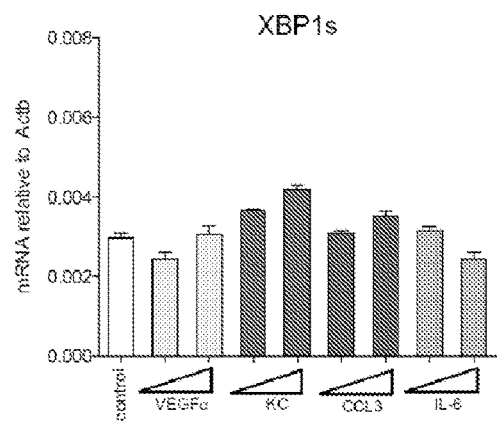
Figure 3E:
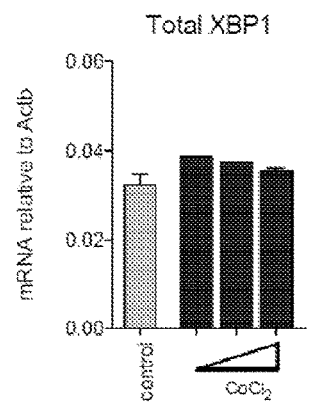
Figure 3F:
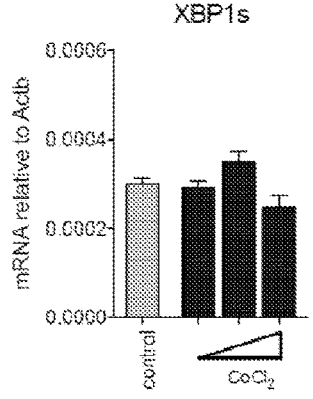

One goal of the present invention was to investigate how the tumor microenvironment influences the functional status of XBP1 in DCs. In particular, one aim of the present invention was to investigate whether cancer-derived factors could participate in triggering ER stress and XBP1 activation in tumor-infiltrating DCs, and determine whether this process could impact the detrimental function of these innate immune cells in hosts with ovarian cancer. Interestingly, neither tumorigenic/immunosuppressive cytokines commonly enriched at tumor sites nor hypoxia-mimicking conditions caused robust XBP1 activation in DCs (FIG. 3). In particular, naïve sDCs were isolated and stimulated for 24 h with cytokines (e.g., IL-10, TGF-β, VEGFα, KC, CCL3. IL-6) at concentrations ranging from 5 ng/ml to 25 ng/ml (FIG. 3A-D). Cells were also exposed for 24 hours to increasing concentrations of cobalt chloride ($CoCl_2$), a chemical inducer of the HIF1α pathway that mimics low oxygen conditions (Piret et al. 2002) (FIG. 3E-F). Splicing and upregulation of XBP1 was determined by RT-qPCR analysis (FIG. 3).

Figure 4A:
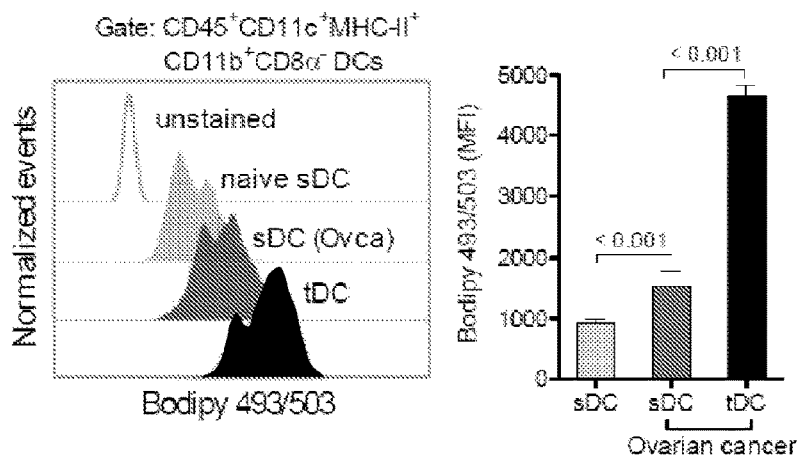
FIG. 4A-J: Provides lipid peroxidation byproduct 4-HNE triggers ER stress in DCs.
Figure 4B:
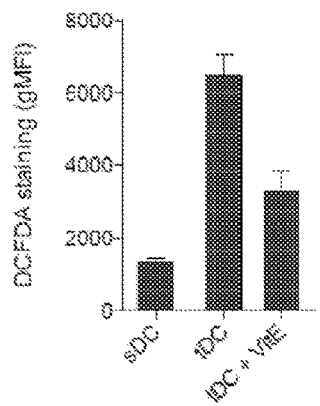
Figure 4C:
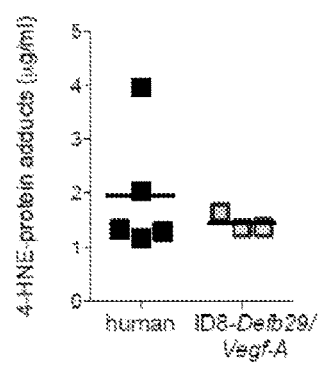
Figure 4D:
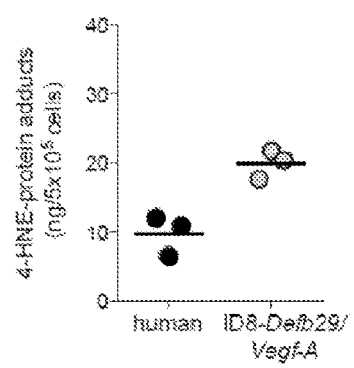
Figure 4E:
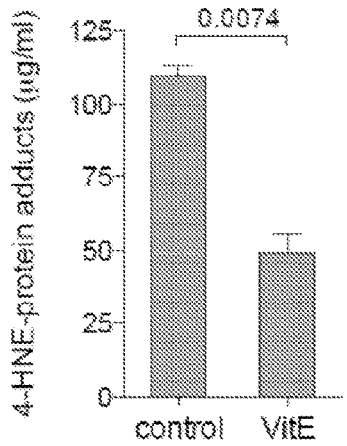
Figure 4F:
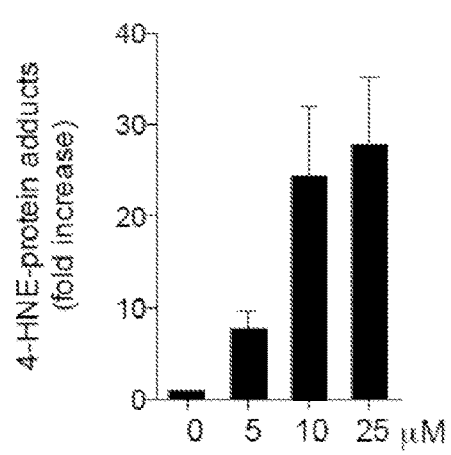
Figure 4G:
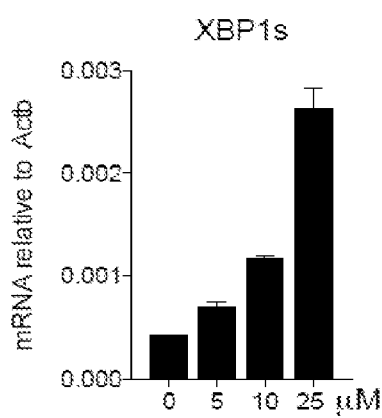
Figure 4H:
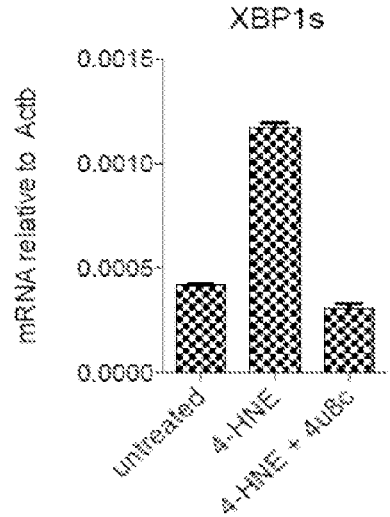
Figure 4I:
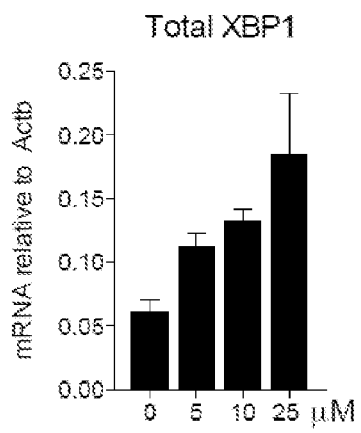
Figure 4I:
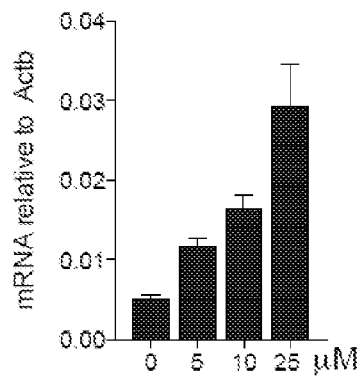
Figure 4J:
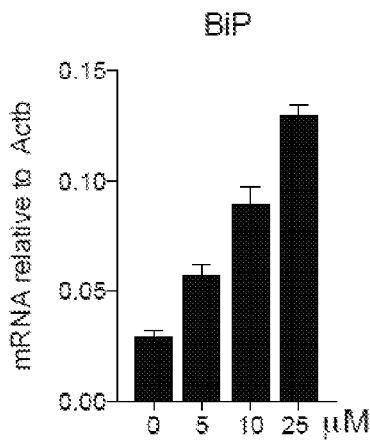
Figure 4J:
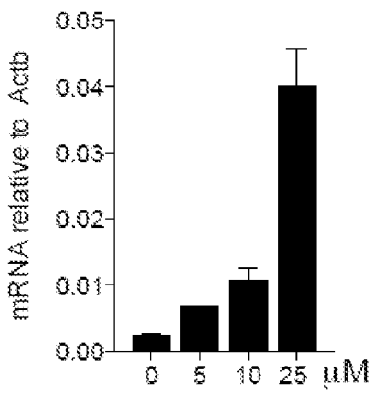

Recent reports demonstrate that abnormal intracellular accumulation of peroxided lipids is a common feature of dysfunctional DCs infiltrating multiple human and mouse cancers (Herber et al., 2010; Ramakrishnan et al., 2014). Importantly, lipid oxidation by reactive oxygen species (ROS) generates reactive byproducts such as the unsaturated aldehyde 4-hydroxy-trans-2-nonenal (4-HNE), which has been shown to induce protein-folding stress by forming stable adducts with ER-resident chaperones (Vladykovskaya et al., 2012). Whether these reactive aldehyde byproducts could trigger ER stress in DCs was investigated. Ovarian cancer-associated DCs demonstrated significantly higher amounts of intracellular lipids and augmented ROS levels in comparison with control non-malignant sDCs isolated from the same host or from naïve mice (FIGS. 4A and 4B). Consistent with active lipid peroxidation taking place at tumor sites, cell-free ovarian cancer ascites of human and mouse origin exhibited high levels of 4-HNE-protein adducts (FIG. 4C). Accordingly, intracellular 4-HNE-protein adducts were also readily found in tDCs isolated from these malignant samples (FIG. 4D). 4-HNE generation in mouse tDCs exposed to cell-free ovarian cancer ascites decreased upon exposure to the common antioxidant Vitamin E (FIG. 4E). Incubation of naïve sDCs with increasing concentrations of purified 4-HNE efficiently formed covalent adducts with intracellular proteins (FIG. 4F) and rapidly triggered splicing of the Xbp1 mRNA in an IRE-1α-dependent manner (FIGS. 4G and 4H). Consistently, upregulation of the canonical XBP1-dependent, ER-resident chaperone ERdj4 (FIG. 4I) as well as robust induction of the general ER stress response markers BiP and CHOP (FIG. 4J) was rapidly evidenced in 4-HNE treated DCs. These data demonstrate that 4-HNE, a lipid peroxidation byproduct readily available in the ovarian cancer microenvironment, triggers strong ER stress and XBP1 activation in DCs.

Figure 5A:
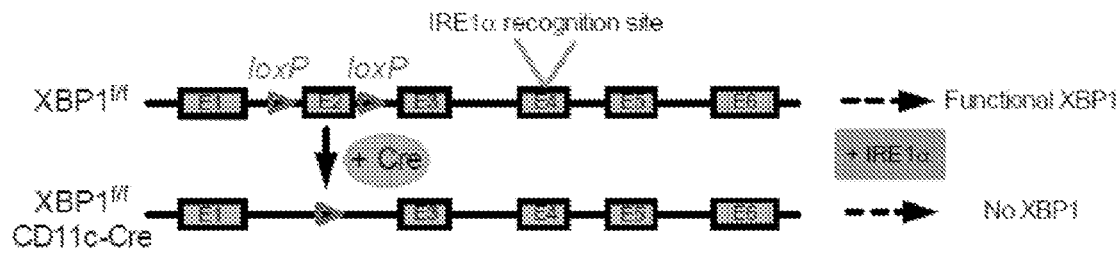
FIG. 5A-C: Shows the efficient and selective XBP1 deletion in DCs via CD11c-controlled Cre expression.
Figure 5B:
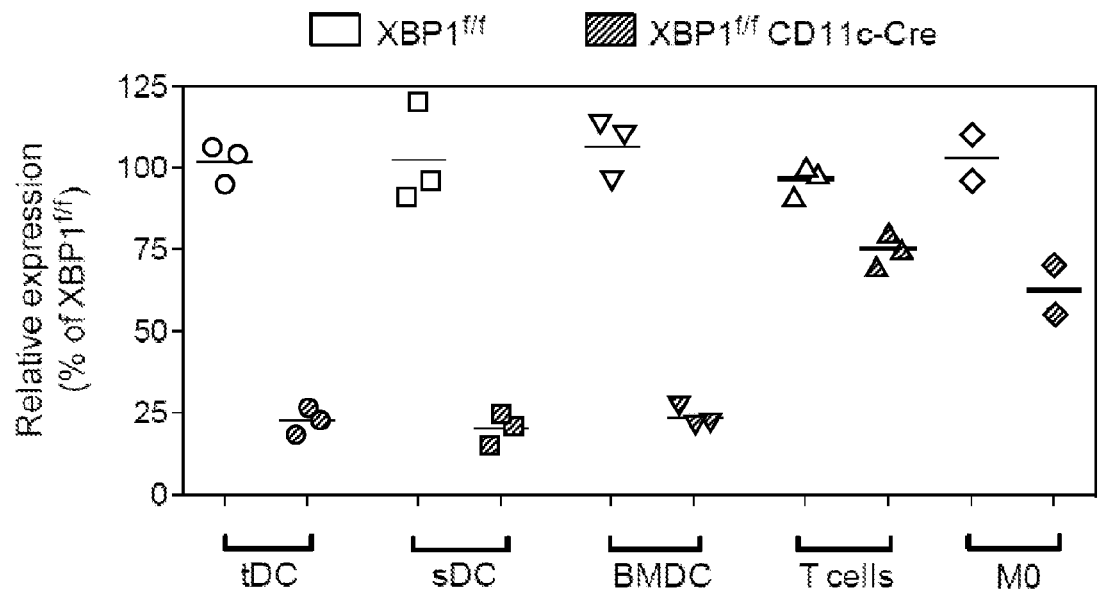
Figure 5C:
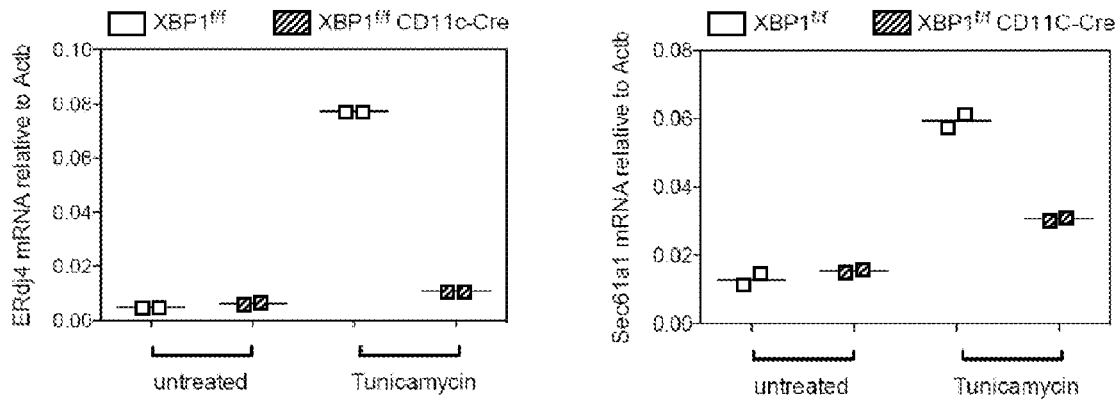

Example 3: DC-Intrinsic XBP1 is Necessary for Optimal Ovarian Cancer Progression To determine how sustained XBP1 activity in tDCs might influence malignant progression, aggressive orthotopic ovarian tumors in conditional knockout female mice lacking functional XBP1 in DCs were developed (FIG. 5). To this end, mice whose exon 2 of Xbp1 is flanked by two loxP sites (Lee et al., 2008) were crossed with mice expressing Cre recombinase under control of the integrin alpha X (Itgax) promoter (hereafter referred to as CD11c-Cre) (FIG. 5). In this system, Cre-mediated recombination is predominant in conventional DCs, while low amounts of recombination are detected in lymphocytes, NK cells and other myeloid cells (Caton et al., 2007).

tDCs were sorted from the peritoneal cavity of mice bearing metastatic ID8-VegfA-Def29b ovarian tumors for 4-5 weeks as described in FIG. 1. Total CD11c$^+$ DCs were magnetically immunopurified from spleens (sDC) or from GMCSF-polarized bone marrow cultures obtained from XBP1$^{f/f}$ (wild type) or XBP1$^{f/f}$ CD11c-Cre (conditional knockout) mice. Total splenic T cells and CD11b$^+$F4/80$^+$ macrophages (M0) were also isolated as control populations. Deletion efficiency was determined by RT-qPCR using primers that selectively amplify exon 2 of Xbp1 (see methods) (FIG. 5B). sDCs from naïve XBP1$^{f/f}$ or XBP1$^{f/f}$ CD11c-Cre mice were left untreated or stimulated for 12 h with the ER stressor Tunicamycin at 1 μg/ml. Induction of canonical XBP1 target genes ERdj4 and Sec61 upon stimulation was determined via RT-qPCR. In all cases, data were normalized to endogenous Actb expression in each sample. Data are representative of at least three independent experiments with similar results (FIG. 5C).

Figure 6H:
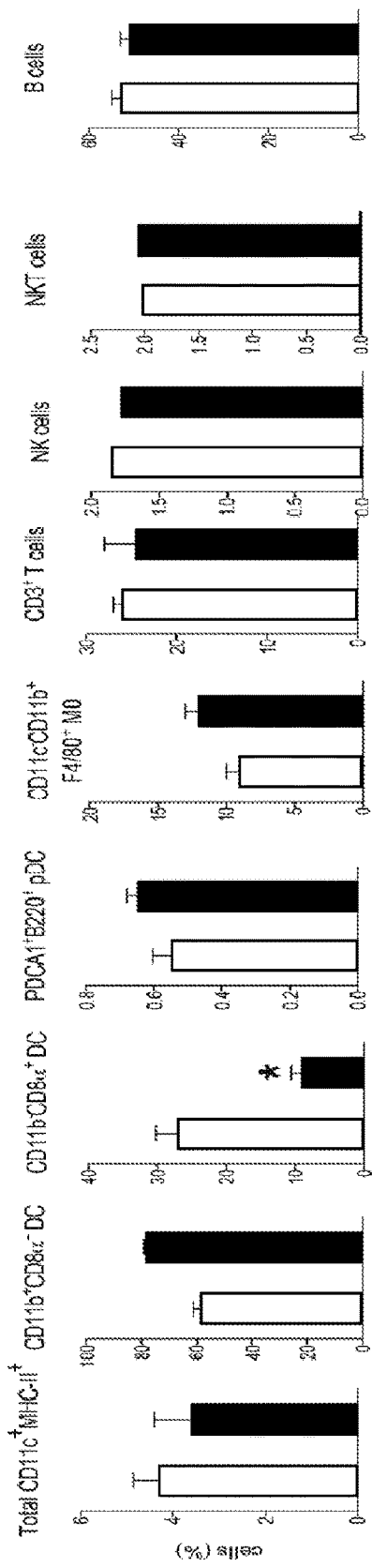
Figure 6I:
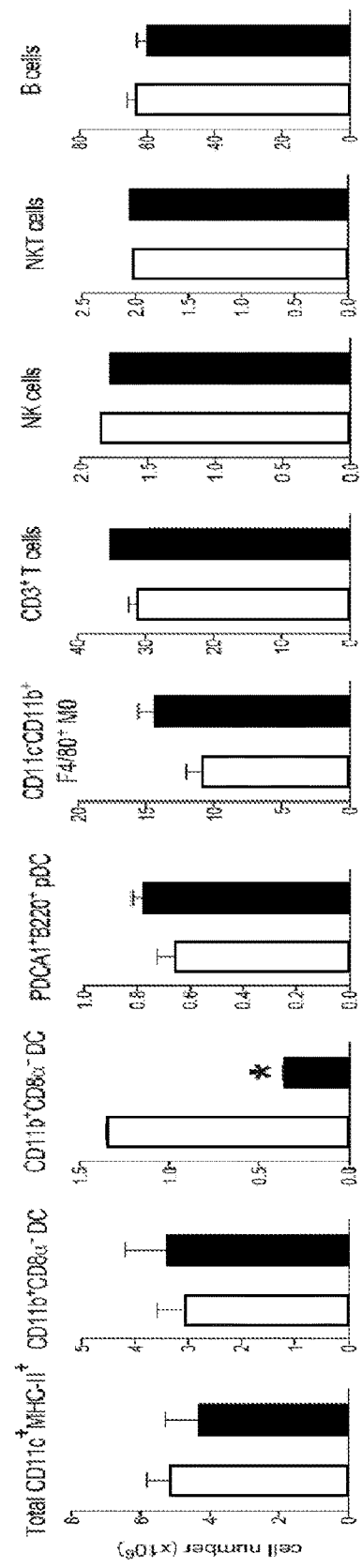
Figure 7A:
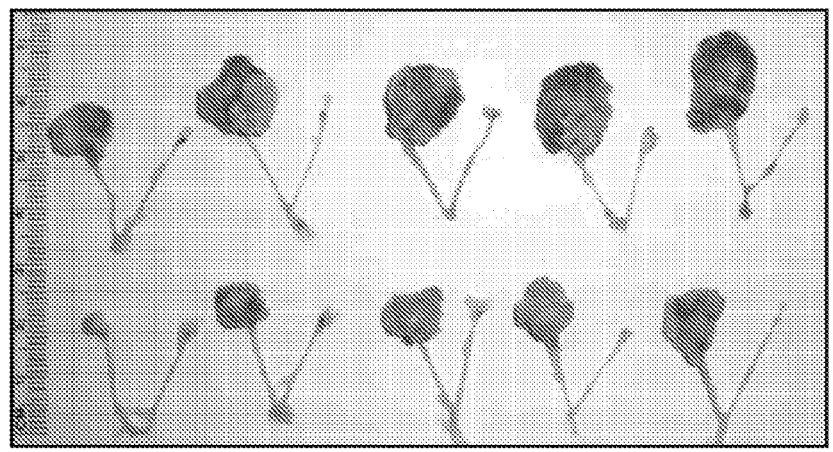
FIG. 7A-I: Shows ovarian cancer progression in hosts lacking XBP1 in DCs.
Figure 7B:
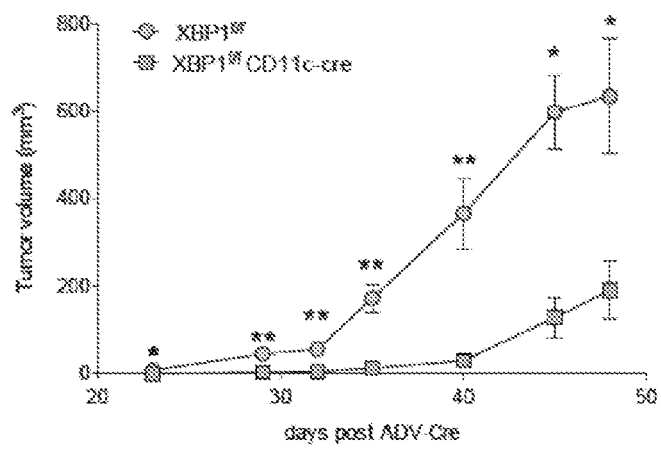
Figure 7C:
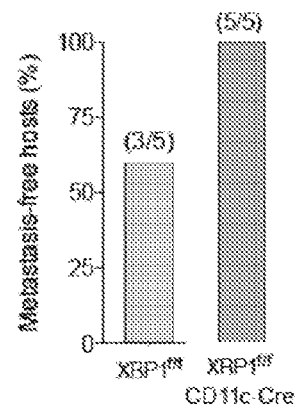

It had been previously been reported that overall DC survival was compromised upon extensive ablation of XBP1 in early hematopoietic precursors (Iwakoshi et al., 2007). In contrast, conditional deletion of XBP1 through CD11c-controlled Cre expression solely affected the proportion and number of splenic CD8α$^+$ DCs (FIG. 6). Other immune cell populations in the spleen remained unaffected (FIG. 6) and the frequency of tumor-infiltrating DCs, which are mainly CD8α$^-$ (FIGS. 1 and 6), was not altered in conditional knockout mice bearing orthotopic ovarian cancers (FIG. 6). These data suggest that XBP1 is dispensable for the optimal survival of DCs in the ovarian cancer microenvironment. Strikingly, the development and metastatic capacity of p53/K-ras-driven primary ovarian tumors (Scarlett et al., 2012) was profoundly compromised in irradiated hosts reconstituted with bone marrow from XBP1-deficient (XBP1$^{f/f}$ CD11c-Cre) donors, compared with control hosts transplanted with bone marrow from XBP1-sufficient (XBP1$^{f/f}$) littermates (FIGS. 7A-7C). These data demonstrate that XBP1 expression in CD11c$^+$ DCs is crucial for the initiation and rapid progression of ovarian tumors.

Figure 7D:
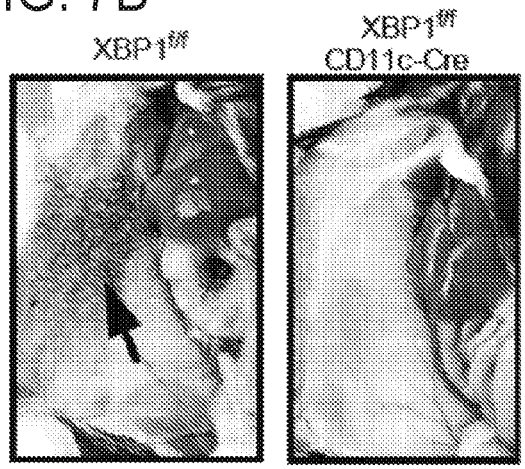
Figure 7E:
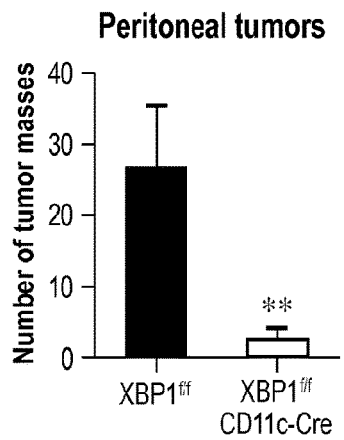
Figure 7F:
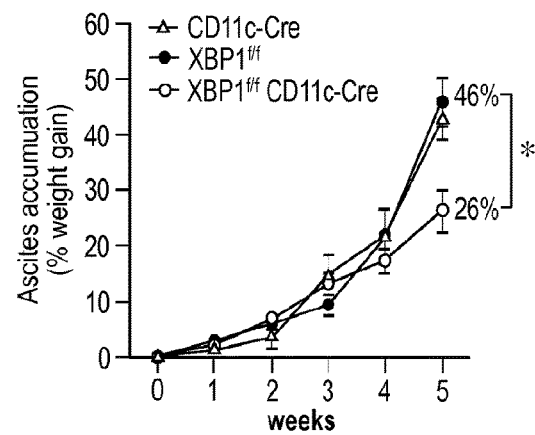
Figure 7G:
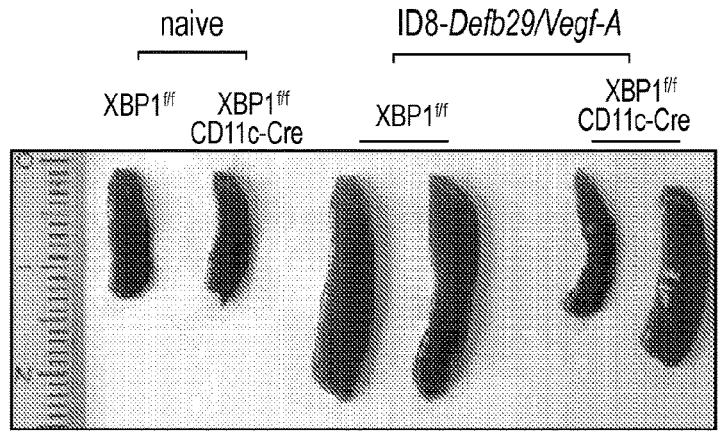
Figure 7H:
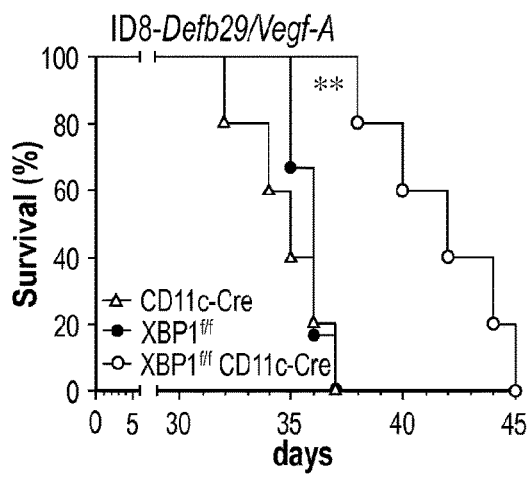
Figure 7I:
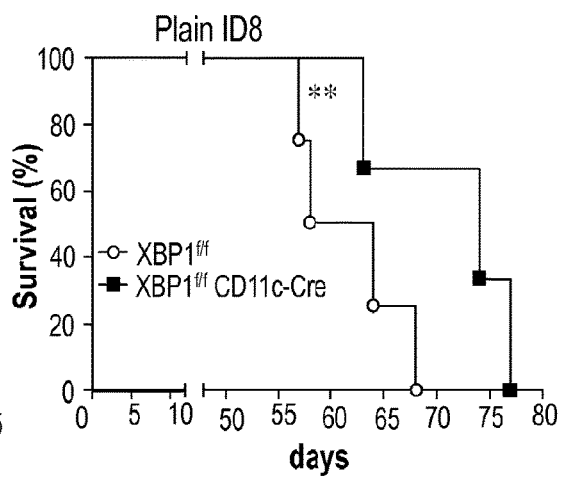

Since the vast majority of ovarian cancers are diagnosed at advanced stages, when the disease has spread throughout the peritoneal cavity, the next goal was to define how DC-derived XBP1 impacts the progression of orthotropic tumors that closely recapitulate the physiopathology of human metastatic ovarian cancer (Conejo-Garcia et al., 2004). Notably, ovarian cancer-bearing female mice lacking functional XBP1 in DCs demonstrated reduced peritoneal tumor burden (FIGS. 7D and 7E), impaired ascites accumulation (FIG. 7F), and diminished tumor-induced splenomegaly (FIG. 7G) compared with control gene-sufficient (XBP1$^{f/f}$) littermates. Consequently, tumor-bearing mice deficient for XBP1 in DCs showed a marked increase in survival compared with control littermates (FIG. 7H). Similar survival results were observed in XBP1$^{f/f}$ CD11c-Cre mice developing parental orthotopic ovarian tumors (Roby et al., 2000) that do not ectopically express Defb29 and Vegf-A (FIG. 7I). Together, these results demonstrate for the first time that XBP1 expression in DCs is necessary for the aggressive and accelerated progression of primary and metastatic ovarian cancers in preclinical models of disease.

Example 4: XBP1 Activation Disrupts Lipid Homeostasis in DCs

Figure 8B:
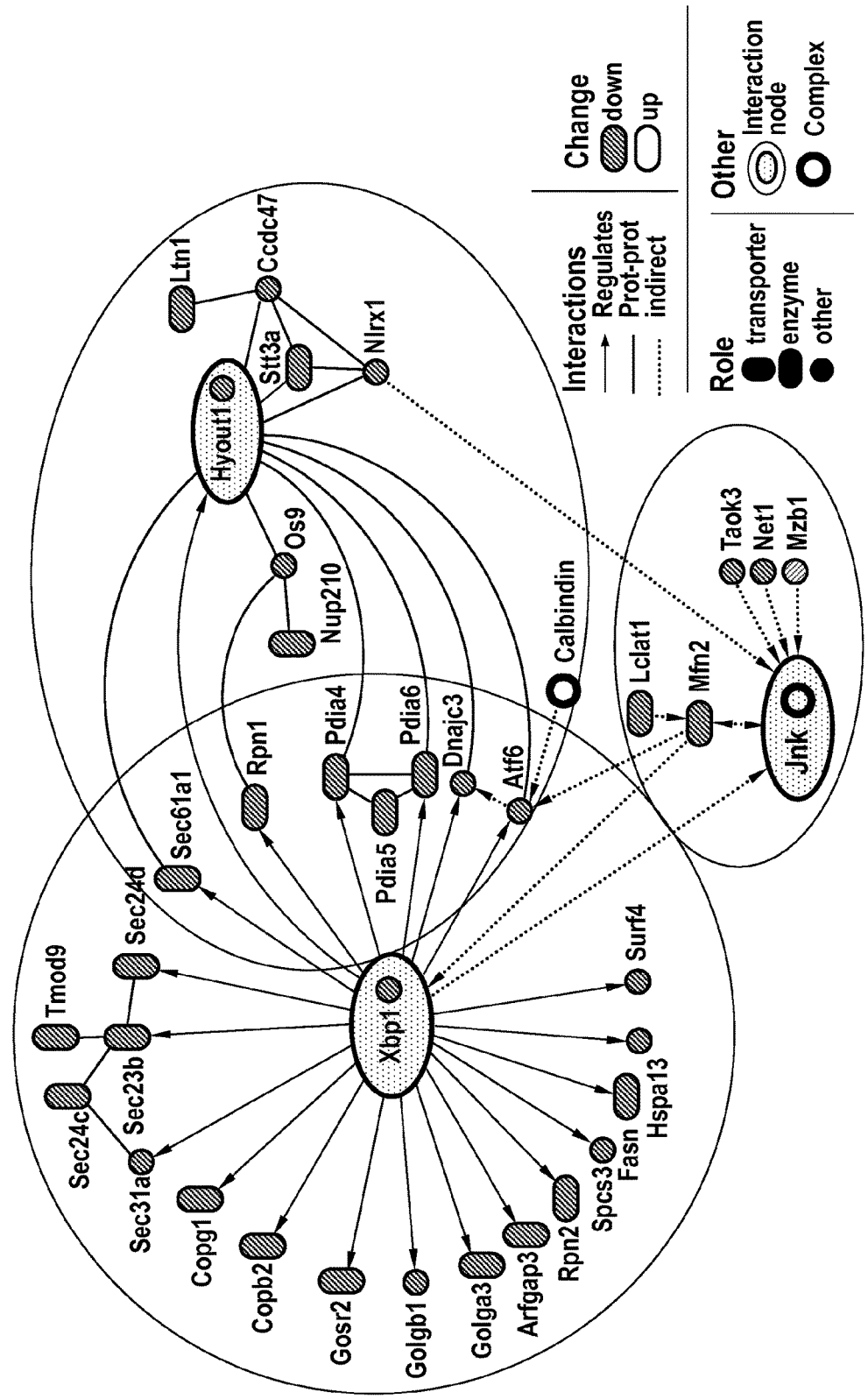
Figure 8C:
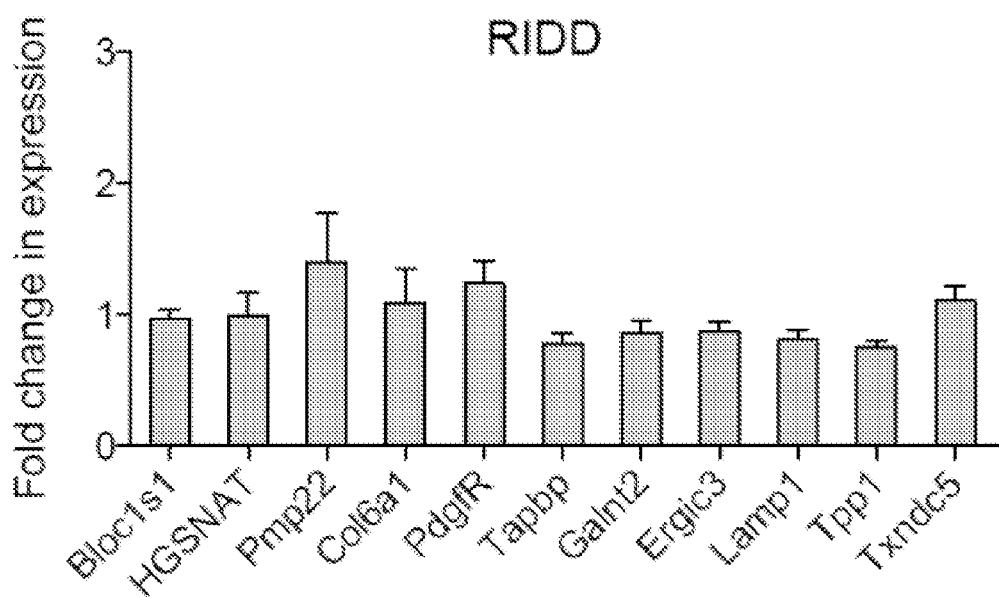
Figure 9A:
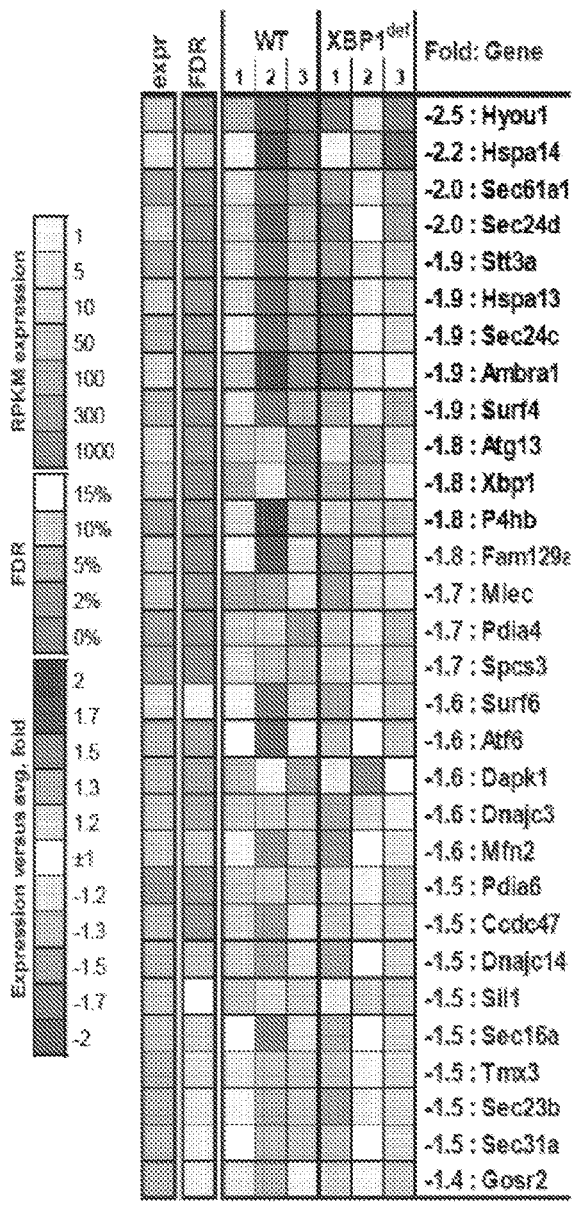
Figure 9B:
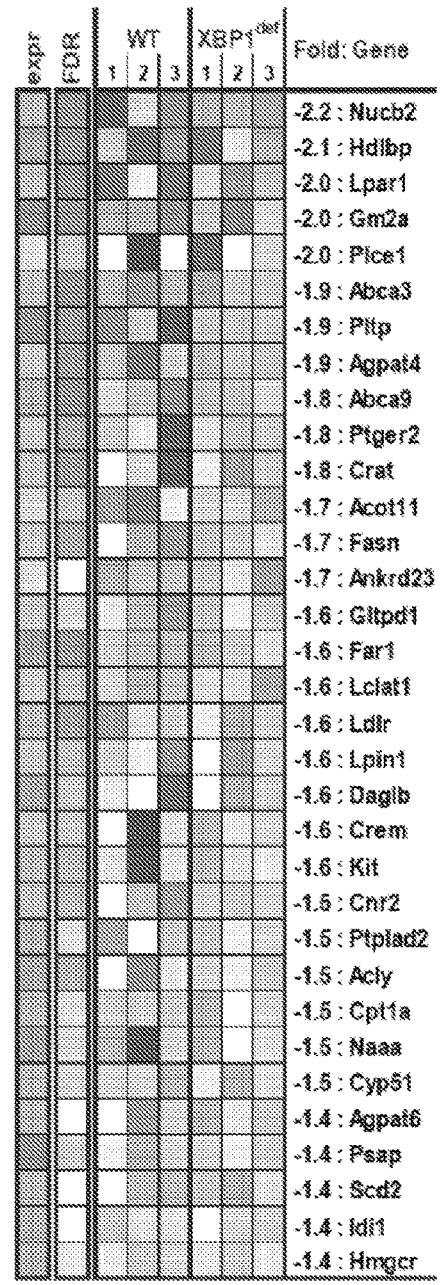
Figure 10A:
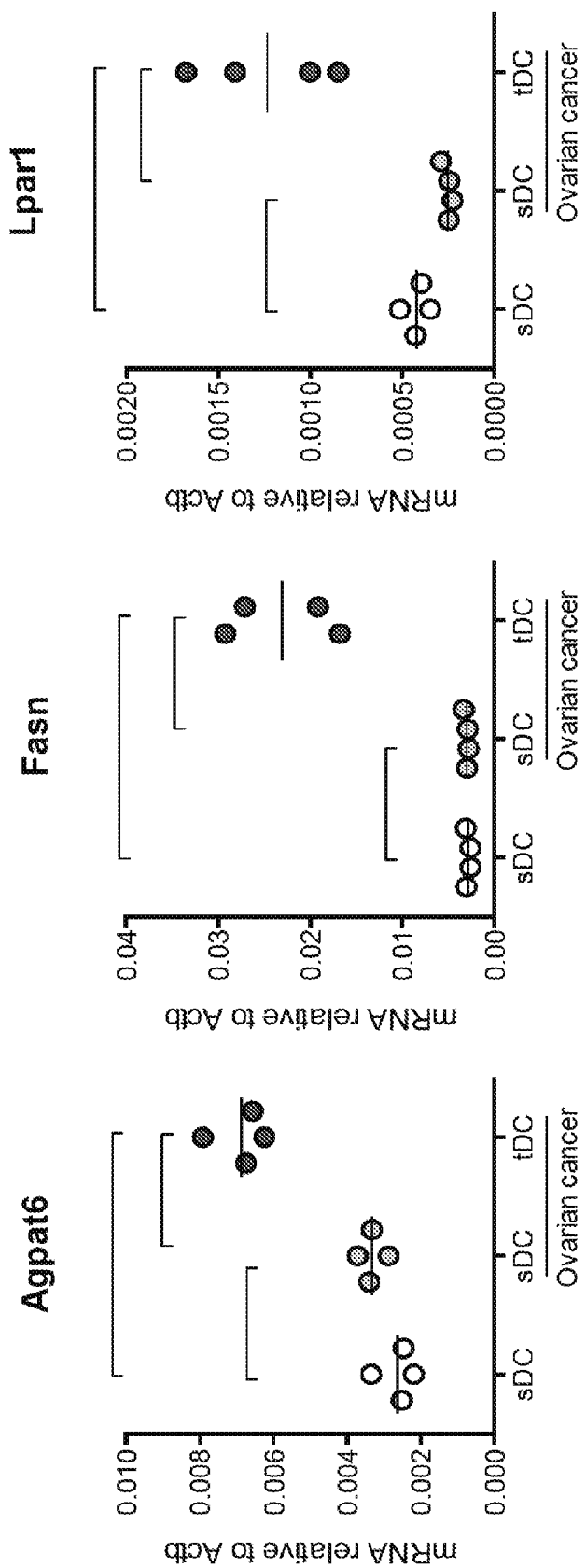
FIG. 10A-F: Shows ER stress and lipid accumulation in tDCs.
Figure 10B:
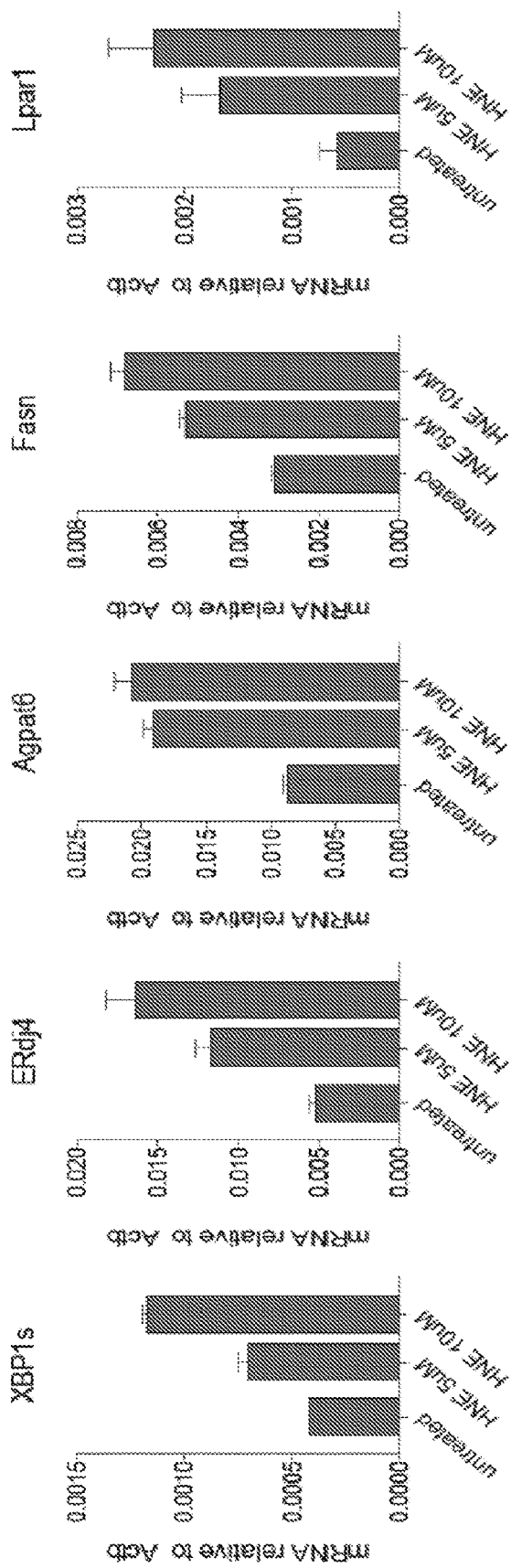
Figure 10C:
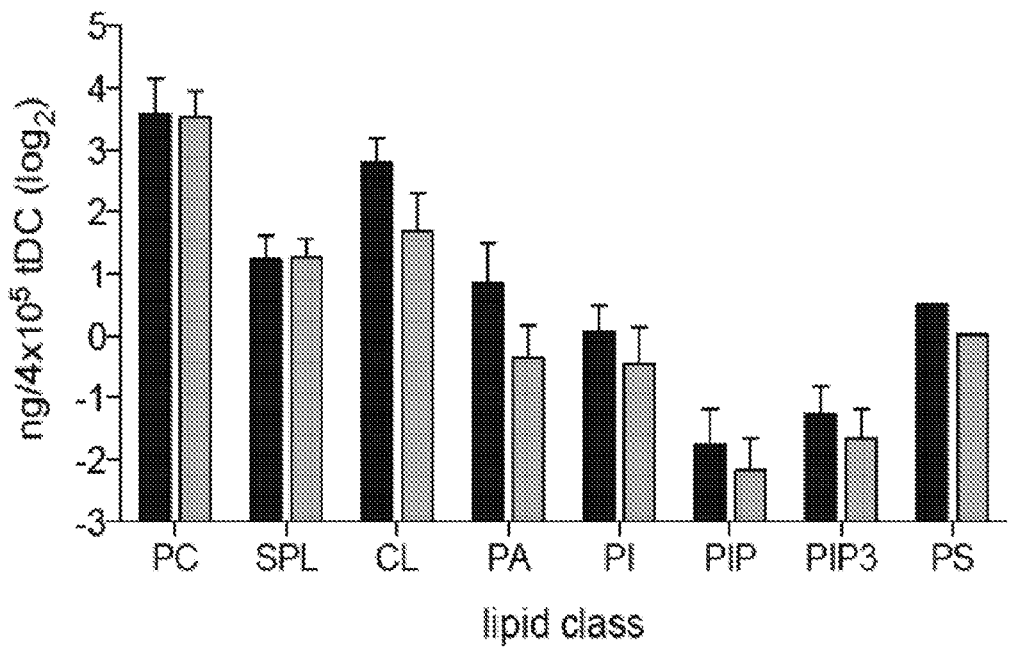
Figure 10D:
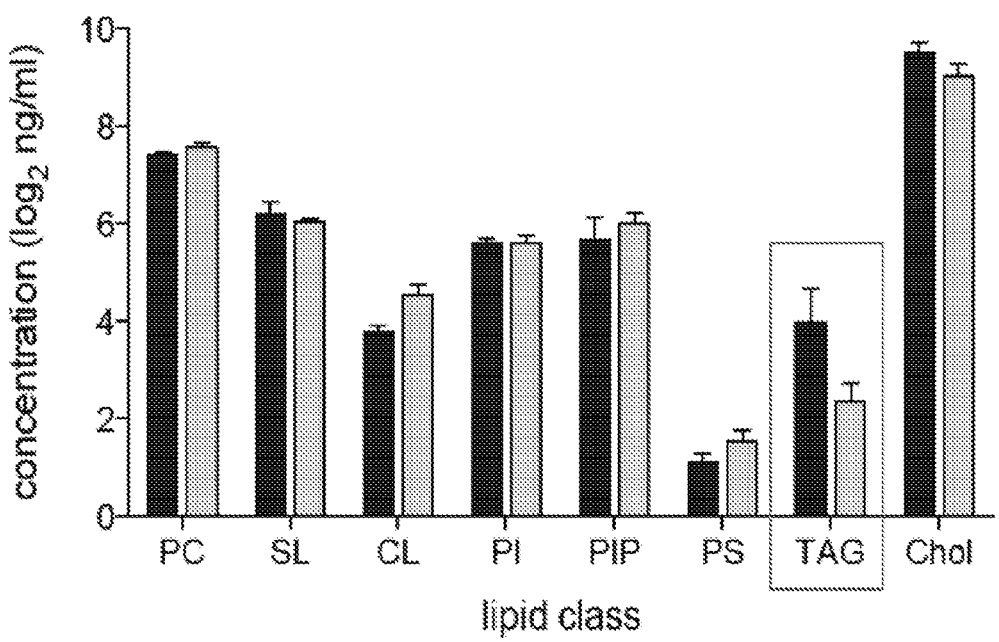
Figure 10E:
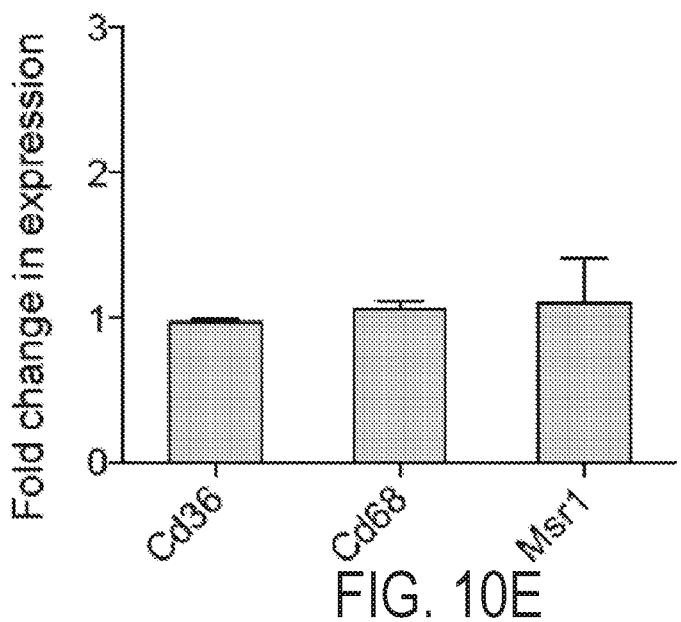
Figure 10F:
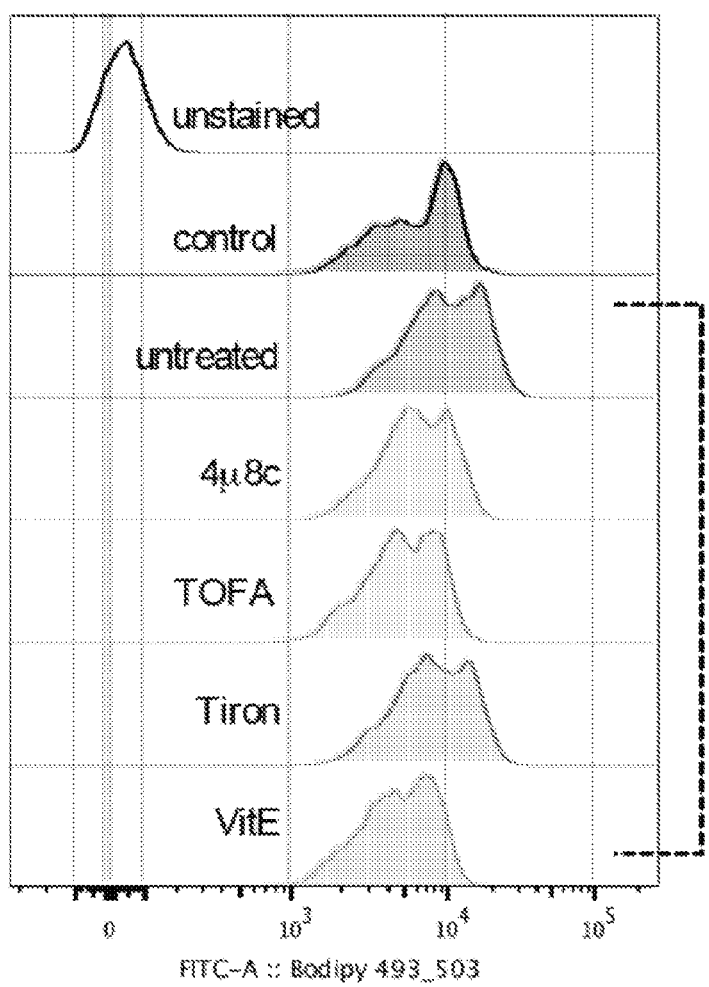

To elucidate how XBP1 confers pro-tumorigenic activity in ovarian cancer-associated DCs, a comparison of the transcriptional profile of wild type vs. XBP1-deficient DCs residing in malignant ovarian cancer ascites was performed. 416 genes that were significantly downregulated were identified, while 237 genes showed significantly higher expression due to XBP1 deficiency (Table 2). Significantly altered gene subsets were analyzed to identify transcriptional regulators that may explain the observed mRNA changes. Several predicted affected regulators were identified (FIG. 8A) with the expected XBP1 as a top hit. Additionally, XBP1 was a key node in the top gene network found from the data (FIG. 8B). Confirming sustained ER stress in DCs infiltrating ovarian cancer, multiple direct XBP1 target genes and genes implicated in the unfolded protein response (Acosta-Alvear et al., 2007; Lee et al., 2003b) were markedly repressed in XBP1-deficient tDCs (FIG. 9A). Expression of known Regulated IRE-1α-dependent Decay (RIDD) target mRNAs (Hetz et al., 2013; Hollien et al., 2009) was indistinguishable between wild type and XBP1-deficient tDCs (FIG. 8C), indicating that IRE-1α is not artificially overactivated in this cell type due to the absence of functional XBP1 (So et al., 2012). A search was then performed for any biological processes affected by XBP1-deficiency and 4 significantly enriched functional categories were found (FIG. 8D). Of particular interest, tDCs devoid of XBP1 displayed marked downregulation of multiple genes involved in lipid metabolic pathways (FIG. 9B). In light of the strong association between enhanced lipid accumulation and DC dysfunction in cancer (Herber et al., 2010; Ramakrishnan et al., 2014), the role of XBP1 as a potential mediator of this process was investigated. Consistent with sustained ER stress at tumor locations, ovarian cancer-associated DCs exhibited severe upregulation of multiple XBP1-controlled lipid metabolism genes (FIG. 9B), including Agpat6, Fasn and Lpar1, compared with control DCs in lymphoid tissue (FIG. 10A). Of note, these lipid biosynthetic genes were rapidly upregulated in naïve sDCs exposed to the XBP1-activating lipid peroxidation byproduct 4-HNE (FIG. 10B). Most importantly, ovarian cancer-associated DCs lacking XBP1 showed reduced intracellular lipid content compared with their wild type counterparts (FIG. 9C). Further supporting these findings, XBP1-deficient tDC demonstrated a marked decrease in the number of cytosolic lipid droplets (FIGS. 9D and 9E) as well as reduced intracellular levels of total triglycerides (FIG. 9F) compared with XBP1-sufficient tDC. Other lipid classes remained unaffected in tDCs lacking XBP1 (FIG. 10C) and these observations were confirmed by analyzing cell-free ascites supernatants (FIG. 10D). Decreased intracellular lipid content in XBP1-deficient tDCs did not occur due to defective expression of genes encoding scavenger receptors implicated in extracellular lipid uptake, including Cd36, Cd68 and Msr1 (FIG. 10E). Notably, exposure to cell-free ovarian cancer ascites augmented the intracellular lipid content of tDCs and this process that was prevented by treatment with TOFA, an inhibitor of fatty acid synthesis blocking the synthesis of malonyl-CoA by acetyl-CoA carboxylase (FIGS. 9G and 10F). Pharmacological inhibition of IRE-1α/XBP1 activation using 4μ8c also restricted the observed ascites-induced lipid biogenesis in tDCs (FIGS. 9G and 10F). In addition, consistent with the function of ROS as key generator of XBP1-activating 4-HNE (FIG. 4), reduced intracellular lipid content was also evidenced in tDCs treated with the global ROS scavenger Vitamin E, but not with the superoxide-specific scavenger Tiron (FIGS. 9G and 10F). Taken together, the transcriptional and functional data indicate that sustained activation of ER stress sensor XBP1 disrupts intracellular lipid homeostasis in ovarian cancer-associated DCs.

Example 5: XBP1-Deficient tDCs Support T Cell Activation

Figure 11A:
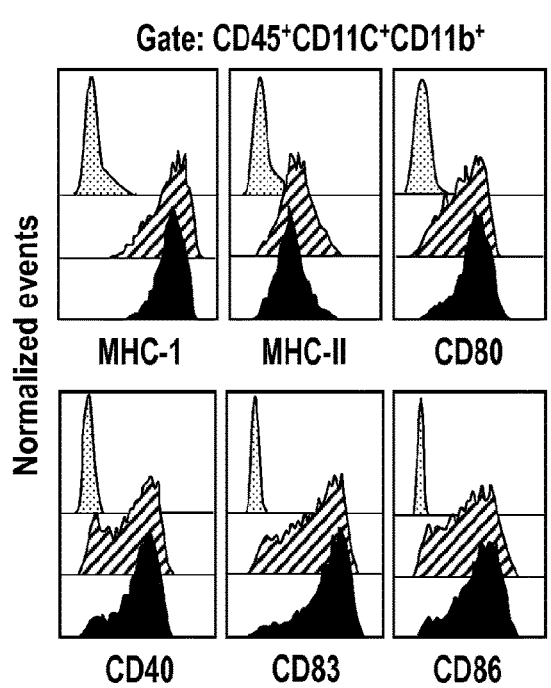
FIG. 11A-F: Shows that XBP1 promotes immune tolerance by DCs in the ovarian cancer microenvironment.
Figure 11B:
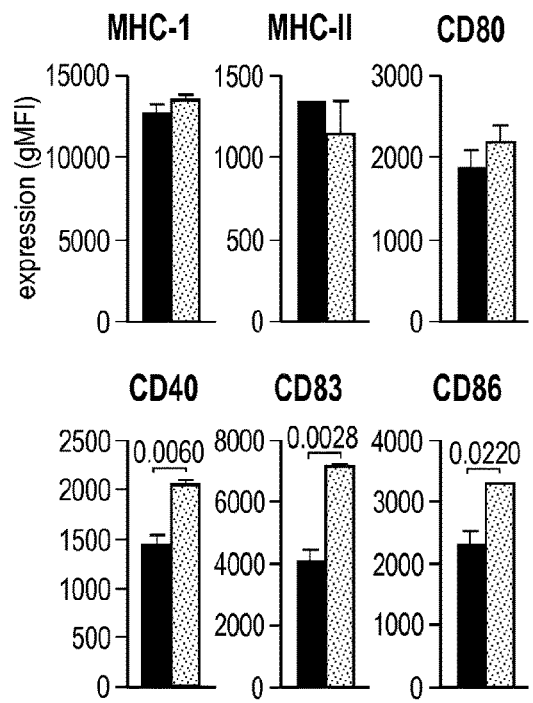
Figure 11C:
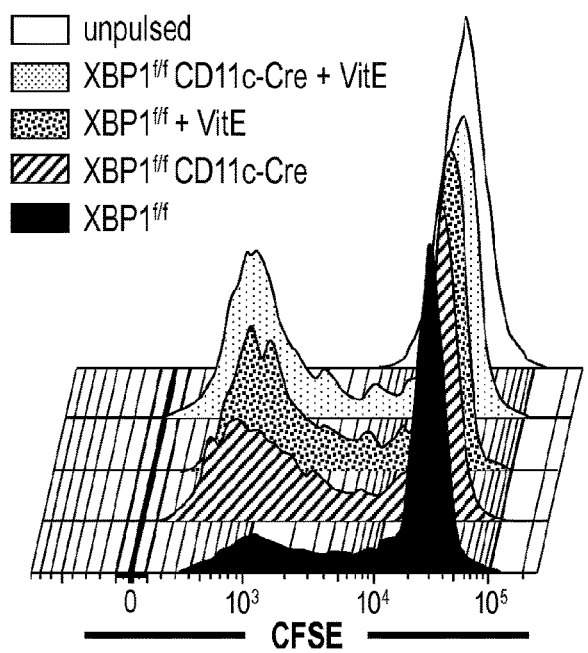
Figure 11D:
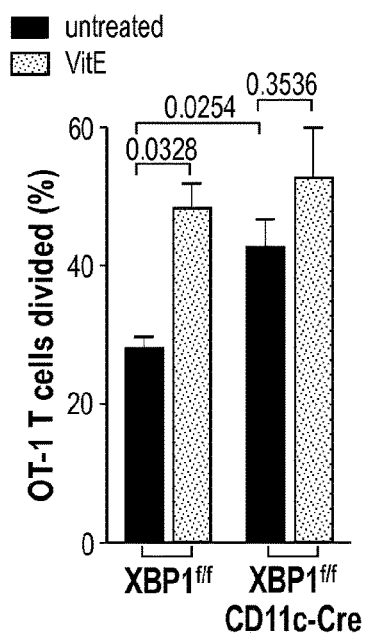
Figure 11E:
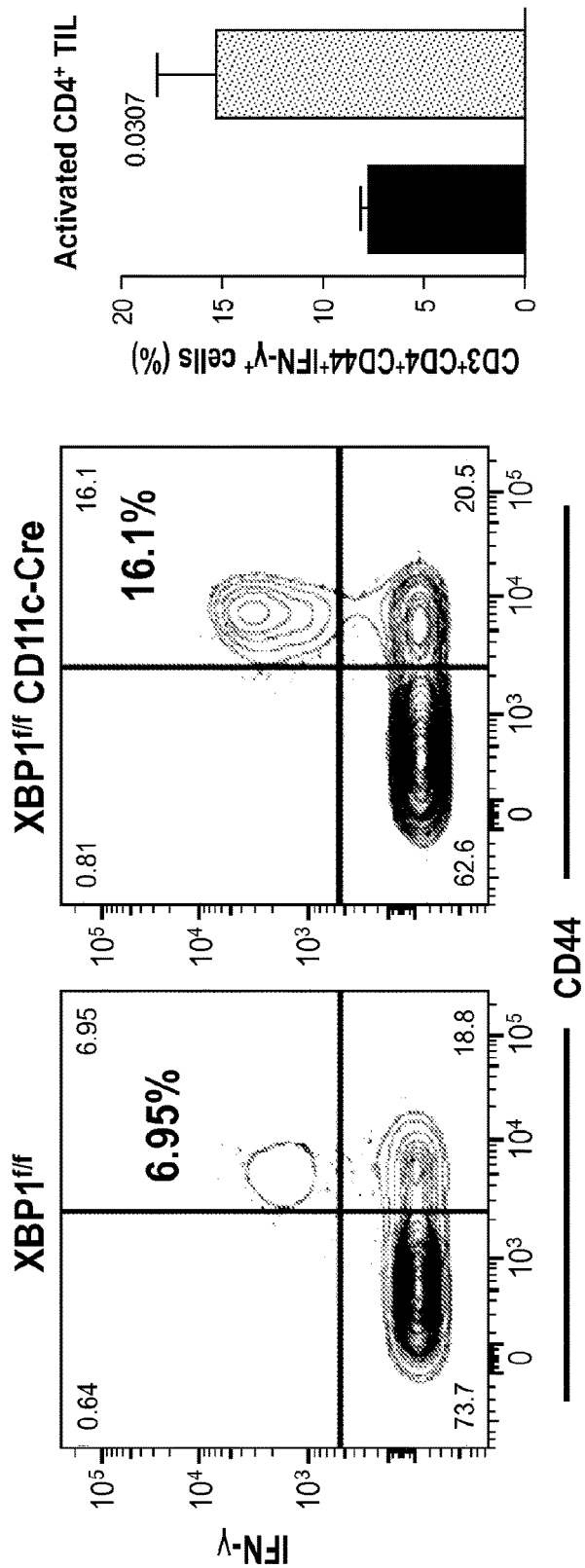
Figure 11F:
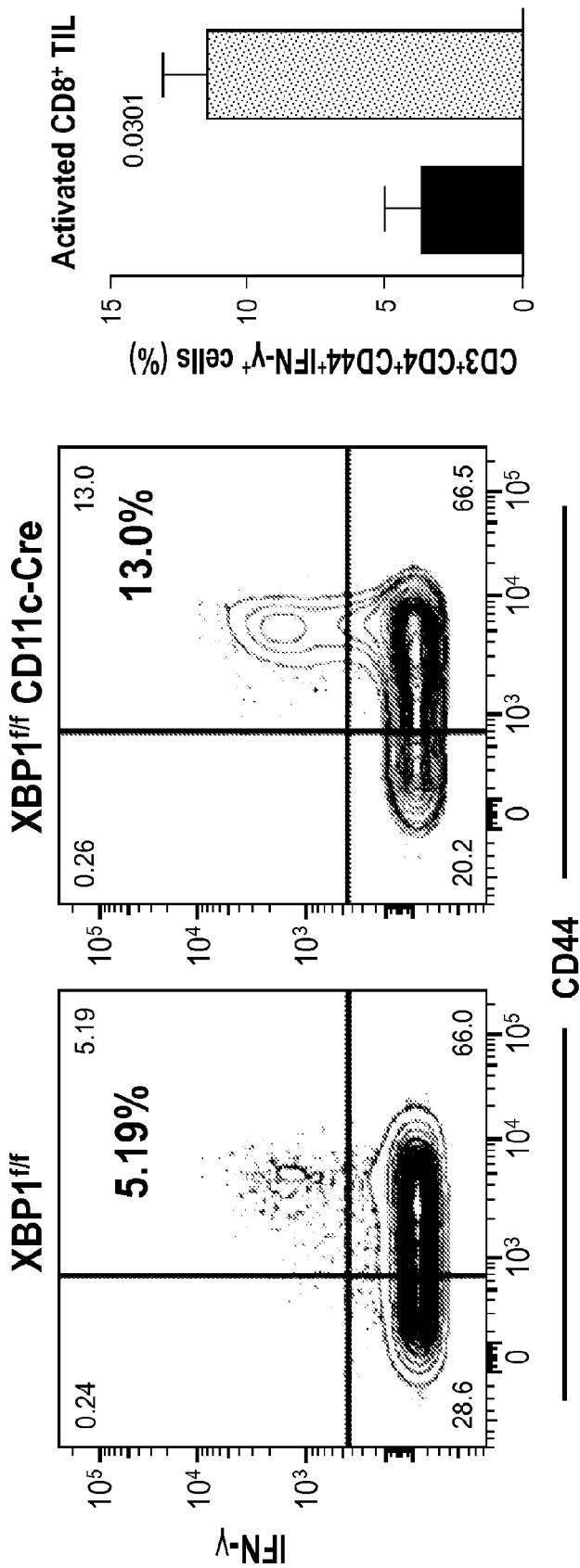
Figure 12A:
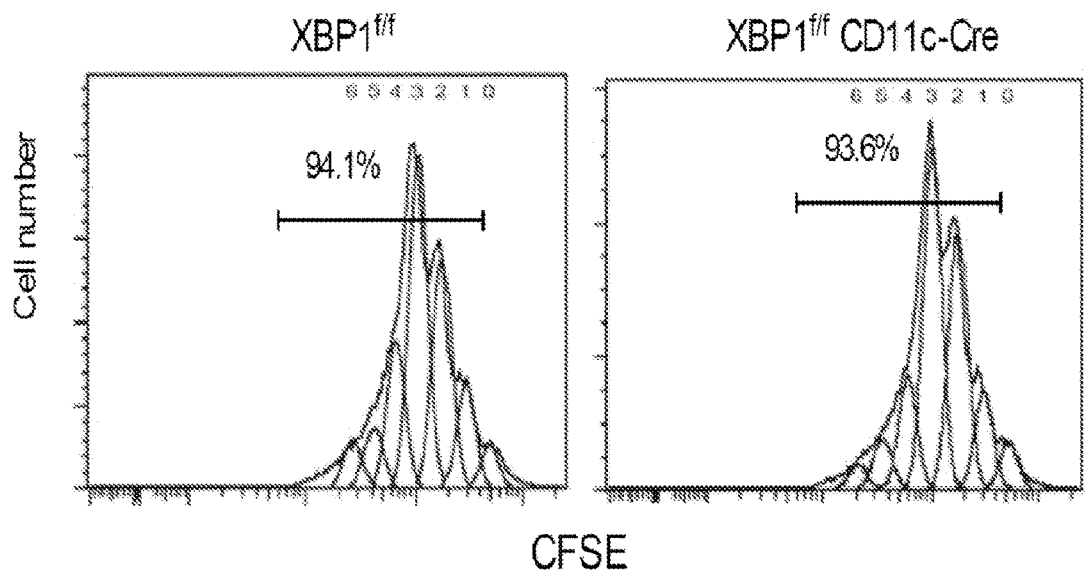
FIG. 12A-B: Shows antigen presentation by XBP1-deficient sDCs
Figure 12B:
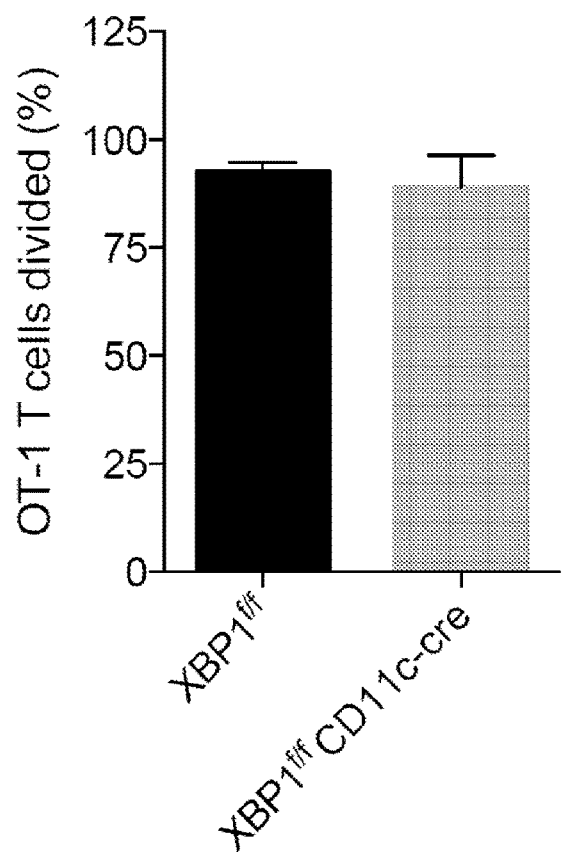

Aberrant lipid accumulation by cancer-associated DCs has been demonstrated to obstruct their normal antigen processing and presentation capacity (Herber et al., 2010; Ramakrishnan et al., 2014). Whether XBP1-deficient tDCs with reduced levels of intracellular lipids might support rather than repress T cell activation and function at tumor sites was investigated. While surface expression of MHC molecules and CD80 remained unaltered, tDCs devoid of XBP1 demonstrated higher levels of costimulatory receptors CD40, CD83 and CD86 (FIGS. 11A and 11B). XBP1-deficiency did not alter the antigen-presenting capacity of control CD8α$^-$ sDCs (FIG. 12). However, XBP1-deficient tDCs pulsed with full-length OVA in the presence of cell-free malignant ascites more efficiently induced the expansion of OT-1 T cells compared with wild type tDCs (FIGS. 11C and 11D). Consistent with impaired lipid accumulation upon global ROS scavenging and IRE-1α/XBP1 inhibition (FIG. 9G), pre-treatment of regulatory wild type tDC with Vitamin E phenocopied the enhanced antigen-presenting capacity exhibited by XBP1-deficient tDCs in this in vitro assay (FIGS. 11C and 11D). Further supporting these findings, conditional knockout mice developing aggressive orthotopic ovarian tumors demonstrated a marked increase in the proportion of infiltrating CD44$^+$IFNγ-secreting CD8$^+$ and CD4$^+$ T cells at tumor sites compared with XBP1-sufficient control littermates (FIGS. 11E and 11F). Together, these data indicate that constitutive XBP1 activation promotes intracellular lipid accumulation in and immune tolerance by ovarian cancer-associated DCs.

Figure 13A:
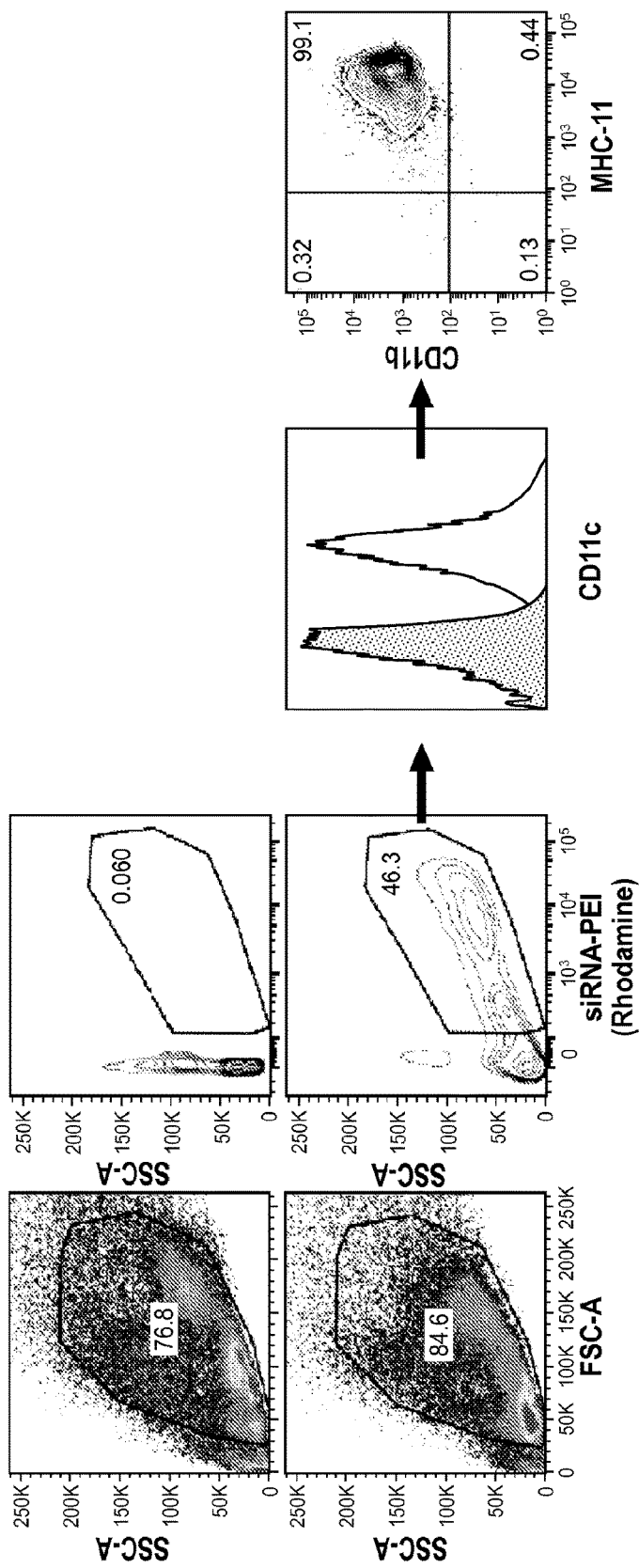
FIG. 13A-C: shows biodistributin and silencing activity of intraperitoneally injected siRNA-PEI nanoparticles
Figures 13B, 13C:
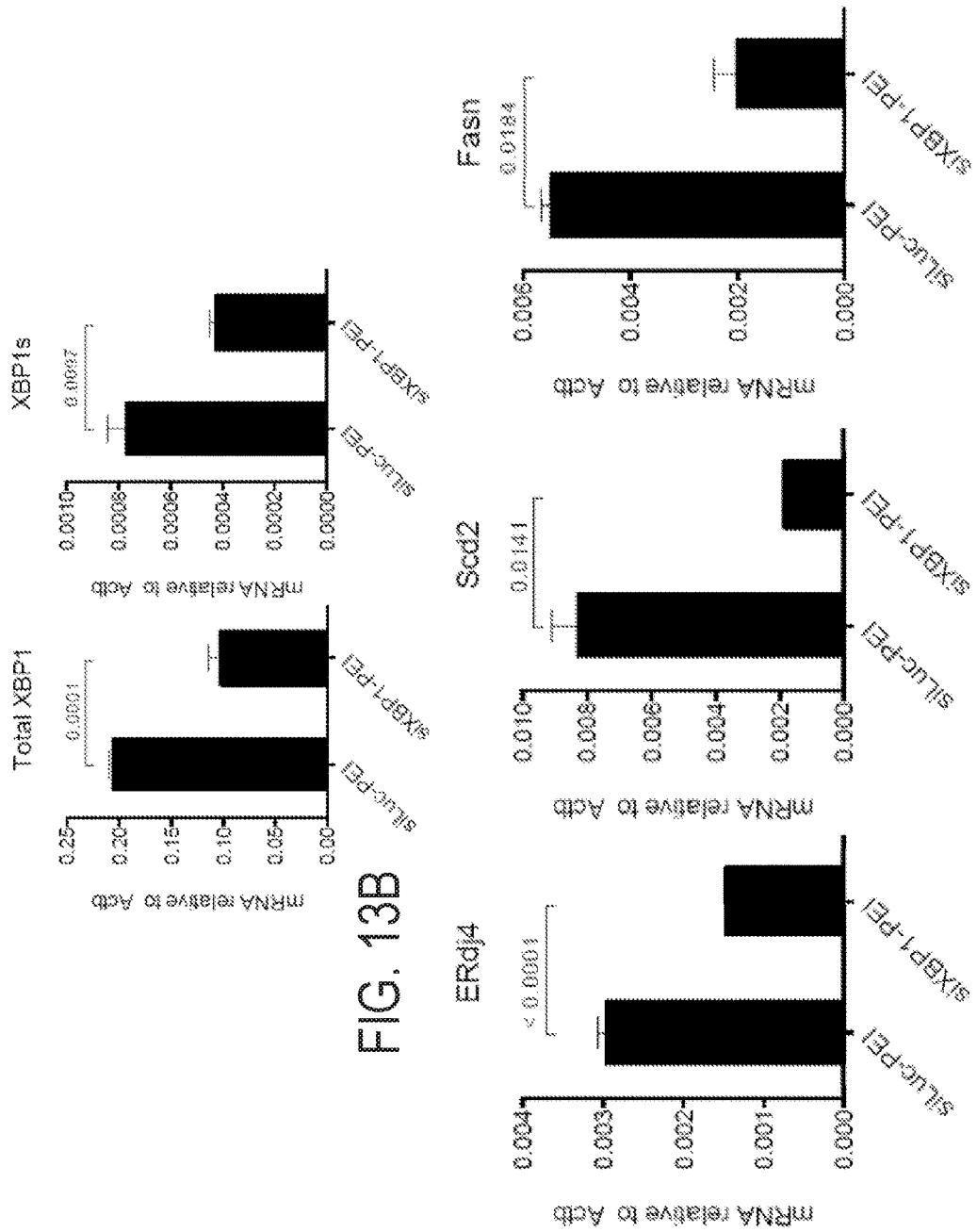
Figure 14A:
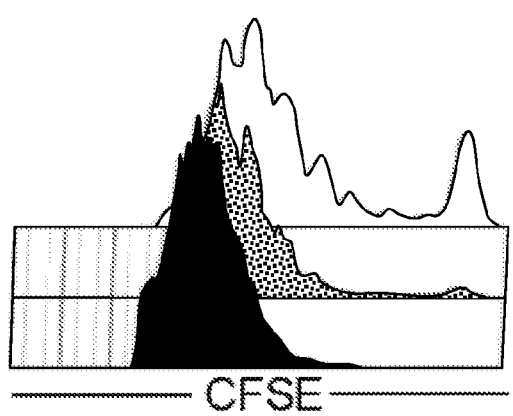
FIG. 14A-J: Shows therapeutic silencing of XBP1 improves tDC function and triggers protective anti-tumor immunity.
Figure 14B:
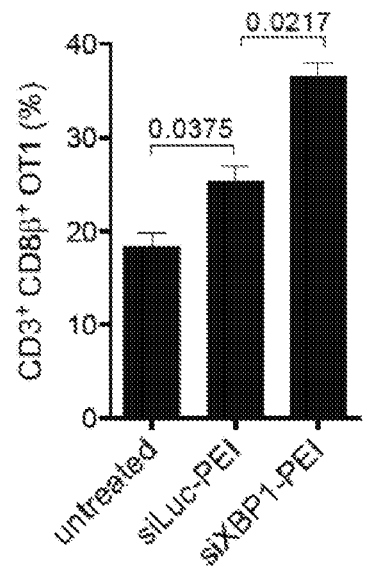
Figure 14C:
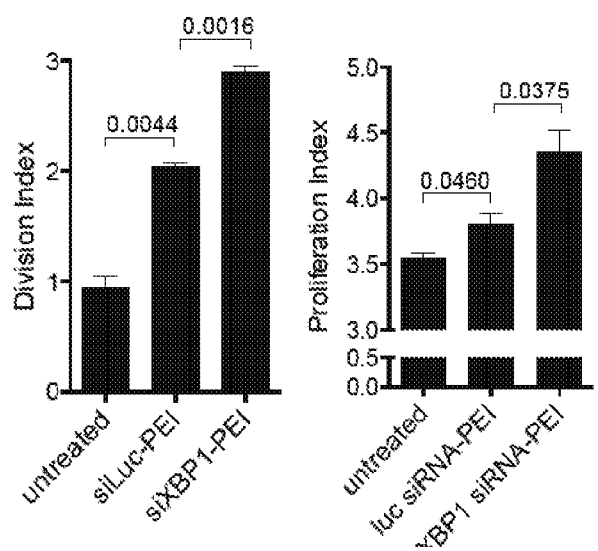
Figure 14D:
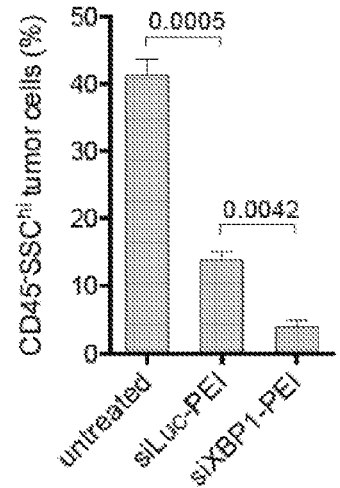
Figure 14E:
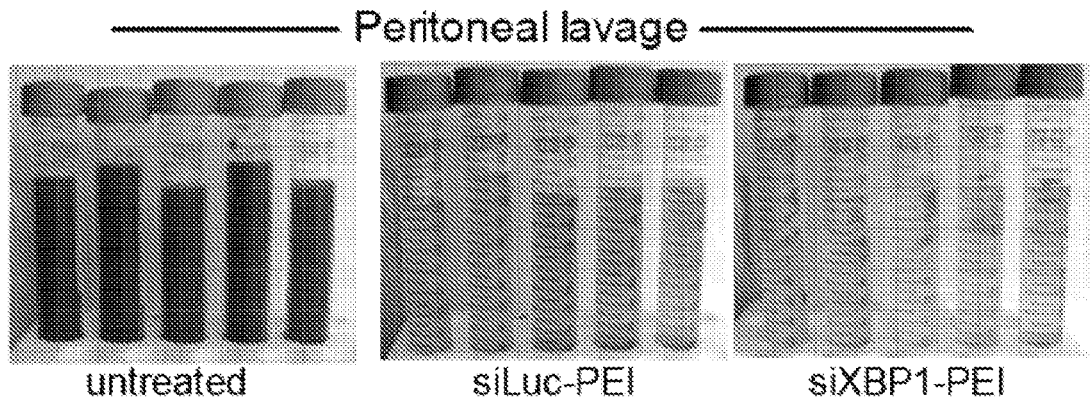
Figure 14F:
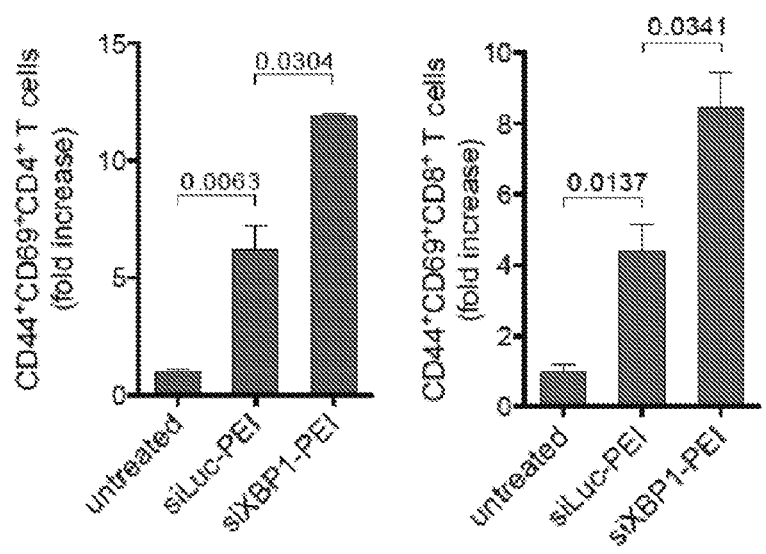
Figure 14G:
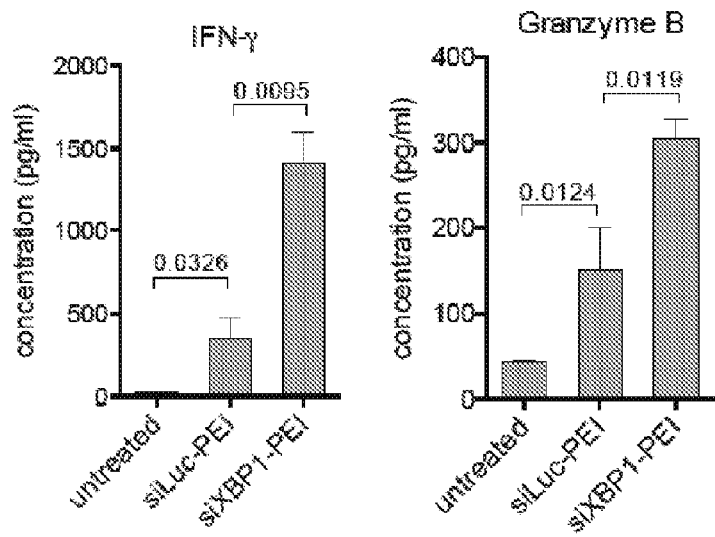
Figure 14H:
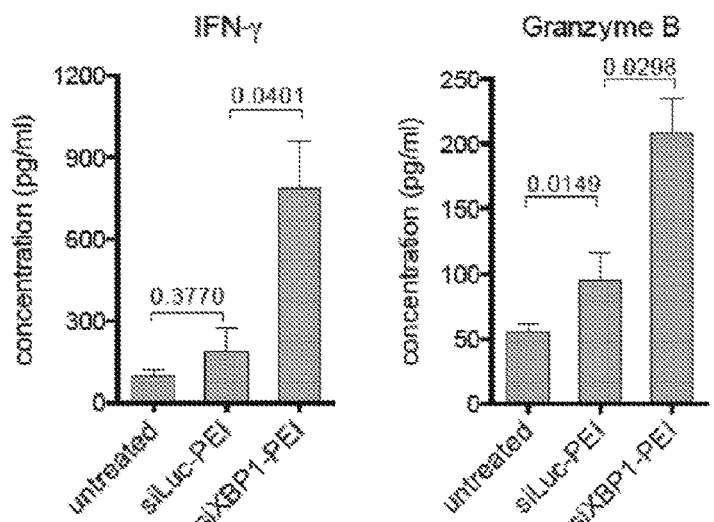

Example 6: Therapeutic XBP1 Silencing in tDCs Extends Host Survival by Inducing Anti-Tumor Immunity T cells are the only immune population known to exert significant pressure against ovarian cancer progression (Callahan et al., 2008; Curiel et al., 2003; Hamanishi et al., 2007; Han et al., 2008; Sato et al., 2005; Zhang et al., 2003). Indeed, it has been demonstrated that the magnitude of intra-tumoral T cell infiltration strongly correlates with a better outcome in ovarian cancer patients (Zhang et al., 2003). To investigate whether targeting XBP1 function in vivo and in situ could be used to restore the immunogenic attributes of ovarian cancer-associated DCs and hence, promote the function of anti-tumor T cells, polyethylenimine (PEI)-based nanoparticles encapsulating siRNA were utilized (Cubillos-Ruiz et al., 2012; Cubillos-Ruiz et al., 2009). Wild type C57BL/6 female mice were injected with 1-2× 10$^6$ ID8-Defb29/Vegf-A ovarian cancer cells and mice received a single injection of control (luciferase-specific) or XBP1-targeting siRNA encapsulated in rhodamine-labeled PEI-based nanocomplexes 3-4 weeks later (FIG. 13). These nanocomplexes are preferentially and avidly engulfed by abundant phagocytic tDCs upon intraperitoneal (i.p.) injection, a process that enables selective in vivo gene silencing in this leukocyte subset (Cubillos-Ruiz et al., 2009). Importantly, PEI-based nanoparticles inherently activate ovarian cancer-associated DCs by triggering TLR signaling and therefore exhibit potent immunoadjuvant activity against tumors (Cubillos-Ruiz et al., 2009). Confirming our previous findings (Cubillos-Ruiz et al., 2012; Cubillos-Ruiz et al., 2009), nanoparticles were selectively taken-up by tDCs present in malignant ascites of mice bearing metastatic ovarian cancer (FIG. 13A). PEI-based nanocomplexes delivering Xbp1-specific siRNA induced 50-60% gene silencing in target tDC compared with control nanoparticles encapsulating luciferase-targeting siRNA (FIG. 13B). The functional effects of gene silencing were confirmed by the decreased expression of the canonical XBP1 target ERdj4, as well as lipid biosynthesis-related Fasn and Scd2 in tDCs engulfing Xbp1-specific nanocomplexes (FIG. 13C). Due to selective tDC targeting in vivo, Xbp1 mRNA levels remained unaltered in non-DC leukocytes or cancer cells of the tumor microenvironment after nanoparticle injection (not shown). Supporting the findings using tDC from conditional XBP1 knockout mice, the in vivo proliferation of adoptively transferred CFSE-labeled OT-1 T cells in the ovarian cancer microenvironment was significantly enhanced in mice pulsed i.p. with full-length OVA when XBP1 expression was specifically silenced in tDCs (FIGS. 14A-14C). Therapeutic administration of siRNA-PEI nanocomplexes selectively targeting tDC-derived XBP1 further reduced the total number of metastatic cancer cells in the peritoneal cavity (FIG. 14D) and consequently diminished the accumulation of malignant ascites (FIG. 14E). Importantly, these effects occurred concomitantly with the enhanced infiltration of endogenous antigen-experienced/activated T cells at tumor locations compared with treatments using control nanoparticles (FIG. 14F). Indeed, silencing XBP1 expression in ovarian cancer-associated DCs markedly enhanced the capacity of infiltrating T cells to respond to tumor antigens, as evidenced by ex vivo IFN-γ and Granzyme B secretion assays using bone marrow-derived DCs pulsed with tumor antigens (FIG. 14G). These data reinforce the concept that abrogating XBP1 function in tDCs drives the activation and expansion of endogenous anti-tumor T cells at tumor sites. Splenic T cells isolated from mice treated with XBP1-silencing nanocomplexes also demonstrated improved responses upon exposure to tumor antigens in similar re-call assays (FIG. 14H), indicating development of enhanced anti-tumor memory responses after targeting XBP1 in tDCs. Together, these results demonstrate that therapeutic silencing of XBP1 in ovarian cancer-associated DCs can boost endogenous anti-tumor immune responses in vivo.

Figure 14I:
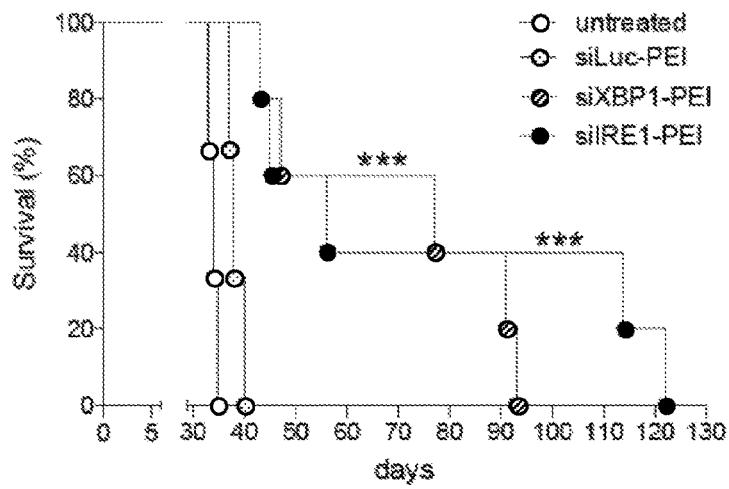
Figure 14J:
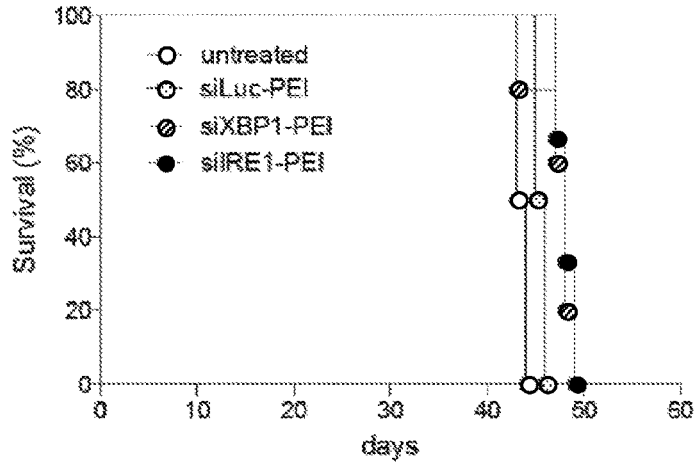

To determine whether selective abrogation of the IRE-1α/XBP1 pathway in tDCs had significant therapeutic effects, mice bearing aggressive orthotopic ovarian tumors were i.p. treated with saline, non-targeting or gene-specific siRNA-PEI nanocomplexes. Treatments started 12 days after tumor implantation and injections were administered every 4 days for a period of 3 weeks. Strikingly, wild type mice treated with either XBP1- or IRE-1α-silencing nanoparticles demonstrated a remarkable increase in survival compared with control groups (FIG. 14I). Most importantly, Rag2-deficient hosts bearing ovarian tumors were totally unable to respond to this treatment, demonstrating that an intact adaptive immune system is necessary for the observed therapeutic benefit (FIG. 14J). Together, these data demonstrate that targeting the IRE-1α/XBP1 branch of the ER stress response in tDCs induces protective anti-tumor immune responses against otherwise lethal ovarian cancer.

TABLE 1

Primers

| Species | Gene | Oligo name | Sequence 5'-3' | Purpose |
|---|---|---|---|---|
| HUMAN | ACTB | bAct-F | GCGAGAAGATGACCCAGATC | RT-qPCR |
| | | bAct-R | CCAGTGGTACGGCCAGAGG | |
| HUMAN | DDIT3/CHOP | bCHOP-F | CTGCTTCTCTGGCTTGGCTG | RT-qPCR |
| | | bCHOP-R | GCTCTGGGAGGTGCTTGTGA | |
| HUMAN | XBP1 | hXBP1-SA-F | CCTGGTTGCTGAAGAGGAGG | Splicing Assay |
| | | hXBP1-SA-R | CCATGGGGAGTTCTGGAG | |
| Mouse | Xbp1 | Xbp1-SA-F | ACACGTTTGGGAATGGACAC | Splicing Assay |
| | | Xbp1-SA-F | CCATGGGAAGATGTTCTGGG | |
| Mouse | Actb | actb1083 | CTCAGGAGGAGCAATGATCCTTGAT | RT-qPCR |
| | | actb987 | TACCACATGTACCCAGGCA | |
| Mouse | Xbp1 | Xbp1.total-F | GACAGAGAGTCAAACTAACGTGG | RT-qPCR |
| | | Xbp1.total-R | GTCCAGCAGGCAAGAAGGT | |
| Mouse | Xbp1s | XBPsA406F | AAGAACACGCTTGGGAATGG | RT-qPCR |
| | | XBPsAa518R | CTGCACCTGCTGCGGAC | |
| Mouse | Xbp1 (exon 2) | XBP1WT205-F | CCTGAGCCCGGAGGAGAA | RT-qPCR (does not amplify deleted exon 2) |
| | | XBP1WT272-R | CTCGAGCAGTCTGCGCTG | |
| Mouse | Dnajb9/ Erdj4 | ERdj4-F | TAAAAGCCCTGATGCTGAAGC | RT-qPCR |
| | | ERdj4-R | TCCGACTATTGGCATCCGA | |
| Mouse | Sec61a1 | Sec61a1-F | CTATTTCCAGGGCTTCCGAGT | RT-qPCR |
| | | Sec61a1-F | AGGTGTTGTACTGGCCTCGGT | |
| Mouse | Hspa5/Bip | Grp78-F | TCATCGGACGCACTTGGAA | RT-qPCR |
| | | Grp78-R | CAACCACCTTGAATGGCAAGA | |
| Mouse | Ddit3/CHOP | CHOP-F | GTCCCTAGCTTGGCTGACAGA | RT-qPCR |
| | | CHOP-R | TGGAGAGCGAGGGCTTTG | |
| Mouse | Agpat6 | Agpat6-F | AGCTTGATTGTCAACCTCCTG | RT-qPCR |
| | | Agpat6-R | CCGTTGGTGTAGGGCTTGT | |
| Mouse | Scd2 | Scd2-F | GCATTTGGGAGCCTTGTACG | RT-qPCR |
| | | Scd2-R | AGCCGTGCCTTGTATGTTCTG | |
| Mouse | Fasn | Fasn-F | GGAGGTGGTGATAGCCGTAT | RT-qPCR |
| | | Fasn-R | TGGGTAATCCATAGAGCCCAG | |
| Mouse | Lpar1 | Lpar1-F | GACCTAGCAGGCTTACAGTTCC | RT-qPCR |
| | | Lpar1-R | GCTGTAGTTTGGGGCGATGA | |
| Mouse | Clec9a | Clec9a-F | GAGCATGGTGTGTTGTGACG | RT-qPCR |
| | | Clec9a-R | TACCTGGAAGAACTTGATGCCC | |
| Mouse | Zbtb46 | Zbtb46.F | CTCACATACTGGAGAGCGGC | RT-qPCR |
| | | Zbtb46.R | TGCTGTGGACCAGAGTATGTC | |

TABLE 2

| Symbol | Description | KO/WT fold |
|---|---|---|
| Fut7 | fucosyltransferase 7 | −2.32 |
| Slc5a3 | solute carrier family 5 (inositol transporters), member 3 | −2.22 |
| Gm2a | GM2 ganglioside activator protein | −1.99 |
| Stt3a | STT3, subunit of the oligosaccharyltransferase complex, homolog A (S. cerevisiae) | −1.94 |
| Uggt1 | UDP-glucose glycoprotein glucosyltransferase 1 | −1.81 |
| Gfpt1 | glutamine fructose-6-phosphate transaminase 1 | −1.77 |
| Mlec | malectin | −1.73 |
| Glce | glucuronyl C5-epimerase | −1.68 |
| Hk1 | hexokinase 1 | −1.59 |
| Aldoc | aldolase C, fructose-bisphosphate | −1.58 |
| Rpn1 | ribophorin I | −1.58 |
| Mgat1 | mannoside acetylglucosaminyltransferase 1 | −1.56 |
| Pfkp | phosphofructokinase, platelet | −1.56 |
| Gaa | glucosidase, alpha, acid | −1.55 |
| Phkb | phosphorylase kinase beta | −1.55 |
| Ogdh | oxoglutarate (alpha-ketoglutarate) dehydrogenase (lipoamide) | −1.52 |
| Ptafr | platelet-activating factor receptor | −1.52 |
| Pgm3 | phosphoglucomutase 3 | −1.52 |
| Pygb | brain glycogen phosphorylase | −1.51 |
| Idua | iduronidase, alpha-L- | −1.49 |
| Acly | ATP citrate lyase | −1.48 |
| Ppip5k2 | diphosphoinositol pentakisphosphate kinase 2 | −1.47 |
| Cpt1a | carnitine palmitoyltransferase 1a, liver | −1.47 |
| Pkm | pyruvate kinase, muscle | −1.46 |
| St3gal4 | ST3 beta-galactoside alpha-2,3-sialyltransferase 4 | −1.45 |
| Ganab | alpha glucosidase 2 alpha neutral subunit | −1.45 |
| Man2b1 | mannosidase 2, alpha B1 | −1.43 |
| Rpn2 | ribophorin II | −1.40 |
| Tram2 | translocating chain-associating membrane protein 2 | −6.39 |
| Zfp781 | zinc finger protein 781 | −4.18 |
| Apol9b | apolipoprotein L 9b | −4.08 |
| Tlr12 | toll-like receptor 12 | −4.06 |
| Zfp791 | zinc finger protein 791 | −3.93 |
| 9530036M11Rik | RIKEN cDNA 9530036M11 gene | −3.71 |
| Leprel1 | leprecan-like 1 | −3.29 |
| Il12b | interleukin 12b | −3.12 |
| Scn4b | sodium channel, type IV, beta | −3.08 |
| Tuba1c | tubulin, alpha 1C | −3.00 |
| Dkk3 | dickkopf homolog 3 (Xenopus laevis) | −2.98 |
| Sardh | sarcosine dehydrogenase | −2.96 |
| Cd226 | CD226 antigen | −2.90 |
| Synpo2 | synaptopodin 2 | −2.87 |
| Fbxo10 | F-box protein 10 | −2.79 |
| Rtkn | rhotekin | −2.75 |
| Fam13c | family with sequence similarity 13, member C | −2.72 |
| Itgb2 | integrin beta 2 | −2.62 |
| Ptgir | prostaglandin I receptor (IP) | −2.61 |
| Bcorl1 | BCL6 co-repressor-like 1 | −2.54 |
| Rnase2a | #N/A | −2.53 |
| Fcrls | Fc receptor-like S, scavenger receptor | −2.47 |
| Hyou1 | hypoxia up-regulated 1 | −2.47 |
| Pdia5 | protein disulfide isomerase associated 5 | −2.45 |
| Sdc1 | syndecan 1 | −2.42 |
| Tmem25 | transmembrane protein 25 | −2.40 |
| Ctnna2 | catenin (cadherin associated protein), alpha 2 | −2.39 |
| F7 | coagulation factor VII | −2.37 |
| Itgae | integrin alpha E, epithelial-associated | −2.35 |
| Extl1 | exostoses (multiple)-like 1 | −2.28 |
| Spryd3 | SPRY domain containing 3 | −2.26 |
| Rps6kc1 | ribosomal protein S6 kinase polypeptide 1 | −2.26 |
| Ear2 | eosinophil-associated, ribonuclease A family, member 2 | −2.24 |
| Fn1 | fibronectin 1 | −2.23 |
| Tenm4 | teneurin transmembrane protein 4 | −2.22 |
| Gfra2 | glial cell line derived neurotrophic factor family receptor alpha 2 | −2.21 |
| Plekhn1 | pleckstrin homology domain containing, family N member 1 | −2.21 |
| Lrrc18 | leucine rich repeat containing 18 | −2.20 |
| Nucb2 | nucleobindin 2 | −2.20 |
| Cacna1d | calcium channel, voltage-dependent, L type, alpha 1D subunit | −2.16 |
| Kctd12b | potassium channel tetramerisation domain containing 12b | −2.16 |
| Hspa14 | heat shock protein 14 | −2.16 |
| Galnt9 | UDP-N-acetyl-alpha-D-galactosamine: polypeptide N-acetylgalactosaminyltransferase 9 | −2.13 |
| Hdlbp | high density lipoprotein (HDL) binding protein | −2.11 |
| Snx22 | sorting nexin 22 | −2.10 |
| Dnmbp | dynamin binding protein | −2.05 |
| Gm8221 | apolipoprotein L 7c pseudogene | −2.04 |
| Lpar1 | lysophosphatidic acid receptor 1 | −2.04 |
| Sec61a1 | Sec61 alpha 1 subunit (S. cerevisiae) | −2.03 |
| Nlrx1 | NLR family member X1 | −2.03 |
| Capn5 | calpain 5 | −2.03 |
| Retnla | resistin like alpha | −2.02 |
| Sec24d | Sec24 related gene family, member D (S. cerevisiae) | −2.02 |
| Atg9b | autophagy related 9B | −2.00 |
| Mpzl2 | myelin protein zero-like 2 | −1.97 |
| Slc13a3 | solute carrier family 13 (sodium-dependent dicarboxylate transporter), member 3 | −1.97 |
| Plce1 | phospholipase C, epsilon 1 | −1.97 |
| Otof | otoferlin | −1.96 |
| F10 | coagulation factor X | −1.96 |
| Unc45b | unc-45 homolog B (C. elegans) | −1.96 |
| Hspa13 | heat shock protein 70 family, member 13 | −1.93 |
| Madd | MAP-kinase activating death domain | −1.92 |
| Nbas | neuroblastoma amplified sequence | −1.92 |
| Sec24c | Sec24 related gene family, member C (S. cerevisiae) | −1.91 |
| Ercc6l | excision repair cross-complementing rodent repair deficiency complementation group 6 like | −1.90 |
| 1700021K19Rik | RIKEN cDNA 1700021K19 gene | −1.88 |
| Abca3 | ATP-binding cassette, sub-family A (ABC1), member 3 | −1.88 |
| Kctd11 | potassium channel tetramerisation domain containing 11 | −1.88 |
| Agpat4 | 1-acylglycerol-3-phosphate O-acyltransferase 4 (lysophosphatidic acid acyltransferase, delta) | −1.87 |
| Ambra1 | autophagy/beclin 1 regulator 1 | −1.87 |
| Xdh | xanthine dehydrogenase | −1.86 |
| Surf4 | surfeit gene 4 | −1.86 |
| Pltp | phospholipid transfer protein | −1.86 |
| Itgam | integrin alpha M | −1.86 |
| Cldn1 | claudin 1 | −1.85 |
| Atg13 | autophagy related 13 | −1.84 |
| Xbp1 | X-box binding protein 1 | −1.83 |
| P4hb | prolyl 4-hydroxylase, beta polypeptide | −1.83 |
| Cdk5rap3 | CDK5 regulatory subunit associated protein 3 | −1.83 |
| Gmppb | GDP-mannose pyrophosphorylase B | −1.83 |
| Zfp872 | zinc finger protein 872 | −1.82 |
| Zfp949 | zinc finger protein 949 | −1.82 |
| Psd4 | pleckstrin and Sec7 domain containing 4 | −1.81 |
| Pidd1 | #N/A | −1.80 |
| Dock2 | dedicator of cyto-kinesis 2 | −1.80 |
| Sidt2 | SID1 transmembrane family, member 2 | −1.80 |
| 4931406H21Rik | RIKEN cDNA 4931406H21 gene | −1.79 |
| Abca9 | ATP-binding cassette, sub-family A (ABC1), member 9 | −1.79 |
| Ppm1f | protein phosphatase 1F (PP2C domain containing) | −1.79 |
| Abcg3 | ATP-binding cassette, sub-family G (WHITE), member 3 | −1.79 |

TABLE 2-continued

| Symbol | Description | KO/WT fold |
|---|---|---|
| Crat | carnitine acetyltransferase | −1.78 |
| Gpr56 | G protein-coupled receptor 56 | −1.78 |
| Bub1b | budding uninhibited by benzimidazoles 1 homolog, beta (S. cerevisiae) | −1.77 |
| Ticam1 | toll-like receptor adaptor molecule 1 | −1.77 |
| Il27ra | interleukin 27 receptor, alpha | −1.77 |
| Fam129a | family with sequence similarity 129, member A | −1.77 |
| Dnase1l3 | deoxyribonuclease 1-like 3 | −1.76 |
| Ptger2 | prostaglandin E receptor 2 (subtype EP2) | −1.75 |
| Gm1966 | predicted gene 1966 | −1.75 |
| Tmem167b | transmembrane protein 167B | −1.75 |
| Nup188 | nucleoporin 188 | −1.75 |
| Tyk2 | tyrosine kinase 2 | −1.75 |
| Asb4 | ankyrin repeat and SOCS box-containing 4 | −1.74 |
| Tom1l2 | target of myb1-like 2 (chicken) | −1.74 |
| Ascc2 | activating signal cointegrator 1 complex subunit 2 | −1.74 |
| Clec4a2 | C-type lectin domain family 4, member a2 | −1.73 |
| Polr3b | polymerase (RNA) III (DNA directed) polypeptide B | −1.73 |
| Igj | immunoglobulin joining chain | −1.73 |
| Acot11 | acyl-CoA thioesterase 11 | −1.73 |
| Ankrd23 | ankyrin repeat domain 23 | −1.73 |
| Mis12 | MIS12 homolog (yeast) | −1.73 |
| Rfwd3 | ring finger and WD repeat domain 3 | −1.73 |
| Ccpg1 | cell cycle progression 1 | −1.72 |
| F2rl2 | coagulation factor II (thrombin) receptor-like 2 | −1.71 |
| Arfgap3 | ADP-ribosylation factor GTPase activating protein 3 | −1.71 |
| Mmp25 | matrix metallopeptidase 25 | −1.71 |
| Ap1g1 | adaptor protein complex AP-1, gamma 1 subunit | −1.70 |
| Cenpi | centromere protein I | −1.70 |
| Tlr8 | toll-like receptor 8 | −1.70 |
| Pdcd1 | programmed cell death 1 | −1.69 |
| Tmem127 | transmembrane protein 127 | −1.69 |
| Plau | plasminogen activator, urokinase | −1.69 |
| Tut1 | terminal uridylyl transferase 1, U6 snRNA-specific | −1.69 |
| Mical1 | microtubule associated monooxygenase, calponin and LIM domain containing 1 | −1.69 |
| Mrc1 | mannose receptor, C type 1 | −1.69 |
| Pdia4 | protein disulfide isomerase associated 4 | −1.69 |
| Zfp738 | zinc finger protein 738 | −1.69 |
| Kat6a | K(lysine) acetyltransferase 6A | −1.69 |
| Mela | melanoma antigen | −1.69 |
| Mettl14 | methyltransferase like 14 | −1.68 |
| Copg1 | coatomer protein complex, subunit gamma 1 | −1.68 |
| Rassf4 | Ras association (RalGDS/AF-6) domain family member 4 | −1.68 |
| Klhl18 | kelch-like 18 | −1.68 |
| Gorab | golgin, RAB6-interacting | −1.68 |
| Rab8b | RAB8B, member RAS oncogene family | −1.67 |
| Spcs3 | signal peptidase complex subunit 3 homolog (S. cerevisiae) | −1.67 |
| Btd | biotinidase | −1.67 |
| Pias3 | protein inhibitor of activated STAT 3 | −1.67 |
| Lysmd3 | LysM, putative peptidoglycan-binding, domain containing 3 | −1.67 |
| Vps8 | vacuolar protein sorting 8 homolog (S. cerevisiae) | −1.67 |
| Calu | calumenin | −1.67 |
| Sdccag8 | serologically defined colon cancer antigen 8 | −1.66 |
| Gpr68 | G protein-coupled receptor 68 | −1.66 |
| Kcnab2 | potassium voltage-gated channel, shaker-related subfamily, beta member 2 | −1.66 |
| Tlr11 | toll-like receptor 11 | −1.66 |
| Slc39a7 | solute carrier family 39 (zinc transporter), member 7 | −1.66 |
| Fasn | fatty acid synthase | −1.65 |
| E2f1 | E2F transcription factor 1 | −1.65 |
| Zc3h12c | zinc finger CCCH type containing 12C | −1.65 |
| Fosl2 | fos-like antigen 2 | −1.65 |
| Mcph1 | microcephaly, primary autosomal recessive 1 | −1.64 |
| Tgoln2 | trans-golgi network protein 2 | −1.64 |
| Dpp7 | dipeptidylpeptidase 7 | −1.64 |
| Golga3 | golgi autoantigen, golgin subfamily a, 3 | −1.63 |
| Far1 | fatty acyl CoA reductase 1 | −1.63 |
| Pank4 | pantothenate kinase 4 | −1.63 |
| Ncapd3 | non-SMC condensin II complex, subunit D3 | −1.63 |
| Ddb1 | damage specific DNA binding protein 1 | −1.62 |
| Map3k14 | mitogen-activated protein kinase kinase kinase 14 | −1.62 |
| Surf6 | surfeit gene 6 | −1.62 |
| Sulf1 | sulfatase 1 | −1.62 |
| Samd9l | sterile alpha motif domain containing 9-like | −1.62 |
| Slc41a2 | solute carrier family 41, member 2 | −1.62 |
| Tnip2 | TNFAIP3 interacting protein 2 | −1.62 |
| Klhl28 | kelch-like 28 | −1.62 |
| Lclat1 | lysocardiolipin acyltransferase 1 | −1.62 |
| Peg13 | paternally expressed 13 | −1.61 |
| Crem | cAMP responsive element modulator | −1.61 |
| Mmp19 | matrix metallopeptidase 19 | −1.61 |
| Copa | coatomer protein complex subunit alpha | −1.61 |
| Rin3 | Ras and Rab interactor 3 | −1.61 |
| Ldlr | low density lipoprotein receptor | −1.61 |
| Nxpe4 | neurexophilin and PC-esterase domain family, member 4 | −1.61 |
| Dock10 | dedicator of cytokinesis 10 | −1.61 |
| Leprot | leptin receptor overlapping transcript | −1.61 |
| Sept9 | septin 9 | −1.61 |
| Fbxo38 | F-box protein 38 | −1.61 |
| Myo1f | myosin IF | −1.60 |
| Znfx1 | zinc finger, NFX1-type containing 1 | −1.60 |
| Ddi2 | DNA-damage inducible protein 2 | −1.60 |
| Anpep | alanyl (membrane) aminopeptidase | −1.60 |
| Lifr | leukemia inhibitory factor receptor | −1.60 |
| Utp20 | UTP20, small subunit (SSU) processome component, homolog (yeast) | −1.60 |
| Lpin1 | lipin 1 | −1.60 |
| Eps8 | epidermal growth factor receptor pathway substrate 8 | −1.60 |
| Zfyve16 | zinc finger, FYVE domain containing 16 | −1.60 |
| Arhgap18 | Rho GTPase activating protein 18 | −1.60 |
| Elmo2 | engulfment and cell motility 2 | −1.60 |
| Daglb | diacylglycerol lipase, beta | −1.59 |
| Elmod2 | ELMO/CED-12 domain containing 2 | −1.59 |
| Abcd1 | ATP-binding cassette, sub-family D (ALD), member 1 | −1.59 |
| Alpk1 | alpha-kinase 1 | −1.59 |
| Ncs1 | neuronal calcium sensor 1 | −1.59 |
| Ticam2 | toll-like receptor adaptor molecule 2 | −1.59 |
| Clasp1 | CLIP associating protein 1 | −1.59 |
| Atxn3 | ataxin 3 | −1.59 |
| Depdc5 | DEP domain containing 5 | −1.58 |
| Cnnm4 | cyclin M4 | −1.58 |
| Steap3 | STEAP family member 3 | −1.58 |
| Kit | kit oncogene | −1.58 |
| 1110037F02Rik | RIKEN cDNA 1110037F02 gene | −1.58 |
| Supt5 | suppressor of Ty 5 | −1.58 |
| Socs6 | suppressor of cytokine signaling 6 | −1.58 |
| Gm5431 | predicted gene 5431 | −1.57 |
| Nup160 | nucleoporin 160 | −1.57 |
| Atf6 | activating transcription factor 6 | −1.57 |
| Net1 | neuroepithelial cell transforming gene 1 | −1.57 |
| Dhdh | dihydrodiol dehydrogenase (dimeric) | −1.57 |
| Dapk1 | death associated protein kinase 1 | −1.57 |
| Taf1 | TAF1 RNA polymerase II, TATA box binding protein (TBP)-associated factor | −1.57 |
| Arhgap11a | Rho GTPase activating protein 11A | −1.57 |
| Supt16 | suppressor of Ty 16 | −1.57 |
| Dnajc3 | DnaJ (Hsp40) homolog, subfamily C, member 3 | −1.57 |

TABLE 2-continued

| Symbol | Description | KO/WT fold |
|---|---|---|
| Ddx10 | DEAD (Asp-Glu-Ala-Asp) box polypeptide 10 | −1.56 |
| Gm8995 | predicted gene 8995 | −1.56 |
| Bsdc1 | BSD domain containing 1 | −1.56 |
| Gpr108 | G protein-coupled receptor 108 | −1.56 |
| Inpp5d | inositol polyphosphate-5-phosphatase D | −1.56 |
| Snrnp200 | small nuclear ribonucleoprotein 200 (U5) | −1.56 |
| Asb6 | ankyrin repeat and SOCS box-containing 6 | −1.56 |
| Mfn2 | mitofusin 2 | −1.56 |
| Ccr2 | chemokine (C-C motif) receptor 2 | −1.56 |
| Cbl | Casitas B-lineage lymphoma | −1.56 |
| Mrvi1 | MRV integration site 1 | −1.56 |
| Tap2 | transporter 2, ATP-binding cassette, sub-family B (MDR/TAP) | −1.56 |
| Mcm3 | minichromosome maintenance deficient 3 (S. cerevisiae) | −1.56 |
| Nol8 | nucleolar protein 8 | −1.56 |
| Gltpd1 | glycolipid transfer protein domain containing 1 | −1.56 |
| Plekho2 | pleckstrin homology domain containing, family O member 2 | −1.56 |
| Il1rl1 | interleukin 1 receptor-like 1 | −1.56 |
| Ankfy1 | ankyrin repeat and FYVE domain containing 1 | −1.56 |
| Gpatch8 | G patch domain containing 8 | −1.55 |
| Nap1l4 | nucleosome assembly protein 1-like 4 | −1.55 |
| Tmed9 | transmembrane emp24 protein transport domain containing 9 | −1.55 |
| Arhgap26 | Rho GTPase activating protein 26 | −1.55 |
| Uspl1 | ubiquitin specific peptidase like 1 | −1.55 |
| Pdia6 | protein disulfide isomerase associated 6 | −1.55 |
| Arrb1 | arrestin, beta 1 | −1.55 |
| Mkl1 | MKL (megakaryoblastic leukemia)/myocardin-like 1 | −1.55 |
| Zfml | zinc finger, matrin-like | −1.55 |
| Fchsd2 | FCH and double SH3 domains 2 | −1.54 |
| Cnr2 | cannabinoid receptor 2 (macrophage) | −1.54 |
| Ccdc47 | coiled-coil domain containing 47 | −1.54 |
| Dok2 | docking protein 2 | −1.54 |
| Taok3 | TAO kinase 3 | −1.54 |
| Tti1 | TELO2 interacting protein 1 | −1.54 |
| Smc5 | structural maintenance of chromosomes 5 | −1.54 |
| Pbxip1 | pre B cell leukemia transcription factor interacting protein 1 | −1.54 |
| Prr5l | proline rich 5 like | −1.54 |
| Stat6 | signal transducer and activator of transcription 6 | −1.54 |
| Hepacam2 | HEPACAM family member 2 | −1.54 |
| 2700049A03Rik | RIKEN cDNA 2700049A03 gene | −1.54 |
| Pkd1 | polycystic kidney disease 1 homolog | −1.54 |
| Lrrk1 | leucine-rich repeat kinase 1 | −1.54 |
| Pan2 | PAN2 polyA specific ribonuclease subunit homolog (S. cerevisiae) | −1.54 |
| Magt1 | magnesium transporter 1 | −1.53 |
| Armcx3 | armadillo repeat containing, X-linked 3 | −1.53 |
| Cd1d1 | CD1d1 antigen | −1.53 |
| Plekhb2 | pleckstrin homology domain containing, family B (evectins) member 2 | −1.53 |
| Bcl2l14 | BCL2-like 14 (apoptosis facilitator) | −1.53 |
| Lmf2 | lipase maturation factor 2 | −1.53 |
| Nhsl2 | NHS-like 2 | −1.53 |
| Timp3 | tissue inhibitor of metalloproteinase 3 | −1.53 |
| Casp3 | caspase 3 | −1.53 |
| Naaa | N-acylethanolamine acid amidase | −1.52 |
| Nfam1 | Nfat activating molecule with ITAM motif 1 | −1.52 |
| Dcp1a | DCP1 decapping enzyme homolog A (S. cerevisiae) | −1.52 |
| Eif3a | eukaryotic translation initiation factor 3, subunit A | −1.52 |
| Mtmr6 | myotubularin related protein 6 | −1.52 |
| Top2a | topoisomerase (DNA) II alpha | −1.52 |
| Dnajc14 | DnaJ (Hsp40) homolog, subfamily C, member 14 | −1.52 |
| Pde4dip | phosphodiesterase 4D interacting protein (myomegalin) | −1.52 |
| Evi2a | ecotropic viral integration site 2a | −1.52 |
| Npat | nuclear protein in the AT region | −1.51 |
| Sil1 | endoplasmic reticulum chaperone SIL1 homolog (S. cerevisiae) | −1.51 |
| Hltf | helicase-like transcription factor | −1.51 |
| Stim2 | stromal interaction molecule 2 | −1.51 |
| Baz2a | bromodomain adjacent to zinc finger domain, 2A | −1.51 |
| Ell | elongation factor RNA polymerase II | −1.51 |
| R3hcc1l | R3H domain and coiled-coil containing 1 like | −1.51 |
| Mybbp1a | MYB binding protein (P160) 1a | −1.51 |
| Myo1c | myosin IC | −1.50 |
| Zfp260 | zinc finger protein 260 | −1.50 |
| Adam19 | a disintegrin and metallopeptidase domain 19 (meltrin beta) | −1.50 |
| Tkt | transketolase | −1.50 |
| Exoc2 | exocyst complex component 2 | −1.50 |
| Sft2d2 | SFT2 domain containing 2 | −1.50 |
| Tuba1a | tubulin, alpha 1A | −1.50 |
| Oat | ornithine aminotransferase | −1.50 |
| Baz2b | bromodomain adjacent to zinc finger domain, 2B | −1.50 |
| Ltn1 | listerin E3 ubiquitin protein ligase 1 | −1.50 |
| Copb2 | coatomer protein complex, subunit beta 2 (beta prime) | −1.50 |
| Cyp51 | cytochrome P450, family 51 | −1.50 |
| Acin1 | apoptotic chromatin condensation inducer 1 | −1.50 |
| Hivep2 | human immunodeficiency virus type I enhancer binding protein 2 | −1.50 |
| Tmem170b | transmembrane protein 170B | −1.49 |
| Stom | stomatin | −1.49 |
| Sec16a | SEC16 homolog A (S. cerevisiae) | −1.49 |
| Krt80 | keratin 80 | −1.49 |
| Malat1 | metastasis associated lung adenocarcinoma transcript 1 (non-coding RNA) | −1.49 |
| Rabgap1 | RAB GTPase activating protein 1 | −1.49 |
| Pja2 | praja 2, RING-H2 motif containing | −1.49 |
| Slamf8 | SLAM family member 8 | −1.49 |
| Tnpo3 | transportin 3 | −1.48 |
| Tmx3 | thioredoxin-related transmembrane protein 3 | −1.48 |
| Rbbp6 | retinoblastoma binding protein 6 | −1.48 |
| Ilf3 | interleukin enhancer binding factor 3 | −1.48 |
| Ctr9 | Ctr9, Paf1/RNA polymerase II complex component, homolog (S. cerevisiae) | −1.48 |
| Anapc1 | anaphase promoting complex subunit 1 | −1.48 |
| Svil | supervillin | −1.48 |
| Ptrf | polymerase I and transcript release factor | −1.48 |
| Tox4 | TOX high mobility group box family member 4 | −1.48 |
| Abi2 | abl-interactor 2 | −1.48 |
| Atp7a | ATPase, Cu++ transporting, alpha polypeptide | −1.48 |
| Cnppd1 | cyclin Pas1/PHO80 domain containing 1 | −1.48 |
| Zc3h7a | zinc finger CCCH type containing 7 A | −1.48 |
| Zfp263 | zinc finger protein 263 | −1.48 |
| Ipo5 | importin 5 | −1.48 |
| Pggt1b | protein geranylgeranyltransferase type I, beta subunit | −1.48 |
| Ptplad2 | protein tyrosine phosphatase-like A domain containing 2 | −1.48 |
| Usp8 | ubiquitin specific peptidase 8 | −1.48 |
| Coro7 | coronin 7 | −1.47 |
| Sept3 | septin 3 | −1.47 |
| Spop | speckle-type POZ protein | −1.47 |
| Aco1 | aconitase 1 | −1.47 |
| Nucb1 | nucleobindin 1 | −1.47 |
| Prpf6 | PRP6 pre-mRNA splicing factor 6 homolog (yeast) | −1.47 |
| Mavs | mitochondrial antiviral signaling protein | −1.47 |
| Cd209c | CD209c antigen | −1.47 |
| Atp8b4 | ATPase, class I, type 8B, member 4 | −1.47 |

TABLE 2-continued

| Symbol | Description | KO/WT fold |
|---|---|---|
| Myof | myoferlin | −1.47 |
| Sec23b | SEC23B (*S. cerevisiae*) | −1.46 |
| Nckap1l | NCK associated protein 1 like | −1.46 |
| Pum1 | pumilio RNA-binding family member 1 | −1.46 |
| Fgl2 | fibrinogen-like protein 2 | −1.46 |
| Sec31a | Sec31 homolog A (*S. cerevisiae*) | −1.46 |
| Txndc16 | thioredoxin domain containing 16 | −1.46 |
| Pdxk | pyridoxal (pyridoxine, vitamin B6) kinase | −1.46 |
| Gga3 | golgi associated, gamma adaptin ear containing, ARF binding protein 3 | −1.46 |
| Kitl | kit ligand | −1.46 |
| Tmcc3 | transmembrane and coiled coil domains 3 | −1.46 |
| Gmppa | GDP-mannose pyrophosphorylase A | −1.46 |
| Ppp1r21 | protein phosphatase 1, regulatory subunit 21 | −1.46 |
| Os9 | amplified in osteosarcoma | −1.46 |
| 4930506M07Rik | RIKEN cDNA 4930506M07 gene | −1.45 |
| Smc1a | structural maintenance of chromosomes 1A | −1.45 |
| Kansl3 | KAT8 regulatory NSL complex subunit 3 | −1.45 |
| 2900097C17RiK | RIKEN cDNA 2900097C17 gene | −1.45 |
| Tmem181b-ps | transmembrane protein 181B, pseudogene | −1.45 |
| Nup210 | nucleoporin 210 | −1.45 |
| Entpd7 | ectonucleoside triphosphate diphosphohydrolase 7 | −1.45 |
| Stag2 | stromal antigen 2 | −1.45 |
| Narf | nuclear prelamin A recognition factor | −1.45 |
| Tmem39a | transmembrane protein 39a | −1.45 |
| Rnf41 | ring finger protein 41 | −1.45 |
| Agpat6 | 1-acylglycerol-3-phosphate O-acyltransferase 6 (lysophosphatidic acid acyltransferase, zeta) | −1.44 |
| Zfp445 | zinc finger protein 445 | −1.44 |
| Ikbkg | inhibitor of kappaB kinase gamma | −1.44 |
| Gripap1 | GRIP1 associated protein 1 | −1.44 |
| Chd2 | chromodomain helicase DNA binding protein 2 | −1.44 |
| Ankrd27 | ankyrin repeat domain 27 (VPS9 domain) | −1.44 |
| Ppp1r15b | protein phosphatase 1, regulatory (inhibitor) subunit 15b | −1.44 |
| Golgb1 | golgi autoantigen, golgin subfamily b, macrogolgin 1 | −1.44 |
| Tmed3 | transmembrane emp24 domain containing 3 | −1.44 |
| Psap | prosaposin | −1.44 |
| Ctnna1 | catenin (cadherin associated protein), alpha 1 | −1.44 |
| Ptbp1 | polypyrimidine tract binding protein 1 | −1.43 |
| Csf2rb | colony stimulating factor 2 receptor, beta, low-affinity (granulocyte-macrophage) | −1.43 |
| Ssrp1 | structure specific recognition protein 1 | −1.43 |
| Cyth4 | cytohesin 4 | −1.43 |
| Tug1 | taurine upregulated gene 1 | −1.43 |
| Scd2 | stearoyl-Coenzyme A desaturase 2 | −1.43 |
| Arhgef6 | Rac/Cdc42 guanine nucleotide exchange factor (GEF) 6 | −1.43 |
| Tbc1d15 | TBC1 domain family, member 15 | −1.42 |
| Mbnl1 | muscleblind-like 1 (*Drosophila*) | −1.42 |
| Eif4g2 | eukaryotic translation initiation factor 4, gamma 2 | −1.42 |
| Rp2h | retinitis pigmentosa 2 homolog (human) | −1.42 |
| Adam8 | a disintegrin and metallopeptidase domain 8 | −1.41 |
| Neat1 | nuclear paraspeckle assembly transcript 1 (non-protein coding) | −1.41 |
| Themis2 | thymocyte selection associated family member 2 | −1.41 |
| Gosr2 | golgi SNAP receptor complex member 2 | −1.40 |
| Idi1 | isopentenyl-diphosphate delta isomerase | −1.40 |
| Psmd2 | proteasome (prosome, macropain) 26S subunit, non-ATPase, 2 | −1.40 |
| Hmgcr | 3-hydroxy-3-methylglutaryl-Coenzyme A reductase | −1.40 |
| Eef2 | eukaryotic translation elongation factor 2 | −1.40 |
| Myo1g | myosin IG | −1.40 |
| Msn | moesin | −1.39 |
| Cfh | complement component factor h | −1.38 |
| C1qc | complement component 1, q subcomponent, C chain | 1.42 |
| A630089N07Rik | RIKEN cDNA A630089N07 gene | 1.43 |
| Traf5 | TNF receptor-associated factor 5 | 1.44 |
| Zfp353-ps | zinc finger protein 352 | 1.45 |
| Fam110b | family with sequence similarity 110, member B | 1.48 |
| Wfdc17 | WAP four-disulfide core domain 17 | 1.48 |
| Fam213b | family with sequence similarity 213, member B | 1.48 |
| Trem2 | triggering receptor expressed on myeloid cells 2 | 1.50 |
| Snx18 | sorting nexin 18 | 1.51 |
| 1500012F01Rik | RIKEN cDNA 1500012F01 gene | 1.51 |
| Tctex1d2 | Tctex1 domain containing 2 | 1.52 |
| Icam2 | intercellular adhesion molecule 2 | 1.53 |
| Gngt2 | guanine nucleotide binding protein (G protein), gamma transducing activity polypeptide 2 | 1.53 |
| Lst1 | leukocyte specific transcript 1 | 1.54 |
| Itsn1 | intersectin 1 (SH3 domain protein 1A) | 1.54 |
| Ltbp1 | latent transforming growth factor beta binding protein 1 | 1.55 |
| Blvrb | biliverdin reductase B (flavin reductase (NADPH)) | 1.57 |
| Hscb | HscB iron-sulfur cluster co-chaperone homolog (*E. coli*) | 1.57 |
| Acot2 | acyl-CoA thioesterase 2 | 1.57 |
| Gimap8 | GTPase, IMAP family member 8 | 1.59 |
| Sept1 | septin 1 | 1.60 |
| C5ar2 | complement component 5a receptor 2 | 1.60 |
| Itga6 | integrin alpha 6 | 1.61 |
| Dcxr | dicarbonyl L-xylulose reductase | 1.61 |
| Mmp12 | matrix metallopeptidase 12 | 1.61 |
| Tmem243 | transmembrane protein 243, mitochondrial | 1.63 |
| Pou2f2 | POU domain, class 2, transcription factor 2 | 1.63 |
| Ly6c2 | lymphocyte antigen 6 complex, locus C2 | 1.63 |
| Hnmt | histamine N-methyltransferase | 1.64 |
| Asns | asparagine synthetase | 1.64 |
| Emp1 | epithelial membrane protein 1 | 1.65 |
| Ets1 | E26 avian leukemia oncogene 1, 5' domain | 1.65 |
| Cirbp | cold inducible RNA binding protein | 1.65 |
| Cbr2 | carbonyl reductase 2 | 1.68 |
| Serpinb10 | serine (or cysteine) peptidase inhibitor, clade B (ovalbumin), member 10 | 1.68 |
| Vsig4 | V-set and immunoglobulin domain containing 4 | 1.69 |
| Fam20c | family with sequence similarity 20, member C | 1.69 |
| Irf2bpl | interferon regulatory factor 2 binding protein-like | 1.71 |
| Cd93 | CD93 antigen | 1.71 |
| Med17 | mediator complex subunit 17 | 1.71 |
| Apoe | apolipoprotein E | 1.72 |
| Cd28 | CD28 antigen | 1.72 |
| Ms4a1 | membrane-spanning 4-domains, subfamily A, member 1 | 1.73 |
| Lpcat2 | lysophosphatidylcholine acyltransferase 2 | 1.73 |
| Plac8 | placenta-specific 8 | 1.73 |
| Rab28 | RAB28, member RAS oncogene family | 1.74 |
| Mzb1 | marginal zone B and B1 cell-specific protein 1 | 1.74 |
| Dok3 | docking protein 3 | 1.75 |
| Arg1 | arginase, liver | 1.76 |
| Cd19 | CD19 antigen | 1.76 |
| Fcna | ficolin A | 1.77 |
| Cd79b | CD79B antigen | 1.77 |
| Tspan4 | tetraspanin 4 | 1.78 |
| Mmp9 | matrix metallopeptidase 9 | 1.80 |
| Itk | IL2 inducible T cell kinase | 1.81 |
| Dppa3 | developmental pluripotency-associated 3 | 1.81 |

TABLE 2-continued

| Symbol | Description | KO/WT fold |
|---|---|---|
| Ninj1 | ninjurin 1 | 1.81 |
| Cxcr5 | chemokine (C-X-C motif) receptor 5 | 1.82 |
| Spry2 | sprouty homolog 2 (Drosophila) | 1.82 |
| Prtn3 | proteinase 3 | 1.82 |
| Snx24 | sorting nexing 24 | 1.83 |
| Ccl3 | chemokine (C-C motif) ligand 3 | 1.83 |
| Gdf3 | growth differentiation factor 3 | 1.86 |
| Ly6d | lymphocyte antigen 6 complex, locus D | 1.86 |
| Cd69 | CD69 antigen | 1.86 |
| Selp | selectin, platelet | 1.86 |
| Apoc2 | apolipoprotein C-II | 1.86 |
| Gimap3 | GTPase, IMAP family member 3 | 1.88 |
| Speer7-ps1 | spermatogenesis associated glutamate (E)-rich protein 7, pseudogene 1 | 1.89 |
| Dusp1 | dual specificity phosphatase 1 | 1.89 |
| Clec4d | C-type lectin domain family 4, member d | 1.90 |
| Cd27 | CD27 antigen | 1.90 |
| Sh2d2a | SH2 domain protein 2A | 1.91 |
| Ly6a | lymphocyte antigen 6 complex, locus A | 1.92 |
| Nt5e | 5' nucleotidase, ecto | 1.94 |
| Txk | TXK tyrosine kinase | 1.96 |
| Saa3 | serum amyloid A 3 | 1.96 |
| Gimap9 | GTPase, IMAP family member 9 | 1.98 |
| Ndufb2 | NADH dehydrogenase (ubiquinone) 1 beta subcomplex, 2 | 1.99 |
| Tfec | transcription factor EC | 2.02 |
| Cxcl13 | chemokine (C-X-C motif) ligand 13 | 2.03 |
| Igfbp4 | insulin-like growth factor binding protein 4 | 2.04 |
| Asb1 | ankyrin repeat and SOCS box-containing 1 | 2.07 |
| Pf4 | platelet factor 4 | 2.07 |
| Xkrx | X Kell blood group precursor related X linked | 2.09 |
| Ypel3 | yippee-like 3 (Drosophila) | 2.09 |
| Ppp3cc | protein phosphatase 3, catalytic subunit, gamma isoform | 2.10 |
| Fam101b | family with sequence similarity 101, member B | 2.10 |
| Slc40a1 | solute carrier family 40 (iron-regulated transporter), member 1 | 2.10 |
| Samd3 | sterile alpha motif domain containing 3 | 2.11 |
| Il2rb | interleukin 2 receptor, beta chain | 2.12 |
| Fam169b | family with sequence similarity 169, member B | 2.12 |
| Mri1 | methylthioribose-1-phosphate isomerase homolog (S. cerevisiae) | 2.15 |
| Gimap6 | GTPase, IMAP family member 6 | 2.15 |
| Alox15 | arachidonate 15-lipoxygenase | 2.17 |
| Tpsb2 | tryptase beta 2 | 2.18 |
| Lef1 | lymphoid enhancer binding factor 1 | 2.18 |
| Tcf7 | transcription factor 7, T cell specific | 2.21 |
| Skap1 | src family associated phosphoprotein 1 | 2.22 |
| Tmprss13 | transmembrane protease, serine 13 | 2.22 |
| Marco | macrophage receptor with collagenous structure | 2.23 |
| Cd79a | CD79A antigen (immunoglobulin-associated alpha) | 2.26 |
| Apoc1 | apolipoprotein C-I | 2.26 |
| Ikzf3 | IKAROS family zinc finger 3 | 2.27 |
| Cd3d | CD3 antigen, delta polypeptide | 2.29 |
| Id1 | inhibitor of DNA binding 1 | 2.29 |
| Gzmb | granzyme B | 2.29 |
| Satb1 | special AT-rich sequence binding protein 1 | 2.29 |
| Lax1 | lymphocyte transmembrane adaptor 1 | 2.32 |
| Gimap4 | GTPase, IMAP family member 4 | 2.34 |
| Cpa3 | carboxypeptidase A3, mast cell | 2.36 |
| Ccr3 | chemokine (C-C motif) receptor 3 | 2.37 |
| Fam189b | family with sequence similarity 189, member B | 2.38 |
| Wnt2 | wingless-related MMTV integration site 2 | 2.38 |
| Vmn2r26 | vomeronasal 2, receptor 26 | 2.39 |
| Ppbp | pro-platelet basic protein | 2.40 |
| Pou2af1 | POU domain, class 2, associating factor 1 | 2.41 |
| Lck | lymphocyte protein tyrosine kinase | 2.42 |
| Gm11346 | X-linked lymphocyte-regulated 5 pseudogene | 2.42 |
| Cma1 | chymase 1, mast cell | 2.42 |
| Ctsw | cathepsin W | 2.43 |
| Gm684 | predicted gene 684 | 2.45 |
| Serpinb2 | serine (or cysteine) peptidase inhibitor, clade B, member 2 | 2.47 |
| Trav3n-3 | T cell receptor alpha variable 3N-3 | 2.48 |
| Prg4 | proteoglycan 4 (megakaryocyte stimulating factor, articular superficial zone protein) | 2.48 |
| Slpi | secretory leukocyte peptidase inhibitor | 2.49 |
| Tmem51os1 | Tmem51 opposite strand 1 | 2.50 |
| Ccl4 | chemokine (C-C motif) ligand 4 | 2.50 |
| Klre1 | killer cell lectin-iike receptor family E member 1 | 2.51 |
| Pear1 | platelet endothelial aggregation receptor 1 | 2.52 |
| Lat | linker for activation of T cells | 2.53 |
| Ptchd4 | patched domain containing 4 | 2.53 |
| Pard6g | par-6 family cell polarity regulator gamma | 2.55 |
| Prf1 | perforin 1 (pore forming protein) | 2.57 |
| Stc1 | stanniocalcin 1 | 2.59 |
| Scn1a | sodium channel, voltage-gated, type I, alpha | 2.60 |
| Plcb4 | phospholipase C, beta 4 | 2.63 |
| Cd3g | CD3 antigen, gamma polypeptide | 2.67 |
| Gpr174 | G protein-coupled receptor 174 | 2.69 |
| Pik3c2b | phosphoinositide-3-kinase, class 2, beta polypeptide | 2.71 |
| Crtam | cytotoxic and regulatory T cell molecule | 2.71 |
| Eomes | eomesodermin homolog (Xenopus laevis) | 2.72 |
| Ebf1 | early B cell factor 1 | 2.72 |
| Tnfsf15 | tumor necrosis factor (ligand) superfamily, member 15 | 2.77 |
| Gimap7 | GTPase, IMAP family member 7 | 2.81 |
| Ifitm10 | interferon induced transmembrane protein 10 | 2.82 |
| Trem3 | triggering receptor expressed on myeloid cells 3 | 2.83 |
| Fasl | Fas ligand (TNF superfamily, member 6) | 2.83 |
| Epha2 | Eph receptor A2 | 2.83 |
| Sh2d1a | SH2 domain protein 1A | 2.85 |
| Tdgf1 | teratocarcinoma-derived growth factor 1 | 2.86 |
| Ncr1 | natural cytotoxicity triggering receptor 1 | 2.88 |
| Fbxl21 | F-box and leucine-rich repeat protein 21 | 2.88 |
| Zdhhc15 | zinc finger, DHHC domain containing 15 | 2.89 |
| Gimap5 | GTPase, IMAP family member 5 | 2.91 |
| Gzma | granzyme A | 2.94 |
| A630023P12Rik | RIKEN cDNA A630023P12 gene | 2.96 |
| Ms4a4b | membrane-spanning 4-domains, subfamily A, member 4B | 2.99 |
| Mgst2 | microsomal glutathione S-transferase 2 | 2.99 |
| Thy1 | thymus cell antigen 1, theta | 2.99 |
| 2900011O08Rik | RIKEN cDNA 2900011O08 gene | 3.01 |
| Cd3e | CD3 antigen, epsilon polypeptide | 3.02 |
| A730060N03Rik | RIKEN cDNA A730060N03 gene | 3.03 |
| Klrc2 | killer cell lectin-like receptor subfamily C, member 2 | 3.04 |
| Phactr3 | phosphatase and actin regulator 3 | 3.10 |
| Retnlg | resistin like gamma | 3.11 |
| Tsix | X (inactive)-specific transcript, opposite strand | 3.12 |
| Rgcc | regulator of cell cycle | 3.13 |
| Dapl1 | death associated protein-like 1 | 3.14 |
| Slitrk4 | SLIT and NTRK-like family, member 4 | 3.20 |
| Cyp26a1 | cytochrome P450, family 26, subfamily a, polypeptide 1 | 3.20 |
| Cd96 | CD96 antigen | 3.21 |
| Mrgpra2b | MAS-related GPR, member A2B | 3.25 |
| Lynx1 | Ly6/neurotoxin 1 | 3.25 |
| Pou1f1 | POU domain, class 1, transcription factor 1 | 3.25 |
| Klrg1 | killer cell lectin-like receptor subfamily G, member 1 | 3.25 |
| S100a9 | S100 calcium binding protein A9 (calgranulin B) | 3.25 |
| Tlr5 | toll-like receptor 5 | 3.26 |
| Klra21 | killer cell lectin-like receptor subfamily A, member 21 | 3.27 |
| Mrgpra2a | MAS-related GPR, member A2A | 3.28 |

TABLE 2-continued

| Symbol | Description | KO/WT fold |
|---|---|---|
| Ptprcap | protein tyrosine phosphatase, receptor type, C polypeptide-associated protein | 3.29 |
| I830127L07Rik | RIKEN cDNA I830127L07 gene | 3.30 |
| 9530053A07Rik | RIKEN cDNA 9530053A07 gene | 3.31 |
| Olfr288 | olfactory receptor 288 | 3.37 |
| Ly6c1 | lymphocyte antigen 6 complex, locus C1 | 3.40 |
| Nkg7 | natural killer cell group 7 sequence | 3.41 |
| Folr4 | folate receptor 4 (delta) | 3.44 |
| Ctsk | cathepsin K | 3.46 |
| Gpr83 | G protein-coupled receptor 83 | 3.47 |
| Unc5cl | unc-5 homolog C (C. elegans)-like | 3.47 |
| Fcer1a | Fc receptor, IgE, high affinity I, alpha polypeptide | 3.58 |
| Klra7 | killer cell lectin-like receptor, subfamily A, member 7 | 3.60 |
| 1810041L15Rik | RIKEN cDNA 1810041L15 gene | 3.62 |
| Nsg2 | neuron specific gene family member 2 | 3.62 |
| G0s2 | G0/G1 switch gene 2 | 3.68 |
| Sall3 | sal-like 3 (Drosophila) | 3.68 |
| S100a8 | S100 calcium binding protein A8 (calgranulin A) | 3.70 |
| Klrc1 | killer cell lectin-like receptor subfamily C, member 1 | 3.71 |
| Gm13363 | predicted gene 13363 | 3.77 |
| Slc2a13 | solute carrier family 2 (facilitated glucose transporter), member 13 | 3.77 |
| Upp1 | uridine phosphorylase 1 | 3.78 |
| Tnik | TRAF2 and NCK interacting kinase | 3.82 |
| Klra1 | killer cell lectin-like receptor, subfamily A, member 1 | 3.85 |
| Tcrd-V1 | T cell receptor delta, variable 1 | 3.86 |
| Lrrn4 | leucine rich repeat neuronal 4 | 3.89 |
| Mycn | v-myc myelocytomatosis viral related oncogene, neuroblastoma derived (avian) | 3.92 |
| Fam155a | family with sequence similarity 155, member A | 3.93 |
| Myo16 | myosin XVI | 3.96 |
| Xcl1 | chemokine (C motif) ligand 1 | 4.01 |
| Lcn2 | lipocalin 2 | 4.10 |
| Gzmk | granzyme K | 4.11 |
| A530013C23Rik | RIKEN cDNA A530013C23 gene | 4.20 |
| Krt75 | keratin 75 | 4.23 |
| 1100001G20Rik | RIKEN cDNA 1100001G20 gene | 4.24 |
| Efna2 | ephrin A2 | 4.24 |
| C330013E15Rik | RIKEN cDNA C330013E15 gene | 4.27 |
| Hecw2 | HECT, C2 and WW domain containing E3 ubiquitin protein ligase 2 | 4.31 |
| March11 | membrane-associated ring finger (C3HC4) 11 | 4.35 |
| 4930588J15Rik | RIKEN cDNA 4930588J15 gene | 4.37 |
| Sucnr1 | succinate receptor 1 | 4.64 |
| Smok4a | sperm motility kinase 4A | 4.85 |
| I730030J21Rik | RIKEN cDNA I730030J21 gene | 5.14 |
| Slc15a2 | solute carrier family 15 (H+/peptide transporter), member 2 | 5.21 |
| Penk | preproenkephalin | 5.25 |
| 1700034I23Rik | FUN14 domain containing 2 pseudogene | 5.30 |
| Tnfsf18 | tumor necrosis factor (ligand) superfamily, member 18 | 5.64 |
| Cox6a2 | cytochrome c oxidase subunit VIa polypeptide 2 | 5.68 |
| Csf2 | colony stimulating factor 2 (granulocyte-macrophage) | 5.81 |
| Actg1 | actin, gamma, cytoplasmic 1 | 5.85 |
| Apold1 | apolipoprotein L domain containing 1 | 6.06 |
| Ip6k2 | inositol hexaphosphate kinase 2 | 7.27 |
| Baiap3 | BAI1-associated protein 3 | 7.29 |
| Hsd3b1 | hydroxy-delta-5-steroid dehydrogenase, 3 beta- and steroid delta-isomerase 1 | 9.34 |
| Sec14l4 | SEC14-like 4 (S. cerevisiae) | 10.28 |
| Itgad | integrin, alpha D | 10.29 |

EQUIVALENTS

Those skilled in the art will recognize, or be able to ascertain using no more than routine experimentation, many equivalents to the specific embodiments of the invention described herein. Such equivalents are intended to be encompassed by the following claims.

REFERENCES

Acosta-Alvear, D., Zhou, Y., Blais, A., Tsikitis, M., Lents, N. H., Arias, C., Lennon, C. J., Kluger, Y., and Dynlacht, B. D. (2007). XBP1 controls diverse cell type- and condition-specific transcriptional regulatory networks. Mol Cell 27, 53-66.

Barnett, B., Kryczek, I., Cheng, P., Zou, W., and Curiel, T. J. (2005). Regulatory T cells in ovarian cancer: biology and therapeutic potential. Am J Reprod Immunol 54, 369-377.

Bhowmick, N. A., Neilson, E. G., and Moses, H. L. (2004). Stromal fibroblasts in cancer initiation and progression. Nature 432, 332-337.

Bollard, C. M., Gottschalk, S., Leen, A. M., Weiss, H., Straathof, K. C., Carrum, G., Khalil, M., Wu, M. F., Huls, M. H., Chang, C. C., et al. (2007). Complete responses of relapsed lymphoma following genetic modification of tumor-antigen presenting cells and T-lymphocyte transfer. Blood 110, 2838-2845.

Callahan, M. J., Nagymanyoki, Z., Bonome, T., Johnson, M. E., Litkouhi, B., Sullivan, E. H., Hirsch, M. S., Matulonis, U. A., Liu, J., Birrer, M. J., et al. (2008). Increased HLA-DMB expression in the tumor epithelium is associated with increased CTL infiltration and improved prognosis in advanced-stage serous ovarian cancer. Clin Cancer Res 14, 7667-7673.

Carrasco, D. R., Sukhdeo, K., Protopopova, M., Sinha, R., Enos, M., Carrasco, D. E., Zheng, M., Mani, M., Henderson, J., Pinkus, G. S., et al. (2007). The differentiation and stress response factor XBP-1 drives multiple myeloma pathogenesis. Cancer Cell 11, 349-360.

Caton, M. L., Smith-Raska, M. R., and Reizis, B. (2007). Notch-RBP-J signaling controls the homeostasis of CD8– dendritic cells in the spleen. J Exp Med 204, 1653-1664.

Chen, X., Iliopoulos, D., Zhang, Q., Tang, Q., Greenblatt, M. B., Hatziapostolou, M., Lim, E., Tam, W. L., Ni, M., Chen, Y., et al. (2014). XBP1 promotes triple-negative breast cancer by controlling the HIF1alpha pathway. Nature 508, 103-107.

Conejo-Garcia, J. R., Benencia, F., Courreges, M. C., Kang, E., Mohamed-Hadley, A., Buckanovich, R. J., Holtz, D. O., Jenkins, A., Na, H., Zhang, L., et al. (2004). Tumor-infiltrating dendritic cell precursors recruited by a beta-defensin contribute to vasculogenesis under the influence of Vegf-A. Nat Med 10, 950-958.

Conejo-Garcia, J. R., Buckanovich, R. J., Benencia, F., Courreges, M. C., Rubin, S. C., Carroll, R. G., and Coukos, G. (2005). Vascular leukocytes contribute to tumor vascularization. Blood 105, 679-681.

Coussens, L. M., Tinkle, C. L., Hanahan, D., and Werb, Z. (2000). MMP-9 supplied by bone marrow-derived cells contributes to skin carcinogenesis. Cell 103, 481-490.

Coussens, L. M., and Werb, Z. (2002). Inflammation and cancer. Nature 420, 860-867.

Cubillos-Ruiz, J. R., Baird, J. R., Tesone, A. J., Rutkowski, M. R., Scarlett, U. K., Camposeco-Jacobs, A. L., Anadon-Arnillas, J., Harwood, N. M., Korc, M., Fiering. S. N., et al. (2012). Reprogramming tumor-associated dendritic cells in vivo using microRNA mimetics triggers protective immunity against ovarian cancer. Cancer Res (Published OnlineFirst February 3).

Cubillos-Ruiz, J. R., Engle, X., Scarlett, U. K., Martinez, D., Barber, A., Elgueta, R., Wang, L., Nesbeth, Y., Durant, Y., Gewirtz, A. T., et al. (2009). Polyethylenimine-based siRNA nanocomplexes reprogram tumor-associated dendritic cells via TLR5 to elicit therapeutic antitumor immunity. J Clin Invest 119, 2231-2244.

Cubillos-Ruiz, J. R., Rutkowski, M., and Conejo-Garcia, J. R. (2010). Blocking ovarian cancer progression by targeting tumor microenvironmental leukocytes. Cell Cycle 9, 260-268.

Curiel, T. J., Wei, S., Dong, H., Alvarez, X., Cheng, P., Mottram, P., Krzysiek, R., Knutson, K. L., Daniel, B., Zimmermann, M. C., et al. (2003). Blockade of B7-H1 improves myeloid dendritic cell-mediated antitumor immunity. Nat Med 9, 562-567.

De Palma, M., Murdoch, C., Venneri, M. A., Naldini, L., and Lewis, C. E. (2007). Tie2-expressing monocytes: regulation of tumor angiogenesis and therapeutic implications. Trends Immunol 28, 519-524.

Dinulescu, D. M., Ince, T. A., Quade, B. J., Shafer, S. A., Crowley, D., and Jacks, T. (2005). Role of K-ras and Pten in the development of mouse models of endometriosis and endometrioid ovarian cancer. Nat Med 11, 63-70.

Dudley, M. E., Wunderlich, J. R., Robbins, P. F., Yang, J. C., Hwu, P., Schwartzentruber, D. J., Topalian, S. L., Sherry, R., Restifo, N. P., Hubicki, A. M., et al. (2002). Cancer regression and autoimmunity in patients after clonal repopulation with antitumor lymphocytes. Science 298, 850-854.

Flesken-Nikitin, A., Choi, K. C., Eng, J. P., Shmidt, E. N., and Nikitin, A. Y. (2003). Induction of carcinogenesis by concurrent inactivation of p53 and Rb1 in the mouse ovarian surface epithelium. Cancer Res 63, 3459-3463.

Gomez, B. P., Riggins, R. B., Shajahan, A. N., Klimach, U., Wang, A., Crawford, A. C., Zhu, Y., Zwart, A., Wang, M., and Clarke, R. (2007). Human X-box binding protein-1 confers both estrogen independence and antiestrogen resistance in breast cancer cell lines. FASEB J 21, 4013-4027.

Hamanishi, J., Mandai, M., Iwasaki, M., Okazaki, T., Tanaka, Y., Yamaguchi, K., Higuchi, T., Yagi, H., Takakura, K., Minato, N., et al. (2007). Programmed cell death 1 ligand 1 and tumor-infiltrating CD8+ T lymphocytes are prognostic factors of human ovarian cancer. Proc Natl Acad Sci USA 104, 3360-3365.

Han, L. Y., Fletcher, M. S., Urbauer, D. L., Mueller, P., Landen, C. N., Kamat, A. A., Lin, Y. G., Merritt, W. M., Spannuth, W. A., Deavers, M. T., et al. (2008). HLA class I antigen processing machinery component expression and intratumoral T-Cell infiltrate as independent prognostic markers in ovarian carcinoma. Clin Cancer Res 14, 3372-3379.

Herber, D. L., Cao, W., Nefedova, Y., Novitskiy, S. V., Nagaraj, S., Tyurin, V. A., Corzo, A., Cho, H. I., Celis, E., Lennox, B., et al. (2010). Lipid accumulation and dendritic cell dysfunction in cancer. Nat Med 16, 880-886.

Hetz, C., Chevet, E., and Harding, H. P. (2013). Targeting the unfolded protein response in disease. Nature reviews Drug discovery 12, 703-719.

Hollien, J., Lin, J. H., Li, H., Stevens, N., Walter, P., and Weissman, J. S. (2009). Regulated Ire1-dependent decay of messenger RNAs in mammalian cells. J Cell Biol 186, 323-331.

Huang da. W., Sherman, B. T., and Lempicki, R. A. (2009). Systematic and integrative analysis of large gene lists using DAVID bioinformatics resources, Nature protocols 4, 44-57.

Huarte, E., Cubillos-Ruiz, J. R., Nesbeth, Y. C., Scarlett, U. K., Martinez, D. G., Buckanovich, R. J., Benencia, F., Stan, R. V., Keler, T., Sarobe, P., et al. (2008). Depletion of dendritic cells delays ovarian cancer progression by boosting antitumor immunity. Cancer Res 68, 7684-7691.

Iwakoshi, N. N., Pypaert, M., and Glimcher, L. H. (2007). The transcription factor XBP-1 is essential for the development and survival of dendritic cells. J Exp Med 204, 2267-2275.

Jackson, E. L., Willis, N., Mercer, K., Bronson, R. T., Crowley, D., Montoya, R., Jacks, T., and Tuveson, D. A. (2001). Analysis of lung tumor initiation and progression using conditional expression of oncogenic K-ras. Genes Dev 15, 3243-3248.

Jonkers, J., Meuwissen, R., van der Gulden, H., Peterse, H., van der Valk, M., and Berns, A. (2001). Synergistic tumor suppressor activity of BRCA2 and p53 in a conditional mouse model for breast cancer. Nat Genet 29, 418-425.

Langmead, B., Trapnell, C., Pop, M., and Salzberg, S. L. (2009). Ultrafast and memory-efficient alignment of short DNA sequences to the human genome. Genome biology 10, R25.

Lee, A. H., Iwakoshi, N. N., Anderson, K. C., and Glimcher, L. H. (2003a). Proteasome inhibitors disrupt the unfolded protein response in myeloma cells. Proc Natl Acad Sci USA 100, 9946-9951.

Lee, A. H., Iwakoshi, N. N., and Glimcher, L. H. (2003b). XBP-1 regulates a subset of endoplasmic reticulum resident chaperone genes in the unfolded protein response. Mol Cell Biol 23, 7448-7459.

Lee, A. H., Scapa, E. F., Cohen, D. E., and Glimcher, L. H. (2008). Regulation of hepatic lipogenesis by the transcription factor XBP1. Science 320, 1492-1496.

Leen, A. M., Myers, G. D., Sili, U., Huls, M. H., Weiss, H., Leung, K. S., Carrum, G., Krance, R. A., Chang, C. C., Molldrem, J. J., et al. (2006). Monoculture-derived T lymphocytes specific for multiple viruses expand and produce clinically relevant effects in immunocompromised individuals. Nat Med 12, 1160-1166.

Li, B., and Dewey, C. N. (2011). RSEM: accurate transcript quantification from RNA-Seq data with or without a reference genome. BMC bioinformatics 12, 323.

Mantovani, A., Allavena, P., Sica, A., and Balkwill, F. (2008). Cancer-related inflammation. Nature 454, 436-444.

Martinon, F., Chen, X., Lee, A. H., and Glimcher, L. H. (2010). TLR activation of the transcription factor XBP1 regulates innate immune responses in macrophages. Nat Immunol 11, 411-418.

Morgan, R. A., Dudley, M. E., Wunderlich, J. R., Hughes, M. S., Yang, J. C., Sherry, R. M., Royal, R. E., Topalian, S. L., Kammula, U. S., Restifo, N. P., et al. (2006). Cancer regression in patients after transfer of genetically engineered lymphocytes. Science 314, 126-129.

Nesbeth, Y., Scarlett, U., Cubillos-Ruiz, J., Martinez, D., Engle, X., Turk, M. J., and Conejo-Garcia, J. R. (2009). CCL5-mediated endogenous antitumor immunity elicited by adoptively transferred lymphocytes and dendritic cell depletion. Cancer Res 69, 6331-6338.

Nesbeth, Y. C., Martinez, D. G., Toraya, S., Scarlett, U. K., Cubillos-Ruiz, J. R., Rutkowski, M. R., and Conejo-Garcia, J. R. (2010). CD4+ T cells elicit host immune responses to MHC class II-negative ovarian cancer through CCL5 secretion and CD40-mediated licensing of dendritic cells. J Immunol 184, 5654-5662.

Piret, J. P., Mottet, D., Raes, M., and Michiels, C. (2002). CoCl2, a chemical inducer of hypoxia-inducible factor-1, and hypoxia reduce apoptotic cell death in hepatoma cell line HepG2. Ann N Y Acad Sci 973, 443-447.

Ramakrishnan, R., Tyurin, V. A., Veglia, F., Condamine, T., Amoscato, A., Mohammadyani, D., Johnson, J. J., Zhang, L. M., Klein-Seetharaman, J., Celis, E., et al. (2014). Oxidized lipids block antigen cross-presentation by dendritic cells in cancer. J Immunol 192, 2920-2931.

Reimold, A. M., Iwakoshi N. N., Manis, J., Vallabhajosyula, P., Szomolanyi-Tsuda, E., Gravallese, E. M., Friend, D., Grusby, M. J., Alt, F., and Glimcher, L. H. (2001). Plasma cell differentiation requires the transcription factor XBP-1. Nature 412, 300-307.

Robinson, M. D., and Oshlack, A. (2010). A scaling normalization method for differential expression analysis of RNA-seq data. Genome biology 11, R25.

Roby, K. F., Taylor, C. C., Sweetwood, J. P., Cheng, Y., Pace, J. L., Tawfik, O., Persons, D. L., Smith, P. G., and Terranova, P. F. (2000). Development of a syngeneic mouse model for events related to ovarian cancer. Carcinogenesis 21, 585-591.

Sato, E., Olson, S. H., Ahn, J., Bundy, B., Nishikawa, H., Qian, F., Jungbluth, A. A., Frosina, D., Gnjatic, S., Ambrosone, C., et al. (2005). Intraepithelial CD8+ tumor-infiltrating lymphocytes and a high CD8+/regulatory T cell ratio are associated with favorable prognosis in ovarian cancer. Proc Natl Acad Sci USA 102, 18538-18543.

Scarlett, U. K., Cubillos-Ruiz, J. R., Nesbeth, Y. C., Martinez, D. G., Engle, X., Gewirtz, A. T., Ahonen, C. L., and Conejo-Garcia, J. R. (2009). In situ stimulation of CD40 and Toll-like receptor 3 transforms ovarian cancer-infiltrating dendritic cells from immunosuppressive to immunostimulatory cells. Cancer Res 69, 7329-7337.

Scarlett, U. K., Rutkowski, M. R., Rauwerdink, A. M., Fields, J., Escovar-Fadul, X., Baird, J., Cubillos-Ruiz, J. R., Jacobs, A. C., Gonzalez, J. L., Weaver, J., et al. (2012). Ovarian cancer progression is controlled by phenotypic changes in dendritic cells. J Exp Med.

Singh, S. P., Niemczyk, M., Saini, D., Awasthi, Y. C., Zimniak, L., and Zimniak, P. (2008). Role of the electrophilic lipid peroxidation product 4-hydroxynonenal in the development and maintenance of obesity in mice. Biochemistry 47, 3900-3911.

Singh, S. P., Niemczyk, M., Zimniak, L., and Zimniak, P. (2009). Fat accumulation in *Caenorhabditis elegans* triggered by the electrophilic lipid peroxidation product 4-hydroxynonenal (4-HNE). Aging 1, 68-80.

So, J. S., Hur, K. Y., Tarrio, M., Ruda, V., Frank-Kamenetsky, M., Fitzgerald, K., Koteliansky, V., Lichtman, A. H., Iwawaki, T., Glimcher, L. H., et al. (2012). Silencing of lipid metabolism genes through IRE1alpha-mediated mRNA decay lowers plasma lipids in mice. Cell Metab 16, 487-499.

Sriburi, R., Jackowski, S., Mori, K., and Brewer, J. W. (2004). XBP1: a link between the unfolded protein response, lipid biosynthesis, and biogenesis of the endoplasmic reticulum. J Cell Biol 167, 35-41.

Vladykovskaya, E., Sithu, S. D., Haberzettl, P., Wickramasinghe, N. S., Merchant, M. L., Hill, B. G., McCracken, J., Agarwal, A., Dougherty, S., Gordon, S. A., et al. (2012). Lipid peroxidation product 4-hydroxy-trans-2-nonenal causes endothelial activation by inducing endoplasmic reticulum stress. J Biol Chem 287, 11398-11409.

Whiteside, T. L. (2008). The tumor microenvironment and its role in promoting tumor growth. Oncogene 27, 5904-5912.

Yoshida, H., Matsui, T., Yamamoto, A., Okada, T., and Mori, K. (2001). XBP1 mRNA is induced by ATF6 and spliced by IRE1 in response to ER stress to produce a highly active transcription factor. Cell 107, 881-891.

Zhang, L., Conejo-Garcia, J. R., Katsaros, D., Gimotty, P. A., Massobrio, M., Regnani, G., Makrigiannakis, A., Gray, H., Schlienger, K., Liebman, M. N., et al. (2003). Intratumoral T cells, recurrence, and survival in epithelial ovarian cancer. N Engl J Med 348, 203-213.

Zou, W. (2005). Immunosuppressive networks in the tumour environment and their therapeutic relevance. Nat Rev Cancer 5, 263-274.

Meredith, M. M., Liu, K., Darrasse-Jeze, G., Kamphorst, A. O., Schreiber, H. A., Guermonprez, P., Idoyaga, J., Cheong, C., Yao, K. H., Niec, R. E., et al. (2012). Expression of the zinc finger transcription factor zDC (Zbtb46, Btbd4) defines the classical dendritic cell lineage. J Exp Med 209, 1153-1165.

Piret, J. P., Mottet, D., Raes, M., and Michiels, C. (2002). CoCl2, a chemical inducer of hypoxia-inducible factor-1, and hypoxia reduce apoptotic cell death in hepatoma cell line HepG2. Ann N Y Acad Sci 973, 443-447.

Satpathy, A. T., Kc, W., Albring, J. C., Edelson, B. T., Kretzer, N. M., Bhattacharya, D., Murphy, T. L., and Murphy, K. M. (2012). Zbtb46 expression distinguishes classical dendritic cells and their committed progenitors from other immune lineages. J Exp Med 209, 1135-1152.

Schraml, B. U., van Blijswijk, J., Zelenay, S., Whitney, P. G., Filby, A., Acton, S. E., Rogers, N. C., Moncaut, N., Carvajal, J. J., and Reis e Sousa, C. (2013). Genetic tracing via DNGR-1 expression history defines dendritic cells as a hematopoietic lineage. Cell 154, 843-858.

The invention claimed is:

1. A method for enhancing or inducing an anti-tumor response in a subject, the method comprising:
administering to the subject an effective amount of a direct inhibitor of IRE1α for enhancing or inducing an anti-tumor immune response in the subject, wherein the effective amount of the direct inhibitor of IRE1α increases antigen presentation in antigen presenting cells, wherein the tumor is a solid tumor, wherein the solid tumor is from an ovarian cancer, epithelial cancer, germ cell cancer, or a stromal tumor, and wherein the direct inhibitor of IRE1α is a small molecule inhibitor of IRE-1α.

2. The method of claim 1, wherein the inhibitor of IRE-1α is administered systemically.

3. The method of claim 1, wherein the inhibitor of IRE-1α, targets tumor-associated dendritic cells (tDCs).

4. The method of claim 1, wherein the inhibitor of IRE-1α is administered in combination with a second cancer therapeutic agent.

5. The method of claim 4, wherein the second cancer therapeutic agent is a chemotherapeutic agent.

6. The method of claim 1, wherein the treatment induces extended survival of the subject.

7. The method of claim 1, wherein the anti-tumor immune response is mediated by adaptive immune cells.

8. The method of claim 7, wherein the adaptive immune cells comprise T cells.

9. The method of claim 1 wherein the solid tumor is from an ovarian cancer.

10. The method of claim 1 wherein the solid tumor is from an epithelial cancer.

11. The method of claim 1 wherein the solid tumor is from a germ cell cancer.

12. The method of claim 1 wherein the solid tumor is a stromal tumor.

* * * * *

SEQUENCE LISTING

```
<160> NUMBER OF SEQ ID NOS: 42

<210> SEQ ID NO 1
<211> LENGTH: 21
<212> TYPE: DNA
<213> ORGANISM: Artificial Sequence
<220> FEATURE:
<223> OTHER INFORMATION: Synthetic oligonucleotide;  siLuc sense
<220> FEATURE:
<221> NAME/KEY: misc_feature
<222> LOCATION: (2)..(2)
<223> OTHER INFORMATION: 2'-OMe modified nucleotide
<220> FEATURE:
```

```
<221> NAME/KEY: misc_feature
<222> LOCATION: (6)..(7)
<223> OTHER INFORMATION: 2'-OMe modified nucleotide
<220> FEATURE:
<221> NAME/KEY: misc_feature
<222> LOCATION: (11)..(13)
<223> OTHER INFORMATION: 2'-OMe modified nucleotide
<220> FEATURE:
<221> NAME/KEY: misc_feature
<222> LOCATION: (17)..(17)
<223> OTHER INFORMATION: 2'-OMe modified nucleotide
<220> FEATURE:
<221> NAME/KEY: misc_feature
<222> LOCATION: (20)..(21)
<223> OTHER INFORMATION: Phosphorothioate linkage

<400> SEQUENCE: 1
cuuacgcuga guacuucgat t                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetic oligonucleotide:  siLuc antisense
<220> FEATURE:
<221> NAME/KEY: misc_feature
<222> LOCATION: (3)..(3)
<223> OTHER INFORMATION: 2'-OMe modified nucleotide
<220> FEATURE:
<221> NAME/KEY: misc_feature
<222> LOCATION: (15)..(15)
<223> OTHER INFORMATION: 2'-OMe modified nucleotide
<220> FEATURE:
<221> NAME/KEY: misc_feature
<222> LOCATION: (20)..(21)
<223> OTHER INFORMATION: Phosphorothioate linkage

<400> SEQUENCE: 2
ucgaaguacu cagcguaagt t                                              21

<210> SEQ ID NO 3
<211> LENGTH: 21
<212> TYPE: DNA
<213> ORGANISM: Artificial Sequence
<220> FEATURE:
<223> OTHER INFORMATION: Synthetic oligonucleotide:  siXBP1 sense
<220> FEATURE:
<221> NAME/KEY: misc_feature
<222> LOCATION: (1)..(1)
<223> OTHER INFORMATION: 2'-OMe modified nucleotide
<220> FEATURE:
<221> NAME/KEY: misc_feature
<222> LOCATION: (3)..(6)
<223> OTHER INFORMATION: 2'-OMe modified nucleotide
<220> FEATURE:
<221> NAME/KEY: misc_feature
<222> LOCATION: (10)..(12)
<223> OTHER INFORMATION: 2'-OMe modified nucleotide
<220> FEATURE:
<221> NAME/KEY: misc_feature
<222> LOCATION: (14)..(15)
<223> OTHER INFORMATION: 2'-OMe modified nucleotide
<220> FEATURE:
<221> NAME/KEY: misc_feature
<222> LOCATION: (17)..(19)
<223> OTHER INFORMATION: 2'-OMe modified nucleotide
<220> FEATURE:
<221> NAME/KEY: misc_feature
<222> LOCATION: (20)..(21)
<223> OTHER INFORMATION: Phosphorothioate linkage

<400> SEQUENCE: 3
cacccugaau ucauugucut t                                              21
```

```
<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide:  siXBP1 antisense
<220> FEATURE:
<221> NAME/KEY: misc_feature
<222> LOCATION: (4)..(4)
<223> OTHER INFORMATION: 2'-OMe modified nucleotide
<220> FEATURE:
<221> NAME/KEY: misc_feature
<222> LOCATION: (13)..(13)
<223> OTHER INFORMATION: 2'-OMe modified nucleotide
<220> FEATURE:
<221> NAME/KEY: misc_feature
<222> LOCATION: (20)..(21)
<223> OTHER INFORMATION: Phosphorothioate linkage

<400> SEQUENCE: 4
agacaaugaa uucagggugt t                                            21

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide:  siIRE1a sense
<220> FEATURE:
<221> NAME/KEY: misc_feature
<222> LOCATION: (2)..(2)
<223> OTHER INFORMATION: 2'-OMe modified nucleotide
<220> FEATURE:
<221> NAME/KEY: misc_feature
<222> LOCATION: (4)..(5)
<223> OTHER INFORMATION: 2'-OMe modified nucleotide
<220> FEATURE:
<221> NAME/KEY: misc_feature
<222> LOCATION: (10)..(12)
<223> OTHER INFORMATION: 2'-OMe modified nucleotide
<220> FEATURE:
<221> NAME/KEY: misc_feature
<222> LOCATION: (16)..(16)
<223> OTHER INFORMATION: 2'-OMe modified nucleotide
<220> FEATURE:
<221> NAME/KEY: misc_feature
<222> LOCATION: (20)..(21)
<223> OTHER INFORMATION: Phosphorothioate linkage

<400> SEQUENCE: 5
augccgaagu ucagauggat t                                            21

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide:  siIRE1a antisense
<220> FEATURE:
<221> NAME/KEY: misc_feature
<222> LOCATION: (3)..(3)
<223> OTHER INFORMATION: 2'-OMe modified nucleotide
<220> FEATURE:
<221> NAME/KEY: misc_feature
<222> LOCATION: (17)..(17)
<223> OTHER INFORMATION: 2'-OMe modified nucleotide
<220> FEATURE:
<221> NAME/KEY: misc_feature
<222> LOCATION: (20)..(21)
<223> OTHER INFORMATION: Phosphorothioate linkage

<400> SEQUENCE: 6
```
uccaucugaa cuucggcaut t                                             21

<210> SEQ ID NO 7
<211> LENGTH: 20
<212> TYPE: DNA
<213> ORGANISM: Artificial Sequence
<220> FEATURE:
<223> OTHER INFORMATION: Synthetic primer: hAct-F

<400> SEQUENCE: 7
gcgagaagat gacccagatc                                               20

<210> SEQ ID NO 8
<211> LENGTH: 19
<212> TYPE: DNA
<213> ORGANISM: Artificial Sequence
<220> FEATURE:
<223> OTHER INFORMATION: Synthetic primer: hAct-R

<400> SEQUENCE: 8
ccagtggtac ggccagagg                                                19

<210> SEQ ID NO 9
<211> LENGTH: 20
<212> TYPE: DNA
<213> ORGANISM: Artificial Sequence
<220> FEATURE:
<223> OTHER INFORMATION: Synthetic primer: hCHOP-F

<400> SEQUENCE: 9
ctgcttctct ggcttggctg                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic primer: hCHOP-R

<400> SEQUENCE: 10
gctctgggag gtgcttgtga                                               20

<210> SEQ ID NO 11
<211> LENGTH: 20
<212> TYPE: DNA
<213> ORGANISM: Artificial Sequence
<220> FEATURE:
<223> OTHER INFORMATION: Synthetic primer: hXBP1-SA-F

<400> SEQUENCE: 11
cctggttgct gaagaggagg                                               20

<210> SEQ ID NO 12
<211> LENGTH: 18
<212> TYPE: DNA
<213> ORGANISM: Artificial Sequence
<220> FEATURE:
<223> OTHER INFORMATION: Synthetic primer: hXBP1-SA-R

<400> SEQUENCE: 12
ccatggggag ttctggag                                                 18

<210> SEQ ID NO 13
<211> LENGTH: 20
<212> TYPE: DNA
<213> ORGANISM: Artificial Sequence

```
<220> FEATURE:
<223> OTHER INFORMATION: Synthetic primer:  Xbp1-SA-F

<400> SEQUENCE: 13
acacgtttgg gaatggacac                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic primer:  Xbp1-SA-F

<400> SEQUENCE: 14
ccatgggaag atgttctggg                                              20

<210> SEQ ID NO 15
<211> LENGTH: 24
<212> TYPE: DNA
<213> ORGANISM: Artificial Sequence
<220> FEATURE:
<223> OTHER INFORMATION: Synthetic primer:  actb1083

<400> SEQUENCE: 15
ctcaggagga gcaatgatct tgat                                         24

<210> SEQ ID NO 16
<211> LENGTH: 20
<212> TYPE: DNA
<213> ORGANISM: Artificial Sequence
<220> FEATURE:
<223> OTHER INFORMATION: Synthetic primer:  actb987

<400> SEQUENCE: 16
taccaccatg tacccaggca                                              20

<210> SEQ ID NO 17
<211> LENGTH: 23
<212> TYPE: DNA
<213> ORGANISM: Artificial Sequence
<220> FEATURE:
<223> OTHER INFORMATION: Synthetic primer:  Xbp1.total-F

<400> SEQUENCE: 17
gacagagagt caaactaacg tgg                                          23

<210> SEQ ID NO 18
<211> LENGTH: 19
<212> TYPE: DNA
<213> ORGANISM: Artificial Sequence
<220> FEATURE:
<223> OTHER INFORMATION: Synthetic primer:  Xbp1.total-R

<400> SEQUENCE: 18
gtccagcagg caagaaggt                                               19

<210> SEQ ID NO 19
<211> LENGTH: 20
<212> TYPE: DNA
<213> ORGANISM: Artificial Sequence
<220> FEATURE:
<223> OTHER INFORMATION: Synthetic primer:  XBPsA406F

<400> SEQUENCE: 19
aagaacacgc ttgggaatgg                                              20
```

```
<210> SEQ ID NO 20
<211> LENGTH: 17
<212> TYPE: DNA
<213> ORGANISM: Artificial Sequence
<220> FEATURE:
<223> OTHER INFORMATION: Synthetic primer: XBPsAa518R

<400> SEQUENCE: 20
ctgcacctgc tgcggac                                                  17

<210> SEQ ID NO 21
<211> LENGTH: 18
<212> TYPE: DNA
<213> ORGANISM: Artificial Sequence
<220> FEATURE:
<223> OTHER INFORMATION: Synthetic primer: XBP1WT205-F

<400> SEQUENCE: 21
cctgagcccg gaggagaa                                                 18

<210> SEQ ID NO 22
<211> LENGTH: 18
<212> TYPE: DNA
<213> ORGANISM: Artificial Sequence
<220> FEATURE:
<223> OTHER INFORMATION: Synthetic primer: XBP1WT272-R

<400> SEQUENCE: 22
ctcgagcagt ctgcgctg                                                 18

<210> SEQ ID NO 23
<211> LENGTH: 21
<212> TYPE: DNA
<213> ORGANISM: Artificial Sequence
<220> FEATURE:
<223> OTHER INFORMATION: Synthetic primer: ERdj4-F

<400> SEQUENCE: 23
taaaagccct gatgctgaag c                                             21

<210> SEQ ID NO 24
<211> LENGTH: 19
<212> TYPE: DNA
<213> ORGANISM: Artificial Sequence
<220> FEATURE:
<223> OTHER INFORMATION: Synthetic primer: ERdj4-R

<400> SEQUENCE: 24
tccgactatt ggcatccga                                                19

<210> SEQ ID NO 25
<211> LENGTH: 21
<212> TYPE: DNA
<213> ORGANISM: Artificial Sequence
<220> FEATURE:
<223> OTHER INFORMATION: Synthetic primer: Sec61a1-F

<400> SEQUENCE: 25
ctatttccag ggcttccgag t                                             21

<210> SEQ ID NO 26
<211> LENGTH: 21
<212> TYPE: DNA
<213> ORGANISM: Artificial Sequence
<220> FEATURE:
<223> OTHER INFORMATION: Synthetic primer: Sec61a1-R
```

<400> SEQUENCE: 26
aggtgttgta ctggcctcgg t         21

<210> SEQ ID NO 27
<211> LENGTH: 19
<212> TYPE: DNA
<213> ORGANISM: Artificial Sequence
<220> FEATURE:
<223> OTHER INFORMATION: Synthetic primer: Grp78-F

<400> SEQUENCE: 27
tcatcggacg cacttggaa         19

<210> SEQ ID NO 28
<211> LENGTH: 21
<212> TYPE: DNA
<213> ORGANISM: Artificial Sequence
<220> FEATURE:
<223> OTHER INFORMATION: Synthetic primer: Grp78-R

<400> SEQUENCE: 28
caaccacctt gaatggcaag a         21

<210> SEQ ID NO 29
<211> LENGTH: 21
<212> TYPE: DNA
<213> ORGANISM: Artificial Sequence
<220> FEATURE:
<223> OTHER INFORMATION: Synthetic primer: CHOP-F

<400> SEQUENCE: 29
gtccctagct tggctgacag a         21

<210> SEQ ID NO 30
<211> LENGTH: 18
<212> TYPE: DNA
<213> ORGANISM: Artificial Sequence
<220> FEATURE:
<223> OTHER INFORMATION: Synthetic primer: CHOP-R

<400> SEQUENCE: 30
tggagagcga gggctttg         18

<210> SEQ ID NO 31
<211> LENGTH: 21
<212> TYPE: DNA
<213> ORGANISM: Artificial Sequence
<220> FEATURE:
<223> OTHER INFORMATION: Synthetic primer: Agpat6-F

<400> SEQUENCE: 31
agcttgattg tcaacctcct g         21

<210> SEQ ID NO 32
<211> LENGTH: 19
<212> TYPE: DNA
<213> ORGANISM: Artificial Sequence
<220> FEATURE:
<223> OTHER INFORMATION: Synthetic primer: Agpat6-R

<400> SEQUENCE: 32
ccgttggtgt agggcttgt         19

<210> SEQ ID NO 33

```
<211> LENGTH: 20
<212> TYPE: DNA
<213> ORGANISM: Artificial Sequence
<220> FEATURE:
<223> OTHER INFORMATION: Synthetic primer: Scd2-F

<400> SEQUENCE: 33
gcatttggga gccttgtacg                                                    20

<210> SEQ ID NO 34
<211> LENGTH: 21
<212> TYPE: DNA
<213> ORGANISM: Artificial Sequence
<220> FEATURE:
<223> OTHER INFORMATION: Synthetic primer: Scd2-R

<400> SEQUENCE: 34
agccgtgcct tgtatgttct g                                                  21

<210> SEQ ID NO 35
<211> LENGTH: 21
<212> TYPE: DNA
<213> ORGANISM: Artificial Sequence
<220> FEATURE:
<223> OTHER INFORMATION: Synthetic primer: Fasn-F

<400> SEQUENCE: 35
ggaggtggtg atagccggta t                                                  21

<210> SEQ ID NO 36
<211> LENGTH: 21
<212> TYPE: DNA
<213> ORGANISM: Artificial Sequence
<220> FEATURE:
<223> OTHER INFORMATION: Synthetic primer: Fasn-R

<400> SEQUENCE: 36
tgggtaatcc atagagccca g                                                  21

<210> SEQ ID NO 37
<211> LENGTH: 22
<212> TYPE: DNA
<213> ORGANISM: Artificial Sequence
<220> FEATURE:
<223> OTHER INFORMATION: Synthetic primer: Lpar1.F

<400> SEQUENCE: 37
gacctagcag gcttacagtt cc                                                 22

<210> SEQ ID NO 38
<211> LENGTH: 20
<212> TYPE: DNA
<213> ORGANISM: Artificial Sequence
<220> FEATURE:
<223> OTHER INFORMATION: Synthetic primer: Lpar1.R

<400> SEQUENCE: 38
gctgtagttt ggggcgatga                                                    20

<210> SEQ ID NO 39
<211> LENGTH: 20
<212> TYPE: DNA
<213> ORGANISM: Artificial Sequence
<220> FEATURE:
<223> OTHER INFORMATION: Synthetic primer: Clec9a.F

<400> SEQUENCE: 39
```

```
gagcatggtg tgttgtgacg                                                    20

<210> SEQ ID NO 40
<211> LENGTH: 22
<212> TYPE: DNA
<213> ORGANISM: Artificial Sequence
<220> FEATURE:
<223> OTHER INFORMATION: Synthetic primer:  Clec9a.R

<400> SEQUENCE: 40
tacctggaag aacttgatgc cc                                                 22

<210> SEQ ID NO 41
<211> LENGTH: 20
<212> TYPE: DNA
<213> ORGANISM: Artificial Sequence
<220> FEATURE:
<223> OTHER INFORMATION: Synthetic primer:  Zbtb46.F

<400> SEQUENCE: 41
ctcacatact ggagagcggc                                                    20

<210> SEQ ID NO 42
<211> LENGTH: 21
<212> TYPE: DNA
<213> ORGANISM: Artificial Sequence
<220> FEATURE:
<223> OTHER INFORMATION: Synthetic primer:  Zbtb46.R

<400> SEQUENCE: 42
tgctgtggac cagagtatgt c                                                  21
```